US008586705B2

(12) United States Patent
Krippner et al.

(10) Patent No.: US 8,586,705 B2
(45) Date of Patent: *Nov. 19, 2013

(54) MACROMOLECULAR COMPOUNDS HAVING CONTROLLED STOICHIOMETRY

(75) Inventors: Guy Yeoman Krippner, Mt Waverley (AU); Gottfried Lichti, Essendon (AU); Pasquale Razzino, South Yarra (AU); Brian Devlin Kelly, Ringwood East (AU); Susanne Pallich, Caroline Springs (AU); Scott Andrew Henderson, Rowville (AU); Angela Michelle Scheppokat, Oakleigh (AU); Charlotte Claire Williams, Carlton (AU); Christopher John Hamilton Porter, Port Melbourne (AU); Benjamin James Boyd, Warrandyte (AU); Lisa Michelle Kaminskas, Brunswick West (AU); Phillip Martin Rendle, Lower Hutt (NZ); Ben William Greatrex, Lower Hutt (NZ)

(73) Assignee: Starpharma Pty Limited, Melbourne, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/570,058

(22) Filed: Aug. 8, 2012

(65) Prior Publication Data

US 2012/0302730 A1 Nov. 29, 2012

Related U.S. Application Data

(63) Continuation of application No. 12/091,233, filed as application No. PCT/AU2006/001591 on Oct. 25, 2006, now Pat. No. 8,258,259.

(30) Foreign Application Priority Data

Oct. 25, 2005 (AU) ................................ 2005905908
Oct. 24, 2006 (AU) ................................ 2006906087

(51) Int. Cl.
*A61K 38/00* (2006.01)
*A61K 9/00* (2006.01)
*A61K 31/74* (2006.01)

(52) U.S. Cl.
USPC ........... 530/323; 530/333; 530/337; 424/400; 424/78.08; 424/DIG. 16

(58) Field of Classification Search
USPC ............... 530/323, 333, 337; 424/400, 78.08, 424/DIG. 16
See application file for complete search history.

(56) References Cited

U.S. PATENT DOCUMENTS 4,289,872 A 9/1981 Denkewalter et al.
5,041,516 A 8/1991 Fréchet et al.
5,229,490 A 7/1993 Tam
5,514,810 A 5/1996 Platzek et al.
5,580,563 A 12/1996 Tam
5,886,126 A 3/1999 Newkome et al.
5,886,127 A 3/1999 Newkome et al.
6,037,444 A 3/2000 Rannard et al.
6,455,071 B1 9/2002 Shchepinov et al.
2002/0123609 A1 9/2002 Frechet et al.

FOREIGN PATENT DOCUMENTS

| JP | 9512264 | 12/1997 |
| JP | 2004515457 | 5/2004 |
| JP | 2005532276 | 10/2005 |
| WO | WO 90/11778 A1 | 10/1990 |
| WO | WO 93/21259 A1 | 10/1993 |
| WO | WO 95/28966 | 11/1995 |
| WO | WO 97/23443 A1 | 7/1997 |
| WO | WO 01/87348 | 11/2001 |
| WO | WO 02/077037 A2 | 10/2002 |
| WO | WO 03/076455 | 9/2003 |

OTHER PUBLICATIONS

Yang et al. ("Penicillin V-conjugated PEG-PAMAM star polymers" in J. Biomater. Sci. Polymer Edn, vol. 14, No. 10, pp. 1043-1056, 2003).*
Page 591, Protective Groups in Organic Synthesis (3rd Ed) by T. Greene and P. Wuts 1999 published by John Wiley & Sons.*
Tetrahedron of 1996, 39, 12839-12852 and Tetrahedron Lett. of 1986, 23, 2599-2602; Troc having the chemical name trichoroethyl carbamate, Can. J. Chem. 1982, 60,976 and Synthesis, 1983, 671 and JOC, 1988.*
Ahlborg, N., 1995 "Synthesis of a Diepitope Multiple Antigen Peptide Containing Sequences from Two Malaria Antigens using Fmoc Chemistry" *Journal of Immunological Methods* 179: 269-275.
Al-Hellani, R. and Schlüter, A.D. 2006 "On the Synthesis and Selective Deprotection of Low-Generation Dendrons with Orthogonally Protected Peripheral Amine Groups and a Possible Impact of the Deprotection Conditions on the Stability of Dendronized Polymers Skeletons" *Helvetica Chimica Acta* 89: 2745-2763.
Ambade, A. V. et al. 2007 "Controlled Functional Group Presentations in dendrimers a tool to probe the Hyperbranched Architecture" *New Journal of Chemistry* 31: 1052-1063.
Dykes, G. M. 2001 "Dendrimers: a Review of Their Appeal and Applications" *Journal of Chemical Technology and Biotechnology* 76: 903-918.
Erlanson, D. A. et al. 2004 "Fragment-Based Drug Discovery" *Journal of Medicinal Chemistry* 47(14): 3463-3482.

(Continued)

*Primary Examiner* — Blessing M Fubara
(74) *Attorney, Agent, or Firm* — Knobbe, Martens, Olson & Bear, LLP

(57) ABSTRACT

The following invention is directed to macromolecules having controlled stoichiometry and topology, processes for their production, and applications for their use. The macromolecules have a controlled functional moiety stoichiometry and include at least one dendritic motif having a surface layer formed from at least one surface building unit and at least one subsurface layer formed from at least one building unit, the surface building unit and building units having a hydrocarbon backbone bearing a carbonyl group and at least one amine group; and at least two different functional moieties on the building unit and/or surface building unit; where functional moiety stoichiometry refers to the number and type of functional moieties.

30 Claims, 23 Drawing Sheets

(56) References Cited

OTHER PUBLICATIONS

Feng, X. et al. 2008 "Janus-Type Dendrimer-Like Poly(ethylene oxide)s" *Journal of American Chemical Society* 130: 11662-11676.
Ganesh, R. N.et al. 2002 "Synthesis of Difunctionalized Dendrimers: an Approach to Main-Chain Poly(Dendrimers)" *Tetrahedron Letters* 43: 7217-7220.
Grayson, S. M. and Frechet J.M.J 2002 "A New Approach to Heterofunctionalized Dendrimer: A Versatile Triallyl Chloride Core" *Organic Letters* 4(19): 3171-3174.
Hawker, C.J. et al. 1990 "Preparation of Polymers with Controlled Molecular Architecture. A New Convergent Approach to Dendritic Macromolecules" *Journal of American Chemical Society* 112(21): 7638-7647.
Hawker, Craig J., "Dendritic and Hyperbranched Macromolecules—Precisely Controlled Macromolecular Architectures", *Advances in Polymer Science*, 1999, 147:113-160.
Horvath, A. et al. 2002 "Lipamino Acid-Based Adjuvant Carrier System: Enhanced Immunogenicity of Group A Strptococcal Peptide Epitopes" *Journal of Medicinal Chemistry* 45: 1387-1390.
Larre, C. et al. 1998 "Chemistry within Megamolecules: Regiospecific Functionalization after Construction of Phosphorus Dendrimers" *Journal of American Chemical Society* 120: 13070-13082.
Lim, J. et al. 2005 "Toward the Next-Generation Drug Delivery Vehicle: Synthesis of a Dendrimer with Four Orthogonally Reactive Groups" *Molecular Pharmaceutics* 2(4): 273-277.
Maraval, V. et al. 2000 "Rapid Synthesis of Phosphorus-Containing Dendrimers with controlled Molecular Architectures: First Example of Surface-Block, Layer-Block, and Segment-Block Dendrimers Issued from the Same Dendron" *Journal of American Chemical Society* 122: 2499-2511.
Maraval, V. et al. 2001 "Varying Topology of Dendrimers—A New Approach toward the Synthesis of Di-Block Dendrimers" *European Journal of Inorganic Chemistry* pp. 1681-1691.
Maruo, N. et al. 1999 "Hemispherical synthesis of dendritic poly(L-lysine) combining sixteen free-base porphyrins and sixteen zinc porphyrins" *Chemical Communications* pp. 2057-2058.
Mihov, G. et al. 2004 "Toward Nanoamphiphiles: Efficient Synthesis of Desymmetrized Polyphenylene Dendrimers" *Journal of Organic Chemistry* 69: 8029-8037.
Morgan, J.R. and Cloninger M.J. 2002 "Heterogeneously Functionalized Dendrimers" *Current Opinion in Drug Discovery & Development* 5(6): 966-973.
Newkome, G. et al. 1998 "Isocyanate-Based Dendritic Building Blocks: Combinatorial Tier Construction and Macromolecular Property Modification" *Agnew Chemistry International Ed* 37(3):307-310.
Newkome, G. et al. 1999 "Dendrimer Construction and Macromolecular Property Modification via Combinatorial Methods" *Biotechnology and Bioengineering (Combinatorial Chemistry)* 6(4): 243-253.
Newkome, G. R. et al. 2003 "Syntheses of New $1\rightarrow(2+1)$ C-Branched Monomers for the Construction of Multifunctional Dendrimers" *Macromolecules* 36: 4345-4354.
Pan, et al. 2000 "Amphiphilic Dendrimers with Both Octyl and Triethylenoxy Methyl Ether Chain Ends" *Macromolecules* 33: 3731-3738.
Qualmann, B. et al, "Synthesis of Boron-Rich Lysine Dendrimers as Protein Labels in electron Microscopy", *Angewandte Chemi International Edition in English*, 1996, 35, (8):909-911.
Salamończyk, G. M. et al. 2002 "Dendrimers Bearing Three Types of Branching Functions" *Tetrahedron Letters* 43: 1747-1749.
Sivanandan, K. et al. 2004 "Sequences in Dendrons an Dendrimers" *Journal of Organic Chemistry* 69: 2937-2944.
Steffensen, M. B. et al. 2004 "Synthesis and Manipulation of Orthogonally Protected Dendrimers: Building Blocks for Library Synthesis" *Agnew Chemistry International Ed* 43: 5178-5180.
Tam, J. P. and Lu, Y.-A. 1989 "Vaccine Engineering: Enhancement of Immunogenicity of Synthetic Peptide Vaccines related to Hepatitis in Chemically defined Models Consisting of T- and B-cell epitope" *Proceedings of the National Academy of Sciences of the United States* 86 (23): 9084-9088.
Virta, P. et al. 2003 "Solid-Supported Synthesis of Cryptand-like Macrobicyclic Peptides" *Journal of Organic Chemistry* 68: 8534-8538.
Vogtle, F. et al 2004 "Towards a Selective Functionalization of amino-terminated Dendrimers" *European Journal of Organic Chemistry* pp. 4717-4724.
Boas and Heegaard, "Dendrimers in drug research", *Critical Review of the Chemical Society Reviews*, Dec. 2003 pp. 43-63.
Liu, et al., Water Soluble Dendrimer-Poly(ethylene glycol) Starlike Conjugates as Potential Drug Carriers, Journal of Polymer Science Part A: Polymer Chemistry, vol. 37, Mar. 25, 1999, pp. 3492-3503.

\* cited by examiner

Figure 2
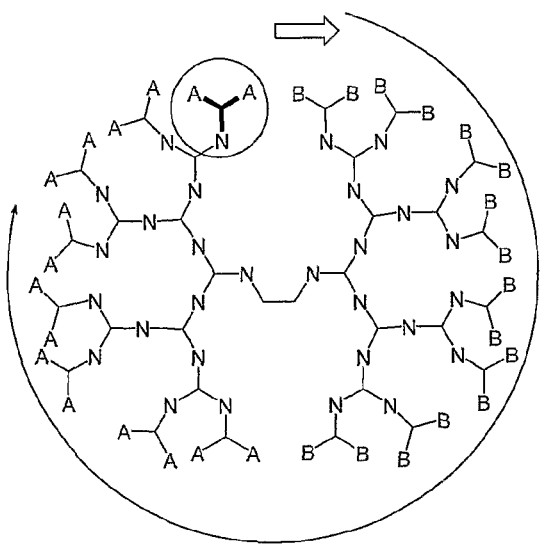
F2.1 (BB)(BB)(BB)(BB)(BB)(BB)(BB)(BB)
(AA)(AA)(AA)(AA)(AA)(AA)(AA)(AA)
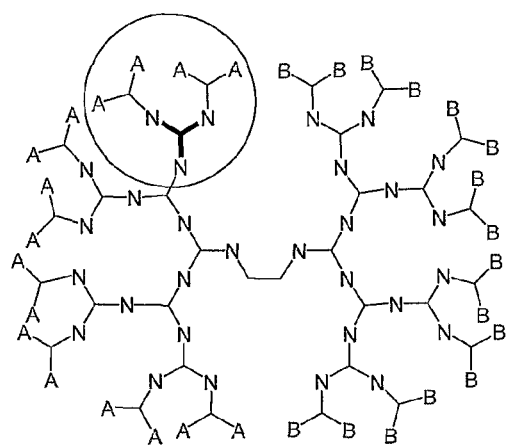
F2.2 ((BB)(BB))$^4$((BB)(BB))$^4$((BB)(BB))$^4$((BB)(BB))$^4$
((AA)(AA))$^4$((AA)(AA))$^4$((AA)(AA))$^4$((AA)(AA))$^4$
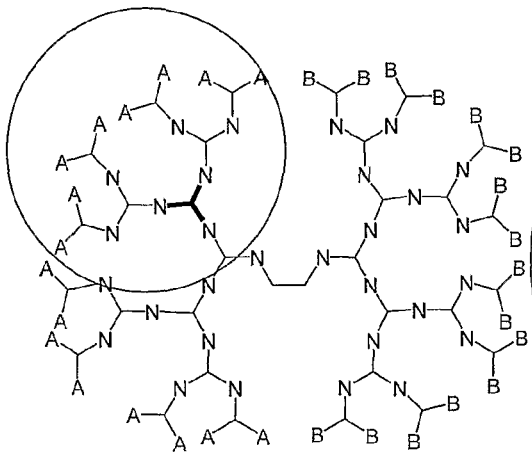
F2.3
(((BB)(BB))$^4$((BB)(BB))$^4$)$^8$(((BB)(BB))$^4$((BB)(BB))$^4$)$^8$
(((AA)(AA))$^4$((AA)(AA))$^4$)$^8$(((AA)(AA))$^4$((AA)(AA))$^4$)$^8$
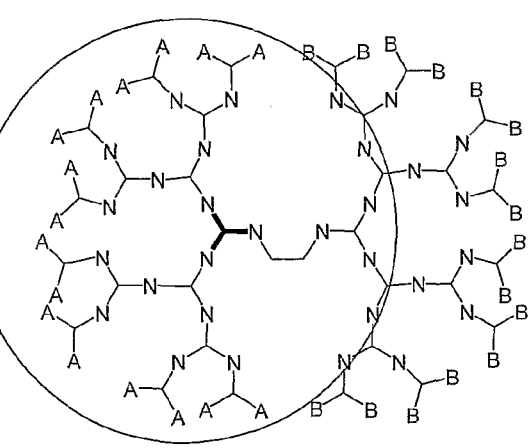
F2.4
((((BB)(BB))$^4$((BB)(BB))$^4$)$^8$(((BB)(BB))$^4$((BB)(BB))$^4$)$^8$)$^{16}$
((((AA)(AA))$^4$((AA)(AA))$^4$)$^8$(((AA)(AA))$^4$((AA)(AA))$^4$)$^8$)$^{16}$
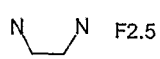 F2.5
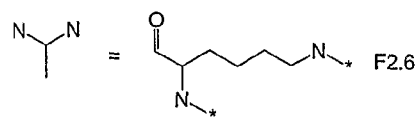 F2.6
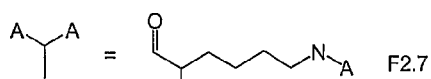 F2.7
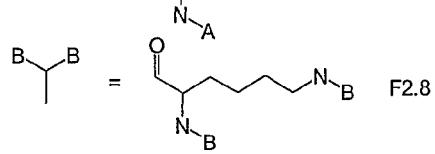 F2.8

Figure 3
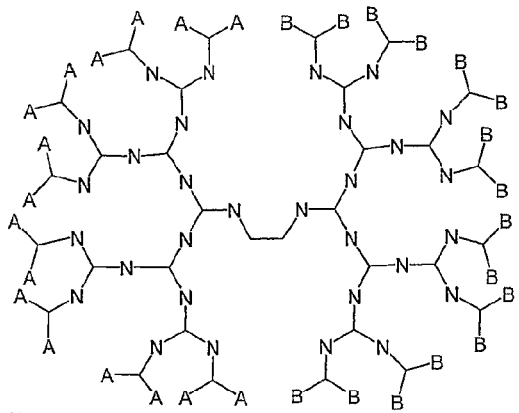
F3.1
((((BB)(BB))⁴((BB)(BB))⁴)⁸(((BB)(BB))⁴((BB)(BB))⁴)⁸)¹⁶
((((AA)(AA))⁴((AA)(AA))⁴)⁸(((AA)(AA))⁴((AA)(AA))⁴)⁸)¹⁶
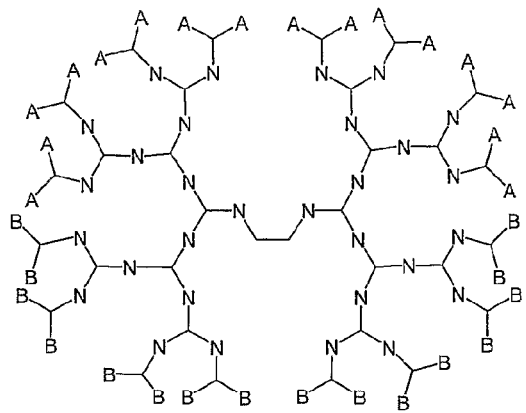
F3.2
((((AA)(AA))⁴((AA)(AA))⁴)⁸(((BB)(BB))⁴((BB)(BB))⁴)⁸)¹⁶
((((BB)(BB))⁴((BB)(BB))⁴)⁸(((AA)(AA))⁴((AA)(AA))⁴)⁸)¹⁶
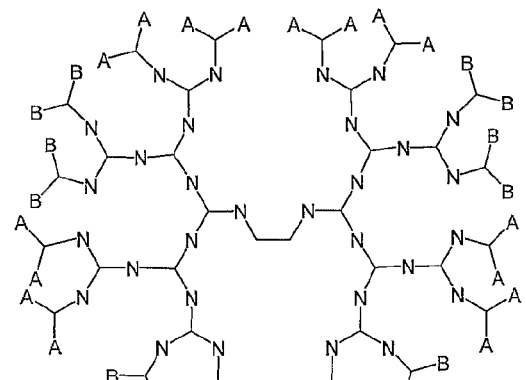
F3.3
((((AA)(AA))⁴((BB)(BB))⁴)⁸((AA)(AA))⁴((BB)(BB))⁴)⁸)¹⁶
((((BB)(BB))⁴((AA)(AA))⁴)⁸((BB)(BB))⁴((AA)(AA))⁴)⁸)¹⁶
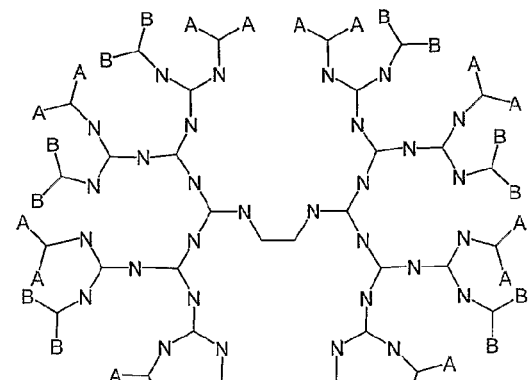
F3.4
((((AA)(BB))⁴((AA)(BB))⁴)⁸(((AA)(BB))⁴((AA)(BB))⁴)⁸)¹⁶
((((BB)(AA))⁴((BB)(AA))⁴)⁸(((BB)(AA))⁴((BB)(AA))⁴)⁸)¹⁶
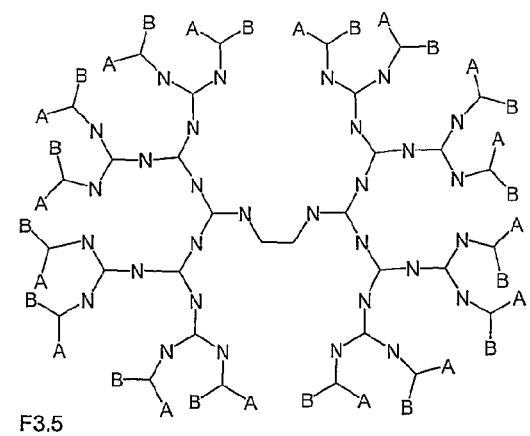
F3.5
((((AB)(AB))⁴((AB)(AB))⁴)⁸(((AB)(AB))⁴((AB)(AB))⁴)⁸)¹⁶
((((AB)(AB))⁴((AB)(AB))⁴)⁸(((AB)(AB))⁴((AB)(AB))⁴)⁸)¹⁶
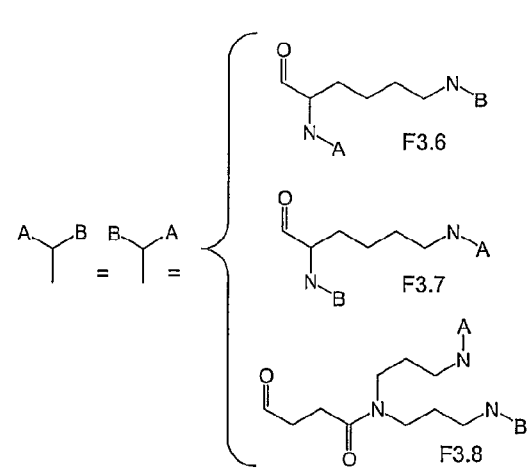

Figure 4
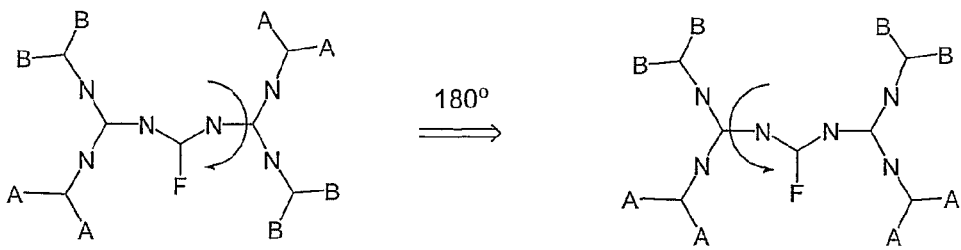
F4.1  $(((AA)(BB))^4((AA)(BB))^4)^8$      F4.2  $(((BB)(AA))^4((AA)(BB))^4)^8$
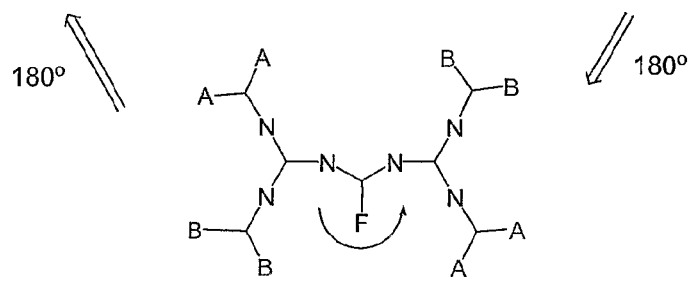
F4.3  $(((BB)(AA))^4((BB)(AA))^4)^8$
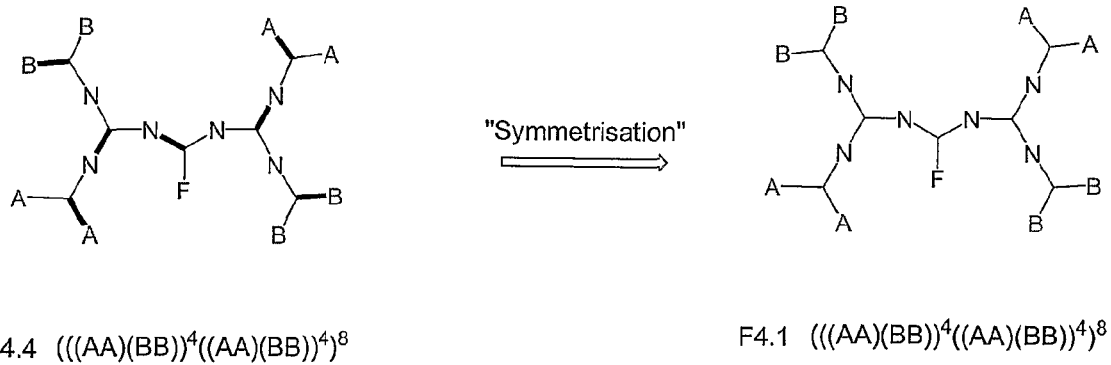
F4.4  $(((AA)(BB))^4((AA)(BB))^4)^8$      F4.1  $(((AA)(BB))^4((AA)(BB))^4)^8$

Figure 5
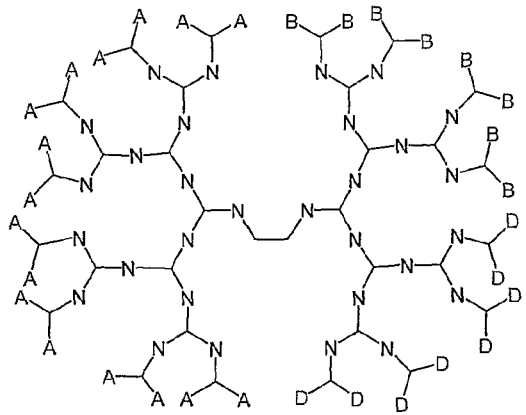
F5.1
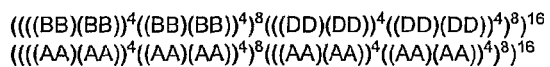
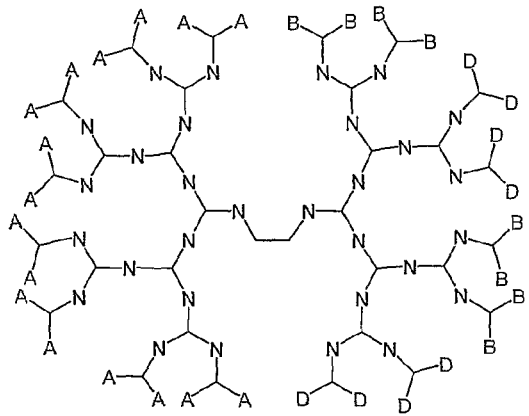
F5.2
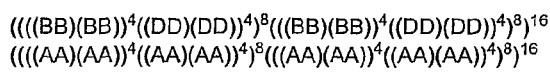
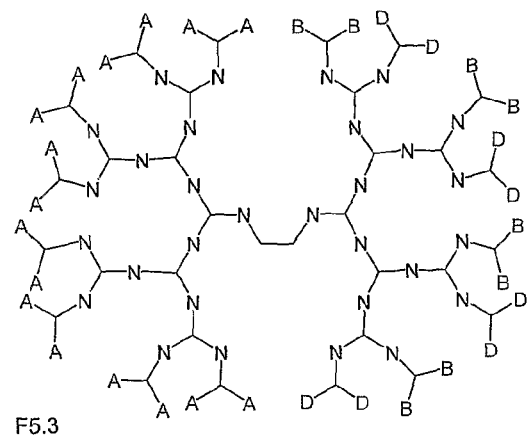
F5.3
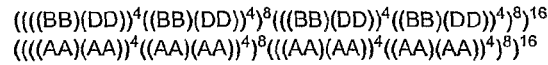
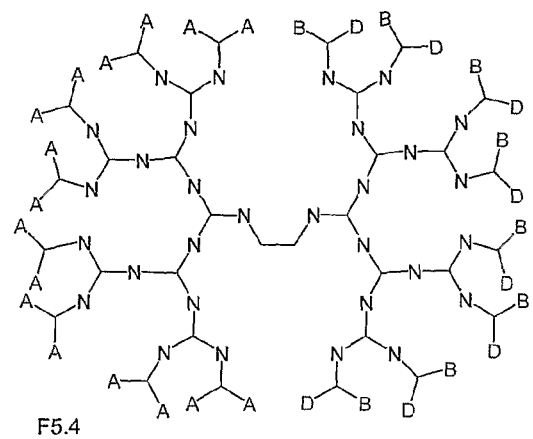
F5.4
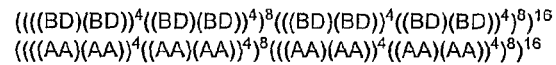
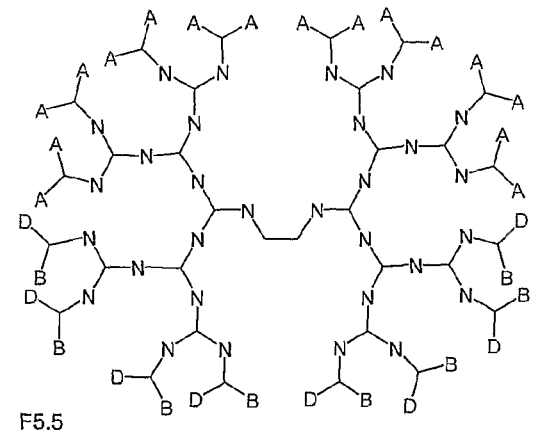
F5.5
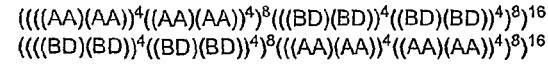

Figure 6

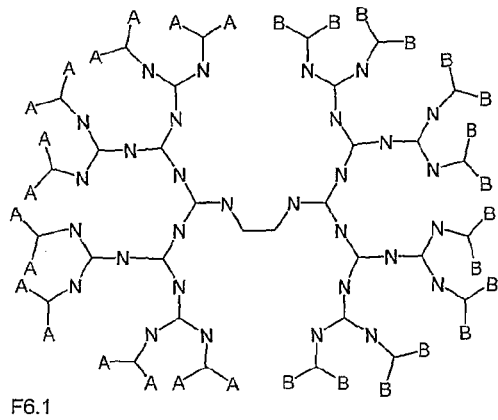

F6.1

$FM_{Max} = FM_{Total} = 32$ (BB)(BB)(BB)(BB)(BB)(BB)(BB)(BB)
(AA)(AA)(AA)(AA)(AA)(AA)(AA)(AA)

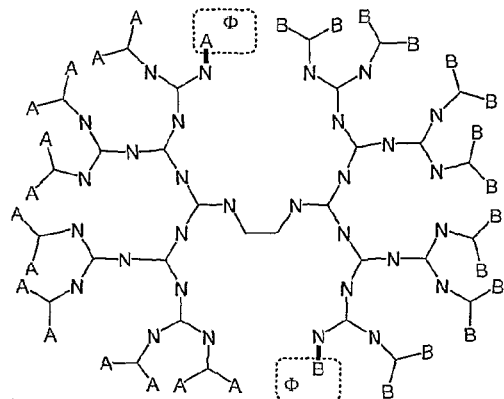

F6.2

$FM_{Max} = FM_{Total} + \Sigma\Phi = 30 + 2 = 32$ $((BB)(BB))^4((BB)(BB))^4((BB)(BB))^4((BB)(B\Phi))^4$
$((AA)(AA))^4((AA)(AA))^4((AA)(AA))^4((AA)(A\Phi))^4$

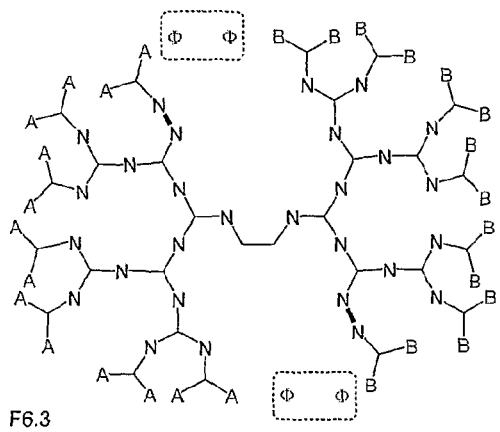

F6.3

$FM_{Max} = FM_{Total} + \Sigma\Phi = 28 + 4 = 32$ $(((BB)(BB))^4((BB)(BB))^4)^8(((BB)(BB))^4((BB)(\Phi\Phi))^4)^8$
$(((AA)(AA))^4((AA)(AA))^4)^8(((AA)(AA))^4((AA)(\Phi\Phi))^4)^8$

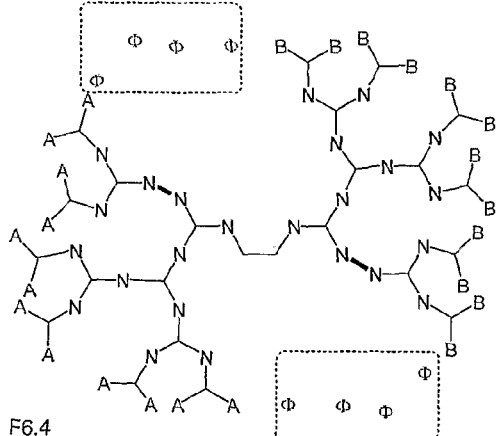

F6.4

$FM_{Max} = FM_{Total} + \Sigma\Phi = 24 + 8 = 32$ $((((BB)(BB))^4((BB)(BB))^4)^8(((BB)(BB))^4((\Phi\Phi)(\Phi\Phi))^4)^8)^{16}$
$((((AA)(AA))^4((AA)(AA))^4)^8(((AA)(AA))^4((\Phi\Phi)(\Phi\Phi))^4)^8)^{16}$

F6.5

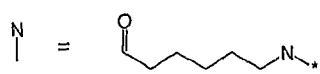

Figure 7
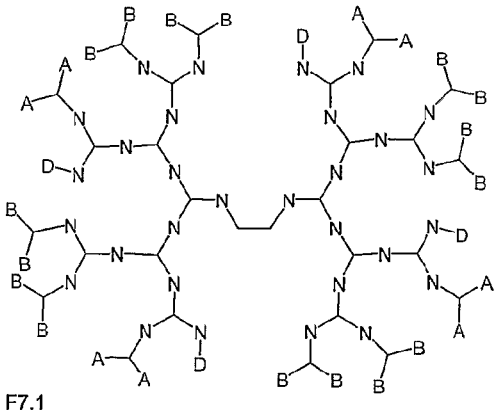
F7.1
((((DΦ)(AA))⁴((BB)(BB))⁴)⁸(((DΦ)(AA))⁴((BB)(BB))⁴)⁸)¹⁶
((((DΦ)(AA))⁴((BB)(BB))⁴)⁸(((DΦ)(AA))⁴((BB)(BB))⁴)⁸)¹⁶
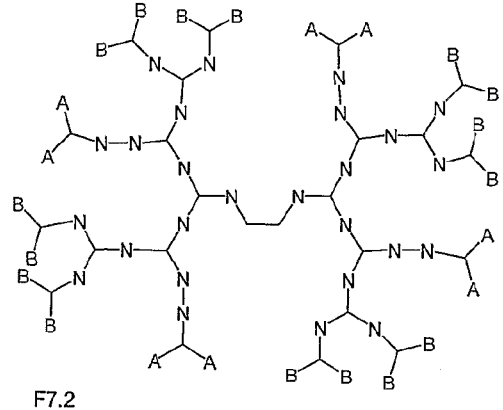
F7.2
((((AA)(ΦΦ))⁴((BB)(BB))⁴)⁸(((AA)(ΦΦ))⁴((BB)(BB))⁴)⁸)¹⁶
((((AA)(ΦΦ))⁴((BB)(BB))⁴)⁸(((AA)(ΦΦ))⁴((BB)(BB))⁴)⁸)¹⁶
F7.3
((((DD)(DD))⁴((ΦΦ)(ΦΦ))⁴)⁸(((AA)(AA))⁴((BB)(BB))⁴)⁸)¹⁶
((((DD)(DD))⁴((ΦΦ)(ΦΦ))⁴)⁸(((AA)(AA))⁴((BB)(BB))⁴)⁸)¹⁶
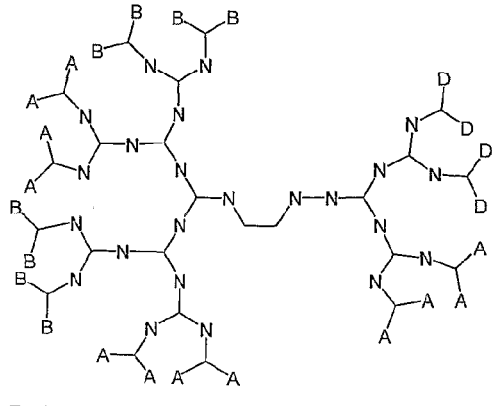
F7.4
((((DD)(DD))⁴((AA)(AA))⁴)⁸(((ΦΦ)(ΦΦ))⁴((ΦΦ)(ΦΦ))⁴)⁸)¹⁶
((((AA)(AA))⁴((BB)(BB))⁴)⁸(((AA)(AA))⁴((BB)(BB))⁴)⁸)¹⁶
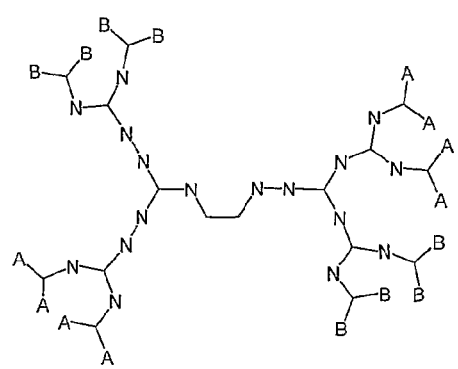
F7.5
((((AA)(AA))⁴((BB)(BB))⁴)⁸(((ΦΦ)(ΦΦ))⁴((ΦΦ)(ΦΦ))⁴)⁸)¹⁶
((((AA)(AA))⁴((ΦΦ)(ΦΦ))⁴)⁸(((BB)(BB))⁴((ΦΦ)(ΦΦ))⁴)⁸)¹⁶

Figure 8

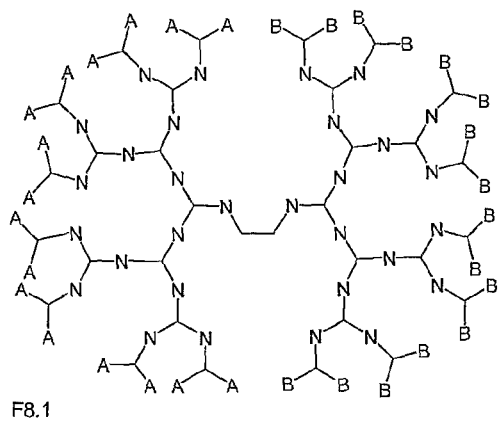

F8.1

$N_{Max} = N_{Total} = 32$ (BB)(BB)(BB)(BB)(BB)(BB)(BB)(BB)
(AA)(AA)(AA)(AA)(AA)(AA)(AA)(AA)

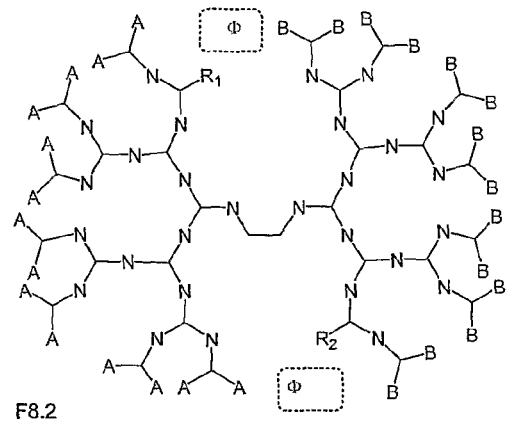

F8.2

$N_{Max} = N_{Total} + \Sigma\Phi = 30 + 2 = 32$ $((BB)(BB))^4((BB)(BB))^4((BB)(BB))^4((BB)(R_2\Phi))^4$
$((AA)(AA))^4((AA)(AA))^4((AA)(AA))^4((AA)(R_1\Phi))^4$

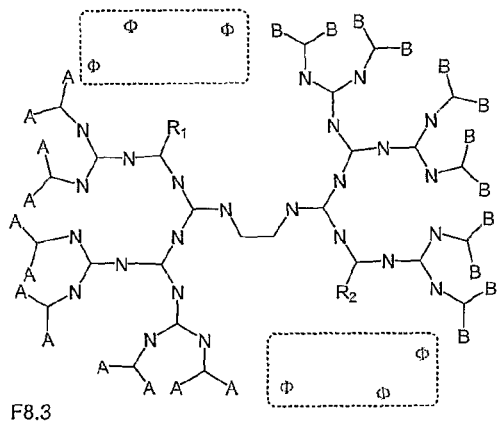

F8.3

$N_{Max} = N_{Total} + \Sigma\Phi = 26 + 6 = 32$ $(((BB)(BB))^4((BB)(BB))^4)^8(((BB)(BB))^4((R_2\Phi)(\Phi\Phi))^4)^8$
$(((AA)(AA))^4((AA)(AA))^4)^8(((AA)(AA))^4((R_1\Phi)(\Phi\Phi))^4)^8$

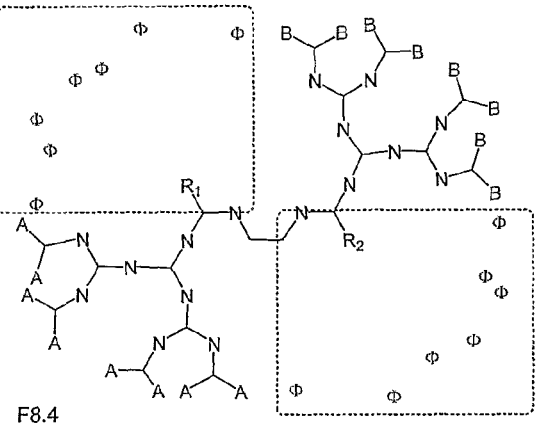

F8.4

$N_{Max} = N_{Total} + \Sigma\Phi = 18 + 14 = 32$ $((((BB)(BB))^4((BB)(BB))^4)^8(((R_2\Phi)(\Phi\Phi))^4((\Phi\Phi)(\Phi\Phi))^4)^8)^{16}$
$((((AA)(AA))^4((AA)(AA))^4)^8(((R_1\Phi)(\Phi\Phi))^4((\Phi\Phi)(\Phi\Phi))^4)^8)^{16}$

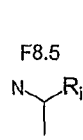 F8.5 = 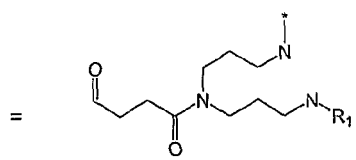 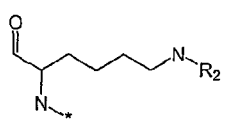

Figure 9

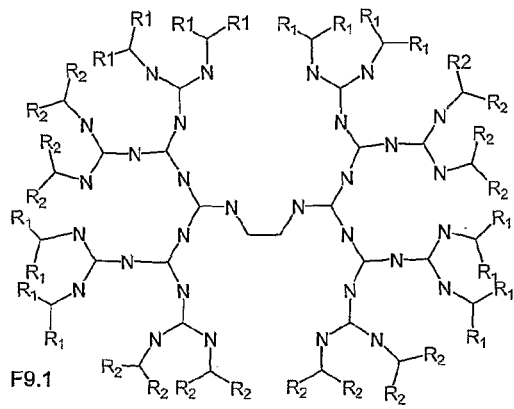

F9.1

$((((R_1R_1)(R_1R_1))^4((R_2R_2)(R_2R_2))^4)^8(((R_1R_1)(R_1R_1))^4((R_2R_2)(R_2R_2))^4)^8)^{16}$
$((((R_2R_2)(R_2R_2))^4((R_1R_1)(R_1R_1))^4)^8(((R_2R_2)(R_2R_2))^4((R_1R_1)(R_1R_1))^4)^8)^{16}$

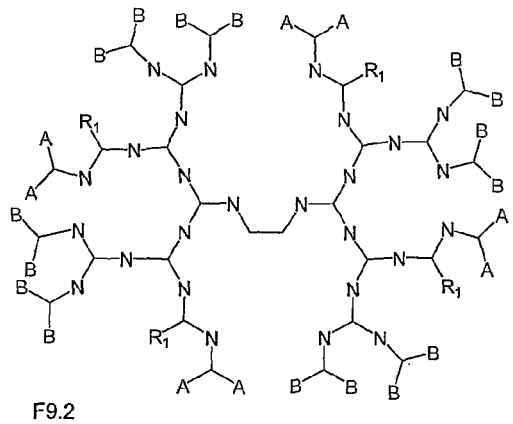

F9.2

$((((AA)(R_1\Phi))^4((BB)(BB))^4)^8(((AA)(R_1\Phi))^4((BB)(BB))^4)^8)^{16}$
$((((AA)(R_1\Phi))^4((BB)(BB))^4)^8(((AA)(R_1\Phi))^4((BB)(BB))^4)^8)^{16}$

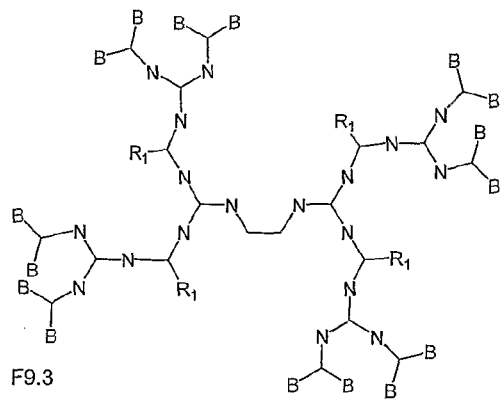

F9.3

$((((R_1\Phi)(\Phi\Phi))^4((BB)(BB))^4)^8(((R_1\Phi)(\Phi\Phi))^4((BB)(BB))^4)^8)^{16}$
$((((R_1\Phi)(\Phi\Phi))^4((BB)(BB))^4)^8(((R_1\Phi)(\Phi\Phi))^4((BB)(BB))^4)^8)^{16}$

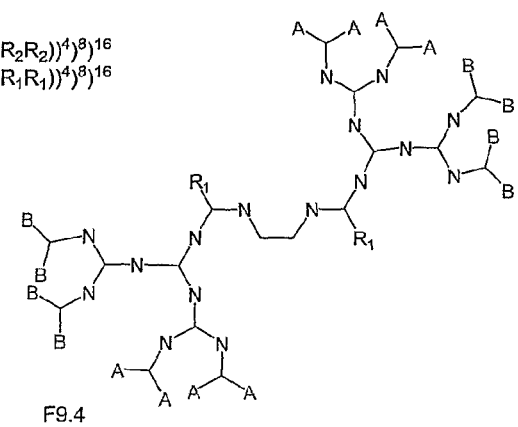

F9.4

$((((AA)(AA))^4((BB)(BB))^4)^8(((R_1\Phi)(\Phi\Phi))^4((\Phi\Phi)(\Phi\Phi))^4)^8)^{16}$
$((((AA)(AA))^4((BB)(BB))^4)^8(((R_1\Phi)(\Phi\Phi))^4((\Phi\Phi)(\Phi\Phi))^4)^8)^{16}$

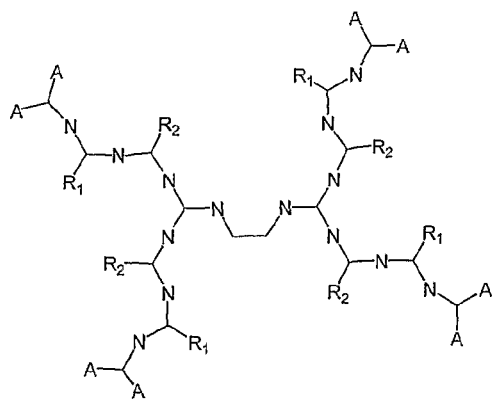

F9.5

$((((R_1\Phi)(AA))^4((R_2\Phi)(\Phi\Phi))^4)^8(((R_1\Phi)(AA))^4((R_2\Phi)(\Phi\Phi))^4)^8)^{16}$
$((((R_1\Phi)(AA))^4((R_2\Phi)(\Phi\Phi))^4)^8(((R_1\Phi)(AA))^4((R_2\Phi)(\Phi\Phi))^4)^8)^{16}$

Figure 16
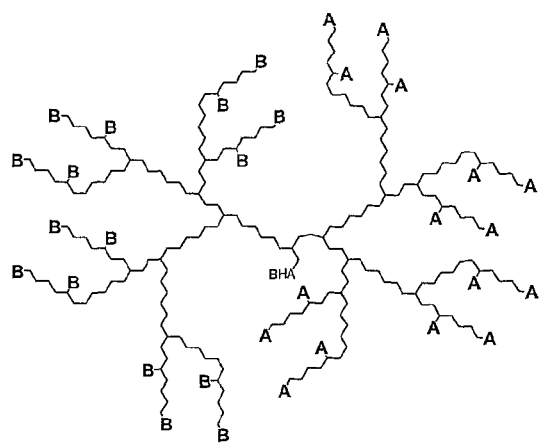
Example 65.1
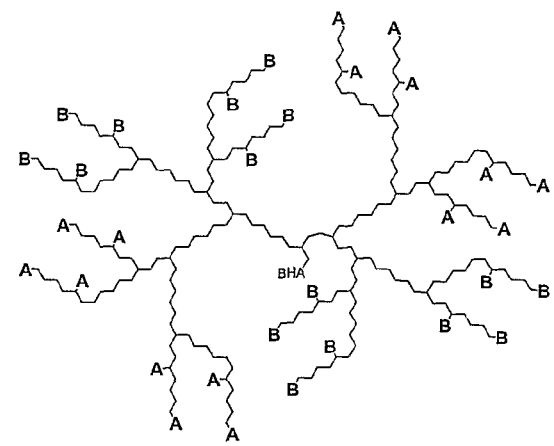
Example 65.2
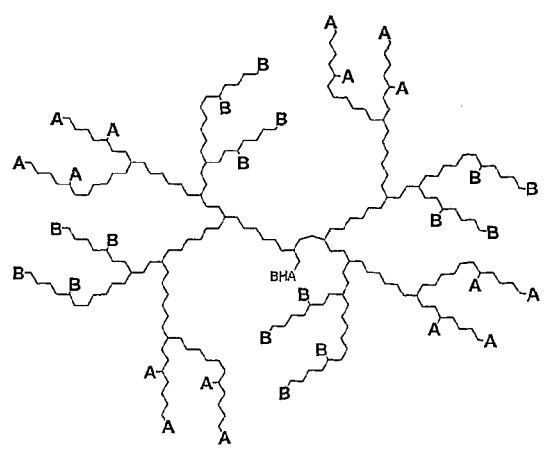
Example 65.3
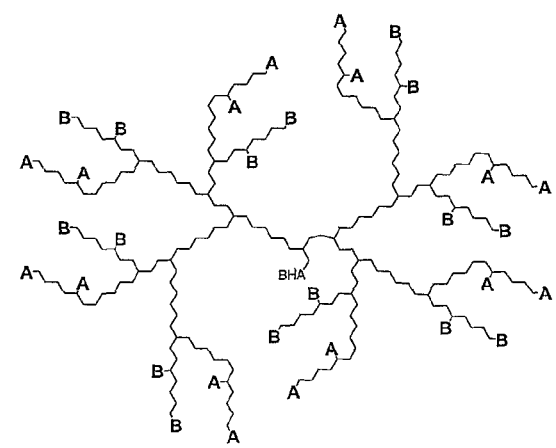
Example 65.4
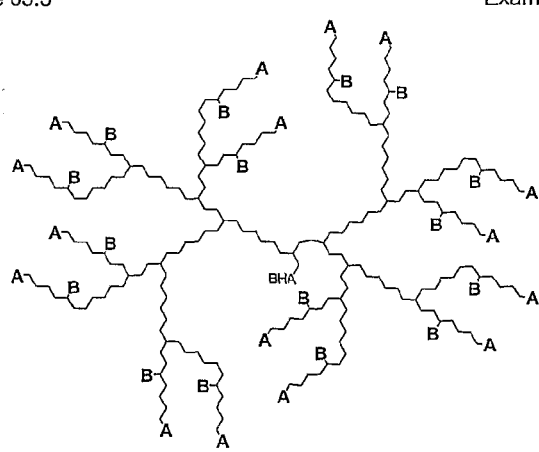
Example 65.5

Figure 17
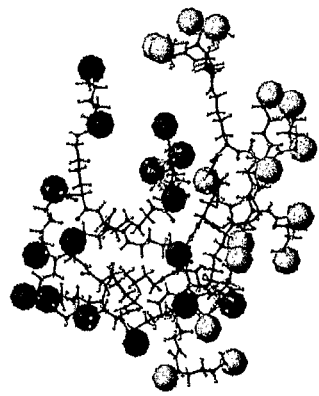
(a) Example 65.1
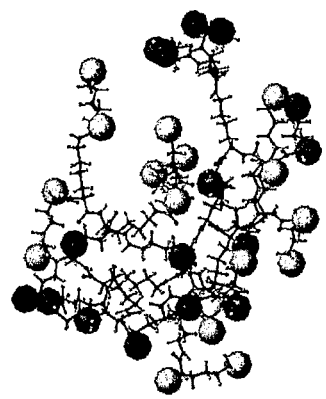
(b) Example 65.2
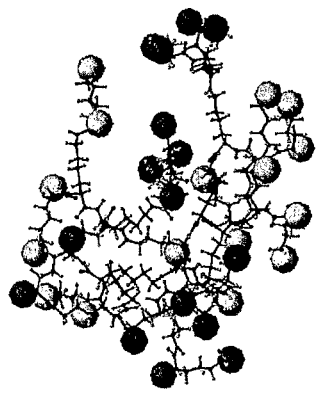
(c) Example 65.3
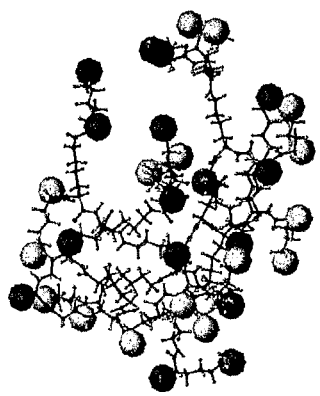
(d) Example 65.4
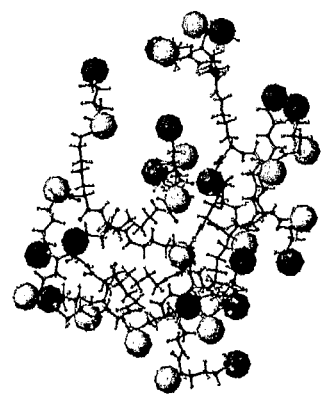
(e) Example 65.5

MACROMOLECULAR COMPOUNDS HAVING CONTROLLED STOICHIOMETRY

REFERENCE TO PRIORITY APPLICATIONS

This application is a continuation of U.S. patent application Ser. No. 12/091,233 filed Apr. 23, 2008 now U.S. Pat. No. 8,258,259 which is U.S. National Phase of International Application PCT/AU2006/001591, filed Oct. 25, 2006 designating the U.S., and published in English as WO 2007/048190 on May 3, 2007, which claims priority to Australian Patent Application 2005905908 filed Oct. 25, 2005 and Australian Patent Application 2006906087 filed Oct. 24, 2006.

FIELD OF THE INVENTION

The present invention relates to macromolecules whose surface architecture may be controlled to produce an enriched proportion of a topological isomer. In particular the macromolecules may be synthesised from lysine or lysine analogue dendritic motifs having two or more surface groups.

BACKGROUND OF THE INVENTION

In recent years, dendritic macromolecules have been found to have increasing applications in biotechnology and pharmaceutical applications on the basis of their unique properties and structure, and subsequently, function. Dendritic macromolecules are a special class of polymers with densely branched structures that are characterized by higher concentrations of functional groups per unit of molecular volume than ordinary polymers. There are three subclasses of dendritic macromolecules (Frechet and Tomalia "Dendrimers and other Dendritic Polymers"): random hyperbranched polymers; dendrigraft polymers and dendrimers (which include dendrons), classified on the basis of the relative degree of structural control present in each of the dendritic architectures. Generally, a dendritic macromolecule includes at least two layers or generations of building units and all contain one or more branches originating from a core molecule.

In particular, peptide-based dendritic molecules, such as those based on polylysine FIG. 1, have been developed as promising vaccine, antiviral and antibacterial candidates. A specific architecture of lysine and lysine analogue dendrimers has been described by Denkewalter in U.S. Pat. No. 4,289,872. This patent describes branched compounds essentially of identical lysine-like trifunctional units.

Denkewalter's methodology has the advantage that a plurality of amide linkages are provided to connect the trifunctional units so that the final dendrimeric moiety tends to be biocompatible and locally protein-like. However the dendrimeric moiety thus provided comprises multiple substantially equivalent outer terminal reactable groups (for example amine groups) as the point of attachment for functional moieties and the following adverse consequences arise:

If a further reagent (e.g. a biological effector molecule) is used to react with the outer terminal reactable groups of the dendrimer moiety in such a way that some of the outer terminal reactable groups remain unreacted, there is a statistical spread of reaction products (i.e. monodispersity in the dendrimer is lost in the dendrimer reaction product).

If a combination of reagents is used to react with the outer terminal reactable groups of the dendrimer moiety there is a statistical spread of reaction products and monodispersity is lost. This situation is described by Newkome et, al. (Combinational Chemistry) Vol 61, No 4 1998/99 "Dendrimer Construction and Macromolecular Property Modification Via Combinational Methods" (p 244) in the following terms: "There is an uncontrolled radial monomer juxtaposition while generational functional group control is retained".

Thus whilst the generational character in the dendrimer is maintained, and whilst the amide linkages are advantageous in the provision of biocompatibility, the inability to provide radial (i.e. surface decoration) monodispersity is a significant disadvantage.

In U.S. Pat. No. 5,229,490 and WO 9011778, Tam teaches that dendritic core molecules of 2 or 3 generations of lysine may be constructed using solid phase peptide synthesis and making use of orthogonally protected lysine at the final step of the process, to provide a composition that has a surface topology of $(PG_1PG_2)_4$. In particular, Tam describes a dendritic polymer bearing multiple B- and T-epitopes, wherein the B- and T-epitopes are arranged as couplets (B-epitope T-epitope) on the surface building unit. The process of solid phase peptide synthesis provides no opportunity for purification until after the final iteration of the synthesis. Materials provided by such a method are often mixtures wherein the target component is contaminated by the components which are of amino acid deletion products.

The preparation of dendritic macromolecules with a homogenous surface comprised of only a single type of functional moiety is now considered to be routine. Furthermore, Tam and others provide teaching for the construction of dendritic macromolecules in which a core or macromolecule has a homogenous surface stoichiometry that is 1:1 for two functional moieties A and B. Furthermore the topology of the two functional moieties is specified as homogenous at the level of (AB) couplets; that is each of the surface building units has two functional moieties A and B attached to the same surface building unit (as for FIG. 3.5).

One key determinant of a dendritic macromolecule's efficacy in any given application is the nature of the macromolecule surface. This application describes macromolecule topological isomers using a hierarchy of descriptive terms which serve to elucidate the way functional moieties, surface building units and building units are interconnected.

It is, accordingly, an object of the present invention to overcome or at least alleviate one or more of the difficulties and deficiencies related to the prior art.

It will be understood that the present invention disclosed and defined in this specification extends to all alternative combinations of two or more of the individual features mentioned or evident from the text or drawings. All of these different combinations constitute various alternative aspects of the present invention.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In a first aspect of the present invention there is provided a macromolecule having a controlled functional moiety stoichiometry including at least one dendritic motif having a surface layer formed from at least one surface building unit and at least one subsurface layer formed from at least one building unit, the surface building unit and building units having a hydrocarbon backbone bearing a carbonyl group and at least one amine group; and at least two different functional moieties on the building unit and/or surface building unit; where functional moiety stoichiometry refers to the number and type of functional moieties.

Preferably, the building units of the dendritic motif are selected from lysine or lysine analogues, and the surface building units are selected from lysine or lysine analogues, glutamate and aspartate.

The macromolecules of the present invention may be selected from a preparation of macromolecules, wherein the preparation is enriched in a selected functional moiety stoichiometry.

In a preferred embodiment, the macromolecule is selected from a preparation of macromolecules that exhibit at least 10%, preferably 20%, and more preferably 40% enrichment in the selected functional moiety stoichiometry compared to random techniques.

Most preferably, the preparations of macromolecules is enriched to the point where at least 80%, preferably 90%, more preferably 95% and most preferably 99% of the macromolecules exhibit the same functional moiety stoichiometry.

In a further preferred embodiment, the macromolecule is a selected topological isomer, where topology describes the relationship between one functional moiety and another in terms of its connection to the subsurface structure.

Preferably the macromolecule that is a selected topological isomer is selected from a preparation of macromolecules exhibiting enrichment in the selected topological isomer. Preferably the macromolecules exhibit a 10%, preferably 20%, more preferably 40% enrichment in the selected topological isomer.

In a further embodiment, there is provided a macromolecule having a controlled functional moiety stoichiometry including at least one dendritic motif having a surface layer formed from at least one surface building unit and at least one subsurface layer formed from at least one building unit, the surface building unit and building units having a hydrocarbon backbone bearing a carbonyl group and at least one amine group; and at least two different functional moieties on the building unit and/or surface building unit; wherein the macromolecule is a selected topological isomer; where functional moiety stoichiometry refers to the number and type of functional moieties, and topology describes the relationship between each functional moiety in terms of its connection to the surface and subsurface layers.

The macromolecules according to this aspect of the present invention may be utilised in various applications, as discussed below, where the ability to control both the surface properties and the overall structure of the macromolecule is advantageous. This is particularly important where more than one functional moiety is included.

For example, the macromolecule may advantageously be utilised to deliver to a desired site a pharmaceutically active compound on its surface, together with a secondary surface compound that may function to modify a specified characteristic, e.g. solubility, pharmacokinetics, targeting, bioavailability, potency, reactivity, plasma life and the like.

Moreover, the capacity to enrich a dendritic macromolecule preparation in molecules of the same topology, where topology describes the relationship between one functional moiety and another in terms of their connection to the subsurface structure, is desirable in the same way that it has been shown to be desirable to enrich organic materials in particular stereoisomers or regioisomers, particularly for biological applications. Thus it will be understood that topological isomerism in the macromolecule represents a subset of the complete set of regio and stereochemical isomers for the macromolecule. That is, the set that specifically pertains to positioning of the surface groups relative to one another, and it will be further understood that as such it may be that one topological isomer may be more effective in a given application than another topological isomer. Even without knowing which topological isomer is the best for a given application, the capacity to prepare macromolecule topological isomers in relatively pure form is very useful in screening for structure-activity relationships.

In a preferred embodiment of this aspect of the present invention, the dendritic motifs of the macromolecule include a lysine or lysine analogue building unit having a carboxylate group or residue thereof at the apex thereof, attached to two amine groups, at least one amine group being attached to a carboxylate group or residue thereof of a second building unit, which is in turn attached directly or indirectly to a first and second functional moiety, at least one of the functional moieties being attached to a surface amine on the second building unit. Preferably, the surface building unit is a lysine or lysine analogue, glutamate or aspartate. When the second building unit is a surface building unit that is a lysine or lysine analogue, the second functional moiety may be attached to a second surface amine on the second building unit.

In addition to the functional moieties attached to the second, surface building unit, a third functional moiety may be attached to the second amine group of the lysine or lysine analogue building unit, resulting in a dendritic motif with functionalisation at the surface and subsurface level.

In another embodiment, the macromolecule may include one or more subsurface layers intermediate the apex carboxylate group or residue thereof and the at least one surface amine groups. Optionally, the macromolecule may include two or more subsurface layers. Preferably, at least one of the subsurface layers includes an apex carboxylate group or residue thereof and two reactable amine groups, at least one amine group in turn being attached to a further carboxylate group or residue thereof.

In a further embodiment, each surface amine may bear a functional moiety A or B, with a pair of adjacent functional moieties on the same surface building unit forming a couplet selected from (AA), (BB) and (AB), or any combination thereof. Optionally, the surface amines may bear a further functional moiety D, with a pair or adjacent functional moieties on the same building unit forming a couplet selected from (AA), (AB), (AD), (BB), (BD), (DD) or any combination thereof.

The macromolecules bearing functional moieties A and B, or A, B and D, may be selected from a preparation of macromolecules exhibiting an enrichment in a selected topological isomer. The enrichment may be at the couplet level; at the quartet level, where a pair of adjacent couplets form a quartet, each quartet having a line of connection to an apex carboxylate group of a surface-but-one building unit; at the octet level where adjacent quartets form an octet, each octet having a line of connection to an apex carboxylate group of a surface-but-two building unit; or at the 16-tet level, where adjacent octets form a 16-tet, each 16-tet having a line of connection to an apex carboxylate group of a surface-but-three building unit.

The surface topology of a macromolecule or dendritic motif bearing functional moieties may also be described in terms of quartets, octets and 16-tets. For example a quartet of the form $((AA)(BD))^4$ is used to represent four functional moieties A,A,B,D which have a line of connection to the same building unit, in particular to a surface-but-one building unit.

An octet of the form $(((AA)(AB))^4((AB)(AA))^4)^8$ is used to represent six functional moieties of type A and two functional moieties of type B which have a line of connection to the same building unit, in particular to a surface-but-two building unit. A 16-tet of the form $((((AA)(AA))^4((AA)(AA))^4)^8(((( AA)(AA))^4((AA)(AA))^4)^8)^{16}$ is used to represent sixteen functional moieties of type A which have a line of connection to the same generation building unit, in particular to a surface-but-three generation-building unit.

In an alternative embodiment, when the macromolecule of the present invention has only two types or functional moiety A and B on the same building unit or surface building unit, the functional moiety stoichiometry is other than 1:1.

The macromolecules or dendritic motifs of the present invention may be attached to cores. In the absence of a core, the dendritic motif may itself be the macromolecule. In a preferred aspect there is provided a macromolecule having a core and at least one dendritic motif of the formula:

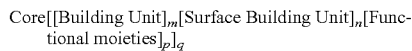

Core[[Building Unit]$_m$[Surface Building Unit]$_n$[Functional moieties]$_p$]$_q$ wherein:
a [Building Unit]$_m$[Surface Building Unit]$_n$[Functional moieties]$_p$ defines a dendritic motif;
the core may be any compound, particle or substrate to which the dendritic motif may be attached;
the Building Unit is selected from a lysine or lysine analogue;
the Surface Building Unit is selected from lysine or lysine analogues, glutamate or aspartate;
the Functional moieties include two or more different functional moieties selected from protecting groups; biological effect moiety ligands for extracellular receptors; property modifiers; biological targeting groups; signalling groups; antigenic materials; genetic materials; pharmaceutically active agents; groups adapted to mediate binding to a second entity, and linkers.
m represents the sum of the building units of the subsurface layers of the dendritic motif and is an integer of value: $1 \leq \text{integer} \leq 64$;
n represents the number of surface building units of the dendritic motif and is an integer of value: $2 \leq \text{integer} \leq 64$;
p represents the total number of functional moieties on the surface of the macromolecule and is an integer of value: $4 \leq \text{integer} \leq 128$; and
q represents the total number of dendritic motifs on the core of the macromolecule and is an integer of value: $1 \leq \text{integer} \leq 10^6$.

In one embodiment, more than one dendritic motif may be attached to a core to enable the construction of larger, more complex macromolecules. For example, two dendritic motifs, each having 3 subsurface layers and 1 surface layer and bearing 16 functional moieties, may be attached to a divalent core, producing a macromolecule having two dendritic motifs and bearing 32 functional moieties.

There are a number of ways of synthesising or "building" a macromolecule of the present invention. Preferably the macromolecule is a dendrimer. One process for synthesising macromolecules of the present invention involves the sequential reaction of a growing macromolecule core moiety and one or more layers of building compounds. Such a process includes:
i) providing
  a growing macromolecule including at least one reactable group;
  a first building compound having a hydrocarbon backbone, and bearing an apex carbonyl group and at least one amine group bearing a functional moiety being a protecting group;

iii) activating the apex carbonyl group of the first building compound; and
iii) reacting the deprotected growing macromolecule with the apex carbonyl group of the first building compound.

The steps of the process will then be reiterated until a macromolecule of the desired subsurface and surface layers is achieved.

In an alternative process, the macromolecule may be prepared by the following steps:
i) providing
  a growing macromolecule including a first reactable group;
  a compound including at least one dendritic motif bearing at least two functional moieties, the motif having a surface layer and at least one subsurface layer, and having a hydrocarbon backbone and bearing an apex carbonyl group;
ii) activating the apex carbonyl group of the dendritic motif; and
iii) reacting the deprotected growing macromolecule with the carbonyl group of the dendritic motif.

The process may further include the preliminary steps of preparing the compound including at least one dendritic motif, the process including:
iv) providing
  a first building compound including an apex carbonyl group, attached directly or indirectly to at least one amine group bearing at least one functional moiety being a protecting group;
  a second building compound including an apex carbonyl group, attached to at least one amine group bearing a first and second functional moiety;
v) activating the amine group on the first building compound by removing the protecting group;
vi) activating the apex carbonyl of the second building compound; and
vii) reacting the deprotected first building compound with the apex carbonyl group of the second building compound.

Depending on the macromolecule and the functional moieties on the building unit or surface building unit, the macromolecules may have a diverse number of prophylactic and/or therapeutic uses, particularly when formulated as a pharmaceutical composition. Accordingly, there is provided a pharmaceutical composition including a macromolecule having a controlled functional moiety stoichiometry according to the invention.

DETAILED DESCRIPTION

As used herein in this specification and claims, the singular forms "a", "an" and "the" include plural referents unless the context clearly dictates otherwise. Thus, for example, reference to a "a macromolecule" includes one or more such macromolecules.

The term "comprises" (or its grammatical variants), as used herein in the specification and claims, is equivalent to the term "includes" and should not be taken as excluding the presence of other elements or features.

By the term "building unit" as used herein in the specification and claims, we mean a unit used in the construction of a dendritic motif. For example, the building unit may be lysine or lysine analogues having a carboxylate at the apex thereof (apex carboxylate). Layers of building units bear at least one amine or other reactable group that may be further reacted with the apex carboxylate group of a further building unit.

By the term "surface building unit" as used herein in the specification and claims we mean a building unit within the outermost layer of building units of the macromolecule. i.e. there are no further building units attached to the surface reactable groups of any of the building units within the layer. A surface building unit has an apex carbonyl moiety and a hydrocarbon framework by which functional moieties may be attached to the macromolecule or dendritic motif.

By the term "dendritic motif", as used herein in the specification and claims, we mean a discrete unit of the macromolecule. When the macromolecule is cut at a bond which connects one of the reactable amines of the building unit or core to the apex carboxylate group of the attached building unit, the dendritic motif will "fall out". The valency of the apex carboxylate group of the dendritic motif is incomplete, as it represents the point at which the dendritic motif would be attached to a growing macromolecule core during the process of synthesising a macromolecule of the invention.

By the term "surface amine" as used herein in the specification and claims we mean any of the outer-most reactable nitrogens of the macromolecule or dendritic motif which derive from the constituent core, building units or linkers. These surface amines represent the points of attachment for additional building units, linkers or functional moieties.

By the term "reactable nitrogen" as used herein in the specification and claims we mean the nitrogen is able to react with a carboxylic acid or activated residue thereof to form a covalent bond.

By the term "functional moiety" as used herein in the specification and claims we mean any group including protecting groups, with the exception of a building unit or a linker, which may be attached at a surface amine with the purpose of serving a particular function.

By the term "end stopping functional moiety" as used herein in the specification and claims we mean a functional moiety that may be attached to a surface amine and which will maintain its functionality through subsequent transformations used to complete the building of the macromolecule or dendritic motif. An end stopping functional moiety may be transformed into a functional moiety once assembly of the macromolecule or dendritic motif is complete in order for it to perform its required function.

By the term "functional moiety stoichiometry", as used herein in the specification and claims, we mean the composition, or number and type, of the functional moieties on the surface of the macromolecule.

By the term "functional moiety topology", as used herein in the specification and claims, we mean the relationship between one functional moiety and another in terms of their connection to the surface and subsurface structure.

By the term "enrichment", as used herein in the specification and claims, we mean the macromolecule composition having macromolecules bearing a specified plurality of functional groups as provided by a process of this invention, that have a greater uniformity of molecular identity, both in terms of functional moiety stoichiometry and functional moiety topology, than a macromolecule composition having macromolecules with an equivalent specified functional group stoichiometry that has been prepared using a random surface functionalisation. There are statistical methods which can be applied to model the theoretical outcome of a random surface functionalisation using two or more functional moieties; and the output of such models can provide a point of reference for the determination of the relative enrichment for the compositions of this invention.

By the term "topological isomer", as used herein in the specification and claims, we mean a macromolecule having a particular topology, wherein topology describes the relationship between one functional moiety and another in terms of its connection to the subsurface structure.

By the term "subsurface", as used herein in the specification and claims, we mean the layer of building units bearing amines reactable with the apex carboxylate group of a further building unit or carbonyl group of a surface building unit. The layers may in turn be described as the surface-but-one layer, meaning the first subsurface immediately adjacent the surface layer; the surface-but-two layer is the second layer below the surface layer; the surface-but-three layer is the third layer below the surface layer; and so on:

By the term "amine-protecting groups", as used herein in the specification and claims, we mean a chemical group attached to an amine moiety of a macromolecule or dendritic motif for the purpose of preventing the amine moiety from forming an amide bond when in the presence of an activated carbonyl group, but which can be removed from the same amine moiety without detriment to amide bond integrity elsewhere in the macromolecule or dendritic motif and, groups for which an order of removal exists such that those groups that are not meant for cleavage removal are inert to the removal cleavage conditions. When protecting groups are defined as "resolvable", this means that the conditions for removal of one group may affect the integrity of the second group whereas conditions exist by which the second group may be removed without affecting the integrity of the first group. When protecting groups are further defined as "orthogonal", this means that each group is inert to the cleavage removal conditions required to remove each of the other groups of the orthogonal set. It is important to note that protecting groups are resolvable or orthogonal only when the appropriate reaction conditions are used.

By the term "linker", as used herein in the specification and claims, we mean a moiety comprising two reactive groups which are connected by one or more carbons or heteroatoms.

Wide-ranging uses have been claimed for dendritic moieties, for example as therapeutic agents per se or as therapeutic agents when macromolecules are combined with bioactive materials. However, the inability to provide monodisperse surface decoration is particularly acute for human pharmaceutical applications, where regulators are moving to insist that macromolecular therapeutic moieties must be as tightly defined (monodisperse) as small-molecule therapeutic moieties.

Furthermore, in macromolecules which carry two or more different functional moieties, and are prepared as different topological isomers, it has been demonstrated that the way in which each topological isomer interacts with a complex system may be different, which indicates that there is a specific benefit to be gained from the ability to control the surface distribution of different functional moieties. For example, the pharmaceutical industry's need to identify drug-like molecules that target clinically relevant pathways by being presented in a controlled fashion to ensure activity. While the development of high-throughput screening methodologies allows large numbers of compounds to be screened, the most conceptually straightforward approach of advancing compounds generally requires highly specific or energetically favourable neighbouring contacts to succeed (Erlanson et al 2004).

Erlanson and co-workers (2004) describe numerous examples whereby known compounds are linked to fragments of newly identified compounds to improve the overall properties of the compound by binding to additional contact points. But while techniques exist for selecting combinations of compounds that can bind concurrently, productively linking them noncompetitively remains a significant technical challenge.

One key determinant of a dendritic macromolecule's efficacy in any given application is the nature of the macromolecule surface. This application describes macromolecule topological isomers using a hierarchy of descriptive terms which serve to elucidate the way the functional moieties are interconnected by the subsurface structure.

In a first aspect of the present invention there is provided a macromolecule having a controlled functional moiety stoichiometry including at least one dendritic motif having a surface layer formed from at least one surface building unit and at least one subsurface layer formed from at least one building unit, the surface building unit and building units having a hydrocarbon backbone bearing a carbonyl group and at least one amine group; and at least two different functional moieties on the building unit and/or surface building unit; where functional moiety stoichiometry refers to the number and type of functional moieties.

In one embodiment the dendritic motif according to the present invention includes at least one building unit, the building unit being selected from lysine and lysine analogues having moiety # to indicate a bond which connects the building unit to a reactable amine, selected from the group consisting of:

Lysine 1: having the structure:

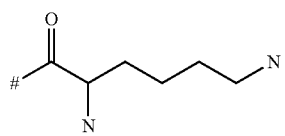

1

Glycyl-Lysine 2 having the structure:

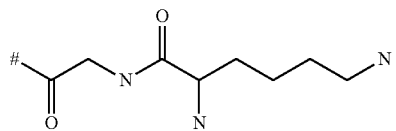

2

Analogue 3, having the structure below, where a is an integer of 1 or 2; b and c are the same or different and are integers of 1 to 4.

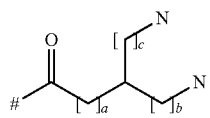

3

Analogue 4, having the structure below, where a is an integer of 0 to 2; b and c are the same or different and are integers of 2 to 6

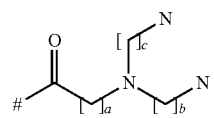

4

Analogue* 5, having the structure below, where a is an integer of 0 to 5; b and c are the same or different and are integers of 1 to 5

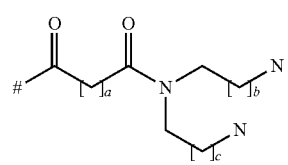

5

Analogue 6, having the structure below, where a is an integer of 0 to 5; b and c are the same or different and are integers of 0 to 5

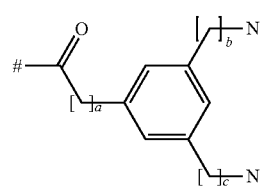

6

Analogue 7, having the structure below, where a is an integer of 0 to 5; b and c are the same or different and are integers of 1 to 5

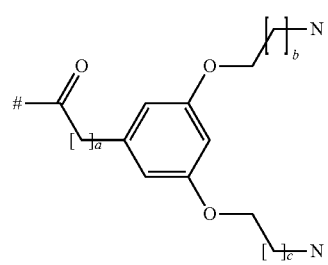

7

Analogue 8, having the structure below, where a is an integer of 0 to 5; b, c and d are the same or different and are integers of 1 to 5

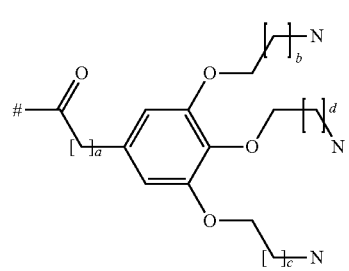

8

Analogue 9, having the structure below, where a is an integer of 0 to 5; b and c are the same or different and are integers of 1 to 5

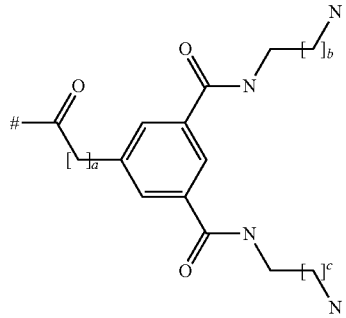

9 and furthermore, the alkyl chain moieties of the building units may be understood to include either alkoxy fragments as C—O—C or C—C—O—C—C but not O—C—X where X is O or N.

In a preferred aspect of the invention, the building units are selected from Lysine 1, Glycyl-Lysine 2 or Lysine analogue 5:

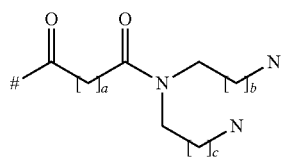

5 where a is an integer of 0 to 2 or the alkyl link is C—O—C; b and c are the same or different and are integers of 1 to 2.

In one embodiment, the surface building unit may be selected from the set of building units 1-9 described above. In an alternative embodiment, the surface building unit may be a compound wherein the reactable nitrogen may be replaced by another reactable moiety.

Chemical reactable groups which provide a useful means of attaching functional moieties to a surface building unit are: amine, carboxylate, hydroxyl, thiol, alkyl halide, allyl halide, heteroaryl halide, aryl halide, vinyl halide, epoxide, aziridine azide, alkyne. Where the chemical functional groups of the surface building unit are the same, as in hydroxyl, thiol, carboxylate, they may be orthogonally protected to achieve attachment of two or more different functional moieties.

Where the chemical reactable groups of the surface building unit may potentially interact with one another under the reaction conditions used to attach the functional moieties, then one or more of the different chemical functional groups may be protected whilst the other chemical functional group is reacted with a functional moiety.

Examples of chemical functional groups that may potentially interact and which may be included in a surface building unit are: carboxylate with any of amine, thiol or hydroxyl; heteroaryl halide with any of amine, thiol or hydroxyl; alkyl halide and any of amine, thiol or hydroxyl; epoxide and any of amine, thiol or hydroxyl; aziridine and any of amine, thiol or hydroxyl.

In yet another embodiment, the surface building unit may be selected from the group consisting of:

Analogue 10, having the structure below, where a is an integer of 0 to 2; b and c are the same or different and are integers of 1 to 4. $A_1$ and $A_2$ are the same or different and selected from $NH_2$, $CO_2H$, OH, SH, X as F, Cl, Br or I, Allyl-X as F, Cl, Br or I, epoxide, aziridine, $N_3$ or alkyne.

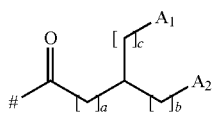

10

Analogue 11, having the structure below, where a is an integer of 0 to 2; b and c are the same or different and are integers of 2 to 6. $A_1$ and $A_2$ are the same or different and selected from $NH_2$, $CO_2H$, OH, SH, epoxide, $N_3$ or alkyne.

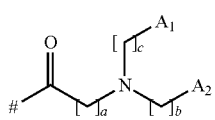

11

Analogue 12, having the structure below, where a is an integer of 0 to 5; b and c are the same or different and are integers of 1 to 5. $A_1$ and $A_2$ are the same or different and selected from $NH_2$, $CO_2H$, OH, SH, X as F, Cl, Br or I, Allyl-X as F, Cl, Br or I, epoxide, aziridine, $N_3$ or alkyne

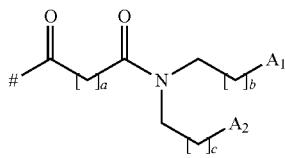

12

Analogue 13, having the structure below, where a is an integer of 0 to 5; b and c are the same or different and are integers of 0 to 5. $A_1$ and $A_2$ are the same or different and selected from $NH_2$, $CO_2H$, OH, SH, X as F, Cl, Br or I, Allyl-X as F, Cl, Br or I, epoxide, aziridine, $N_3$ or alkyne

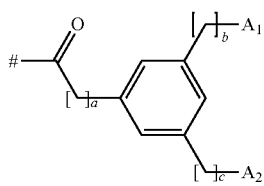

13

Analogue 14, having the structure below, where a is an integer of 0 to 5; b and c are the same or different and are integers of 1 to 5. $A_1$ and $A_2$ are the same or different and selected from $NH_2$, $CO_2H$, OH, SH, X as F, Cl, Br or I, Allyl-X as F, Cl, Br or I, epoxide, aziridine, $N_3$ or alkyne

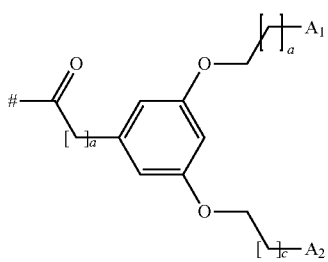

Analogue 15, having the structure below, where a is an integer of 0 to 5; b, c and d are the same or different and are integers of 1 to 5. $A_1$ and $A_2$ are the same or different and selected from $NH_2$, $CO_2H$, OH, SH, X as F, Cl, Br or I, Allyl-X as F, Cl, Br or I, epoxide, aziridine, $N_3$ or alkyne

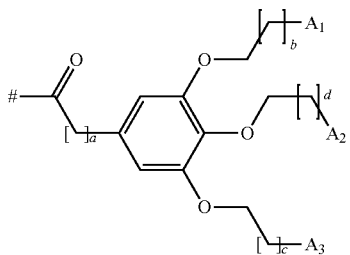

Analogue 16 having the structure below, where a is an integer of 0 to 5; b and c are the same or different and are integers of 1 to 5. $A_1$ and $A_2$ are the same or different and selected from $NH_2$, $CO_2H$, OH, SH, X as F, Cl, Br or I, Allyl-X as F, Cl, Br or I, epoxide, aziridine, $N_3$ or alkyne

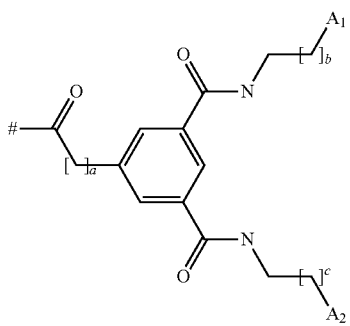

and furthermore, the alkyl chain moieties of the building units may be understood to include either alkoxy fragments as C—O—C or C—C—O—C—C but not O—C—X where X is O or N. Groups $A_1$ and $A_2$ may be further protected where required.

Preferred surface building units include glutamate and aspartate.

The type of building units and surface building units allows attachment of different functional moieties to the surface and subsurface by a number of ways. In one embodiment, where the dendritic motifs of the macromolecule include a lysine or lysine analogue building unit having a carboxylate group or residue thereof at the apex thereof, attached to two amine groups, at least one amine group may in turn be attached to a carboxylate group or residue thereof of a second building unit. When the second building unit is a surface building unit that is glutamate or aspartate for example, and bears two functional moieties, one of those functional moieties may be attached via a surface amine. When the second building unit is a surface building unit that is a lysine or lysine, analogue having two amine groups, two functional moieties may be attached to the amines.

In addition to the functional moieties attached to the second, surface building unit, a third functional moiety may be attached to the second amine group of the lysine or lysine analogue building unit, resulting in a dendritic motif with functionalisation at the surface and subsurface level.

The present invention is directed to macromolecules having controlled functional moiety stoichiometry and topology and will now be described in more detail.

In a preferred embodiment, the surface amines or other reactable groups of the building units and/or surface building units bear a functional moiety A or B, with a pair of adjacent functional moieties on the same surface building unit or building unit forming a couplet selected from (AA), (BB) and (AB), or any combination thereof. When there are only two types of functional moiety A and B on the same building unit or surface building unit, the functional moiety stoichiometry is other than 1:1.

When a macromolecule having two or more different functional moieties is synthesised using random surface functionalisation methods, two approaches may be considered, e.g. an equal mixture of two functional moieties is required.

In a first prior art approach using lysine or lysine analogues as an example of a surface building unit, a substoichiometric amount of the first activated functional moiety is used in an attempt to cap only half the reactive surface amine groups on the surface of the macromolecule. The remaining reactive surface amines may then be reacted, and in this second reaction, an excess of the second activated functional moiety may be used to force the reaction to completion. In this approach, there is a statistical distribution of products which vary in the number of attached first functional moieties arising from the first stage of the reaction, and furthermore there is little or no control over the topology of the two different functional moieties.

In a second prior art approach, both activated functional moieties may be simultaneously reacted with the reactive surface amine groups. In such an approach, it may be possible to adjust the stoichiometries of each surface derivatising agent to account for their differing reactivities, but molecule to molecule variability will still arise because more than one type of functional moiety is available to react with the reactive surface amine groups and so the likely outcome of each reaction may only be described by a statistical distribution, and again, there is no control over the topological outcome of the reaction.

In contrast to the random prior art approaches, the present invention is concerned with controlled surface and subsurface functionalisation methods. This difference is more clearly illustrated in the sets below.

Set 1 represents a preparation of macromolecules in which four macromolecules, each with 16 reactable terminal groups, has been allowed to react with a mixture of 32 dark and 32 light functional moieties. Whilst the outcome is only illustrative, it can be seen that whilst the "average" property of each molecule of the preparation is a 1:1 stoichiometry of light and dark; the actual likelihood of any individual molecule of the preparation having a 1:1 stoichiometry is determined by statistics.

For comparison, Set 2 represents a preparation of macromolecules with a controlled stoichiometry and topology of light and dark functional moieties, as is the subject of the present invention. It can be seen that for this preparation, each macromolecule is identical.

Set 1: Random stoichiometry and topology

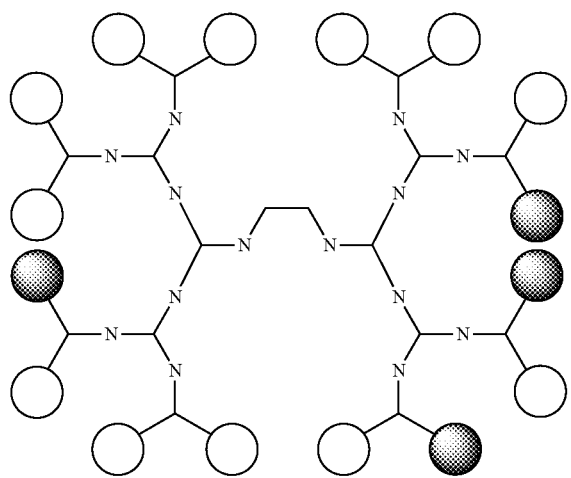

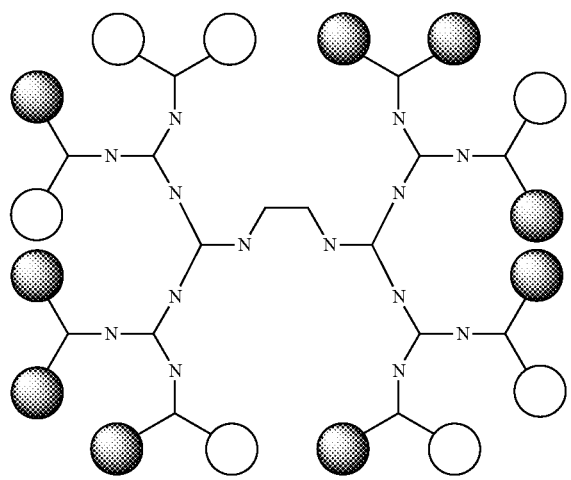

-continued

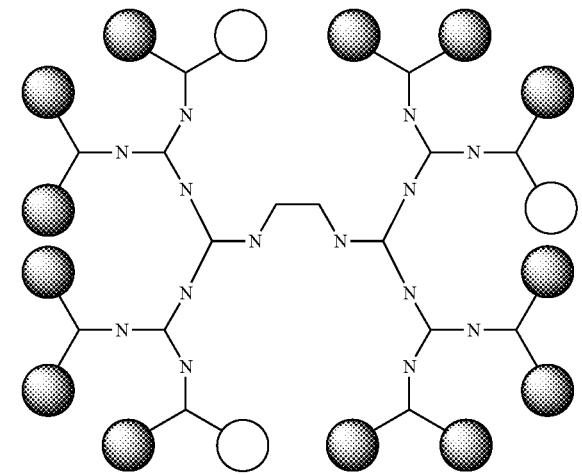

Set 2: Control over stoichiometry and topology

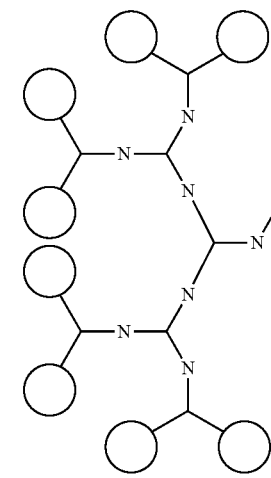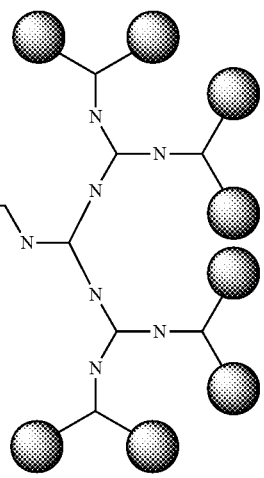

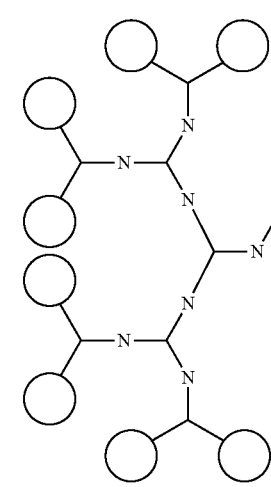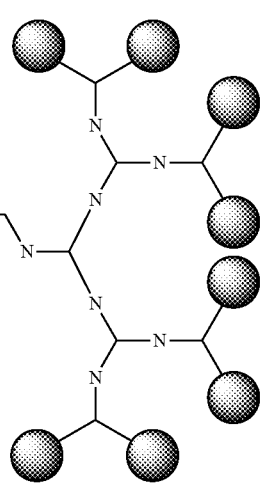

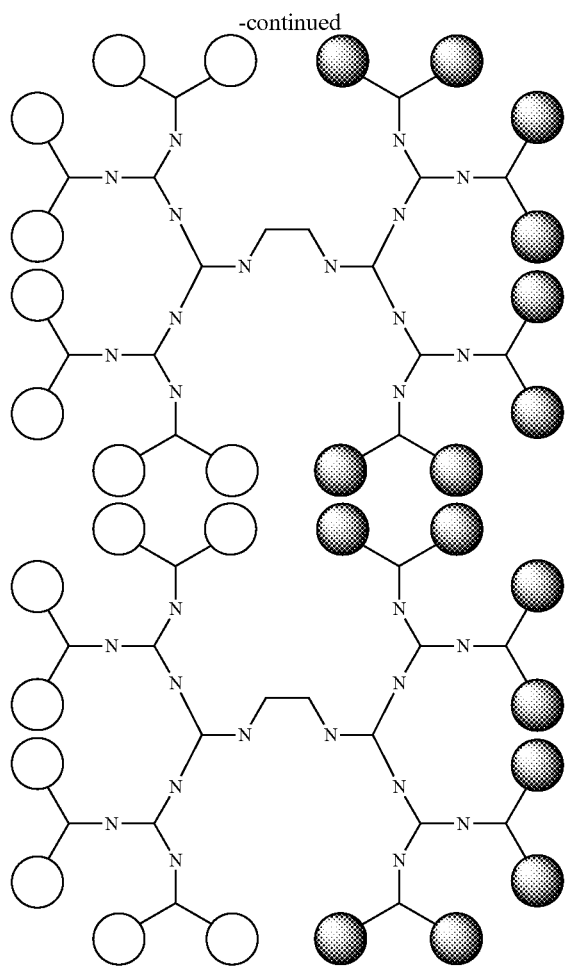

A macromolecule composition is considered "enriched" if the fractional abundance of macromolecules with precisely specified composition of functional moieties is greater than the fractional abundance in a randomly surface functionalised material by a factor of at least 2 (2-fold enriched monodispersity) and preferably 4 (4-fold enriched monodispersity). This enrichment may be specified by comparing the precisely specified composition with a randomly functionalised macromolecule composition. Suppose that this random method provides a particular functional moiety stoichiometry in 5% of the macromolecules. Then enrichment would constitute an increase in the macromolecule with a particular functional moiety stoichiometry over this 5% level. For example a two-fold enrichment would mean that 10% of the macromolecules exhibited the particular functional moiety stoichiometry.

At an extreme level of stoichiometric enrichment each macromolecule will have the same number and type of functional moieties. A more moderate level of enrichment, such as enrichment at 20%, is taken to mean that 20% of the macromolecules will have the same number and type of functional moieties. Accordingly, in one embodiment of the present invention there is provided a preparation of macromolecules having at least 10% enrichment in a selected functional moiety stoichiometry. In turn, in a preferred embodiment, there is provided a preparation wherein at least 80% of the macromolecules have the same functional moiety stoichiometry.

The concept of enrichment, which has been illustrated for functional moieties, may also be applied to "topological enrichment", being the number and type of couplets, quartets and octets etc, which are described in detail below. Even if the general make up of the surface of the macromolecule is maintained, at 100% enrichment, for example with 50% functional moiety A and 50% functional moiety B, it does not follow that there is 100% topological enrichment. This is because the functional moieties A and B may be grouped into couplets, quartets, octets and 16-tets in a multitude of ways. Accordingly, in another embodiment, there is provided a preparation of macromolecules, wherein the macromolecules further exhibit enrichment in a selected topological isomer, wherein topology describes the relationship between functional moiety and another in terms of its connection to the surface and subsurface layers.

There are many stereochemical and regiochemical consequences that may arise when the carbonyl-to-amine bond sequence is asymmetric within a building unit, as it is for native lysine 1. For the purposes of the present invention, such consequences will not be analysed. The present invention will identify the relative configuration of the different topological elements. The order of functional moieties within a couplet is then, for the present analysis, redundant. That is (AB) is equivalent to (BA), and this also holds true for couplets within quartets, quartets within octets and octets within 16-tets.

The simplest type of topological enrichment is enrichment at the level of couplets i.e., two functional moieties attached to the same surface building unit or building unit. A macromolecule composition may be fully enriched at the level of functional moieties, but not fully enriched at the level of couplets. This is because the same functional moieties may be grouped into couplets in a number of ways. For example in FIGS. 3.1 to 3.5, where A and B represent different functional moieties, the macromolecules contain 16 A groups and 16 B groups. However in FIGS. 3.1, 3.2, 3.3 and 3.4 there are eight (AA) couplets and eight (BB) couplets while in FIG. 3.5 there are sixteen (AB) couplets.

Topological enrichment at 20% is taken to mean that 20% of the macromolecules will have the same composition (number and type) of couplets.

Alternatively as described above in relation to stoichiometric enrichment this enrichment may be specified by comparing the enriched composition with a randomly functionalised macromolecule composition, from which has been selected all macromolecules with the specified couplet stoichiometry. Assuming this selection provides a particular composition of couplets at a level of 5% of the total number of macromolecules, then, a two-fold enrichment at the level of couplets would mean that 10% of the macromolecules had the required couplet composition. Accordingly, in one embodiment, there is provided a macromolecule composition having at least 10% enrichment in a selected functional moiety topology.

A higher order of topological enrichment is enrichment at the level of quartets.

A macromolecule composition with at least two layers of building units may be fully enriched at the level of functional moieties and couplets, but not fully enriched at the level of quartets. This is because the same couplets may be grouped into quartets in a multitude of ways. For example in FIGS. 3.1 to 3.5 the macromolecules contain 16 A groups and 16 B groups, however in FIGS. 3.1, 3.2 and 3.3 there are four $((AA)(AA))^4$ quartets and four $((BB)(BB))^4$ quartets while in FIG. 3.4 there are eight $((AA)(BB))^4$ quartets and in FIG. 3.5 there are eight $((AB)(AB))^4$ quartets.

A higher order specification of topological enrichment would thus require a specification of enrichment at the level of quartets. This enrichment may be specified in two ways, as described previously, i.e. either enrichment at 20% means that 20% of the macromolecules will have the same quartet composition (number and type) or two fold enrichment at the level of quartets means that there are twice as many macromolecules with specified quartet composition than is achievable from a random functionalisation experiment.

Thus the topological enrichment is specified in terms of a hierarchy of enrichment values that will correspond to couplet enrichment, quartet enrichment, octet enrichment, 16-tet enrichment etc. In a preferred embodiment, there is provided a macromolecule according to claim 17 wherein the macromolecule exhibits topological enrichment at:

the couplet level;

at the quartet level, where a pair of adjacent couplets form a quartet, each quartet having a line of connection to an apex carboxylate group of a surface-but-one building unit;

at the octet level where adjacent quartets form an octet, each octet having a line of connection to an apex carboxylate group of a surface-but-two building unit; or at the 16-tet level, where adjacent octets form a 16-tet, each 16-tet having a line of connection to an apex carboxylate group of a surface-but-three building unit. The hierarchy of enrichment values is determined by the number of layers in the macromolecule. The order at which a macromolecule is specified, i.e. at the couplet, quartet, octet level, or 16-tet provides a level of information about the structure for various dendrimer motifs. A couplet represents a minimal dendritic motif, whilst a 16-tet represents a much larger dendritic motif.

The macromolecules of the invention may bear two or more different functional moieties on the building unit and/or surface building unit. Each functional moiety may be independently chosen from protecting groups including Boc, CBz, 4-nitrobenzyloxycarbamate (4-NO$_2$-Nitro-CBz), Fmoc, Dde, CF$_3$CO$_2$, 2-halo-CBz, Aloc, Me$_3$SiEtSO$_2$, Troc, o-NO$_2$PhSO$_2$ and, 2,4-dinitrobenzene-sulfonyl and t-butyldimethylsilyl chloride, and preferably from Boc, CBz, 4-NO$_2$-Nitro-CBz, Fmoc 2-halo-CBz, Alloc, Me$_3$SiEtSO$_2$, Troc, o-NO$_2$PhSO$_2$, 2,4-dinitrobenzene-sulfonyl.

The functional moieties may also be selected from the types listed in Table 1A.

TABLE 1A

| | Functional moieties |
|---|---|
| Ligands for extracellular receptors | Mono and oligosaccharides or analogues thereof<br>Peptide ligands or fragments or analogues: Chemokines or cytokines or binding motifs eg RGD peptide<br>Known small molecule agonists or antagonists, fragments thereof |
| Property modifiers | Hydrophilic groups: PEG's or other hydrophilic polymers, polyhydroxyl chains, oligosaccharides, aryl or heteroaryl groups,<br>Hydrophobic groups: long chain alkyl groups, steroids,<br>Charged surface groups: groups with negative charge at pH ≤1, ≤3, ≤5, ≤7, ≤9 etc; groups with positive charge at pH ≤1, ≤3, ≤5, ≤7, ≤9 etc, groups that are zwitterionic at pH ≤1, ≤3, ≤5, ≤7, ≤9 etc. |
| Pharmaceutically active agents (see Table 1B) attached by cleavable linker | Cleavable linker: acid labile, photocleavable, reductively labile, enzymatically cleavable (protease, esterase);<br>Pharmaceutically active agents conjugated for release to facilitate delivery via increased solubility, decreased toxicity |
| Groups to effect targeting | Ligands to extracellular receptors; receptors to extracellular ligands eg lectins or antibodies or functional fragments thereof; cell surface antigen recognising antibodies or antibody fragments prepared either through cleavage of whole antibodies or through protein expression systems. |
| Groups to effect signalling | Radioactive label, PET label, ligand-metal complex where metal is radioactive, PET active, MRI active; fluorescent label; labels that are quiescent but signal upon activation (cleavage, chemical reaction, excitation via irradiation) |
| Antigenic material | Known peptide or glycopeptide or carbohydrate epitope, or protein comprising known epitope. |
| Genetic material | Sequence of DNA or RNA |
| Group to mediate binding to second entity | Known partners in high affinity ligand-receptor interactions, such as biotin-streptavidin, digoxin-antibody, nickel-histidine-binding motifs, complimentary single stranded DNA, RNA or PNA |

When the functional moiety is a pharmaceutically active agent, a derivative thereof, or a precursor thereof, the pharmaceutically active agent may be exemplified by, but not limited to one or more selected from the groups in Table 1B:

TABLE 1B

| Pharmaceutically active agents | |
|---|---|
| Acetonemia preparations | Anabolic agents |
| Anaesthetics | Analgesics |
| Anti-acid agents | Anti-arthritic agents |
| Antibodies | Anti-convulsants |
| Anti-fungals | Anti-histamines |
| Anti-infectives | Anti-inflammatories |
| Anti-metabolites | Anti-microbials |
| Anti-mitotics | Anti-parasitic agents |
| Anti-protozoals | Anti-ulcer agents |
| Antiviral pharmaceuticals | Behaviour modification drugs |
| Biologicals | Blood and blood substitutes |
| Bronchodilators and expectorants | Cancer therapy and related pharmaceuticals |
| Cardiovascular pharmaceuticals | Central nervous system pharmaceuticals |
| Contrast agents | Contraceptives |
| Diuretics | Diabetes therapies |
| Growth hormones | Fertility pharmaceuticals |
| Hematinics | Growth promoters |
| Hormone replacement therapies | Hemostatics |
| Immune suppressives | Immunostimulants |
| Hormones and analogs | Muscle relaxants |
| Minerals | Natural products |
| Nutraceuticals and nutritionals | Obesity therapeutics |
| Ophthalmic pharmaceuticals | Osteoporosis drugs |
| Pain therapeutics | Peptides and polypeptides |
| Proteins | Respiratory pharmaceuticals |

TABLE 1B-continued

Pharmaceutically active agents

| | |
|---|---|
| Sedatives and tranquilizers | Transplantation products |
| Urinary acidifiers | Vaccines and adjuvants |
| Vitamins | |

The present invention is particularly appropriate for pharmaceutically active agents that are very, active even in extremely small quantities and whose sustained long-term administration is sought, particularly to overcome toxicity problems with standard doses.

In a preferred embodiment the functional moieties are independently selected from functional groups such as those listed in Table 1A and 1B and functional groups that are protecting groups. The stoichiometric ratio between one type of functional moiety and all other functional moieties is approximately 1:1 or 1:2 or 1:3 or 1:4 or 1:5 or 1:6 or 1:7 or 1:8 or 1:9 1:10 or 1:16, more preferably 1:1 or 1:3 or 1:7. In turn, the stoichiometric ratio between a selected couplet to all other couplets, a selected quartet to all other quartets, and selected octet to all other octets, and a selected 16-tet to all other 16-tets is approximately 1:1 or 1:2 or 1:3 or 1:4 or 1:5 or 1:6 or 1:7 or 1:8 or 1:9 1:10 or 1:16, more preferably 1:1 or 1:3 or 1:7.

In many cases of practical interest, the relative configuration of the different functional groups and their pattern of connectedness (topological isomeric character) is of principal interest. The topological isomeric character of a macromolecule or dendritic motif may readily be shown from planar representations of the motif when the building units are all symmetric. By this we mean that the building units are treated as if the bond path from apex to each reactable amine is identical, as exemplified in FIG. 4.

It is possible to rotate by 180° the chemical bond joining a non-surface amine to the apex carboxylate group of the attached building unit. The macromolecule or dendritic motif, containing this rotated dendritic motif component will also fit on the same plane of representation. After rotation, the macromolecule or dendritic motif may appear different because the location of functional moieties at the surface of the motif are different relative to each other, as for F4.1, F4.2 and F4.3 in FIG. 4. In order to check if two apparently different planar representations of a macromolecule or dendritic motif actually represent the same thing, the planar representation of the first macromolecule or dendritic motif should be taken as a reference and all permissible 180° degree rotations carried out within the planar representation of the second macromolecule or dendritic motif to form a rotation set. If the first planar representation is contained in the rotation set of the second, the two dendritic motifs are the same.

In order to facilitate the description of the embodiments, an alpha-numeric topological nomenclature of couplets, quartets, octets and beyond has been introduced. In particular the nomenclature makes it possible to identify the preferred quartets, octets and 16-tets which are components of macromolecules and which are a preferred embodiment of this invention.

It should be understood that this alpha-numeric nomenclature is a transcription of one of many potential planar two-dimensional representations of a particular topological isomer. Before a planar representation is transcribed into the topological nomenclature, it should be positioned on a page such that an unhindered line can be drawn from outside the planar representation to meet the shortest bond sequence that joins two reactable amine groups of the core. This is demonstrated by example in FIG. 1.1: reading clockwise from the vertical line the functional moieties are AAAABBB-BAAAABBBB. If the core is monovalent or macroscopic, or if a dendritic motif is being transcribed, then this line should meet the shortest bond sequence that joins the two reactable amine groups of the first building unit i.e. that building unit with the apex carboxylate (F) is demonstrated by example in FIG. 1.3: reading clockwise from the line the functional moieties are AAAABBBB. In those circumstances where a dendritic motif is described the apex carboxylate is represented as, it is often helpful to include this feature in the alpha-numeric nomenclature, and this is done as a prefix F as in FIG. 1.3; where F represents the chemical functional moiety at the apex.

In the event that one or more of the building units is asymmetric, for example in terms of the sequence of bonds from the apex of the building unit to the amines of the building unit capable of further reaction, or in terms of the presence of chirality, the description of the dendritic motif as a topological isomer may be determined by representing each building unit as a symmetric unit on the diagram (even if it is not), and then checking to see if one representation is contained in the rotation set of the other. An example of this approach is demonstrated in FIG. 4 for F4.4, symmetrised to F4.1 prior to bond rotation analysis. While there are many stereochemical and regiochemical consequences that may arise when the carboxylate-to-amine bond sequence is asymmetric within a building unit, as it is for native lysine 1. Such consequences will not be analysed for the purposes of the present invention. The present invention will identify the relative configuration of the different topological elements. The order of functional moieties within a couplet is then, for the present analysis, redundant. That is (AB) is equivalent to (BA), and this also holds true for couplets within quartets, quartets within octets and octets within 16-tets.

The total number of functional moieties in a macromolecule or dendritic motif can be represented by $FM_{Total}$. The composition of functional moieties of a macromolecule or dendritic motif, wherein all the surface amines and/or surface building units groups are attached to functional moieties, can be provided in a formula of the form $\Sigma FM_i = FM_{total}$ where the surface of the macromolecule or dendritic motif has an integral quantity FM, of functional moieties of type i. Consider FIG. 3 which provides schematic diagrams of five different topological isomers of macromolecules which have the same $FM_{Total}$ and furthermore have the same equal number of two functional moieties A and B. For these systems, $FM_A = FM_B = 16$ and $\Sigma FM_i = (FM_A + FM_B) = 32$. However it is important to note that each of these examples has a different surface topology and it is the purpose of the alpha-numeric topological nomenclature to identify and distinguish between these topological isomers even where the number and type of functional moieties of a macromolecule or dendritic motif is the same.

In one embodiment, two different functional moieties A and B are attached to the same surface building unit. In the alpha-numeric topological nomenclature of this invention the functional moieties attached to a particular surface building unit are represented within a single layer of, parentheses, and can be described in terms of couplets. Preferred couplets are (AA), (BB) and (AB) and any combination thereof. For example, (AA) would represent that functional moiety A and a second functional moiety A are attached to the same surface building unit. This connectivity is demonstrated in FIG. 2.1. The macromolecules of FIG. 3 are represented using couplets in the alpha-numeric topological nomenclature as follows:

TABLE 2

| Figure | alpha-numeric topological nomenclature | Composition |
|---|---|---|
| 3.1 | (BB)(BB)(BB)(BB)(BB)(BB)(BB)(BB)(AA)(AA)(AA)(AA)(AA)(AA)(AA)(AA) | 8 (AA) couplets and 8 (BB) couplets |
| 3.2 | (AA)(AA)(AA)(AA)(BB)(BB)(BB)(BB)(BB)(BB)(BB)(BB)(AA)(AA)(AA)(AA) | 8 (AA) couplets and 8 (BB) couplets |
| 3.3 | (AA)(AA)(BB)(BB)(AA)(AA)(BB)(BB)(BB)(BB)(AA)(AA)(BB)(BB)(AA)(AA) | 8 (AA) couplets and 8 (BB) couplets |
| 3.4 | (AA)(BB)(AA)(BB)(AA)(BB)(AA)(BB)(BB)(AA)(BB)(AA)(BB)(AA)(BB)(AA) | 8 (AA) couplets and 8 (BB) couplets |
| 3.5 | (AB)(AB)(AB)(AB)(AB)(AB)(AB)(AB)(AB)(AB)(AB)(AB)(AB)(AB)(AB)(AB) | 16 (AB) couplets |

It is then possible to describe the macromolecules or dendritic motifs of this invention in terms of the composition (number and type) of couplets. This is demonstrated for clarity in the examples of FIG. 3 and summarised in the "composition" column of Table 2.

The surface topology of a macromolecule or dendritic motif bearing functional moieties A and B may also be described in terms of couplets and quartets. For example in the alpha-numeric topological nomenclature a quartet of the form $((AA)(AA))^4$ is used to represent four functional moieties A,A,A,A which have a line of connection to the same building unit, in particular to a surface-but-one building unit. This connectivity is demonstrated by FIG. F2.2. A description of the topology of a macromolecule or dendritic motif in terms of quartets can provide structural information about the lines of connectivity between the functional moieties and the surface-but-one building units to which they are attached.

The macromolecules of FIG. 3 are represented using quartets in the alpha-numeric topological nomenclature as follows:

When a quartet is to be assembled from two functional moieties, represented by A and B this may be done by making use of the preferred couplets (AA), (AB) and (BB). The preferred composition of quartets can be of the form:

TABLE 3B

| Ratio | Type of quartet | Equivalent quartet |
|---|---|---|
| Homogenous | $((AA)(AA))^4$ | $((BB)(BB))^4$ |
| 3:1 | $((AA)(AB))^4$ | $((AB)(BB))^4$ |
| 1:1 | $((AB)(AB))^4$; $((AA)(BB))^4$ | |

In a preferred embodiment, the compositions of macromolecules or dendritic motifs include at least one quartet selected from Table 3B, including those quartets which can be considered equivalent by way of their topology and relative composition of two different functional moieties.

The surface topology of a macromolecule or dendritic motif bearing functional moieties A and B may also be described in terms of couplets, quartets and octets. For

TABLE 3A

| Figure | alpha-numeric topological nomenclature | Composition |
|---|---|---|
| 3.1 | $((BB)(BB))^4((BB)(BB))^4((BB)(BB))^4((BB)(BB))^4$ $((AA)(AA))^4((AA)(AA))^4((AA)(AA))^4((AA)(AA))^4$ | 4 quartets $((AA)(AA))^4$ and 4 quartets $((BB)(BB))^4$ |
| 3.2 | $((AA)(AA))^4((AA)(AA))^4((BB)(BB))^4((BB)(BB))^4$ $((BB)(BB))^4((BB)(BB))^4((AA)(AA))^4((AA)(AA))^4$ | 4 quartets $((AA)(AA))^4$ and 4 quartets $((BB)(BB))^4$ |
| 3.3 | $((AA)(AA))^4((BB)(BB))^4((AA)(AA))^4((BB)(BB))^4$ $((BB)(BB))^4((AA)(AA))^4((BB)(BB))^4((AA)(AA))^4$ | 4 quartets $((AA)(AA))^4$ and 4 quartets $((BB)(BB))^4$ |
| 3.4 | $((AA)(BB))^4((AA)(BB))^4((AA)(BB))^4((AA)(BB))^4$ $((BB)(AA))^4((BB)(AA))^4((BB)(AA))^4((BB)(AA))^4$ | 8 quartets $((AA)(BB))^4$ |
| 3.5 | $((AB)(AB))^4((AB)(AB))^4((AB)(AB))^4((AB)(AB))^4$ $((AB)(AB))^4((AB)(AB))^4((AB)(AB))^4((AB)(AB))^4$ | 8 quartets $((AB)(AB))^4$ |

It is then possible to describe the macromolecules or dendritic motifs of this invention in terms of the composition (number and type) of quartets. This is demonstrated for clarity in the examples of FIG. 3 and summarised in the "composition" column of Table 3A.

example in the alpha-numeric topological nomenclature an octet of the form: $(((AA)(AA))^4((AA)(AA))^4)^8$ is used to represent eight functional moieties A,A,A,A,A,A,A,A which have a line of connection to the same building unit, in fact to a surface-but-two building unit. This connectivity is demonstrated by FIG. F2.3. A description of the topology of a macromolecule or dendritic motif in terms of octets can provide structural information about the lines of connectivity between the functional moieties and the surface-but-two building units to which they are attached.

The macromolecules of FIG. 3 are represented using octets in the alpha-numeric topological nomenclature as follows:

motif in terms of 16-tets can provide structural information about the lines of connectivity between the functional moieties and the surface-but-three building units to which they are attached.

The macromolecules of FIG. 3 are represented using 16-tets in the alpha-numeric topological nomenclature as follows:

TABLE 4A

| Figure | alpha-numeric topological nomenclature | Composition |
|---|---|---|
| 3.1 | $(((BB)(BB))^4((BB)(BB))^4)^8(((BB)(BB))^4((BB)(BB))^4)^8$ $(((AA)(AA))^4((AA)(AA))^4)^8(((AA)(AA))^4((AA)(AA))^4)^8$ | 2 octets $(((AA)(AA))^4((AA)(AA))^4)^8$ and 2 octets $(((BB)(BB))^4((BB)(BB))^4)^8$ |
| 3.2 | $(((AA)(AA))^4((AA)(AA))^4)^8(((BB)(BB))^4((BB)(BB))^4)^8$ $(((BB)(BB))^4((BB)(BB))^4)^8(((AA)(AA))^4((AA)(AA))^4)^8$ | 2 octets $(((AA)(AA))^4((AA)(AA))^4)^8$ and 2 octets $(((BB)(BB))^4((BB)(BB))^4)^8$ |
| 3.3 | $(((AA)(AA))^4((BB)(BB))^4)^8(((AA)(AA))^4((BB)(BB))^4)^8$ $(((BB)(BB))^4((AA)(AA))^4)^8(((BB)(BB))^4((AA)(AA))^4)^8$ | 4 octets $(((AA)(AA))^4((BB)(BB))^4)^8$ |
| 3.4 | $(((AA)(BB))^4((AA)(BB))^4)^8(((AA)(BB))^4((AA)(BB))^4)^8$ $(((BB)(AA))^4((BB)(AA))^4)^8(((BB)(AA))^4((BB)(AA))^4)^8$ | 4 octets $(((AA)(BB))^4((AA)(BB))^4)^8$ |
| 3.5 | $(((AB)(AB))^4((AB)(AB))^4)^8(((AB)(AB))^4((AB)(AB))^4)^8$ $(((AB)(AB))^4((AB)(AB))^4)^8(((AB)(AB))^4((AB)(AB))^4)^8$ | 4 octets $(((AB)(AB))^4((AB)(AB))^4)^8$ |

It is then possible to describe the macromolecules or dendritic motifs of this invention in terms of the composition (number and type) of octets. This is demonstrated for clarity in the examples of FIG. 3 and summarised in the "composition" column of Table 4A.

When an octet is to be assembled from two functional moieties, represented by A and B this may be done by making use of the preferred quartets from Table 3B. The preferred composition of octets can be of the form:

TABLE 4B

| Ratio | Type of octet | Equivalent octet |
|---|---|---|
| homogenous | $(((AA)(AA))^4((AA)(AA))^4)^8$ | $(((BB)(BB))^4((BB)(BB))^4)^8$ |
| 7:1 | $(((AA)(AA))^4((AA)(AB))^4)^8$ | $(((BB)(BB))^4((BB)(AB))^4)^8$ |
| 6:2 | $(((AA)(AA))^4((AA)(BB))^4)^8$, | $(((BB)(BB))^4((BB)(AA))^4)^8$ |
|  | $(((AA)(AA))^4((AB)(AB))^4)^8$, | $(((BB)(BB))^4((AB)(AB))^4)^8$ |
|  | $(((AA)(AB))^4((AA)(AB))^4)^8$. | $(((BB)(BA))^4((BB)(AB))^4)^8$ |
| 5:3 | $(((AA)(AA))^4((AB)(BB))^4)^8$, | $(((BB)(BB))^4((AA)(AB))^4)^8$ |
|  | $(((AA)(AB))^4((AA)(BB))^4)^8$, | $(((BB)(AB))^4((AA)(BB))^4)^8$ |
|  | $(((AA)(AB))^4((AB)(AB))^4)^8$. | $(((BB)(AB))^4((AB)(AB))^4)^8$ |
| 4:4 (1:1) | $(((AA)(AA))^4((BB)(BB))^4)^8$, |  |
|  | $(((AA)(AB))^4((AB)(BB))^4)^8$, |  |
|  | $(((AA)(BB))^4((AA)(BB))^4)^8$, |  |
|  | $(((AA)(BB))^4((AB)(AB))^4)^8$, |  |
|  | $(((AB)(AB))^4((AB)(AB))^4)^8$. |  |

In a preferred embodiment, the compositions of macromolecules or dendritic motifs include at least one octet selected from Table 4B, including those octets which can be considered equivalent by way of their topology and relative composition of two different functional moieties.

The surface topology of a macromolecule or dendritic motif bearing functional moieties A and B may also be described in terms of couplets, quartets, octets and 16-tets. For example in the alpha-numeric topological nomenclature a 16-tet of the form: $((((AA)(AA))^4((AA)(AA))^4)^8(((AA)(AA))^4((AA)(AA))^4)^8)^{16}$ is used to represent sixteen functional moieties of type A which have a line of connection to the same building unit, in fact to a surface-but-three building unit. This connectivity is demonstrated by FIG. F2.4. A description of the topology of a macromolecule or dendritic

TABLE 5A

| Figure | alpha-numeric topological nomenclature |
|---|---|
| 3.1 | $((((BB)(BB))^4((BB)(BB))^4)^8(((BB)(BB))^4((BB)(BB))^4)^8)^{16}$ $((((AA)(AA))^4((AA)(AA))^4)^8(((AA)(AA))^4((AA)(AA))^4)^8)^{16}$ |
| 3.2 | $((((AA)(AA))^4((AA)(AA))^4)^8(((BB)(BB))^4((BB)(BB))^4)^8)^{16}$ $((((BB)(BB))^4((BB)(BB))^4)^8(((AA)(AA))^4((AA)(AA))^4)^8)^{16}$ |
| 3.3 | $((((AA)(AA))^4((BB)(BB))^4)^8(((AA)(AA))^4((BB)(BB))^4)^8)^{16}$ $((((BB)(BB))^4((AA)(AA))^4)^8(((BB)(BB))^4((AA)(AA))^4)^8)^{16}$ |
| 3.4 | $((((AA)(BB))^4((AA)(BB))^4)^8(((AA)(BB))^4((AA)(BB))^4)^8)^{16}$ $((((BB)(AA))^4((BB)(AA))^4)^8(((BB)(AA))^4((BB)(AA))^4)^8)^{16}$ |
| 3.5 | $((((AB)(AB))^4((AB)(AB))^4)^8(((AB)(AB))^4((AB)(AB))^4)^8)^{16}$ $((((AB)(AB))^4((AB)(AB))^4)^8(((AB)(AB))^4((AB)(AB))^4)^8)^{16}$ |

When a 16-tet is to be assembled from two functional moieties, represented by A and B this may be done by making use of the preferred couplets, quartets and octets. The preferred composition of 16-tets can be of the form:

$$((((AA)(AA))^4((AA)(AB))^4)^8(((AA)(AA))^4((AA)(AB))^4)^8)_{16}$$

$$((((AA)(AA))^4((AA)(AA))^4)^8(((AB)(AB))^4((AB)(AB))^4)^8)_{16}$$

$$((((AA)(AA))^4((AB)(AB))^4)^8(((AB)(AB))^4((AB)(AB))^4)^8)_{16}$$

$$((((AA)(BB))^4((AA)(BB))^4)^8(((AA)(BB))^4((AA)(BB))^4)^8)_{16}$$

In a preferred embodiment, the compositions of macromolecules or dendritic motifs include at least one 16-tet.

In another embodiment, the functional moieties attached to the surface building units of a macromolecule or dendritic motif are selected from A, B and D. Consider FIG. 5 which provides schematic diagrams of five different topological isomers of macromolecules with the same ratio, 2:1:1, of three functional moieties A, B and D. Furthermore these macromolecules have the same $FM_{Total}$ and the same number of three functional moieties A, B and D, represented by $FM_A=16$, $FM_B=8$, $FM_D=8$, providing a description of the macromolecules in the form: $\Sigma FM_i=(FM_A+FM_B+FM_D)=16A+8B+8D=32$. However it is important to note that each of these examples has a different surface topology and it is the purpose of the alpha-numeric topological nomenclature to identify and distinguish between these topological isomers where the number/type of functional moieties of a macromolecule or dendritic motif is the same.

When three different functional moieties A, B and D are attached to the surface building units of a macromolecule or dendritic motif, preferred couplets are selected from (AA), (BB), (DD), (AB), (AD) and (BD), and combinations thereof.

The macromolecules of FIG. 5 are represented using couplets in the alpha-numeric topological nomenclature as follows:

TABLE 6

| Fig | alpha-numeric topological nomenclature | Composition |
| --- | --- | --- |
| 5.1 | (BB)(BB)(BB)(BB)(DD)(DD)(DD)(DD)(AA)(AA)(AA)(AA)(AA)(AA)(AA)(AA) | 8 (AA), 4 (BB) and 4 (DD) couplets |
| 5.2 | (BB)(BB)(DD)(DD)(BB)(BB)(DD)(DD)(AA)(AA)(AA)(AA)(AA)(AA)(AA)(AA) | 8 (AA), 4 (BB) and 4 (DD) couplets |
| 5.3 | (BB)(DD)(BB)(DD)(BB)(DD)(BB)(DD)(AA)(AA)(AA)(AA)(AA)(AA)(AA)(AA) | 8 (AA), 4 (BB) and 4 (DD) couplets |
| 5.4 | (BD)(BD)(BD)(BD)(BD)(BD)(BD)(BD)(AA)(AA)(AA)(AA)(AA)(AA)(AA)(AA) | 8 (AA) couplets and 4 (BD) couplets |
| 5.5 | (AA)(AA)(AA)(AA)(BD)(BD)(BD)(BD)(BD)(BD)(BD)(BD)(AA)(AA)(AA)(AA) | 8 (AA) couplets and 4 (BD) couplets |

It is then possible to describe the macromolecules or dendritic motifs of this invention in terms of the composition (number and type) of couplets containing functional moieties selected from A, B and D. This is demonstrated for clarity in the examples of FIG. 5 and summarised in the "composition" column of Table 6.

The surface topology of a macromolecule or dendritic motif bearing functional moieties A, B and D may also be described in terms of couplets and quartets. For example in the alpha-numeric topological nomenclature a quartet of the form $((AA)(BD))^4$ is used to represent four functional moieties A,A,B,D which have a line of connection to the same building unit, in particular to a surface-but-one building unit.

The macromolecules of FIG. 5 are represented using quartets in the alpha-numeric topological nomenclature as follows:

When a quartet is to be assembled from three functional moieties, represented by A, B and D, this may be done by making use of preferred couplets. The preferred composition of quartets additional to those in Table 3B can be of the form:

TABLE 7B

| Ratio | Type of quartet | Equivalent quartet |
| --- | --- | --- |
| 2:1:1 | $((AA)(BD))^4$ | $((BB)(AD))^4$ |
| | | $((DD)(AB))^4$ |
| 2:1:1 | $((AB)(AD))^4$ | $((BD)(AB))^4$ |
| | | $((BD)(AD))^4$ |

In a preferred embodiment, the compositions of macromolecules or dendritic motifs include at least one quartet selected from Table 3B or 7B, including those quartets which can be considered equivalent by way of their topology and relative composition of two or three different functional moieties.

The surface topology of a macromolecule or dendritic motif bearing functional moieties A, B and D may also be

TABLE 7A

| Fig. | alpha-numeric topological nomenclature | Composition |
| --- | --- | --- |
| 5.1 | $((BB)(BB))^4((BB)(BB))^4((DD)(DD))^4((DD)(DD))^4$ | 2 ((BB)(BB)) and 2 ((DD)(DD)) quartets; |
| | $((AA)(AA))^4((AA)(AA))^4((AA)(AA))^4((AA)(AA))^4$ | 4 ((AA)(AA)) quartets |
| 5.2 | $((BB)(BB))^4((DD)(DD))^4((BB)(BB))^4((DD)(DD))^4$ | 2 ((BB)(BB)) and 2 ((DD)(DD)) quartets; |
| | $((AA)(AA))^4((AA)(AA))^4((AA)(AA))^4((AA)(AA))^4$ | 4 ((AA)(AA)) quartets |
| 5.3 | $((BB)(DD))^4((BB)(DD))^4((BB)(DD))^4((BB)(DD))^4$ | 4 ((BB)(DD)) quartets; |
| | $((AA)(AA))^4((AA)(AA))^4((AA)(AA))^4((AA)(AA))^4$ | 4 ((AA)(AA)) quartets |
| 5.4 | $((BD)(BD))^4((BD)(BD))^4((BD)(BD))^4((BD)(BD))^4$ | 4 ((BD)(BD)) quartets |
| | $((AA)(AA))^4((AA)(AA))^4((AA)(AA))^4((AA)(AA))^4$ | 4 ((AA)(AA)) quartets |
| 5.5 | $((AA)(AA))^4((AA)(AA))^4((BD)(BD))^4((BD)(BD))^4$ | 4 ((BD)(BD)) quartets |
| | $((BD)(BD))^4((BD)(BD))^4((AA)(AA))^4((AA)(AA))^4$ | 4 ((AA)(AA)) quartets |

It is also possible to describe the macromolecules or dendritic motifs of this invention in terms of the composition (number and type) of quartets. This is demonstrated for clarity in the examples of FIG. 5 and summarised in the "composition" column of Table 7.

described in terms of couplets, quartets and octets. For example in the alpha-numeric topological nomenclature an octet of the form $(((AA)(AA))^4((BB)(DD))^4)^8$ is used to represent eight functional moieties A,A,A,A,B,B,D,D which have a line of connection to the same building unit, in particular to a surface-but-two unit.

The macromolecules of FIG. 5 are represented using octets in the alpha-numeric topological nomenclature as follows:

described in terms of couplets, quartets, octets and 16-tets For example in the alpha-numeric topological nomenclature a

TABLE 8A

| Figure | alpha-numeric topological nomenclature | Composition |
|---|---|---|
| 5.1 | $(((BB)(BB))^4((BB)(BB))^4)^8(((DD)(DD))^4((DD)(DD))^4)^8$ $(((AA)(AA))^4((AA)(AA))^4)^8(((AA)(AA))^4((AA)(AA))^4)^8$ | 2 $(((AA)(AA))^4((AA)(AA))^4)^8$ octets 1 $(((BB)(BB))^4((BB)(BB))^4)^8$ octet 1 $(((DD)(DD))^4((DD)(DD))^4)^8$ octet |
| 5.2 | $(((BB)(BB))^4((DD)(DD))^4)^8(((BB)(BB))^4((DD)(DD))^4)^8$ $(((AA)(AA))^4((AA)(AA))^4)^8(((AA)(AA))^4((AA)(AA))^4)^8$ | 2 $(((AA)(AA))^4((AA)(AA))^4)^8$ octets 2 $(((BB)(BB))^4((DD)(DD))^4)^8$ octets |
| 5.3 | $(((BB)(DD))^4((BB)(DD))^4)^8(((BB)(DD))^4((BB)(DD))^4)^8$ $(((AA)(AA))^4((AA)(AA))^4)^8(((AA)(AA))^4((AA)(AA))^4)^8$ | 2 $(((AA)(AA))^4((AA)(AA))^4)^8$ octets 2 $(((BB)(DD))^4((BB)(DD))^4)^8$ octets |
| 5.4 | $(((BD)(BD))^4((BD)(BD))^4)^8(((BD)(BD))^4((BD)(BD))^4)^8$ $(((AA)(AA))^4((AA)(AA))^4)^8(((AA)(AA))^4((AA)(AA))^4)^8$ | 2 $(((AA)(AA))^4((AA)(AA))^4)^8$ octets 2 $(((BD)(BD))^4((BD)(BD))^4)^8$ octets |
| 5.5 | $(((AA)(AA))^4((AA)(AA))^4)^8(((BD)(BD))^4((BD)(BD))^4)^8$ $(((BD)(BD))^4((BD)(BD))^4)^8(((AA)(AA))^4((AA)(AA))^4)^8$ | 2 $(((AA)(AA))^4((AA)(AA))^4)^8$ octets 2 $(((BD)(BD))^4((BD)(BD))^4)^8$ octets |

It is then possible to describe the macromolecules or dendritic motifs of this invention in terms of the composition (number and type) of octets. This is demonstrated for clarity in the examples of FIG. 5 and summarised in the "composition" column of Table 8A.

When an octet is to be assembled from three functional moieties, represented by A, B and D, this may be done by making use of preferred quartets from Table 3B or 7B. The preferred composition of octets additional to those in Table 4B can be of the form:

TABLE 8B

| Ratio | Type of Octet | Examples of Equivalent Octets |
|---|---|---|
| homogenous | $(((DD)(DD))^4((DD)(DD))^4)^8$ | |
| 6:1:1 | $(((AA)(AA))^4((AA)(BD))^4)^8$ $(((AA)(AA))^4((AB)(AD))^4)^8$ $(((AA)(AB))^4((AA)(AD))^4)^8$ | $(((BB)(BB))^4((BB)(AD))^4)^8$ $(((BB)(BB))^4((AB)(BD))^4)^8$ $(((BB)(AB))^4((BB)(BD))^4)^8$ |
| 5:2:1 | $(((AA)(AA))^4((AD)(BB))^4)^8$ $(((AA)(AA))^4((AB)(BD))^4)^8$ $(((AA)(AB))^4((AA)(BD))^4)^8$ $(((AA)(AB))^4((AB)(AD))^4)^8$ | $(((BB)(BB))^4((BD)(AA))^4)^8$ $(((BB)(BB))^4((AB)(AD))^4)^8$ $(((BB)(AB))^4((BB)(AD))^4)^8$ $(((BB)(AB))^4((AB)(BD))^4)^8$ |
| 4:3:1 | $(((AA)(AA))^4((BB)(BD))^4)^8$ $(((AA)(AD))^4((BB)(BA))^4)^8$ $(((AA)(AB))^4((AB)(BD))^4)^8$ $(((AA)(AB))^4((BB)(AD))^4)^8$ $(((AA)(BD))^4((AA)(BB))^4)^8$ $(((AA)(BD))^4((AB)(AB))^4)^8$ $(((AB)(AD))^4((AA)(BB))^4)^8$ $(((AB)(AD))^4((AB)(AB))^4)^8$ | $(((AA)(AB))^4((DD)(BD))^4)^8$ $(((AA)(BD))^4((DD)(DD))^4)^8$ $(((AA)(BD))^4((AD)(DD))^4)^8$ $(((AD)(BD))^4((AD)(DD))^4)^8$ $(((AA)(DD))^4((AB)(DD))^4)^8$ $(((AA)(DD))^4((AD)(BD))^4)^8$ $(((AD)(AD))^4((AB)(DD))^4)^8$ $(((AD)(AD))^4((AD)(BD))^4)^8$ |
| 4:2:2 | $(((AA)(AA))^4((BB)(DD))^4)^8$ $(((AA)(AA))^4((BD)(BD))^4)^8$ $(((AA)(AB))^4((BB)(DD))^4)^8$ $(((AA)(AB))^4((AD)(BD))^4)^8$ $(((AA)(BB))^4((AA)(DD))^4)^8$ $(((AA)(BB))^4((AD)(AD))^4)^8$ $(((AB)(AB))^4((AA)(DD))^4)^8$ $(((AB)(AB))^4((AD)(AD))^4)^8$ | $(((BB)(BB))^4((AA)(DD))^4)^8$ $(((BB)(BB))^4((AD)(AD))^4)^8$ $(((BB)(AB))^4((AB)(DD))^4)^8$ $(((BB)(AB))^4((AD)(BD))^4)^8$ $(((AA)(BB))^4((BB)(DD))^4)^8$ $(((AA)(BB))^4((BD)(BD))^4)^8$ $(((AB)(AB))^4((BB)(DD))^4)^8$ $(((AB)(AB))^4((AD)(BD))^4)^8$ |
| 3:3:2 | $(((AA)(AB))^4((BB)(DD))^4)^8$ $(((AA)(AB))^4((BD)(BD))^4)^8$ $(((AA)(BB))^4((AB)(DD))^4)^8$ $(((AA)(BB))^4((AD)(BD))^4)^8$ $(((AB)(AB))^4((AB)(DD))^4)^8$ $(((AB)(AB))^4((AD)(BD))^4)^8$ | $(((BB)(AB))^4((AA)(DD))^4)^8$ $(((BB)(AB))^4((AD)(AD))^4)^8$ $(((AA)(DD))^4((AD)(BB))^4)^8$ $(((AA)(DD))^4((AB)(BD))^4)^8$ $(((AD)(AD))^4((AB)(BB))^4)^8$ $(((AD)(AD))^4((AB)(BD))^4)^8$ |

In a preferred embodiment, the compositions of macromolecules or dendritic motifs include at least one octet selected from Table 4B or 8B, including those octets which can be considered equivalent by way of their topology and relative composition of two or three different functional moieties.

The surface topology of a macromolecule or dendritic motif bearing functional moieties A, B and D may also be 16-tet of the form $((((AA)(AA))^4((AA)(AA))^4)^8(((BB)(DD))^4((BB)(DD))^4)^8)^{16}$ is used to represent the sixteen functional moieties which have a line of connection to the same building unit, in fact to a surface-but-three building unit.

The macromolecules of FIG. 5 are represented using 16-tets in the alpha-numeric topological nomenclature as follows:

TABLE 9A

| Figure | alpha-numeric topological nomenclature |
|---|---|
| 5.1 | $((((BB)(BB))^4((BB)(BB))^4)^8((DD)(DD))^4((DD)(DD))^4)^8)^{16}$ $((((AA)(AA))^4((AA)(AA))^4)^8(((AA)(AA))^4((AA)(AA))^4)^8)^{16}$ |
| 5.2 | $((((BB)(BB))^4((DD)(DD))^4)^8(((BB)(BB))^4((DD)(DD))^4)^8)^{16}$ $((((AA)(AA))^4((AA)(AA))^4)^8(((AA)(AA))^4((AA)(AA))^4)^8)^{16}$ |
| 5.3 | $((((BB)(DD))^4((BB)(DD))^4)^8(((BB)(DD))^4((BB)(DD))^4)^8)^{16}$ $((((AA)(AA))^4((AA)(AA))^4)^8(((AA)(AA))^4((AA)(AA))^4)^8)^{16}$ |
| 5.4 | $((((BD)(BD))^4((BD)(BD))^4)^8(((BD)(BD))^4((BD)(BD))^4)^8)^{16}$ $((((AA)(AA))^4((AA)(AA))^4)^8(((AA)(AA))^4((AA)(AA))^4)^8)^{16}$ |
| 5.5 | $((((AA)(AA))^4((AA)(AA))^4)^8(((BD)(BD))^4((BD)(BD))^4)^8)^{16}$ $((((BD)(BD))^4((BD)(BD))^4)^8(((AA)(AA))^4((AA)(AA))^4)^8)^{16}$ | where:
there is one $((((AA)(AA))^4((AA)(AA))^4)^8(((AA)(AA))^4((AA)(AA))^4)^8)^{16}$ and one $((((BB)(BB))^4((BB)(BB))^4)^8(((DD)(DD))^4((DD)(DD))^4)^8)^{16}$ 16-tet in FIG. 5.1;
there is one $((((AA)(AA))^4((AA)(AA))^4)^8(((AA)(AA))^4((AA)(AA))^4)^8)^{16}$ and one $((((BB)(BB))^4((DD)(DD))^4)^8(((BB)(BB))^4((DD)(DD))^4)^8)^{16}$ 16-tet in FIG. 5.2;
there is one $((((AA)(AA))^4((AA)(AA))^4)^8(((AA)(AA))^4((AA)(AA))^4)^8)^{16}$ and one $((((BB)(DD))^4((BB)(DD))^4)^8(((BB)(DD))^4((BB)(DD))^4)^8)^{16}$ 16-tet in FIG. 5.3;
there is one $((((AA)(AA))^4((AA)(AA))^4)^8(((AA)(AA))^4((AA)(AA))^4)^8)^{16}$ and one $((((BD)(BD))^4((BD)(BD))^4)^8(((BD)(BD))^4((BD)(BD))^4)^8)^{16}$ 16-tet in FIG. 5.4; and
there are two $((((AA)(AA))^4((AA)(AA))^4)^8(((BD)(BD))^4((BD)(BD))^4)^8)^{16}$ 16-tets in FIG. 5.5.

It is then possible to describe the macromolecules or dendritic motifs of this invention in terms of the composition (number and type) of 16-tets. This is demonstrated for clarity in the examples of FIG. 5 and summarised in dot point form above.

When a 16-tet is to be assembled from three functional moieties, represented by A, B and D, this may be done by making use of the preferred couplets, quartets and octets.

In a preferred embodiment, the compositions of macromolecules or dendritic motifs include at least one 16-tet.

Linkers

It may be desirable to alter the surface composition and/or topology of a macromolecule or to provide an additional property to a functional moiety or macromolecule by way of the means through which the functional moiety is attached to the surface amine or surface building unit. This may be achieved by introducing linkers to the dendritic motif. Accordingly the macromolecules of the present invention as described herein may include functional moieties optionally attached to the surface or subsurface layers via linkers.

Linker moieties may be incorporated into the synthesis of a dendritic motif by substitution for a building unit. A linker moiety comprises two reactive groups, F and Y, which are connected by one or more carbons or heteroatoms, preferably by a hydrocarbon backbone. The functional group F may be activated to react with reactive amine moieties such as those on a core or dendritic motif. Typically the functional group F is a carboxylate group or residue thereof. The other functional group, Y, may be either an amine carrying a protecting group, or it is selected such that it has a specific reactivity that is complementary to a reactive group of a desired functional moiety that is to be attached to the surface of a dendritic motif. Typical examples of Y include amine, carboxylate, amine, hydroxyl, thiol, alkyl halide, allyl halide, heteroaryl halide, aryl halide, vinyl halide, epoxide, aziridine azide, alkene or alkyne.

When linker moieties are incorporated in a dendritic motif, and the group Y is intended for further reaction with a building unit, then the group Y is a protected amine. Where linker moieties are used to connect functional moieties to the surface building units or building units of dendritic motifs, the reaction between the linker and the functional moiety may be carried out either before, or after, the linker moiety is reacted with the surface building unit or building unit of the dendritic motif.

Linkers by definition maintain but do not amplify the number of surface amine groups of a macromolecule or dendritic motif. The surface composition and topology of a macromolecule which includes a complete layer of linkers, either attached to the surface amine groups or to the amine groups of a subsurface building unit, is equivalent to a macromolecule or dendritic motif which lacks this complete layer of linkers.

The number of functional moieties on the surface of a macromolecule or dendritic motif is reduced when a building unit is replaced a linker.

For example:

| Description of structure | Resulting Surface Stoichiometry |
|---|---|
| Linker replaces one surface building unit: 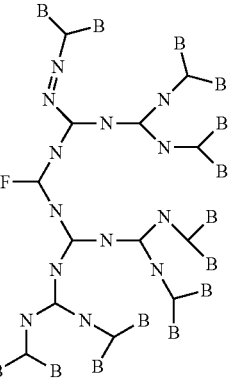 | 1 functional moiety in affected couplet<br>3 functional moieties in affected quartet<br>7 functional moieties in affected octet<br>15 functional moieties in affected 16-tet |
| Linker replaces one surface-but-one building unit: 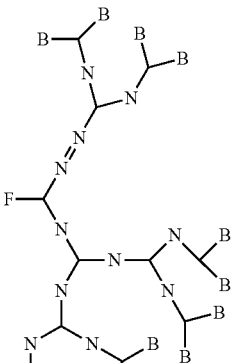 | 2 functional moieties affected quartet<br>6 functional moieties in affected octet<br>14 functional moieties in affected 16-tet |
| Linker replaces one surface-but-two building unit: 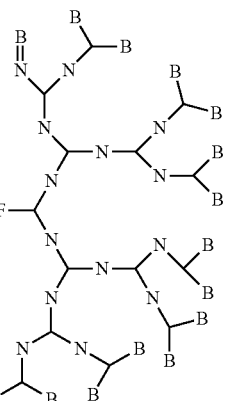 | 4 functional moieties in affected octet<br>12 functional moieties in affected 16-tet |

Incorporation of linkers is described in more detail below.

When linker moieties are incorporated in a macromolecule or dendritic motif, and the group Y is intended for further reaction with a building unit, then the group Y is a protected amine. Once a linker has been added to a macromolecule or dendritic motif the reactable amine group of the linker serves the same purpose as a surface amine group and is defined as such. Where linker moieties are used to connect functional moieties to the surface amine groups and/or surface building units of macromolecules or dendritic motifs, the reaction between the linker and the functional moiety may be carried out either before, or after, the linker moiety is reacted with the surface building units or building units of the dendritic motif.

A reaction which is used to introduce one or more linker moieties to a dendritic motif is conducted to ensure the complete reaction of all deprotected surface amines of a macromolecule or dendritic motif with the linker moieties. Typically this is done by using an excess of the chosen linker moiety.

The total number of functional moieties in a macromolecule or dendritic motif in which linkers have been used can be represented by $FM_{Total}$. The composition of functional moieties of a macromolecule or dendritic motif, wherein all the surface amine groups and/or surface building units are attached to functional moieties, can also be provided in terms of $FM_{Total}$ in a formula of the form $\Sigma FM_i = FM_{total}$ where the surface of the macromolecule or dendritic motif has an integral quantity $FM_i$ of functional moieties of type i: ($FM_i=FM_A$, $FM_B \ldots FM_Z$). Consider FIG. 7 which provides schematic diagrams of five different topological isomers of macromolecules wherein linkers have been used at various stages in the macromolecule synthesis. Each of these macromolecules can be described by a formula $\Sigma FM_i=_iFM_{total}$, for example $\Sigma FM_i=(8A+16B+4D)=28$ for FIG. 7.1; $\Sigma FM_i=(8A+16B)=24$ for FIG. 7.2; $\Sigma FM_i=(8A+8B+8D)=24$ for FIG. 7.3; $\Sigma FM_i=(12A+8B+4D)=24$ for FIG. 7.4 and $\Sigma FM_i=(8A+8B)=16$ for FIG. 7.5.

The alpha-numeric topological nomenclature of couplets, quartets, octets and beyond is able to provide a description of the functional moiety composition in addition to the topology of macromolecules and dendritic motifs in which linkers have been used by making use of the maximum functional moiety number $FM_{MAX}$ in addition to utilising the null symbol Ø. The null groups can also be used in descriptions of "work in progress" intermediates or growing macromolecules or dendritic motifs, which have an incomplete surface layer of building units due to subsurface building units having not yet been reacted (as illustrated in the examples). The use of null symbols maintains the integrity of the outer $FM_{MAX}$.

The term $FM_{MAX}$ is used to represent the number of functional moieties that would be present on a macromolecule or dendritic motif in a scenario wherein the layer of surface building units is complete and no building units have been replaced by linkers in the preparation thereof, and can be calculated using the formula:

$$FM_{Max}=N_{Core} \times N_{First\ Building\ Unit} \times \ldots \times FM_{Surface\ Building\ Unit}$$

where:

$N_{Core}$ is the number of reactable amines on the core to which building units could be attached (this value is deleted when $FM_{Max}$ is calculated for dendritic motifs);

$N_{First\ building\ unit}$ is the number of reactable amines on the building unit used in the first layer out from the core (when $FM_{Max}$ is calculated for a dendritic motif, $N_{First\ building\ unit}$ is that building unit with the apex carboxylate);

$FM_{Surface\ building\ unit}$ is the number of reactable amines on the surface building unit used in the preparation of the macromolecule or dendritic motif;

In one example of a calculation of $FM_{Max}$ for a dendritic motif, consider that lysine has two reactable amines and so from the apex carboxylate a motif with two additional layers of lysine would have an $FM_{MAX}$ of $2 \times 2 \times 2 = 8$.

In a second example of a calculation of $FM_{max}$ for a macromolecule, consider FIG. 7.1 which is a macromolecule comprising 4 layers of lysine, each with two reactable amine groups from a core with two reactable amine groups. The $FM_{MAX}$ for this macromolecule is thus $2 \times 2 \times 2 \times 2 \times 2 = 32$.

Identifiable differences between dendritic motifs which are enriched with respect to surface composition and in which linkers have been used may be described utilising the null symbol Ø in concert with knowledge of the maximum functional moiety number $FM_{MAX}$. The null symbols and their inclusion in the alpha-numeric topological nomenclature make it possible to describe the connectivity between the functional moieties and the subsurface layers of building units when building units have been replaced by linkers. The use of the null symbol Ø in the alpha-numeric topological descriptions of macromolecules or dendritic motifs that include linkers is demonstrated by example, making use of the schematic diagrams of FIGS. 6 and 7.

The examples of FIG. 7 are included to demonstrate how the alpha-numeric topological nomenclature can be used to provide a description of macromolecules that include linkers which have a defined surface topology in addition to a defined composition of functional moieties. In particular the nomenclature makes it possible to identify the preferred couplets, quartets, octets and 16-tets which are components of macromolecules, and which are a preferred embodiment of this invention.

The use of the null symbols enables concepts such as doublets, quartets, octets and 16-tets to be retained in the alpha-numeric topological nomenclature when end stopping functional moieties (see below) or linkers are used in the synthesis of a dendritic motif. The null symbols and their inclusion in the topological nomenclature describe that part of a dendritic motif which has been lost as a result of replacing building units with linkers or end stopping moieties in end stopping reactions.

Consider FIG. 6.1 which represents a macromolecule comprising 4 layers of building units each with two reactable amine groups from a core with two reactable amine groups. The $FM_{MAX}$ for this macromolecule is thus $2 \times 2 \times 2 \times 2 \times 2 = 32$. In those circumstances where linkers are used only to attach functional moieties to the surface building units, $FM_{Max}=FM_{Total}$. There is no requirement for the Ø null symbol unless a linker replaces a building unit or end stopping reaction has been used on the surface amine group of a subsurface building unit.

A description of topology to the level of quartets is required to describe the subsurface connectivity for macromolecules wherein surface building units have been replaced by linkers. It may be seen in FIG. 6.2 that for each surface building unit that is replaced by a linker, a value of 1 represented by Ø is lost from the final outer surface $FM_{Total}$ so that $FM_{Total} + \Sigma Ø = FM_{MAX}$. The use of the null symbols restores the integrity of the outer $FM_{Total}$. In F6.2, the use of Ø is demonstrated as the functional moieties and null symbols related to the surface-but-one building units are gathered into their related couplets and quartets. When one surface building unit is replaced by a linker, one of the couplets will contain a functional moiety and a null symbol, and the other couplet will contain two functional moieties, providing quartets of the form: $((AA)(AØ))^4$ and $((BB)(BØ))^4$. The quartet $((AA)(AØ))^4$ indicates that there are three functional moieties A,A,A and all have a line of connection to the same building unit, in particular to the surface-but-one building unit and further indicates that couplet (AA) and functional moiety A are attached to the same building unit. Couplets that contain one or more null symbols Ø may be grouped together with other couplets to provide quartet, octet and 16-tet descriptions of surface topology.

When three different functional moieties A, B and D are attached to the surface building units of a macromolecule or dendritic motif, and at least one building unit has been replaced by a linker, preferred couplets are selected from (AA), (BB), (DD), (AB), (AD), (BD), (AØ), (BØ) and (DØ) and combinations thereof.

The macromolecules of FIG. 7 are described in terms of couplets making use of the alpha-numeric topological nomenclature as follows:

TABLE 10

| Figure | alpha-numeric topological nomenclature | Composition |
|---|---|---|
| 7.1 | (DØ)(AA)(BB)(BB)(DØ)(AA)(BB)(BB) (DØ)(AA)(BB)(BB)(DØ)(AA)(BB)(BB) | 4 (AA), 8 (BB) and 4 (DØ) couplets |
| 7.2 | (AA)(ØØ)(BB)(BB)(AA)(ØØ)(BB)(BB) (AA)(ØØ)(BB)(BB)(AA)(ØØ)(BB)(BB) | 4 (AA), 8 (BB) and 4 (ØØ) couplets |

TABLE 10-continued

| Figure | alpha-numeric topological nomenclature | Composition |
|---|---|---|
| 7.3 | (DD)(DD)(ØØ)(ØØ)(AA)(AA)(BB)(BB) (DD)(DD)(ØØ)(ØØ)(AA)(AA)(BB)(BB) | 4 (AA), 4 (BB), 4 (DD) and 4 (ØØ) couplets |
| 7.4 | (DD)(DD)(AA)(AA)(ØØ)(ØØ)(ØØ)(ØØ) (AA)(AA)(BB)(BB)(AA)(AA)(BB)(BB) | 6 (AA), 4 (BB), 2 (DD) and 4 (ØØ) couplets |
| 7.5 | (AA)(AA)(BB)(BB)(ØØ)(ØØ)(ØØ)(ØØ) (AA)(AA)(ØØ)(ØØ)(BB)(BB)(ØØ)(ØØ) | 4 (AA), 4 (BB) and 8 (ØØ) couplets |

It is possible to describe the macromolecules or dendritic motifs of this invention that contain linkers in terms of the composition (number and type) of couplets containing functional moieties A, B and D and making use of the null symbol Ø. This is demonstrated for clarity in the examples of FIG. 7 and summarised in the "composition" column of Table 10.

The macromolecules of FIG. 7 are described in terms of quartets making use of the alpha-numeric topological nomenclature as follows:

TABLE 11A

| Figure | alpha-numeric topological nomenclature | Composition |
|---|---|---|
| 7.1 | ((DØ)(AA))$^4$((BB)(BB))$^4$((DØ)(AA))$^4$((BB)(BB))$^4$ ((DØ)(AA))$^4$((BB)(BB))$^4$((DØ)(AA))$^4$((BB)(BB))$^4$ | 4 ((BB)(BB))$^4$ and 4 ((DØ)(AA))$^4$ quartets |
| 7.2 | ((AA)(ØØ))$^4$((BB)(BB))$^4$((AA)(ØØ))$^4$((BB)(BB))$^4$ ((AA)(ØØ))$^4$((BB)(BB))$^4$((AA)(ØØ))$^4$((BB)(BB))$^4$ | 4 ((AA)(ØØ))$^4$ and 4 ((BB)(BB))$^4$ quartets |
| 7.3 | ((DD)(DD))$^4$((ØØ)(ØØ))$^4$((AA)(AA))$^4$((BB)(BB))$^4$ ((DD)(DD))$^4$((ØØ)(ØØ))$^4$((AA)(AA))$^4$((BB)(BB))$^4$ | 2 ((AA)(AA))$^4$, 2 ((BB)(BB))$^4$, 2 ((DD)(DD))$^4$ and 2 ((ØØ)(ØØ))$^4$ quartets |
| 7.4 | ((DD)(DD))$^4$((AA)(AA))$^4$((ØØ)(ØØ))$^4$((ØØ)(ØØ))$^4$ ((AA)(AA))$^4$((BB)(BB))$^4$((AA)(AA))$^4$((BB)(BB))$^4$ | 3 ((AA)(AA))$^4$, 2 ((BB)(BB))$^4$, 1 ((DD)(DD))$^4$ and 2 ((ØØ)(ØØ))$^4$ quartets |
| 7.5 | ((AA)(AA))$^4$((BB)(BB))$^4$((ØØ)(ØØ))$^4$((ØØ)(ØØ))$^4$ ((AA)(AA))$^4$((ØØ)(ØØ))$^4$((BB)(BB))$^4$((ØØ)(ØØ))$^4$ | 2 ((AA)(AA))$^4$, 2 ((BB)(BB))$^4$, and 4 ((ØØ)(ØØ))$^4$ quartets |

It is possible to describe the macromolecules or dendritic motifs of this invention that contain linkers in terms of the composition (number and type) of quartets. This is demonstrated for clarity in the examples of FIG. 7 and summarised in the "composition" column of Table 11A.

When a quartet is to be assembled from three functional moieties represented by A, B and D; and at least one building unit has been replaced by a linker, this may be done by making use of the preferred couplets, in addition to using the null couplet (ØØ).

In a preferred embodiment, the composition of macromolecules or dendritic motifs includes at least one quartet selected from the set:

TABLE 11B

| Ratio | Type of quartet | Examples of equivalent quartets |
|---|---|---|
| homogenous | ((AA)(AØ))$^4$ | ((BB)(BØ))$^4$ ((DD)(DØ))$^4$ |
| homogenous | ((AA)(ØØ))$^4$ | ((BB)(ØØ))$^4$ |
| homogenous | ((AØ)(AØ))$^4$ | ((BØ)(BØ))$^4$ |
| homogenous | ((AØ)(ØØ))$^4$ | ((DØ)(ØØ))$^4$ |
| 2:1 | ((AA)(BØ))$^4$ | ((AA)(DØ))$^4$ ((BB)(AØ))$^4$ ((BB)(DØ))$^4$ |
| 2:1 | ((AB)(AØ))$^4$ | ((AD)(AØ))$^4$ ((AB)(BØ))$^4$ ((BD)(BØ))$^4$ |
| 1:1 | ((AB)(ØØ))$^4$ | ((BD)(ØØ))$^4$ |

TABLE 11B-continued

| Ratio | Type of quartet | Examples of equivalent quartets |
|---|---|---|
| 1:1 | ((AØ)(BØ))$^4$ | ((BØ)(DØ))$^4$ |
| 1:1:1 | ((AB)(DØ))$^4$ | ((AD)(BØ))$^4$ ((BD)(AØ))$^4$ |

In a preferred embodiment, the compositions of macromolecules or dendritic motifs include at least one quartet selected from Table 3B or 7B or 11B, including those quartets which can be considered equivalent by way of their topology and relative composition of two or three different functional moieties.

A description of topology to the level of octets is required to describe the subsurface connectivity for macromolecules wherein surface-but-one building units have been replaced by linkers. It may be seen in FIG. 6.3 that for each surface-but-one, building units that is replaced by a linker, a value of 2 represented by ØØ is lost from the final outer surface $FM_{Total}$ so that $FM_{Total} + \Sigma Ø = FM_{MAX}$. The use of the null symbols restores the integrity of the outer $FM_{Total}$.

In F6.3, the use of ØØ is demonstrated as the functional moieties and null symbols related to the surface-but-two building units are gathered into their related couplets, quartets and octets. When one surface-but-one building unit is replaced by a linker, one of the quartets of the octet will contain a null couplet (ØØ), and the other couplet will contain two functional moieties. The second quartet will be complete, providing octets of the form: $(((AA)(AA))^4((AA)(ØØ))^4)^8$ and $(((BB)(BB))^4((BB)(ØØ))^4)^8$. The octet $(((AA)(AA))^4 ((AA)(ØØ))^4)^8$ indicates that there are six functional moieties A,A,A,A,A,A all having a line of connection to the same building unit, in particular to the surface-but-two building unit and further indicates that quartet $((AA)(AA))^4$ and couplet (AA) are attached to the same building unit. Quartets that contain one or more null symbols Ø may be grouped together with other quartets to provide octet and 16-tet descriptions of surface topology.

The macromolecules of FIG. 7 are described in terms of octets making use of the alpha-numeric topological nomenclature as follows:

TABLE 12A

| Figure | alpha-numeric topological nomenclature | Composition |
|---|---|---|
| 7.1 | (((DØ)(AA))$^4$((BB)(BB))$^4$)$^8$(((DØ)(AA))$^4$((BB)(BB))$^4$)$^8$ (((DØ)(AA))$^4$((BB)(BB))$^4$)$^8$(((DØ)(AA))$^4$((BB)(BB))$^4$)$^8$ | 4 (((DØ)(AA))$^4$((BB)(BB))$^4$)$^8$ octets |
| 7.2 | (((AA)(ØØ))$^4$((BB)(BB))$^4$)$^8$(((AA)(ØØ))$^4$((BB)(BB))$^4$)$^8$ (((AA)(ØØ))$^4$((BB)(BB))$^4$)$^8$(((AA)(ØØ))$^4$((BB)(BB))$^4$)$^8$ | 4 (((AA)(ØØ))$^4$((BB)(BB))$^4$)$^8$ octets |
| 7.3 | (((DD)(DD))$^4$((ØØ)(ØØ))$^4$)$^8$(((AA)(AA))$^4$((BB)(BB))$^4$)$^8$ (((DD)(DD))$^4$((ØØ)(ØØ))$^4$)$^8$(((AA)(AA))$^4$((BB)(BB))$^4$)$^8$ | 2 (((DD)(DD))$^4$((ØØ)(ØØ))$^4$)$^8$ and 2 (((AA)(AA))$^4$((BB)(BB))$^4$)$^8$ |
| 7.4 | (((DD)(DD))$^4$((AA)(AA))$^4$)$^8$(((ØØ)(ØØ))$^4$((ØØ)(ØØ))$^4$)$^8$ (((AA)(AA))$^4$((BB)(BB))$^4$)$^8$(((AA)(AA))$^4$((BB)(BB))$^4$)$^8$ | 2 (((AA)(AA))$^4$((BB)(BB))$^4$)$^8$ octets, 1 (((DD)(DD))$^4$((AA)(AA))$^4$)$^8$ and 1 (((ØØ)(ØØ))$^4$((ØØ)(ØØ))$^4$)$^8$ octet |
| 7.5 | (((AA)(AA))$^4$((BB)(BB))$^4$)$^8$(((ØØ)(ØØ))$^4$((ØØ)(ØØ))$^4$)$^8$ (((AA)(AA))$^4$((ØØ)(ØØ))$^4$)$^8$(((BB)(BB))$^4$((ØØ)(ØØ))$^4$)$^8$ | 1 (((AA)(AA))$^4$((BB)(BB))$^4$)$^8$, 1 (((AA)(AA))$^4$((ØØ)(ØØ))$^4$)$^8$, 1 (((BB)(BB))$^4$((ØØ)(ØØ))$^4$)$^8$, and 1 (((ØØ)(ØØ))$^4$((ØØ)(ØØ))$^4$)$^8$ octet |

It is possible to describe the macromolecules or dendritic motifs of this invention that contain linkers in terms of the composition (number and type) of octets. This is demonstrated for clarity in the examples of FIG. 7 and summarised in the "composition" column of Table 12A.

When an octet is to be assembled from three functional moieties represented by A, B and D; and at least one building unit has been replaced by a linker, this may be done by making use of the preferred quartets from Table 3B, 7B and 11B, in addition to using the null quartet ((ØØ)(ØØ))$^4$ in the manner which has been demonstrated for combining quartets to provide octets above.

In a preferred embodiment, the composition of macromolecules or dendritic motifs includes at least one octet selected from the set: (((AA)(AA))$^4$((AB)(AØ))$^4$)$^8$, (((AA)(AB))$^4$((AA)(DØ))$^4$)$^8$, (((AA)(AB))$^4$((AD)(BØ))$^4$)$^8$, (((AB)(AD))$^4$((AB)(DØ))$^4$)$^8$, (((AA)(AØ))$^4$((AB)(AØ))$^4$)$^8$, (((AB)(AD))$^4$((AØ)(AØ))$^4$)$^8$ or (((AB)(AD))$^4$((AØ)(BØ))$^4$)$^8$.

A description of topology to the level of 16-tets is required to describe the subsurface connectivity for macromolecules wherein surface-but-two building units have been replaced by linkers. It may be seen in FIG. 6.4 that for each surface-but-two building unit that is replaced by a linker, a value of 4 represented by ØØØØ is lost from the final outer surface FM$_{Total}$ so that FM$_{Total}$+ΣØ=FM$_{MAX}$. The use of the null symbols restores the integrity of the outer FM$_{Total}$.

In F6.4, the use of ØØØØ is demonstrated as, the functional moieties and null symbols related to the surface-but-three building units are gathered into their related couplets, quartets, octets and 16-tets. When one surface-but-two building unit is replaced by a linker, one of the octets will contain a null quartet ((ØØ)(ØØ))$^4$, and the other quartet will contain four functional moieties. The second octet will be complete, providing 16-tets of the form: ((((AA)(AA))$^4$((AA)(AA))$^4$)$^8$ (((AA)(AA))$^4$((ØØ)(ØØ))$^4$)$^8$)$^{16}$ and ((((BB)(BB))$^4$((BB)(BB))$^4$)$^8$(((BB)(BB))$^4$((ØØ)(ØØ))$^4$)$^8$)$^{16}$. The 16-tet ((((AA)(AA))$^4$((AA)(AA))$^4$)$^8$(((AA)(AA))$^4$((ØØ)(ØØ))$^4$)$^8$)$^{16}$ indicates that there are 12 functional moieties of type A all having a line of connection to the same building unit, in particular to the surface-but-three building unit and further indicates that octet (((AA)(AA))$^4$((AA)(AA))$^4$)$^8$ and quartet ((AA)(AA))$^4$ are attached to the same building unit. Octets that contain one or more null symbols Ø may be grouped together with other octets to provide 16-tet descriptions of surface topology.

The macromolecules of FIG. 7 are described in terms of 16-tets making use of the alpha-numeric topological nomenclature as follows:

TABLE 13

| Figure | alpha-numeric topological nomenclature |
|---|---|
| 7.1 | ((((DØ)(AA))$^4$((BB)(BB))$^4$)$^8$(((DØ)(AA))$^4$((BB)(BB))$^4$)$^8$)$^{16}$ ((((DØ)(AA))$^4$((BB)(BB))$^4$)$^8$(((DØ)(AA))$^4$((BB)(BB))$^4$)$^8$)$^{16}$ |
| 7.2 | ((((AA)(ØØ))$^4$((BB)(BB))$^4$)$^8$(((AA)(ØØ))$^4$((BB)(BB))$^4$)$^8$)$^{16}$ ((((AA)(ØØ))$^4$((BB)(BB))$^4$)$^8$(((AA)(ØØ))$^4$((BB)(BB))$^4$)$^8$)$^{16}$ |
| 7.3 | ((((DD)(DD))$^4$((ØØ)(ØØ))$^4$)$^8$(((AA)(AA))$^4$((BB)(BB))$^4$)$^8$)$^{16}$ ((((DD)(DD))$^4$((ØØ)(ØØ))$^4$)$^8$(((AA)(AA))$^4$((BB)(BB))$^4$)$^8$)$^{16}$ |
| 7.4 | ((((DD)(DD))$^4$((AA)(AA))$^4$)$^8$(((ØØ)(ØØ))$^4$((ØØ)(ØØ))$^4$)$^8$)$^{16}$ ((((AA)(AA))$^4$((BB)(BB))$^4$)$^8$(((AA)(AA))$^4$((BB)(BB))$^4$)$^8$)$^{16}$ |
| 7.5 | ((((AA)(AA))$^4$((BB)(BB))$^4$)$^8$(((ØØ)(ØØ))$^4$((ØØ)(ØØ))$^4$)$^8$)$^{16}$ ((((AA)(AA))$^4$((ØØ)(ØØ))$^4$)$^8$(((BB)(BB))$^4$((ØØ)(ØØ))$^4$)$^8$)$^{16}$ | where:
there are two ((((DØ)(AA))$^4$((BB)(BB))$^4$)$^8$(((DØ)(AA))$^4$((BB)(BB))$^4$)$^8$)$^{16}$ 16-tets in FIG. 7.1;
there are two ((((AA)(ØØ))$^4$((BB)(BB))$^4$)$^8$(((AA)(ØØ))$^4$((BB)(BB))$^4$)$^8$)$^{16}$ 16-tets in FIG. 7.2;
there are two ((((DD)(DD))$^4$((ØØ)(ØØ))$^4$)$^8$(((AA)(AA))$^4$((BB)(BB))$^4$)$^8$)$^{16}$ 16-tets in FIG. 7.3;
there is one ((((DD)(DD))$^4$((AA)(AA))$^4$)$^8$(((ØØ)(ØØ))$^4$((ØØ)(ØØ))$^4$)$^8$)$^{16}$ and one ((((AA)(AA))$^4$((BB)(BB))$^4$)$^8$(((AA)(AA))$^4$((BB)(BB))$^4$)$^8$)$^{16}$ 16-tet in FIG. 7.4; and
there is one ((((AA)(AA))$^4$((BB)(BB))$^4$)$^8$(((ØØ)(ØØ))$^4$((ØØ)(ØØ))$^4$)$^8$)$^{16}$ and one ((((AA)(AA))$^4$((ØØ)(ØØ))$^4$)$^8$(((BB)(BB))$^4$((ØØ)(ØØ))$^4$)$^8$)$^{16}$ 16-tet in FIG. 7.5.

It is possible to describe the macromolecules or dendritic motifs of this invention that contain linkers in terms of the composition (number and type) of 16-tets. This is demonstrated for clarity in the examples of FIG. 7 and summarised in dot point form above.

When an 16-tet is to be assembled from three functional moieties represented by A, B and D; and at least one building unit has been replaced by a linker, this may be done by making use of the preferred octets including homogenous octets, in addition to using the null octet (((ØØ)(ØØ))$^4$((ØØ)(ØØ))$^4$)$^8$ in the manner which has been demonstrated for combining quartets to provide octets above.

Summary of Various Cleavable Linkers

Cleavable linkers may be designed to be enzymatically cleaved, and may for example, be used in dendrimers targeted to tissues expressing those enzymes. Alternatively, an acid labile linker may be preferred such that the compound attached to it is released under acid conditions, such as in hypoxic tissue. In a further alternative, photocleavable linkers may be used.

The linker moiety may be selected from one or more of the following:

| Linker type | Linker |
|---|---|
| Stable | Amide; PEG-peptide |
| Acid Labile | Hydrazone, Oxime, Imine; Ester and Orthoester; Aconitic amide; Acetal/Ketal. |

| Linker type | Linker |
|---|---|
| Thiol Labile | Disulfide |
| Enzyme Labile | Esters (Esterases and proteases); Peptide sequences |

Stable Linkers

Amide Linkers:

The nature of an amide bond is important in determining whether the functional moiety will be released from a conjugate. The release of free drug from protein carriers bound via a direct amide linker will only be achievable in rare circumstances where the drug is itself a peptide-like molecule and the bond between drug and carrier is enzymatically cleavable.

PEG-Peptide:

PEG-peptides are used in a similar way to conventional peptides, except the PEG moiety provides additional in vivo stability and mass for the carrier. It has the advantage of increasing the distance between a carrier and a drug for example while exposing the site of enzymatic cleavage, decrease immunogenicity of the conjugate, increase blood circulation times and increasing the solubility of the complex.

Acid Labile

Hydrazone, Oxime and Imine Linkers:

Hydrazone, oxime and imine bonds do not require the presence of enzymes to allow cleavage of the drug from the carrier. They are able to be cleaved hydrolytically at the C=N bond in low pH environments such as in the tumour extravascular space or within lysosomes.

Ester Linkers:

Both acid labile and metabolisable ester linkers can be made: Orthoesters have been used to conjugate PEG to lipids which bind anionic membrane carriers. The stability of the conjugate in acidic conditions (pH 4-6) depends on the structure of the ester or orthoester linker. In terms of simple ester conjugation to small molecules, diester functionalities provide more sites for metabolic cleavage compared with monoesters which are more stable than disulfides but less stable than amide bonds.

Acetals and Ketals:

This kind of linker is particularly useful when the pharmaceutically active agent includes a hydroxyl moiety. In general ketals are more acid labile than acetal linkages.

Thiol Labile

Disulfide Linkers:

Disulfide linkers are the most unstable linkers currently used and undergo rapid reductive cleavage in vitro. Their in vivo stability is generally higher, however, than their in vitro stability. They may be formed via disulfide linkages between sulphur containing amino acids or at non peptide based disulfide bonds. They also show greater reactivity with other nucleophilic thiols in the body and hence show rapid plasma clearance.

Enzyme Labile

Peptide Linkers:

Peptide linkers are by far the most versatile of all cleavable linkers in that many different combinations of amino acids can be used to control the rate of cleavage and the cleavage enzyme. While there are a number of problems associated with their use as conjugates for drug and carrier, it may be controlled by choosing an appropriate peptide bound directly to the drug molecule, e.g. proline. Generally, cathepsin B cleavable linkers have been designed to be cleaved by cathepsin (located in lysosomes and not free in the cytosol) following endocytosis of the complex. Non-specific proteases (i.e. proteases that are not specific for a particular peptide sequence) may cleave a drug from a PEGylated dendrimer after it has undergone sufficient extravasation and accumulation in tumour tissue.

Summary of Non-Cleavable Linkers

Non-cleavable linkers may be selected from the group consisting of polypeptides (i.e. amino acid residues, oligomeric polyamines and polyamine amides), peptide nucleic acids (PNAs), synthetic polymers (PEG, PEOX, N-(2-hydroxypropyl)methacrylamide (HPMA) copolymers, poly(vinyl-pyrrolidone)(PVP), poly(ethyleneimine)(PEI), linear polyamidoamines and DIVEMA); natural polymers (dextran (alpha-1,6 polyglucose), dextrin (alpha-1,4 polyglucose), hyaluronic acid, chitosans); and pseudosynthetic polymers, such as the man-made poly(amino acids) poly(L-lysine), poly(glutamic acid) (PGA), poly(malic acid), poly(aspartamides), poly(lactides), poly(glycolides) and poly(lactides co glycolides).

In a preferred embodiment, the linker may include a hydrocarbon, PEG or PEOX backbone, or a combination thereof.

Another preferred embodiment of the linker is described in formula 1

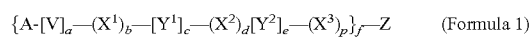

{A-[V]$_a$—(X$^1$)$_b$—[Y$^1$]$_c$—(X$^2$)$_d$[Y$^2$]$_e$—(X$^3$)$_p$}$_f$—Z  (Formula 1)

| | |
|---|---|
| a | a = 0 or 1 (see V below) provides optional CH or CH$_2$ linker, to facilitate hydrazone, oxime or ether type linkages. |
| b | b = 0 then linker section Y$^1$ or Y$^2$ to connect directly to ligand A |
| | b = 1 allows use of X$^1$: preferred. |
| c | c = 0 eliminates first linker section, and would most likely require b = 0 as well |
| | c = 1 allows use of Y$^1$: preferred. |
| d | d = 0 then linker section Y$^2$ connects directly to linker section Y$^1$ etc. |
| | d = 1 allows use of X$^2$: preferred. |
| e | e = 0 eliminates second linker section, and d = 0 as well preferred |
| | e = 1 allows use of Y$^2$: preferred. |
| p | p = 0 then dendrimer Z connects directly to linker section Y$^2$ (or Y$^1$ or V or A) and allows for f = 2. |
| | p = 1 allows use of X$^3$: preferred. |
| f | f = 1 when X$^3$ is used: preferred. |
| | f = 2 when X$^3$ is not used, allows for two linkers per dendrimer Z. |

| | -continued |
|---|---|
| $X^3$ | $C(W^3)$, $OC(W^3)$, $NRC(W^3)$, $SC(W^3)$; preferably $C(W^3)$ where W = O<br>In the preferred embodiment, the join $X^3$ is an amide connection between the dendrimer Z and the second linker section $Y^2$. |
| $X^n$ ($X^1$ and $X^2$) | O, S, NR, NRO, ONR<br>$C(W^n)$, $OC(W^n)$, $C(W^n)O$, $NRC(W^n)$, $C(W^n)NR$,<br>$OC(W^n)O$, $OC(W^n)NR$, $NRC(W^n)O$, $NRC(W^n)NR$<br>Preferably $C(W^n)NR$ where W = O and R = H.<br>There are two joins, $X^1$ and $X^2$.<br>$X^2$ "joins" the two linker sections ($Y^1$ to $Y^2$), and preferably an amide, carboxyl from $Y^1$.<br>$X^1$ "joins" the ligand to the first linker section ($Y^1$) and preferably an amide, carboxyl from A; or an ether where a = 0 or 1. |
| R | hydrogen or small group, each R is same or different, small group defined as: an alkyl chain of 1 to 10 atoms which may incorporate within the chain an aryl moiety of 5 to 10 atoms, where the alkyl chain and/or aryl moiety may include one or more O, N or S atoms exchanged for one or more C atoms; preferably R = H. |
| W | O or S; preferably O |
| $Y^n$ ($Y^1$ and $Y^2$) | The linker section may be made up from a combination of one or more fragment types.<br>$Y^1$ is the first linker section and functions to connect ligand to longer linker section, sensitive to needs of receptor; possibly more hydrophobic, with potential H bond donor/acceptor.<br>$Y^2$ is the second linker fragment and provides water solubility, length and possibly rigidity.<br>fragment 1: $(CH_2)_g$ where g = 1-12<br>fragment 2: $[O—(CH_2)_h]_i$ where h = 2-6 and i = 1-30<br>fragment 3: $[(O)_j—(CH_2)_k\text{-Aryl-}(CH_2)_l—(O)_m]_o$ where j = 0-1, k = 0-3, l = 0-3, m = 0-1, o = 1-10<br>fragment 4: oligopeptides of up to 30 amino acids preferably including Glycine, Serine, Glutamate, Aspartate or β-alanine<br>fragment 5: linear oligosaccharides of up to 10 hexose units, preferably including Glucose, N-acetylglucosamine, mannose, galactose; interconnected by glycosidic bonds selected from 1-2, 1-4 or 1-6. |
| V | $CH(R)_r$ where r = 1 if bond to $X^n$ or $Y^n$ is saturated; r = 0 if bond to $X^n$ or $Y^n$ is unsaturated. |
| A | A is a functional moiety:<br>optionally modified to include V; or<br>optionally modified to provide a new functional group for attachment to $X^n$ or $Y^n$; or<br>optionally modified to convert an existing functional group into a functional group for attachment to $X^n$ or $Y^n$ |
| Z | Z is a lysine dendrimer terminal nitrogen group (which may form one or two bonds, so f = 1 or 2); |

The length of the linker will vary depending on the functional moiety being used.

The use of the null symbols enables concepts such as doublets, quartets, octets and 16-tets to be retained in the alpha-numeric topological nomenclature when end stopping reactions (see below) or linkers have been used in the synthesis of a dendritic motif. The null symbols and their inclusion in the topological nomenclature describe that part of a dendritic motif which has been lost as a result of replacing building units with linkers or end stopping reactions.

End-Stopping Reactions

It may be desirable to alter the surface topology of a macromolecule or to provide a particular encapsulated site therein. This may be achieved by utilising functional moieties that function as end stopping moieties (or groups) to introduce modifications to the macromolecule or dendritic motif.

An end stopping reaction is defined as the complete reaction of all deprotected surface amine groups of a macromolecule or dendritic motif with an end stopping functional moiety R where the moiety R is then inert to subsequent chemical transformations that are carried out on the macromolecule or dendritic motif for the purposes of the addition of further building units, linker groups or end stopping reactions. The end stopping functional moiety may be transformed into a functional moiety by a chemical or other stimulus at a chosen stage in the process of preparing the macromolecule or dendritic motif.

A reaction which is used to introduce one or more end stopping moieties to a dendritic motif is conducted to ensure the complete reaction of all deprotected surface amine groups of a macromolecule or dendritic motif with the reactive end stopping functional moieties. Typically this is done by using an excess of the end stopping functional moiety. The reaction is described in more detail in Example 72.

The total number of functional moieties in a macromolecule or dendritic motif in which end stopping has occurred can be represented by $FM_{Total}$. The composition of functional moieties of a macromolecule or dendritic motif, wherein all the surface amine groups and/or surface building units are attached to functional moieties, can also be provided in terms of $FM_{Total}$ in a formula of the form $\Sigma FM_i = FM_{total}$ where the surface of the macromolecule or dendritic motif has an integral quantity $FM_i$ of functional moieties of type i: ($FM_i = FM_A$, $FM_B \ldots FM_Z$) and where $FM_i$ may comprise one or more functional moieties R of type i: ($R_i = R_1, R_2 \ldots R_n$). Consider FIG. 9 which provides schematic diagrams of five different topological isomers of macromolecules wherein end stopping reactions have been used at various stages in the macromolecule synthesis. Each of these macromolecules can be described by a formula $\Sigma FM_i = FM_{total}$, for example $\Sigma FM_i = (16R_1 + 16R_2) = 32$ for FIG. 9.1; $\Sigma FM_i = (8A + 16B + 4R_1) = 28$ for FIG. 9.2; $\Sigma FM_i = (16B + 4R_1) = 20$ for FIG. 9.3; $\Sigma FM_i = (8A + 8B + 2R_1) = 18$ for FIG. 9.4 and $\Sigma FM_i = (8A + 4R_1 + 4R_2) = 16$ for FIG. 9.5.

The alpha-numeric topological nomenclature of couplets, quartets, octets and beyond is able to provide a description of the functional moiety composition in addition to the topology of macromolecules and dendritic motifs in which end stopping reactions have been used by making use of the maximum functional moiety number $FM_{MAX}$ in addition to utilising the null symbol Ø.

The term $FM_{MAX}$ is used to represent the number of functional moieties that would be present on a macromolecule or dendritic motif in a scenario where no end stopping functional moieties or linkers are attached at or below a surface-but-one building unit in the preparation thereof.

Identifiable differences between dendritic motifs which are enriched with respect to surface stoichiometry and in which end stopping reactions have been used may be described utilising the null symbol Ø in concert with knowledge of the maximum functional moiety number $FM_{MAX}$.

The null symbols and their inclusion in the alpha-numeric topological nomenclature make it possible to describe the connectivity between the functional moieties and the subsurface layers of building units when end stopping has been used. The use of the null symbol Ø in the alpha-numeric topological descriptions of macromolecules or dendritic motifs that contain end stopping moieties is demonstrated by example, making use of the schematic diagrams of FIGS. 8 and 9.

The examples of FIG. 9 are included to demonstrate how the alpha-numeric topological nomenclature can be used to provide a description of macromolecules that include end stopping functional moieties and which have a defined surface topology in addition to a defined surface composition of functional moieties. In particular the nomenclature makes it possible to identify the preferred couplets, quartets, octets and 16-tets which are components of macromolecules, and which are a preferred embodiment of this invention.

The use of the null symbols enables concepts such as couplets, quartets, octets and 16-tets to be retained in the alpha-numeric topological nomenclature when end stopping reactions or linkers have been used in the synthesis of a dendritic motif. The null symbols and their inclusion in the topological nomenclature describe that part of a dendritic motif which has been lost as a result of end stopping reactions or by replacing building units with linkers.

A description of topology to the level of quartets is required to describe the subsurface connectivity for macromolecules wherein end stopping functional moieties have been attached at the surface-but-one layer building units. It may be seen in FIG. 8.2 that for each end stopping functional moiety $R_i$ that is attached to a surface amine group of a surface-but-one building unit, a value of 1 represented by Ø is lost from the final outer surface $FM_{Total}$ so that $FM_{Total}+\Sigma Ø=FM_{MAX}$. The use of the null symbols restores the integrity of the outer $FM_{Total}$. In F8.2, the use of Ø is demonstrated as the functional moieties and null symbols related to the surface-but-one building units are gathered into their related couplets and quartets. When one end stopping functional moiety is attached to the surface-but-one building unit, one of the couplets will contain a end stopping functional moiety and a null symbol $(R_i Ø)$, and the other couplet will contain two functional moieties, providing quartets of the form: $((AA)(R_1Ø))^4$ and $((BB)(R_2Ø))^4$. The quartet $((AA)(R_1Ø))^4$ indicates that there are three functional moieties $A,A,R_1$ and all have a line of connection to the same building unit, in particular to the surface-but-one building unit and further indicates that couplet (AA) and end stopping functional moiety $R_1$ are attached to the same building unit. Couplets that contain one or more null symbols Ø may be grouped together with other couplets to provide quartet, octet and 16-tet descriptions of surface topology.

The macromolecules of FIG. 9 are described in terms of couplets making use of the alpha-numeric topological nomenclature as follows:

TABLE 14

| Figure | alpha-numeric topological nomenclature | Composition |
|---|---|---|
| 9.1 | $(R_1R_1)(R_1R_1)(R_2R_2)(R_2R_2)(R_1R_1)(R_1R_1)(R_2R_2)(R_2R_2)$ $(R_1R_1)(R_1R_1)(R_2R_2)(R_2R_2)(R_1R_1)(R_1R_1)(R_2R_2)(R_2R_2)$ | 8 $(R_1R_1)$ and 8 $(R_2R_2)$ couplets |
| 9.2 | $(AA)(R_1Ø)(BB)(BB)(AA)(R_1Ø)(BB)(BB)$ $(AA)(R_1Ø)(BB)(BB)(AA)(R_1Ø)(BB)(BB)$ | 4 (AA), 8 (BB) and 4 $(R_1Ø)$ couplets |
| 9.3 | $(R_1Ø)(ØØ)(BB)(BB)(R_1Ø)(ØØ)(BB)(BB)$ $(R_1Ø)(ØØ)(BB)(BB)(R_1Ø)(ØØ)(BB)(BB)$ | 8 (BB), 4 $(R_1Ø)$ and 4 (ØØ) couplets |
| 9.4 | $(AA)(AA)(BB)(BB)(R_1Ø)(ØØ)(ØØ)(ØØ)$ $(AA)(AA)(BB)(BB)(R_1Ø)(ØØ)(ØØ)(ØØ)$ | 4 (AA), four (BB), 2 $(R_1Ø)$ and 6 (ØØ) couplets |
| 9.5 | $(R_1Ø)(AA)(R_2Ø)(ØØ)(R_1Ø)(AA)R_2Ø)(ØØ)$ $(R_1Ø)(AA)(R_2Ø)(ØØ)(R_1Ø)(AA)(R_2Ø)(ØØ)$ | 4 (AA), 4 $(R_1Ø)$, 4 $(R_2Ø)$ and 4 (ØØ) couplets |

Consider FIG. 8.1 which represents a macromolecule comprising 4 layers of building units each with two reactable amine groups from a core with two reactable amine groups. The $FM_{MAX}$ for this macromolecule motif is thus $2\times2\times2\times2=32$. In those circumstances where linkers and end stopping functional moieties are attached only on the surface building units, $FM_{Max}=FM_{Total}$ and there is no requirement for the Ø null symbol.

It is possible to describe the macromolecules or dendritic motifs of this invention that contain end stopping moieties in terms of the composition (number and type) of couplets. This is demonstrated for clarity in the examples of FIG. 9 and summarised in the "composition" column of Table 14.

The macromolecules of FIG. 9 are described in terms of quartets making use of the alpha-numeric topological nomenclature as follows:

TABLE 15A

| Figure | alpha-numeric topological nomenclature | Composition |
|---|---|---|
| 9.1 | $((R_1R_1)(R_1R_1))^4((R_2R_2)(R_2R_2))^4((R_1R_1)(R_1R_1))^4((R_2R_2)(R_2R_2))^4$ $((R_1R_1)(R_1R_1))^4((R_2R_2)(R_2R_2))^4((R_1R_1)(R_1R_1))^4((R_2R_2)(R_2R_2))^4$ | 4 $((R_1R_1)(R_1R_1))^4$ and 4 $((R_2R_2)(R_2R_2))^4$ quartets |
| 9.2 | $((AA)(R_1Ø))^4((BB)(BB))^4((AA)(R_1Ø))^4((BB)(BB))^4$ $((AA)(R_1Ø))^4((BB)(BB))^4((AA)(R_1Ø))^4((BB)(BB))^4$ | 4 $((AA)(R_1Ø))^4$ and 4 $((BB)(BB))^4$ quartets |
| 9.3 | $((R_1Ø)(ØØ))^4((BB)(BB))^4((R_1Ø)(ØØ))^4((BB)(BB))^4$ $((R_1Ø)(ØØ))^4((BB)(BB))^4((R_1Ø)(ØØ))^4((BB)(BB))^4$ | 4$((R_1Ø)(ØØ))^4$ and 4 $((BB)(BB))^4$ quartets |
| 9.4 | $((AA)(AA))^4((BB)(BB))^4((R_1Ø)(ØØ))^4((ØØ)(ØØ))^4$ $((AA)(AA))^4((BB)(BB))^4((R_1Ø)(ØØ))^4((ØØ)(ØØ))^4$ | 2 $((AA)(AA))^4$, 2 $((BB)(BB))^4$, 2 $((R_1Ø)(ØØ))^4$ and 2 $((ØØ)(ØØ))^4$ quartets |

TABLE 15A-continued

| Figure | alpha-numeric topological nomenclature | Composition |
|---|---|---|
| 9.5 | $((R_1Ø)(AA))^4((R_2Ø)(ØØ))^4((R_1Ø)(AA))^4((R_2Ø)(ØØ))^4$ $((R_1Ø)(AA))^4((R_2Ø)(ØØ))^4((R_1Ø)(AA))^4((R_2Ø)(ØØ))^4$ | $4\ ((R_1Ø)(AA))^4$ and $4\ ((R_2Ø)(ØØ))^4$ quartets |

It is possible to describe the macromolecules or dendritic motifs of this invention that contain end stopping moieties in terms of the composition (number and type) of quartets. This is demonstrated for clarity in the examples of FIG. 9 and summarised in the "composition" column of Table 15A.

The macromolecules of FIG. 9 are described in terms of octets making use of the alpha-numeric topological nomenclature as follows:

TABLE 16A

| Fig | alpha-numeric topological nomenclature | Composition |
|---|---|---|
| 9.1 | $(((R_1R_1)(R_1R_1))^4((R_2R_2)(R_2R_2))^4)^8(((R_1R_1)(R_1R_1))^4((R_2R_2)(R_2R_2))^4)^8$ $(((R_1R_1)(R_1R_1))^4((R_2R_2)(R_2R_2))^4)^8(((R_1R_1)(R_1R_1))^4((R_2R_2)(R_2R_2))^4)^8$ | $4\ (((R_1R_1)(R_1R_1))^4((R_2R_2)(R_2R_2))^4)^8$ octets |
| 9.2 | $(((AA)(R_1Ø))^4((BB)(BB))^4)^8(((AA)(R_1Ø))^4((BB)(BB))^4)^8$ $(((AA)(R_1Ø))^4((BB)(BB))^4)^8(((AA)(R_1Ø))^4((BB)(BB))^4)^8$ | $4\ (((AA)(R_1Ø))^4((BB)(BB))^4)^8$ octets |
| 9.3 | $(((R_1Ø)(ØØ))^4((BB)(BB))^4)^8(((R_1Ø)(ØØ))^4((BB)(BB))^4)^8$ $(((R_1Ø)(ØØ))^4((BB)(BB))^4)^8(((R_1Ø)(ØØ))^4((BB)(BB))^4)^8$ | $4\ (((R_1Ø)(ØØ))^4((BB)(BB))^4)^8$ octets |
| 9.4 | $(((AA)(AA))^4((BB)(BB))^4)^8(((R_1Ø)(ØØ))^4((ØØ)(ØØ))^4)^8$ $(((AA)(AA))^4((BB)(BB))^4)^8(((R_1Ø)(ØØ))^4((ØØ)(ØØ))^4)^8$ | $2\ (((AA)(AA))^4((BB)(BB))^4)^8$ and $2\ (((R_1Ø)(ØØ))^4((ØØ)(ØØ))^4)^8$ octets |
| 9.5 | $(((R_1Ø)(AA))^4((R_2Ø)(ØØ))^4)^8(((R_1Ø)(AA))^4((R_2Ø)(ØØ))^4)^8$ $(((R_1Ø)(AA))^4((R_2Ø)(ØØ))^4)^8(((R_1Ø)(AA))^4((R_2Ø)(ØØ))^4)^8$ | $4\ (((R_1Ø)(AA))^4((R_2Ø)(ØØ))^4)^8$ octets |

When a quartet is to be assembled from three functional moieties or end stopping functional moieties represented by A, B and D; and at least one building unit has been replaced by a linker or end stopping reactions have been used, this may be done by making use of the preferred couplets in addition to using the null couplet (ØØ) in the manner which has been demonstrated for combining couplets to provide quartets above.

In a preferred embodiment, the compositions of macromolecules or dendritic motifs include at least one quartet selected from Table 3B or 7B or 11B, including those quartets which can be considered equivalent by way of their topology and relative composition of two or three different functional moieties. In this preferred embodiment, the symbols A, B and D are taken to represent different functional moieties or end stopping functional moieties.

A description of topology to the level of octets is required to describe the subsurface connectivity for macromolecules wherein end stopping moieties have been attached at the surface-but-two layer building units. It may be seen in FIG. 8.3 that for each end stopping functional moiety Ri that is attached to a surface amine group of a surface-but-two building unit, a value of 3 represented by ØØØ is lost from the final outer surface $FM_{Total}$ so that $FM_{Total}+\Sigma Ø=FM_{MAX}$. The use of the null symbols restores the integrity of the outer $FM_{Total}$. In F8.3, the use of ØØØ is demonstrated as the functional moieties and null symbols related to the surface-but-two building units gathered into their related couplets, quartets and octets. When an end stopping functional moiety R is attached to a surface-but-two building unit, one of the quartets will contain a null couplet (ØØ), and the other couplet will contain $R_i$ and a null symbol as $(R_1Ø)$. The second quartet will be complete, providing octets of the form: $(((AA)(AA))^4((R_1Ø)(ØØ))^4)^8$ and $(((BB)(BB))^4((R_2Ø)(ØØ))^4)^8$. The octet $(((AA)(AA))^4((R_1Ø)(ØØ))^4)^8$ indicates that there are five functional moieties A,A,A,A,$R_1$ all having a line of connection to the same building unit, in particular to the surface-but-two building unit. Quartets that contain one or more null symbols Ø may be grouped together with other quartets to provide octet and 16-tet descriptions of surface topology.

The macromolecules of FIG. 9 are described in terms of octets making use of the alpha-numeric topological nomenclature as follows:

It is possible to describe the macromolecules or dendritic motifs of this invention that contain end stopping moieties in terms of the composition (number and type) of octets. This is demonstrated for clarity in the examples of FIG. 9 and summarised in the "composition" column of Table 16A.

When an octet is to be assembled from three functional moieties or end stopping functional moieties represented by A, B and D; and at least one building unit has been replaced by a linker or end stopping reactions have been used, this may be done by making use of the preferred quartets from Tables 3B, 7B and 11B, in addition to using the null quartet $((ØØ)(ØØ))^4$ in the manner which has been demonstrated for combining quartets to provide octets above.

A description of topology to the level of 16-tets is required to describe the subsurface connectivity for macromolecules wherein end stopping functional moieties have been attached at the surface-but-three layer building units. It may be seen in FIG. 8.4 that for each end stopping functional moiety Ri that is attached to a surface amine group, a value of 7 represented by ØØØØØØØ is lost from the final outer surface $FM_{Total}$ so that $FM_{Total}+\Sigma Ø=FM_{MAX}$. When one end stopping functional moiety is attached to a surface-but-three building unit, one of the octets will contain a null quartet $((ØØ)(ØØ))^4$, and the other quartet will contain only the $R_i$ and null symbols as $((R_1Ø)(ØØ))^4$. The second octet will be complete, providing 16-tets of the form: $((((AA)(AA))^4((AA)(AA))^4)^8(((R_1Ø)(ØØ))^4((ØØ)(ØØ))^4)^8)^{16}$ and $((((BB)(BB))^4((BB)(BB))^4)^8(((R_2Ø)(ØØ))^4((ØØ)(ØØ))^4)^8)^{16}$. The 16-tet $((((AA)(AA))^4((AA)(AA))^4)^8(((R_1Ø)(ØØ))^4((ØØ)(ØØ))^4)^8)^{16}$ indicates that there are 8 functional moieties of type A and an end stopping functional moiety $R_1$ all having a line of connection to the same building unit, in particular to the surface-but-three building unit. Octets that contain one or more null symbols Ø may be grouped together with other octets to provide 16-tet descriptions of surface topology.

The macromolecules of FIG. 9 are described in terms of 16-tets making use of the alpha-numeric topological nomenclature as follows:

TABLE 17A

| Figure | alpha-numeric topological nomenclature |
|---|---|
| 9.1 | $((((R_1R_1)(R_1R_1))^4((R_2R_2)(R_2R_2))^4)^8(((R_1R_1)(R_1R_1))^4((R_2R_2)(R_2R_2))^4)^8)^{16}$ <br> $((((R_1R_1)(R_1R_1))^4((R_2R_2)(R_2R_2))^4)^8(((R_1R_1)(R_1R_1))^4((R_2R_2)(R_2R_2))^4)^8)^{16}$ |
| 9.2 | $((((AA)(R_1\emptyset))^4((BB)(BB))^4)^8(((AA)(R_1\emptyset))^4((BB)(BB))^4)^8)^{16}$ <br> $((((AA)(R_1\emptyset))^4((BB)(BB))^4)^8(((AA)(R_1\emptyset))^4((BB)(BB))^4)^8)^{16}$ |
| 9.3 | $((((R_1\emptyset)(\emptyset\emptyset))^4((BB)(BB))^4)^8(((R_1\emptyset)(\emptyset\emptyset))^4((BB)(BB))^4)^8)^{16}$ <br> $((((R_1\emptyset)(\emptyset\emptyset))^4((BB)(BB))^4)^8(((R_1\emptyset)(\emptyset\emptyset))^4((BB)(BB))^4)^8)^{16}$ |
| 9.4 | $((((AA)(AA))^4((BB)(BB))^4)^8(((R_1\emptyset)(\emptyset\emptyset))^4((\emptyset\emptyset)(\emptyset\emptyset))^4)^8)^{16}$ <br> $((((AA)(AA))^4((BB)(BB))^4)^8(((R_1\emptyset)(\emptyset\emptyset))^4((\emptyset\emptyset)(\emptyset\emptyset))^4)^8)^{16}$ |
| 9.5 | $((((R_1\emptyset)(AA))^4((R_2\emptyset)(\emptyset\emptyset))^4)^8(((R_1\emptyset)(AA))^4((R_2\emptyset)(\emptyset\emptyset))^4)^8)^{16}$ <br> $((((R_1\emptyset)(AA))^4((R_2\emptyset)(\emptyset\emptyset))^4)^8(((R_1\emptyset)(AA))^4((R_2\emptyset)(\emptyset\emptyset))^4)^8)^{16}$ | where:
there are two $((((R_1R_1)(R_1R_1))^4((R_2R_2)(R_2R_2))^4)^8(((R_1R_1)(R_1R_1))^4((R_2R_2)(R_2R_2))^4)^8)^{16}$ 16-tets in FIG. 9.1;
there are 2 $((((AA)(R_1\emptyset))^4((BB)(BB))^4)^8(((AA)(R_1\emptyset))^4((BB)(BB))^4)^8)^{16}$ 16-tets in FIG. 9.2;
there are two $((((R_1\emptyset)(\emptyset\emptyset))^4((BB)(BB))^4)^8(((R_1\emptyset)(\emptyset\emptyset))^4((BB)(BB))^4)^8)^{16}$ 16-tets in FIG. 9.3;
there are two $((((AA)(AA))^4((BB)(BB))^4)^8(((R_1\emptyset)(\emptyset\emptyset))^4((\emptyset\emptyset)(\emptyset\emptyset))^4)^8)^{16}$ 16-tets in FIG. 9.4; and
there are two $((((R_1\emptyset)(AA))^4((R_2\emptyset)(\emptyset\emptyset))^4)^8(((R_1\emptyset)(AA))^4((R_2\emptyset)(\emptyset\emptyset))^4)^8)^{16}$ 16-tets in FIG. 9.5.

It is then possible to describe the macromolecules or dendritic motifs of this invention that contain end stopping moieties in terms of the composition (number and type) of 16-tets. This is demonstrated for clarity in the examples of FIG. 9 and summarised in dot point form above.

When an 16-tet is to be assembled from three functional moieties or end stopping functional moieties represented by A, B and D; and at least one building unit has been replaced by a linker or end stopping reactions have been used, this may be done by making use of the preferred octets, in addition to using the null octet $(((\emptyset\emptyset)(\emptyset\emptyset))^4((\emptyset\emptyset)(\emptyset\emptyset))^4)^8$ in the manner which has been demonstrated for combining quartets to provide octets above.

In a preferred embodiment, the compositions of macromolecules or dendritic motifs include at least one 16-tet assembled from preferred octets including those octets which can be considered equivalent by way of their topology and relative composition of two or three different functional moieties. In this preferred embodiment, the symbols A, B and D are taken to represent different functional moieties or end stopping functional moieties.

The macromolecules or dendritic motifs of the invention may be attached to cores. In a preferred aspect of the present invention, there is provided a macromolecule having a core and at least one dendritic motif of the formula:

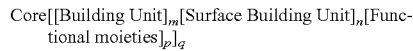

wherein:
a [Building Unit]$_m$[Surface Building Unit]$_n$[Functional moieties]$_p$ defines a dendritic motif;
the core may be any compound, particle or substrate to which the dendritic motif may be attached. Preferably the core contains one or more reactive nitrogens and is selected from the group consisting of lysine, a derivative thereof, a diamine compound, a triamine compound, or a tetramine compound.
the Building Unit is selected from a lysine or lysine analogue;
the Surface Building Unit, which may be the same as, or different to that of the building unit, is selected from lysine or lysine analogue or a building unit selected from the sets herein described;
the Functional moieties include two or more different functional moieties selected from protecting groups; biological effect moiety ligands for extracellular receptors; property modifiers; biological targeting groups; signalling groups; antigenic materials; genetic materials; pharmaceutically active agents; groups adapted to mediate binding to a second entity, and linkers.

m represents the sum of the building units of the subsurface layers of the dendritic motif and is an integer of value: $1 \leq \text{integer} \leq 64$;

n represents the number of surface building units of the dendritic motif and is an integer of value: $2 \leq \text{integer} \leq 64$;

p represents the total number of functional moieties on the surface of the macromolecule and is an integer of value: $4 \leq \text{integer} \leq 128$; and q represents the total number of dendritic motifs on the core of the macromolecule and is an integer of value: $1 \leq \text{integer} \leq 10^6$.

Depending on the type of core, the number of dendritic motifs that may be attached to the core is quite variable. In one embodiment, more than one dendritic motif may be attached to a core to enable the construction of larger, more complex macromolecules. For example, two dendritic motifs, each having 3 subsurface layers and 1 surface layer and bearing 16 functional moieties, may be attached to a divalent core, producing a macromolecule having two dendritic motifs and bearing 32 functional moieties.

In yet another embodiment, wherein the core is the reactive amine groups of a macroscopic surface, for example: the surface of a diagnostic device that is utilised for detection of one or more analytes, (see below for further options) a very large number of dendritic motifs may be attached.

Preferably the core is a diamine compound selected from the benzhydrylamide of lysine or other lysine amide or:

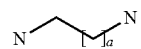

17 where a is an integer of 1 to 9, preferably 1 to 5;

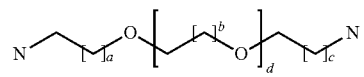

18 where a, b and c, which may be the same or different, are integers of 1-5, preferably 2 or 3 and d is an integer from 0-100, preferably 1-30;

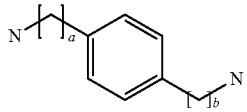

(19)

where a and b, which may be the same or different, are integers of 0 to 5;

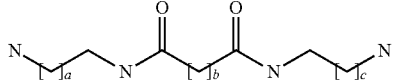

(20)

where a and c, which may be the same or different, are integers of 1 to 6 and where c is an integer from 0-6;

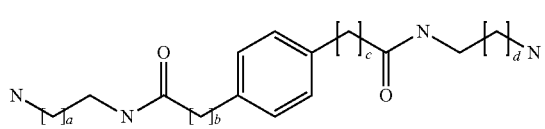

(21)

where a and d, which may be the same or different, are integers of 1 to 6 and where b and c, which may be the same or different, are integers from 0-6.

a triamine compound selected from:

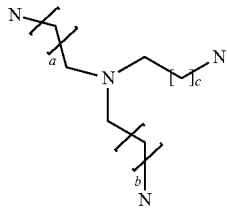

(22)

where a, b and c, which may be the same or different, are integers of 1 to 6;

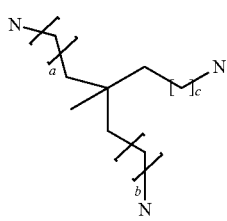

(23)

where a, b and c, which may be the same or different, are integers of 0 to 6;

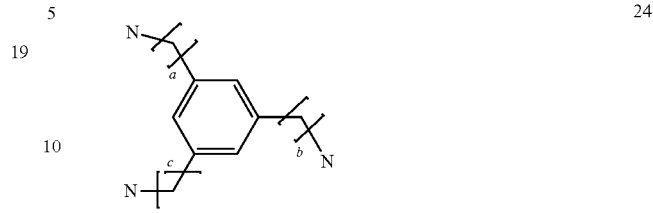

(24)

(25)

(26)

where a, b and c, which may be the same or different, are integers of 0 to 6;

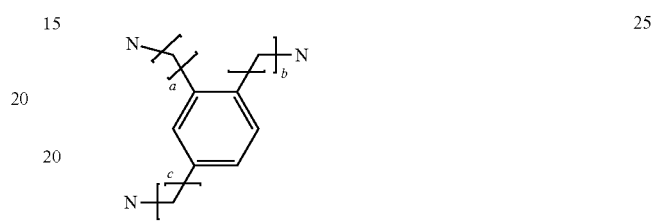

(27)

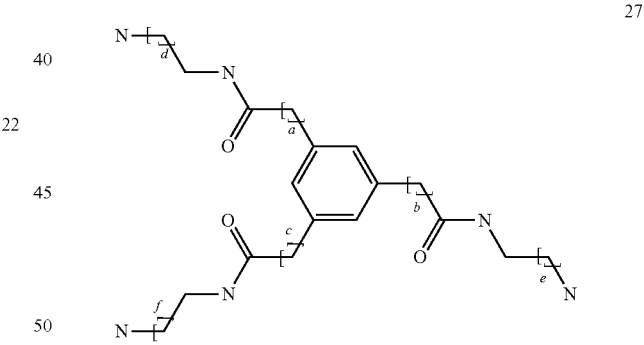

where a, b and c, which may be the same or different, are integers of 0 to 6; and d, e and f, which may be the same or different, are integers of 1 to 6.

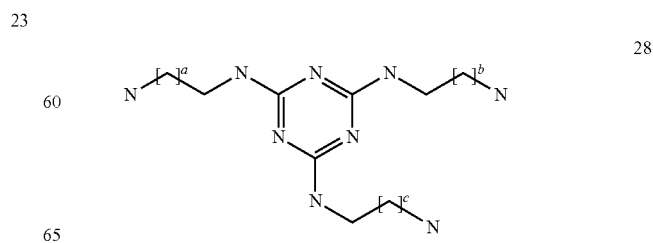

(28)

where a, b and c, which may be the same or different, are integers of 1 to 6.

or a tetramine compound selected from

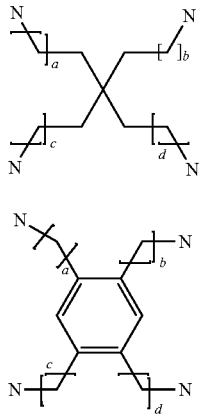

where a, b, c and d, which may be the same or different, are integers of 0 to 6

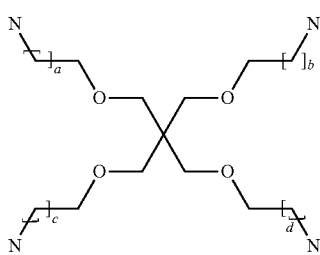

where a, b, c and d, which may be the same or different, are integers of 1 to 6

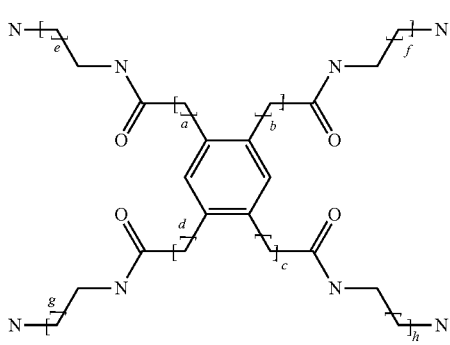

where a, b, c and d, which may be the same or different, are integers of 0 to 6; and e, f, g and h, which may be the same or different, are integers of 1 to 6.

and furthermore, the alkyl chain moieties of the core may be understood to include either alkoxy fragments as C—O—C or C—C—O—C—C but not O—C—X where X is O or N.

More preferably the core is benzhydrylamido-lysine (BHALys), or a compound selected from the following:

where a is an integer of 1 to 5;

where a, b and c, which may be the same or different, are integers of 2 or 3 and d is an integer from 1-30;

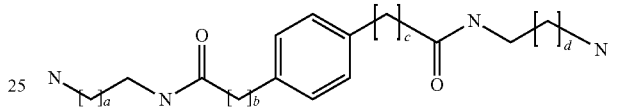

where a and d, which may be the same or different, are integers of 1 or 2 and where b and c, which may be the same or different, are integers from 0-2.

a triamine compound selected from:

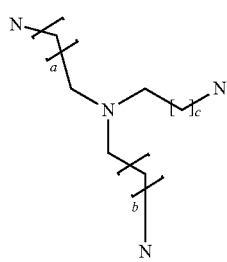

where a, b and c, which may be the same or different, are integers of 1 to 2;

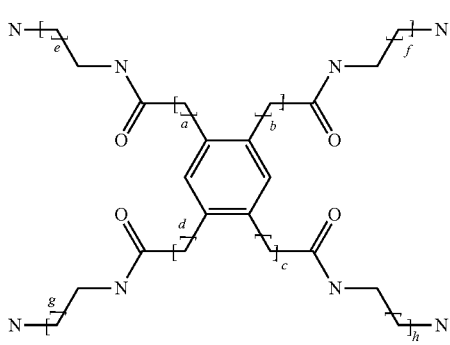

where a, b and c, which may be the same or different, are integers of 0 to 2; and d, e and f, which may be the same or different, are integers of 1 to 2.

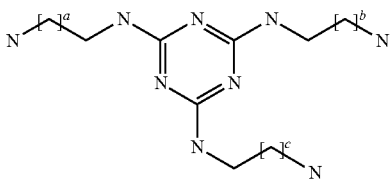

where a, b and c, which may be the same or different, are integers of 1 to 3.

or a tetramine compound

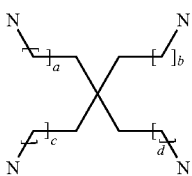

where a, b, c and d, which may be the same or different, are integers of 0 to 1

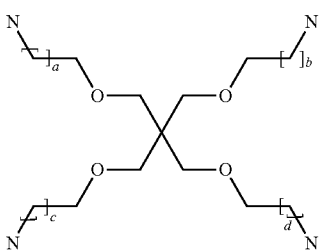

where a, b, c and d, which may be the same or different, are integers of 1 to 2

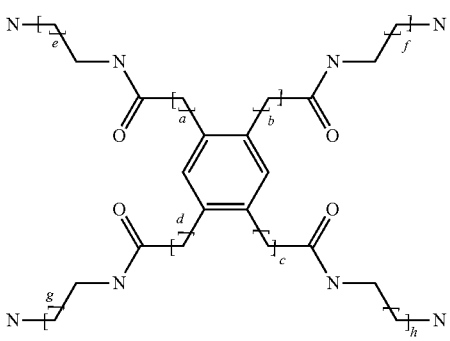

where a, b, c and d, which may be the same or different, are integers of 0 to 2; and e, f, g and h, which may be the same or different, are integers of 1 to 2.

In an alternative embodiment, the core may itself be a non-lysine dendrimer. A poly(amidoamine) (PAMAM), poly (propyleneimine) POPAM or polyethyleneimine (PEI) dendrimer, dendrigrafts, arborols or the like may form the core. In a further embodiment, the core may be a linear polymer, for example poly-lysine, poly-vinylamine or poly-ω-aminoalkylmethacrylamides.

In yet another embodiment, the core may be a metallic or non-metallic particle, for example a gold particle or colloid, latex, a metal oxide, a micelle, a vesicle, a liposome, a buckball, a carbon nanotube (single and double wall), carbon fibre and silica. The cores may be reactable groups, or the dendritic motif may be modified to be attachable to any surface.

In a further embodiment, the core may be the reactive amine groups of a macroscopic surface, for example: the surface of a diagnostic device that is utilised for detection of one or more analytes; the surfaces of medical devices; the surfaces of components used in separation technologies such as chromatographic media or membranes; the surfaces of semiconductor components used in electronic devices. In another embodiment, the dendritic motif may be modified to allow attachment of the motif to the core, wherein the core does not have reactive amine groups.

Synthesis of Macromolecules

There are a number of ways of synthesising or "building" a macromolecule of the present invention. Preferably the macromolecule is a dendrimer. One process for synthesising macromolecules of the present invention involves the sequential reaction of a growing macromolecule core moiety and one or more layers of building compounds.

Accordingly, in one aspect, there is provided a process for preparing a macromolecule, which process includes i) providing
   a growing macromolecule including at least one reactable group;
   a first building compound having a hydrocarbon backbone, and bearing an apex carbonyl group and at least one amine group bearing a functional moiety being a protecting group;

ii) activating the apex carbonyl group of the first building compound; and iii) reacting the deprotected growing macromolecule with the apex carbonyl group of the first building compound.

The steps of the process will then be reiterated until a macromolecule of the desired subsurface and surface layers is achieved.

Preferably the building compounds are lysine or lysine analogues selected from the compounds 1-9 described earlier; the surface building compound is preferably a lysine or lysine analogue selected from the same compounds as the building unit, or compounds 10-16 as also described earlier. Most preferably, it is glutamate or aspartate. Taking a lysine analogue as an example for use in the above process, the apex carboxylate F of the lysine analogues will necessarily be activated prior to reaction with an unprotected amine moiety, and each of the reactable amine groups of the lysine analogue is protected to prevent self condensation. Reactable amines of the building compounds are always protected when the apex carboxylate of a building compound is reacted with unprotected nitrogens of a growing macromolecule. Furthermore the reaction between unprotected amines and activated lysine analogues is always carried out in such a way so as to ensure that the unprotected amines are completely reacted with the chosen lysine analogue. This is most simply done by using a stoichiometric excess of the activated lysine analogue.

A growing macromolecule may be a core including reactable moieties or modified to have reactable moieties bearing protecting groups, or a core having at least one layer of building compounds, to which further layers of building compounds may be reacted. The core may be selected from compounds 17 to 32 as described earlier. Alternatively the core may be a non-lysine dendrimer such as a poly(amidoamine) (PAMAM), poly(propyleneimine) POPAM or polyethyleneimine (PEI) dendrimer, dendrigrafts, arborols or the like may form the core, or a linear polymer, such as poly-lysine, poly-vinylamine or poly-ω-aminoalkylmethacrylamides.

In a further embodiment, the core may be a metallic or non-metallic particle, for example a gold particle or colloid, latex, a metal oxide, a micelle, a vesicle, a liposome, a buckball, a carbon nanotube (single and double wall), carbon fibre and silica.

In a further embodiment, the core may be the reactive amine groups of a macroscopic surface, for example: the surface of a diagnostic device that is utilised for detection of one or more analytes; the surfaces of medical devices; the surfaces of components used in separation technologies such as chromatographic media or membranes; the surfaces of semiconductor components used in electronic devices.

An alternative process for synthesising the macromolecule of the present invention includes the preliminary step of providing a dendritic motif for attachment to the growing macromolecule.

Accordingly, in one aspect of the invention, there is provided a process for preparing a macromolecule, which process includes
i) providing
    a growing macromolecule including a first reactable group, at least one of which bears a first functional moiety being a protecting group;
    a compound including at least one dendritic motif bearing at least two functional moieties, the motif having a surface layer and at least one subsurface layer, and having a hydrocarbon backbone and bearing an apex carbonyl group;
ii) activating the first reactable group by removing the first protecting group;
iii) activating the apex carbonyl group of the dendritic motif; and
iv) reacting the deprotected growing macromolecule with the carbonyl group of the dendritic motif.

In one embodiment, the two functional moieties may be the same or different on each of the growing macromolecule and the compound having at least one dendritic motif. In turn, depending on what the functional moieties are, the functional moiety stoichiometry can be controlled at the surface and subsurface level. The functional moiety stoichiometry can be controlled through the use of a dendritic motif in which the surface amine protecting group stoichiometry and topology has been established. It has been observed that such an approach can provide macromolecules of the present invention that are of high purity.

Preferably there is provided a preparation of macromolecules, wherein at least 80% of the macromolecules exhibit the same functional moiety stoichiometry prior to any end stage or final purification processes, as a result of the process for preparation.

The compound including at least one dendritic motif for use in the process of the present invention may be prepared in any suitable manner. In one embodiment, there is provided a process for preparing a compound including at least one dendritic motif which process includes:
iv) providing
    a first building compound including an apex carbonyl group, attached directly or indirectly to at least one amine group bearing at least one functional moiety;
    a second building compound including an apex carbonyl group, attached to at least one amine group, the building compound bearing a first and second functional moiety one of which is attached to the amine group;
v) activating the amine group on the first building compound by removing the protecting group;
vi) activating the apex carbonyl of the second building compound; and
vii) reacting the deprotected first building compound with the apex carbonyl group of the second building compound.

The dendritic motif preferably has a surface layer and two or more layers, and can be built by reiterating the steps above.

Alternatively, the first building compound may already include at least layers i.e. when the carbonyl group is indirectly attached to the at least one functional moiety.

The order of removal of protecting groups may be an important factor in determining the sequence of reactions that may be used to prepare macromolecules and the dendritic motifs thereof comprising different amine protecting groups, particularly in those cases where the cleavage conditions for one amine protecting group can lead to the loss of a spectator amine protecting group. Accordingly, when the growing macromolecule includes a second reactable group that bears a functional moiety being a protective group, and the second protecting group is different to the first, the second protecting group is inert to the activating conditions for removing the first protecting group. The protecting group table below provides the preferred set of resolvable, and orthogonal, amine protecting groups.

A set of resolvable amine protecting groups are defined as those for which an order of removal exists such that those groups that are not meant for cleavage are inert to the cleavage conditions. When protecting groups are defined as orthogonal, this means that each group is inert to the cleavage conditions required to remove each of the other groups of the orthogonal set. Illustrative amine protecting groups may be sourced in the following references: Protective groups in Organic Synthesis, 3$^{rd}$ Edition, John Wiley and Sons, New York 1999, Greene, T. W. and Wuts, P. G. M., Protecting Groups 3$^{rd}$ Edition, Thieme Stuttgart 2004, Kocienski, P. J. Preferred amine protecting groups may be selected from Table 18.

TABLE 18

Preferred Amine Protecting Groups

| Protecting Group [1] | Boc | CBz | Fmoc | 2-halo-CBz * | Alloc | SES | Troc | Ns | DNP | 4-Nitro-CBz |
|---|---|---|---|---|---|---|---|---|---|---|
| Boc | | O | O | O | O | O | O | O | O | O |
| CBz | O | | R (Fmoc) | [3] | O | O | R (Troc) | R (Ns) | R (DNP) | [3] |
| Fmoc | O | R (Fmoc) | | R (Fmoc) | R (Fmoc) | O | O | [3] | [3] | R (Fmoc) |
| 2-halo-CBz [2] | O | [3] | R (Fmoc) | | O | O | R (Troc) | R (Ns) | R (DNP) | [3] |
| Alloc | O | O | R (Fmoc) | R (Fmoc) | | O | O | O | O | R (Alloc) |
| Me$_3$SiEtSO$_2$ (SES) | O | O | O | O | O | | O | O | O | O |
| Troc | O | R (Troc) | O | R (Troc) | O | O | | O | O | R (Troc) |
| o-NO$_2$PhSO$_2$ (Ns) | O | R (Ns) | [3] | R (Ns) | O | O | O | | [3] | O |

TABLE 18-continued

Preferred Amine Protecting Groups

| Protecting Group [1] | Boc | CBz | Fmoc | 2-halo-CBz * | Alloc | SES | Troc | Ns | DNP | 4-Nitro-CBz |
|---|---|---|---|---|---|---|---|---|---|---|
| 2,4-dinitrobenzene-sulfonyl (DNP) | O | R (DNP) | [3] | R (DNP) | O | O | O | [3] |  | O |
| 4-Nitro-CBz | O | [3] | R (Fmoc) | [3] | R (Alloc) | O | R (Troc) | O | O |  |

Notes:
[1] The combinations of the protecting groups listed in the first column of the table with the protecting groups listed across the top row of the table are defined as being either "resolvable" (R) or "orthogonal" (O). When a combination is deemed "resolvable", the protecting group in parentheses denotes the group which should be removed first.
[2] Refers to 2-chloro-CBz and 2-bromo-CBz.
[3] Combination neither resolvable nor orthogonal.

The process for synthesis of the compound including a dendritic motif according to the present invention may include the removal of one or more surface amine protecting groups to provide one or more reactive amine groups. These reactive amine groups are then reacted with a carbonyl moiety. In an example using lysine or a lysine analogue, the carboxylate moiety of the functional moiety precursor will either be activated for amide bond formation either prior to the reaction or in situ.

Both the carboxylate group and the reactable amine groups may be derivatised to enhance or diminish the reactivity of these groups. For example the carboxylate group may be activated as in an acyl halide derivative or an activated ester derivative (The Peptides, Analysis, Synthesis and Biology Vol 1 Major Methods of Peptide Bond Formation; Academic Press New York 1979 eds Gross, E. and Meienhofer, J., Peptides: Chemistry and Biology. Wiley-VCH Weinheim 2002, Sewald, N. and Jakubke, H-D., The Chemical Synthesis of Peptides Clarendon Press, Oxford 1994, Jones, J.), and the reactable amine groups may be protected (deactivated) using amine-protecting groups such as Boc, CBz, 4-nitrobenzyloxycarbamate (4-$NO_2$—CBz) Fmoc, Dde, $CF_3CO_2$, 2-halo-CBz, Alloc, $Me_3SiEtSO_2$, Troc, o-$NO$-$_2PhSO_2$ and 2,4-dinitrobenzene-sulfonyl.groups.CBz.

In general, a free carboxylate group is not sufficiently reactive to react with an amine to form the amide bond, so some means is preferably provided that facilitates the dehydration and so drives the reaction to completion. This may be achieved, for example, by utilising one of two related methods.

In the first activation method, the reagent which contains the carboxylic acid is reacted with a second reagent containing a hydroxyl moiety in the presence of a dehydrating reagent and, where required, other activating agents, to provide a product in which the acid containing moiety and the hydroxyl containing moiety are joined by an ester bond. This product is known as an "active ester". The reagent containing the hydroxyl moiety is chosen such that the product ester will readily react with primary amines to form amides with liberation of the aforementioned reagent containing the hydroxyl moiety. In some cases, the active ester is sufficiently stable to enable it to be isolated, purified and stored prior to use.

Preferred reagents containing the hydroxy moiety are: p-nitrophenol (and other nitro phenol derivatives); N-hydroxysuccinimide; pentafluorophenol and trifluorophenol. A more complete list is provided in Sewald page 197. Preferred dehydrating agents are dicyclohexylcarbodiimide (DCC) and N-(3-Dimethylaminopropyl)-N'-ethylcarbodiimide (EDC).

In a second activation method, the reagent which contains the carboxylate group may be reacted "in situ" with an activating agent to form an acyl species which further reacts with primary amines also present "in situ" or added after an appropriate prior activation time to lead to the formation of the required amide bond. Preferred activating agents are (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), O-(7-Azabenzotriazol-1-yl)-N,N,N',N'-tetramethyluronium hexafluorophosphate (HATU), O-(Benzotriazol-1-yl)-N,N,N',N'-tetramethyluronium tetrafluoroborate (TBTU), O-(Benzotriazol-1-yl)-N,N,N',N'-tetramethyluronium hexafluorophosphate (HBTU). Ancillary reagents like 1-hydroxybenzotriazole (HOBt) may be required to facilitate this reaction, for example through the formation of activated intermediates which are known to react further with amines to form amide bonds.

Any compound containing one or more reactive amines may be reacted with an activated apex carboxylate of either a building unit or a dendritic motif to provide a macromolecule. The reactable amines of the building unit or dendritic motif need to be prevented from reacting with the activated apex carboxylate either through appropriate use of amine protecting groups, or through prior reaction with a functional moiety. The functional moiety needs to be inert to the reactive amine-activated apex carboxylate reaction.

Any compound containing one or more reactive amines may be reacted with an activated dendritic motif to provide a macromolecule.

In one embodiment, the process for the preparation of the compound including at least one dendritic motif may optionally include the protection of a selected carboxylate group prior to removal of protecting groups on surface amines present on the lysine or lysine analogue backbone. The protecting group used for the protected carboxylate group is preferably stable to the conditions required to remove the protecting groups present on the surface amines. Carboxylate protecting groups such as methyl or more preferably ethyl esters are suitable. Illustrative carboxylate protecting groups may be sourced in the following references: Protective groups in Organic Synthesis, 3rd Edition, John Wiley and Sons, New York 1999, Greene, T. W. and Wuts, P. G. M., Protecting Groups 3rd Edition, Thieme Stuttgart 2004, Kocienski, P. J.

Where the synthesis of the compound including at least one dendritic motif requires a further deprotection step subsequent to the addition of a functional moiety that is not a protecting group, it is important to take the stability of this functional moiety toward subsequent reactions into consideration. In a preferred sequence of functional moiety additions, the second functional moiety, which is selected, for example, to modify the pharmacokinetics of the pharmaceutically active agent and/or macromolecule, is added first to the lysine or lysine analogue backbone. Accordingly, a non-protecting group functional moiety may be activated and reacted with an amine group on the building compound that has been deprotected. The building compound-functional moiety may then be reacted with a further building unit that is preferably already attached to a growing macromolecule, i.e., non-protecting functional moiety reacted with building compound then reacted with building compound on growing macromolecule. Furthermore, in those situations where the pharmaceutically active agent is to be attached to the lysine or lysine analogue backbone via a labile linker (see below), it may be necessary to activate the selected carboxylate of the building compound prior to the reaction of the unprotected surface amine groups of the lysine or lysine analogue backbone, and furthermore where the selected carboxylate of the lysine or lysine analogue backbone is unprotected it will be necessary for the carboxylate group of the pharmaceutically active agent-linker moiety to be activated prior to the presence of the unprotected surface amine groups.

The process for synthesising a macromolecule of the present invention is then continued by the reaction of unprotected amines of a growing macromolecule with the compound including at least one dendritic motif, or individual building compounds. The carboxylate moieties will either be activated for amide bond formation either prior to the reaction or in situ. In a preferred method, the carboxylate moiety is activated in situ. This method is preferred and it is possible, through the inclusion of water or other hydroxyl donors, to limit the adventitious formation of ester bonds to the macromolecule where unmasked hydroxyl moieties are present on either the growing macromolecule core or compound Including at least one dendritic motif or individual building compounds.

In one embodiment, the compound including at least one dendritic motif or individual building compounds may be attached to the growing macromolecule via a linker moiety.

A process for synthesising macromolecules of this invention may include the reaction of unprotected amines of a growing macromolecule with linker moieties. The carbonyl group of the linker is activated for amide bond formation either prior to the reaction or in situ. If the linker group includes a reactable amine then it is protected. Furthermore, the reaction between unprotected amines of the growing macromolecule and the activated linkers is carried out in such a way as to ensure that the unprotected amines are completely reacted with the activated group, typically by using the activated group in excess.

An example of this approach may be seen in FIG. 16, wherein PNPO-Lys(Boc)$_2$, the reactive building compound, reactable nitrogens are protected with the Boc group, and the carboxylate is activated as a para-nitrophenol ester.

Accordingly, in an alternative embodiment of the present invention there is provided a process for preparing a macromolecule having controlled functional moiety stoichiometry including the steps of:
(i) providing
a growing macromolecule including a first reactable group, at least one of which bears a first functional moiety being a protecting group; and
a linker including a carbonyl group and a reactable group;
(ii) activating the carbonyl group on the linker;
(iii) activating the first reactable group on the growing macromolecule; and
(iv) reacting the deprotected growing macromolecule with the activated carbonyl group on the linker.
The process may then further include the steps of:
(v) providing a compound including at least one dendritic motif bearing at least two functional moieties, the motif having a surface layer and at least one sub-surface layer, and having a hydrocarbon backbone and bearing an apex carbonyl group;
(vi) activating the carbonyl group of the dendritic motif;
(vii) activating the reactable group of the linker; and
(viii) reacting the activated carbonyl group and linker, either before or after step (iv) of the process above.

In one embodiment the reactable group of the linker is a reactable amine that is protected, and the activating step involves deprotecting the linker using suitable conditions as have been discussed herein.

In yet another embodiment, the growing macromolecule may be reacted with an end-stopping functional moiety, optionally on a linker bearing the end-stopping functional moiety. The end-stopping functional moiety may also be activated for amide bond formation either prior to the reaction or in situ.

The macromolecule of the present invention may include a unique point of attachment for either of the first or second functional moiety. In this way, a macromolecule may be synthesised with a single first or second functional moiety.

In an alternative embodiment the macromolecule of the present invention may include a selected single point of attachment for either the first or second functional moiety.

There are general methods described in the art for the selective mono-protection of polyamine molecules. Such methods are described in Krapcho and Kuell Synthetic Commun. 1990 20 2559. In a preferred method macromolecules with a unique point of attachment are prepared from a di- or tri-valent core wherein only one of the reactive amine groups is protected, and with a protecting group that is inert, or orthogonal, to the conditions that are used to remove other amine protecting groups during the process by which a macromolecule is constructed. It is then possible to conduct the iterative cycles of condensation and amine deprotection, to build a macromolecule of 1 to 6 generations, more preferably 3 to 5 generations, and in which there exists a single surface amine group that is distinguished from the other surface amine groups by its unique amine protecting group. This unique surface amine group represents a site at which a single selected molecule, e.g. a protein or peptide, a pharmaceutically active agent, a signalling moiety, an anchoring moiety or a targeting molecule may be attached to the macromolecule.

In a preferred form of this embodiment, there is provided a macromolecule having a controlled surface group composition, the macromolecule including a surface layer, at least one subsurface layer and at least two functional moieties including
a first functional moiety attached to a single selected point of attachment on the macromolecule; and
a second functional moiety group;
wherein functional moiety composition refers to the number and type of functional moieties.

In a preferred method, the protecting group of the unique surface amine group is removed, and the surface amine group is reacted with a haloacetic acid derivative, or a maleimide derivative such as 3-maleimidopropionic acid or 4-maleimidobutyric acid under conditions where the amide bond is formed. General methods for the coupling of thiol containing peptides and proteins to such thiol active groups are described in Hermanson, G. T. Bioconjugate Techniques (Academic Press 1996) and the references cited therein, Blatter et al, Biochem., 24: 1517 (1985) and Jue et al, Biochem., 17:5399 (1978).

Computer Modelling

In addition to the couplet, quartet, octet, and 16-tet notation used to describe each different topological isomer, the macromolecules may be represented graphically.

Computer simulation of the macromolecules may be used to illustrate the distribution of functional moieties, and the three-dimensional structure adopted by the macromolecule. Such an illustration helps to demonstrate the differences that exist between different topological isomers of macromolecules which have the same surface group stoichiometry.

The molecular modelling of a set (see Table 19) of asymmetric macromolecules which were constructed entirely from asymmetric lysine building units is described in Example 65.

Each of asymmetric sets contained the following topological isomers:

TABLE 19

Topological Isomers used in Example 65

| Macro-molecule | Topological description |
|---|---|
| Type 1: 16-tet cluster | $((((AA)(AA))^4((AA)(AA))^4)^8(((AA)(AA))^4((AA)(AA))^4)^8)^{16}$<br>$((((BB)(BB))^4((BB)(BB))^4)^8(((BB)(BB))^4((BB)(BB))^4)^8)^{16}$ |
| Type 2: Octet cluster | $((((AA)(AA))^4((AA)(AA))^4)^8(((BB)(BB))^4((BB)(BB))^4)^8)^{16}$<br>$((((AA)(AA))^4((AA)(AA))^4)^8(((BB)(BB))^4((BB)(BB))^4)^8)^{16}$ |
| Type 3: Quartet cluster | $((((AA)(AA))^4((BB)(BB))^4)^8(((AA)(AA))^4((BB)(BB))^4)^8)^{16}$<br>$((((AA)(AA))^4((BB)(BB))^4)^8(((AA)(AA))^4((BB)(BB))^4)^8)^{16}$ |
| Type 4: Couplet cluster | $((((AA)(BB))^4((AA)(BB))^4)^8(((AA)(BB))^4((AA)(BB))^4)^8)^{16}$<br>$((((AA)(BB))^4((AA)(BB))^4)^8(((AA)(BB))^4((AA)(BB))^4)^8)^{16}$ |
| Type 5: No cluster | $((((AB)(AB))^4((AB)(AB))^4)^8(((AB)(AB))^4((AB)(AB))^4)^8)^{16}$<br>$((((AB)(AB))^4((AB)(AB))^4)^8(((AB)(AB))^4((AB)(AB))^4)^8)^{16}$ |

In general, simulation of the macromolecules of Example 65 exhibited significantly different distributions of functional moieties A and B dependent on the topological isomer.

TABLE 20

Means and standard deviations of A-B distances and their variation with Cluster Pattern.

| Cluster Pattern | Mean A-B distance (Å) | Standard Deviation of A-B distance (Å) |
|---|---|---|
| Type 1 | 23.16 | 7.57 |
| Type 2 | 20.81 | 7.09 |
| Type 3 | 20.83 | 7.42 |
| Type 4 | 20.62 | 7.38 |
| Type 5 | 20.14 | 7.88 |

FIG. 18 shows the distribution of all functional moiety-functional moiety distances. The most significant difference is between the Type 1 clustering where the Functional Moieties are clustered in 16-tets; and Type 5 where there is no clustering. These topological isomers are graphically depicted in FIGS. 16 and 17.

In cases where the end groups possess different electrostatic charges, a division of the dendrimer into distinct regions will result in a polarised dendrimer molecule. This may be measured by calculating the distances between the centres of charge of the various functional moiety/functional moieties. The results of these calculations are depicted in FIG. 19, it can be seen from this graph that Clustering at the level of 16-tet and octet provides a significantly larger distance between the centre of mass of the different Functional Moieties than does smaller clustering topologies.

Applications of the Macromolecules

Depending on the macromolecule and the functional moieties on the building unit or surface building unit, the macromolecules may have a large number of prophylactic and/or therapeutic uses, particularly when formulated as a pharmaceutical composition. Accordingly, there is provided a pharmaceutical composition including a macromolecule having a controlled functional moiety stoichiometry including at least one dendritic motif having a surface layer formed from at least one surface building unit and at least one subsurface layer formed from at least one building unit, the surface building unit and building units having a hydrocarbon backbone bearing a carbonyl group and at least one amine group; and at least two different functional moieties on the building unit and/or surface building unit;

where functional moiety stoichiometry refers to the number and type of functional moieties;

and a pharmaceutically acceptable carrier, or excipient.

In one embodiment of this aspect of the invention, the macromolecule has a controlled topology, wherein topology refers to the relationship between the functional moieties.

The pharmaceutically acceptable carriers or excipients may be selected from any known carriers or excipients depending on the delivery route selected for the active.

The pharmaceutical composition may be formulated for oral, injectable, rectal, parenteral, subcutaneous, intravenous, intramuscular or other delivery. The pharmaceutical composition may be formulated in tablet, capsule, caplet, injectable ampoule vial, or ready-to-use solution, lyophilised material, suppository, bolus or implant form.

The macromolecules and compositions of the present invention are suitable for administration in any suitable manner, e.g. parenteral (including intravenously, intramuscularly, subcutaneous), orally, intraperitoneally, topically (skin), buccal, vaginally, rectally, to the surface of the skin, transdermal (slow release preparation), into the joint space, intranasally, by aerosol, by pulmonary administration, and directly to a body part.

It is especially advantageous to formulate the pharmaceutical composition of the present invention in unit dosage form for ease of administration and uniformity of dosage. The specifications for the dosage unit forms of the present invention may be determined by a person skilled in the art depending on, for example (a) the unique characteristics of the active ingredient and the particular therapeutic effect to be achieved, and (b) the limitations inherent in the art of compounding such an active ingredient for the particular treatment.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may for example be in the form of aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles, which may include edible oils, or preservatives.

The macromolecule according to the present invention may also be formulated for parenteral administration by injection, for example bolus injection, or continuous infusion, and may be presented in unit dosage form in ampoules, pre-filled syringes, small volume infusion or in multi-dose containers with an added preservative. The compositions may take such forms as suspensions, solutions, or emulsions in oily or aqueous vehicles, and may contain formulating agents such as suspending, stabilising and/or dispersing agents.

Alternatively, the active ingredient may be in powder form, obtained by aseptic isolation of sterile solid or by lyophilisation from solution, for constitution with a suitable vehicle, eg. sterile, pyrogen-free water, before use.

For topical administration to the epidermis, the macromolecule according to the invention may be formulated as an ointment, cream or lotion, or as a transdermal patch.

Ointments and creams may, for example, be formulated with an aqueous or oily base with the addition of suitable thickening and/or gelling agents. Lotions may be formulated with an aqueous or oily base, and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and gum acacia or gum tragacanth; pastilles comprising the active ingredient in an inert base such as gelatin or sucrose and gum acacia; and mouthwashes comprising the active ingredient in a suitable liquid carrier.

Pharmaceutical formulations suitable for rectal administration wherein the carrier is a solid are most preferably presented as unit dosage suppositories. Suitable carriers include cocoa butter and other materials commonly used in the art, and the suppositories may be conveniently formed by admixture of the macromolecule with the softened or melted carrier(s) followed by chilling and shaping moulds.

Formulations suitable for vaginal administration may be presented as pessaries, tampons, creams, gels, pastes, foams or sprays containing in addition to the active ingredient such carriers as are known in the art to be appropriate.

For administration to the respiratory tract, including intranasal administration, the macromolecule according to the present invention may be administered by any of the methods and formulations employed in the art for administration to the respiratory tract.

Thus in general the macromolecule according to the present invention may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump Administration to the respiratory tract may also be achieved by means of an aerosol formulation in which the macromolecule according to the present invention is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. More preferably the propellant is an HCFC such as R134a or R125. The aerosol may conveniently also contain a surfactant such as lecithin. The dose of drug may be controlled by provision of a metered valve.

Alternatively the macromolecule according to the present invention may be provided in the form of a dry powder, for example a powder mix of the macromolecule according to the present invention in a suitable powder base such as lactose, starch, starch derivatives such as hydroxypropylmethyl cellulose-14 and polyvinylpyrrolidine (PVP). Conveniently the powder carrier will form a gel in the nasal cavity. The powder composition may be presented in unit dosage form, for example in capsules or cartridges of eg. gelatin, or blister packs from which the powder may be administered by means of an inhaler.

Compositions of the present invention may also be used in combination with existing and accepted therapeutic approaches as adjuvant therapy. For example, they may be used with antibacterial drugs, antiviral drugs or antifungal drugs. In rheumatoid arthritis and related conditions, Behcet's disease, inflammatory bowel disease and psoriasis, they may be used with steroids and disease modifying drugs such as methotrexate or disease modifying therapeutic antibodies. In the treatment of organ transplant rejection, and in graft versus host disease, they may be used with steroids and/or cyclosporine and/or FK506 and/or azathioprine and/or tacrolimus and/or sirolimus and/or basiliximab and/or daclizumab.

Suitable pharmaceutically acceptable carriers, diluents and/or excipients include conventional solvents, dispersion media, fillers, solid carriers, aqueous solutions, coatings, antibacterial and antifungal agents, isotonic, and absorption enhancing or delaying agents, and the like. The use of such media and agents for pharmaceutically active substances is well known in the art, and it is described, by way of example, in Remington's Pharmaceutical Sciences, 18th Edition, Mack Publishing Company, Pennsylvania, USA, the relevant disclosure of which is incorporated herein by reference. Except insofar as any conventional media or agent is incompatible with the active ingredient, use thereof in the pharmaceutical composition of the present invention is contemplated. Supplementary active ingredients may also be incorporated into the composition.

The pharmaceutical composition may be prepared by any of the methods well known in the art of pharmacy. Such methods include the step of bringing the active component into association with a carrier, diluent or excipient, which may include one or more accessory excipients. For example, the composition may be prepared by uniformly and intimately bringing the active component into association with a liquid carrier, a finely divided solid carrier, or both, and then, if necessary, shaping the product.

The macromolecule of the present invention may be administered in prophylactically or therapeutically effective amounts. A prophylactically or therapeutically effective amount means that amount necessary to at least partly attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and may be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily doses of the macromolecule may be from about 0.01 mg/kg per day to 1000 mg/kg per day. Small doses (0.01-1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

In a further preferred embodiment, pharmaceutically acceptable carriers or excipients may be selected from one or more of sterile aqueous salt solutions, suspensions and emulsions, including saline and buffered media, Ringer's dextrose, dextrose and sodium chloride, and lactated Ringer's solution. Intravenous vehicles include fluid and nutrient replenishers, electrolyte replenishers, such as those based on Ringer's dextrose, and the like. For administration by non-intravenous routes, the carrier can be in the form of clotted plasma, preferably the patient's clotted plasma. Alternatively the carrier can be a plasma-free, physiologically compatible, biodegradable solid or semi-solid, such as a gel, suspension or water soluble jelly. Acacia, methylcellulose and other cellulose derivatives, sodium alginate and tragacanth suspensions or gels are suitable for use as carriers in the practice of this invention, for example, sodium carboxymethylcellulose 2.5%, tragacanth 1.25% and guar gum 0.5%.

A number of non-limiting applications for the macromolecules according to the present invention may be illustrated as follows:

1. Anti-Sexually Transmitted Microbial Macromolecule

In a further aspect of the present invention, there is provided a macromolecule, having a controlled functional moiety stoichiometry including at least one dendritic motif having a surface layer formed from at least one surface building unit and at least one subsurface layer formed from at least one building unit, the surface building unit and building units having a hydrocarbon backbone bearing a carbonyl group and at least one amine group and at least two different functional moieties on the building unit and/or surface building unit, at least one of the functional moieties bearing an aromatic or heterocyclic sulphate, sulphonate, phosphate, phosphonate, carboxyl or carbonyl residue, or derivative thereof, and exhibiting an enrichment in a selected functional moiety stoichiometry, where functional moiety stoichiometry refers to the number and type of functional moieties.

International patent application no PCT/AU02/00407 (WO 02/079299), to applicants, the entire contents of which are incorporated herein by reference, discloses a class of dendrimers (highly branched macromolecules with a defined envelope of polyanionic or cationic surface groups) which have been shown to exhibit a range of antiviral and antimicrobial activity with minimal toxicity. These macromolecules act to prevent infection of cells of the host organism by interfering with the binding of the infectious microbe to the host.

Despite these advances in the art, difficulties remain in respect of the potency of these macromolecules, in particular with regard to the differences in potency between in vitro test systems and in vivo test systems. These macromolecules are primarily formulated as compositions with a single functional moiety on the surface.

The presentation of a multiplicity of functional moieties on the surface of a macromolecule with control over topology and stoichiometry of the different functional moieties is made possible through the application of this invention. In a preferred embodiment the first functional moiety is an aromatic or heteroaromatic moiety which includes at least one and preferably two anionic residues per functional moiety. The role of the second functional moiety is to provide a second mechanism by which the macromolecule may bind to the targets through which the microbial infection is mediated, and antimicrobial efficacy is achieved when this binding is enhanced. In a preferred embodiment of this invention the second functional moiety has lipophilic properties.

For example, the macromolecule according to this aspect of the present invention may be useful in the prophylactic and/or therapeutic treatment of STI's including one or more of Human Immunodeficiency Viruses—I and II (HIV), Herpes Simplex viruses 1 and 2 (HSV), Cytomegalovirus (CMV), Varicella Zoster Virus (VZV), Epstein-Barr Virus (EBV), Hepatitis Viruses A, B, C & D, Human Papilloma Virus (HPV), *Chlamydia trachomatis, Candida albicans, Trichomonas vaginalis, Neisseria gonorrhoeae, Treponema pallidum, Calymmato bacterium granulomatis, Haemophilus Ducreyi, Sarcoptes scabiei, Phthirus pubis, Mycoplasma, Gardnerella vaginalis*, and other microbial pathogens.

The macromolecule according to the present invention may exhibit significant in vivo efficacy, improved toxicity and pharmacokinetics relative to the prior art.

In a preferred embodiment, there is provided a composition for prophylactic or therapeutic treatment of sexually transmitted infections which includes a macromolecule having a controlled functional moiety stoichiometry including at least one dendritic motif having a surface layer formed from at least one surface building unit and at least one subsurface layer formed from at least one building unit, the surface building unit and building units having a hydrocarbon backbone bearing a carbonyl group and at least one amine group; and at least two different functional moieties on the building unit and/or surface building unit; where functional moiety stoichiometry refers to the number and type of functional moieties; and optionally a pharmaceutically acceptable carrier or excipient.

An example of such a macromolecule is BHALys [Lys]$_8$ [α-COCH$_2$O-3,6-Naph(SO$_3$Na)$_2$]$_8$ [ε-Boc]$_8$ which is described in Example antimicrobial 9 and is illustrated in FIG. 11.

Desirably, the second functional moiety(s) may be selected from one or more of the following: alkyl moieties of C1 to C20 either branched or straight chain, cycloalkyl ring systems such as cyclohexyl, decalin, and the various steroid scaffolds including cholic acids and deoxycholic acids, benzyl, naphthyl, thiophenes or other polycyclic aromatic moieties; pyridines, quinolines and isoquinolines, pyrroles and indoles, imidazoles, oxazoles, pyrazoles, pyridazines, pyrimidines and quinazolines, pyrazines and quinoxalines; all optionally further substituted with amine, hydroxyl alkyl or halo moieties where such substitution does not lead to a chemically labile material.

A hydrophobic group, such as an alkyl C1 to C10, ring systems such as cyclohexyl, and the various steroid scaffolds including cholic acids and deoxycholic acids, benzyl, pyridine or imidazole is preferred.

In a further preferred embodiment, the macromolecules are enriched in a relative stoichiometry of the anionic functional moiety to the hydrophobic functional moiety in the range from 63:1 through to 16:48, more preferably the relative stoichiometry is in the range of 60:4 through to 1:1.

In a further preferred embodiment, the macromolecules may be selected from a preparation of macromolecules enriched in topologies selected from: anionic moieties clustered at the level of couplets or quartets or octets or couplets of the form (AB) where A is an anionic functional moiety and B is a hydrophobic moiety.

The second functional moiety may be directly connected to the macromolecule or may be connected to the macromolecule by a non-cleavable linker.

In a preferred aspect of this embodiment of the present invention, there is provided a macromolecule of the formula:

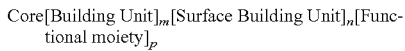

wherein:
the Core is selected from the group consisting of lysine, or a derivative thereof, a diaminoalkane compound, or a trialkyltetramine compound to which the first layer of building units (below) is added;
the Building Unit is selected from lysine or lysine analogue;
the Surface Building Unit, which may be the same as, or different to that of the building unit is selected from lysine or lysine analogue;
the Functional moieties include two or more different groups, a first functional moiety having the structure of one or more of the following:

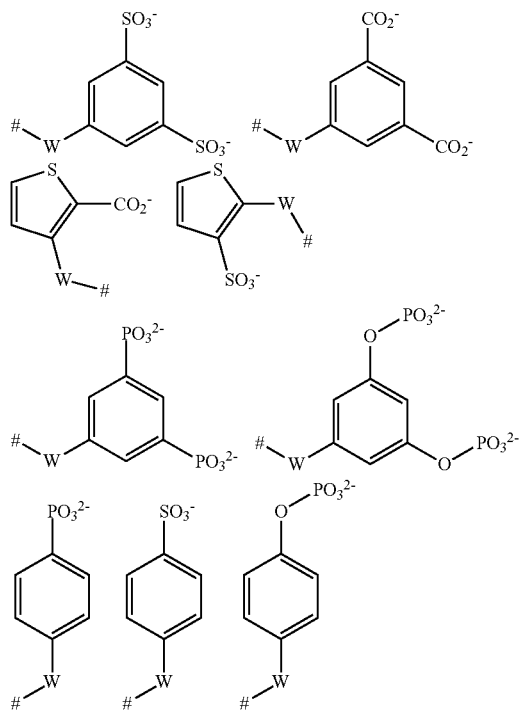

wherein W represents a functional group attached to a surface amine of the macromolecule and is selected from C(O) or S(O)2 and;
a second functional moiety selected from one or more of the group consisting of: property modifiers; alkyl moieties of C1 to C20 either branched or straight chain, cycloalkyl ring systems such as cyclohexyl, decalin, and the various steroid scaffolds including cholic acids and deoxycholic acids, benzyl, naphthyl, thiophenes or other polycyclic aromatic moieties; pyridines, quinolines and isoquinolines, pyrroles and indoles, imidazoles, oxazoles, pyrazoles, pyridazines, pyrimidines and quinazolines, pyrazines and quinoxalines; all optionally further substituted with amine, hydroxyl alkyl or halo moieties where such substitution does not lead to a chemically labile material;

m represents the sum of building units of the subsurface layers of the macromolecule and is an integer between 1 to 64;
n represents the number of surface building units with surface layer(s) of the macromolecule and is an integer between 2 and 64;
p represents the number of functional moieties on the surface layer of building units and is an integer between 0 to 64.

The macromolecule, or precursor therefor may be selected from the following

BHALys [Lys]$_4$ [α-COCH$_2$O-3,6-Naph(SO$_3$Na)$_2$]$_4$ [ε-COC$_5$H$_{11}$]$_4$
BHALys [Lys]$_4$ [α-COC$_5$H$_{11}$]$_4$ [ε-COCH$_2$O-3,6-Naph(SO$_3$Na)$_2$]$_4$
BHALys [Lys]$_4$ [α-CO-4-PhSO$_3$Na]$_4$ [ε-Hexyl]$_4$
DAH [Lys]$_8$ [α-COCH$_2$O-3,6-Naph(SO$_3$Na)$_2$]$_8$ [ε-COC$_5$H$_{11}$]$_8$
BHALys [Lys]$_8$ [ε-COCH$_2$O-3,6-Naph(SO$_3$Na)$_2$]$_8$ [ε-CBz]$_8$
BHALys [Lys]$_8$ [α-CO-3,5-Ph(SO$_3$Na)$_2$]$_8$ [ε-CBz]$_8$
DAH [Lys]$_8$ [α-CO-3,6-Ph(SO$_3$Na)$_2$]$_8$ [ε-COC$_5$H$_{11}$]$_8$
BHALys [Lys]$_8$ [α-CO-4-Ph(SO$_3$Na)]$_8$ [ε-CBz]$_8$
BHALys [Lys]$_{16}$ [α-COCH$_2$O-3,6-Naph(SO$_3$Na)$_2$]$_{16}$ [ε-CBz]$_{16}$
BHALys [Lys]$_{16}$ [α-CO-3,5-Ph(SO$_3$Na)$_2$]$_{16}$ [ε-CBz]$_{16}$
BHALys [Lys]$_{16}$ [α-CO-4-Ph(SO$_3$Na)]$_{16}$ [ε-CBz]$_{16}$
BHALys [GlyLys]2 [Lys]$_4$ [α,α-Boc]$_2$ [α,ε-Boc]$_2$ [ε,α-COCH$_2$O-3,6-Naph(SO$_3$Na)$_2$]$_2$ [ε,ε-COCH$_2$O-3,6-Naph(SO$_3$Na)$_2$]$_2$
BHALys [GlyLys]$_2$ [Lys]$_4$ [α,α-COCH$_2$O-3,6-Naph(SO$_3$Na)$_2$]$_2$ [α,ε-COCH$_2$O-3,6-Naph(SO$_3$Na)$_2$]$_2$ [ε,α-COC$_5$H$_{12}$]$_2$ [ε,ε-COC$_5$H$_{12}$]$_2$
BHALys [Lys]$_2$ [GlyLys]$_4$ [Lys]$_8$ [α,α-Boc]$_4$ [α,ε-Boc]$_4$ [ε,α-COCH$_2$O-3,6-Naph(SO$_3$Na)$_2$]$_4$ [ε,ε-COCH$_2$O-3,6-Naph(SO$_3$Na)$_2$]$_4$
BHALys [Lys]$_2$ [GlyLys]$_4$ [Lys]$_8$ [α,α-COCH$_2$O-3,6-Naph(SO$_3$Na)$_2$]$_4$ [α,ε-COCH$_2$O-3,6-Naph(SO$_3$Na)$_2$]$_4$ [ε,α-COC$_5$H$_{12}$]$_4$ [ε,ε-COC$_5$H$_{12}$]$_4$
BHALys [Lys]$_2$ [α,ε-Lys] [CBz]$_2$ [Lys]$_3$ [COCH$_2$O-3,6-Naph(SO$_3$Na)$_2$]$_6$
BHALys [Lys]$_2$ [α,ε-Lys] [COCH$_2$O-3,6-Naph(SO$_3$Na)$_2$]$_2$ [Lys]$_3$ [Boc]$_6$
BHALys [GlyLys]$_2$ [Lys]$_4$ [COCH$_2$O-3,6-Naph(SO$_3$Na)$_2$]$_6$ [ε,ε-CBz]$_2$
BHALys [GlyLys]$_2$ [Lys]$_4$ [Boc]$_6$ [ε,ε-COCH$_2$O-3,6-Naph(SO$_3$Na)$_2$]$_2$ The macromolecule may be utilised in a composition for use method for the prophylactic or therapeutic treatment of sexually transmitted infections including administering to a mammalian patient an effective amount of the composition as described above. The anti-sexually transmitted microbial macromolecule may also be used in a composition for the prophylactic or therapeutic treatment of a sexually transmitted infection in a mammalian patient. Preferably the mammal is a human.

2. Drug Sustenance Macromolecule

A macromolecule according to the present invention may serve as an improved drug delivery platform with defined pharmacokinetics and release profiles.

Many drugs fail in clinical trials either because their physical properties (particularly solubility) make them difficult to formulate; or because of a poor therapeutic index that leads to toxic effects during the high drug concentrations that occur just after dosing.

There are many emerging technologies which seek to provide a drug delivery vehicle which will act to overcome poor drug solubility by capturing the drug in some kind of soluble matrix or particle; and reduce toxicity through controlled release or targeting drug to the site of disease prior to release.

We have demonstrated that it is possible to control the pharmacokinetics of a macromolecule by manipulation of the surface PEG group size. In the macromolecule of FIG. 15 the drug of interest is covalently attached to the macromolecule through a linker that cleaves in a manner consistent with the disease treatment (i.e. either hydrolyses slowly in plasma or is cleaved specifically at the disease site).

In a preferred embodiment, the macromolecule according to the present invention includes one or more different pharmaceutically active agents, derivatives thereof, precursors therefore, or residues thereof, as functional moieties. The macromolecules according to this aspect of the present invention may have application in combination therapy.

The pharmaceutically active agent may be an anti-tumor agent selected from one or more of the following: rituximab, oxaliplatin, docetaxel, gemcitabine, trastuzumab, irinotecan, paclitaxel, bevacizumab, carboplatin, cetuximab, doxorubicin, pemetrexed, epirubicin, bortezomib, topotecan, azacitidine, vinorelbine, mitoxantrone, fludarabine, doxorubicin, alemtuzumab, carmustine, ifosfamide, idarubicin, mitomycin, fluorouracil, cisplatin, methotrexate, melphalan, arsenic, denileukin diftitox, cytarabine, calcium levofolinate, cyclophosphamide, etoposide, *viscum album*, mesna, gemtuzumab, ozogamicin, busulfan, pentostatin, cladribine, bleomycin, daunorubicin, bendamustine, dacarbazine, raltitrexed, vincristine, fotemustine, etoposide phosphate, porfimer sodium and vinblastine.

The pharmaceutically active agents may be a combination of any one or more of the categories exemplified in Table 1A or B, and/or anti-tumor agents listed above.

Exemplary combinations include, but are not limited to, combinations of: chemotherapeutic pharmaceuticals; anti-inflammatory pharmaceuticals and anti-arthritic pharmaceuticals; obesity therapeutics and diabetes therapeutics; growth hormones and growth promoters; muscle relaxants and anti-inflammatories; respiratory pharmaceuticals and bronchodilators or anti-microbials; chemotherapeutics and vitamins and the like.

3. Anti-Inflammatory Macromolecule

An inflammatory response is produced in response to infection, immune responses and trauma. The various cellular processes involved in the inflammation response provide targets for potential anti-inflammatory therapies. The most commonly used anti-inflammatory drugs are the non-steroidal anti-inflammatory drugs (NSAIDs). Most NSAIDS act as non-selective inhibitors of the enzyme cyclooxygenase (COX), meaning that both COX-1 and COX-2 isoforms of the enzyme are targeted. However a subset of NSAIDs selectively target COX-2. Steroidal anti-inflammatory drugs act by binding to cortisol receptors.

Protein binding to cell surface carbohydrates is a key trigger of the inflammatory response. Therefore, receptor-ligand interactions between carbohydrates and proteins are also a potential mechanism to be targeted in the modification of the inflammatory response.

Treatments to inhibit an inflammatory response are often limited by the inability to target the area of inflammation with a high enough concentration of an anti-inflammatory drug and/or the low water solubility of the anti-inflammatory drug. Other short comings include poor absorption, poor bioavailability, instability, systemic side effects due to an inability to target the drugs, and the inability to control their biodistribution, metabolism and renal or hepatic clearance once administered. Furthermore the therapeutic profile of many anti-inflammatory drugs already on the market could be improved by providing formulations with better bioavailability, targeting etc.

It would be useful to be able to provide anti-inflammatory agents desirably in a form with reduced toxicity and/or improved targeting to the site of action and/or improved bioavailability.

Accordingly, the macromolecule of the present invention may be used as delivery vehicles for inflammatory response-modulating agents, such as anti-inflammatory drugs or carbohydrates. Such macromolecules have the potential to provide multivalent delivery systems for agents that have a potential anti-inflammatory function, due to the ability of single or multiple agents to participate in polyvalent interactions with, for example, cell surface receptors. The macromolecule of the present invention also may be used to simultaneously target different aspects of the inflammatory response and related responses by combining two or more active agents in the same delivery vehicle to achieve a faster and more effective treatment.

An example of such a macromolecule is illustrated in FIG. 21; see also Example 66.

The macromolecules of the present invention may include functional moieties that are inflammatory response-modulating agent. These act to inhibit the production of proinflammatory chemokines and/or cytokines, or may inhibit the action of a second messenger involved in the inflammatory response, such as a prostaglandin. Suitable inhibitors of prostaglandin include non-selective and selective cyclooxygenase (COX) inhibitors. The inflammatory response-modulating agent may alternatively act by inhibiting phospholipid metabolism and suppressing the immune response or by inhibiting the receptor-mediated synthesis of proinflammatory cytokines and/or chemokines.

The inflammatory response-modulating agent may be a steroid; a non-steroidal anti-inflammatory drug; an agent that modulates cell-surface receptor-ligand interactions or other agent capable of modulating cellular activities responsible for the inflammatory response. For example, the inflammatory response-modulating agent may be a saccharide or oligosaccharide containing carbohydrate moieties selected from: glucosamine, sialic acid, mannose, furanose, glucuronic acid, iduronic acid, galactose; or analogues or O- or N-sulfated derivatives thereof.

Further examples of inflammatory response-modulating agents that may be used in the present invention include, but are not limited to the following:
diclofenac; diflunisal; etodolac; fenoprofen; floctafenine; flurbiprofen; ibuprofen; indomethacin; ketoprofen; meclofenamate; menamic acid; molicam; nabumentone; naproxen; oxaprozin; phenylbutazone; piroxicam; sulindac; tenoxicam; tiaprofenic acid; tolmetin; celecoxib; valdecoxib; rofecoxib; glucosamine; glucocorticoids; and corticosteroids, such as beclomethasone, budesonide, dexamethasone, fluticasone, prednisone, methylprednisolone, mometasone furoate, triamcinolone and hydrocortisone.

The macromolecule may be modified to include a second functional moiety. The second moiety may be capable of modulating an inflammatory response. Alternatively, the second moiety may have a complementary therapeutic or prophylactic activity, or may modify the characteristics of the macromolecule by providing, for example, targeting of the macromolecule, increased plasma half life, or reduced toxicity.

Scar formation following injury or surgery results from a combination of an inflammatory response and an angiogenesis response that promotes fibroblast proliferation. Using a combination of an anti-inflammatory agent together with an anti-angiogenesis agent as terminus groups in the macromolecule according to the present invention may allow the simultaneous targeting of both mechanisms responsible for scar formation. An examples of anti-angiogenic agents that may be included as a terminus group is glucosamine-6-sulphate (Shaunak et al., 2004). A further example of a functional moiety having anti-angiogenic function is provided in AU2005905858 (the entire contents of which is incorporated herein by reference) and is represented as follows:

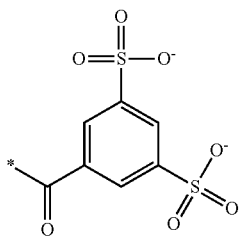 [SMILES: *C(=O)c1cc(S(=O)(=O)[O-])cc(S(=O)(=O)[O-])c1]

In a further embodiment, the macromolecule includes a second functional group that targets the macromolecule to a specific cell and/or tissue type. Examples of targeting groups include ligands for cell surface markers specific to particular cell types, for example: Cellular adhesion molecules (CAMs) such as E-selectin, P-selectin, VCAM-1, ICAM-1, integrins, chemokine receptors such as CCR3, CXCR1, CXCR3; receptors for cytokine such as IL-1, TNF-alpha, TGF-beta, IL-6, IL-2; receptors for growth factors such as VEGF and FGF; Toll-like receptors; CD40 ligand (TNF superfamily); Heat shock protein 70 (HSP70); Fc receptors such as FcRII; procoagulant molecules such as tissue factor (TF) and platelet glycoproteins such as collagen, fibronectin, von Willebrands factor.

Some embodiments of the invention will now be described more fully with reference to the following non-limiting examples and figures:

In the figures:

FIG. 1 illustrates a lysine macromolecule according to a preferred embodiment of the invention with a lysine benzylhydrylamide divalent core, and three layers of building units. Cleavage of the linkage L shown provides dendritic motif F1.2, which is a 3 layer lysine dendritic motif (note the eight bold N moieties represent the surface amines). The apex carbonyl moiety is now at L. R can either be a functional moiety that is a protecting group or any other type of functional moiety. Another form of this dendritic motif is described in F1.3 wherein the apex carbonyl is in the form of a carboxylate moiety is described in full: such a motif may be prepared and used as part of the embodiments of this invention.

FIG. 2 is a schematic representation of a selected topological isomer of a lysine dendritic macromolecule according to a preferred embodiment of the invention having four layers of building units from the ethylenediamine core, and bearing a total of 32 functional moieties A and B in a ratio of 1:1. A, B represent two different functional moieties that may be protecting groups or other functional moieties. Bold bonds indicate the outermost building unit to which all the encircled functional moieties are connected, and the functional moieties of the circled dendritic motif are underlined in the nomenclature. Further note in 2.1. the arrow to indicate the origin, and reading frame, that is used to generate the alphanumeric topological nomenclature discussed in the text. 2.1 use of couplets; 2.2 use of quartets; 2.3 use of octets; 2.4 use of 16-tets. building units (Lysine analogues): F2.5 Core; F2.6 subsurface building unit; F2.7 surface building unit bearing functional moieties (AA); and F2.8 (BB).

FIG. 3 is a schematic representation of selected topological isomers of lysine dendritic macromolecules according to a preferred embodiment of the invention having four layers of building units from the ethylenediamine core and bearing a total of 32 functional moieties A and B in a ratio of 1:1. A, B represent two different functional moieties that may be protecting groups or other functional moieties. The topological isomers are defined using nomenclature described in the text at the level of 16-tet building units (Lysine analogues): Topological equivalence of F3.6 and F3.7 asymmetric lysine surface units bearing functional moieties (AB) and symmetric lysine building unit F3.8.

FIG. 4 is a schematic representation of equivalent topological isomers according to a preferred embodiment of the invention of three layers of lysine or lysine analogue building units from the apex F having a 1:1 surface stoichiometric ratio of A and B. A, B represent two different functional moieties that may be protecting groups or other functional moieties and F represents the carbonyl moiety at the apex. Each representation differs by a 180° rotation of the indicated inter-building unit bond. F4.4 is a representation of a dendritic motif with asymmetric building units. Such a structure is simplified by "symmetrising" the building unit prior to undertaking the bond rotation analysis.

FIG. 5 is a schematic representation of selected topological isomers of lysine dendritic macromolecules according to a preferred embodiment of the invention having four layers of building units from the ethylenediamine core and bearing a total of 32 functional moieties A, B and D in a ratio of 2:1:1. The topological isomers are defined using nomenclature described in the text at the level of 16-tet.

FIG. 6 is a schematic representation of selected topological isomers according to a preferred embodiment of the invention of lysine variegated dendritic macromolecules of four layers from the ethylenediamine core in which linkers have been used. A and B represent two different functional moieties that may be protecting groups or other functional moieties and Ø is the null symbol used to represent functional moieties lost from an ideal $FM_{MAX}$ due to linkers replacing building units. F6.1 use of couplets and the dendritic macromolecule in which $FM_{total}=FM_{MAX}$; F6.2 use of quartets with linkers replacing surface building units; F6.3 use of octets and linkers replacing surface-but-one building units; F6.4 use of 16-tets and linkers replacing surface-but-two building units. Rectangles highlight functional moieties as Ø lost due to use of linkers. F6.5 internal linker.

FIG. 7 is a schematic representation of selected topological isomers according to a preferred embodiment of the invention of lysine variegated dendritic macromolecules of four layers from the ethylenediamine core in which linkers have been used. A, B and D represent three different functional moieties that may be protecting groups or other functional moieties. The topological isomers are defined using nomenclature described in the text at the level of 16-tet. F7.1 shows a variegated dendritic macromolecule in which linkers replace surface building units to provide a surface stoichiometry of 8A:16B:4D; F7.2 shows a dendritic macromolecule in which linkers replace surface-but-one building units to provide a surface stoichiometry of 8A:16B; F7.3 a dendritic macromolecule in which linkers replace surface-but-two building units to provide a surface stoichiometry of 8A:8B:81D, F7.4 shows a dendritic macromolecule in which a linker replaces a surface-but-three building unit to provide a surface stoichiometry of 12A:8B:4D; F7.5 shows a dendritic macromolecule in which linkers replace both surface-but-two and surface-but-three building units to provide a surface stoichiometry of 8B:8A.

FIG. 8 is a schematic representation of selected topological isomers according to a preferred embodiment of the invention of lysine variegated dendritic macromolecules of four layers from the ethylenediamine core in which end stopping functional moieties have been used. A and B represent two different functional moieties that may be protecting groups or other functional moieties and Ø is the null symbol used to represent functional moieties lost from an ideal $FM_{MAX}$ due to an end stopping functional moiety at a subsurface building unit. F8.1 use of couplets and the dendritic motifs in which $FM_{total}=FM_{MAX}$; F8.2 use of quartets with end stopping functional moieties R1 and R2 at surface-but-one building unit; F8.3 use of octets and end stopping functional moieties R1 and R2 at surface-but-two building unit; F8.4 use of 16-tets and end stopping functional moieties at surface-but-three building unit. Rectangles highlight functional moieties as Ø lost due to end stopping. F8.5 Building units bearing end stopping functional moieties.

FIG. 9 is a schematic representation of selected topological isomers according to a preferred embodiment of the invention of lysine variegated dendritic macromolecules of four layers from the ethylenediamine core in which linkers have been used. A and B represent two different functional moieties and R1, R2 represent end stopping functional moieties. The topological isomers are defined using nomenclature described in the text at the level of 16-tet. F9.1 shows a variegated dendritic macromolecule in which end stopping reactions have been used at the surface layer of building units to provide a surface stoichiometry of 16R1:16R2; F9.2 shows a dendritic macromolecule in which end stopping reactions have been used at the surface-but-one layer of building units to provide a surface stoichiometry of 4R1:16B:8A; F9.3 shows a dendritic macromolecule in which end stopping reactions have been used at the surface-but-two layer of building units to provide a surface stoichiometry of 4R1:16B; F9.4 shows a dendritic macromolecule in which end stopping reactions have been used at the surface-but-three layer of building units to provide a surface stoichiometry of 2R1:8B:8A; F9.5 shows a dendritic macromolecule in which end stopping reactions have been used at both the surface-but-one and surface-but-two layers of building units to provide a surface stoichiometry of 4R1:4R2:8A.

In Scheme 1: i. Reaction of BHALys [Boc]$_2$ with trifluoroacetic acid in dichloromethane; ii. Reaction of BHALys [NH$_2$.TFA]$_2$ with excess PFP-Lys-α-Fmoc-ε-Boc and base in DMF; iii. Reaction of BHALys [Lys]$_2$ [α-Fmoc]$_2$ [ε-Boc]$_2$ with trifluoroacetic acid in dichloromethane; iv. Reaction of BHALys [Lys]$_2$ [α-Fmoc]$_2$ [ε-NH$_2$.TFA]$_2$ with excess PNPO-Lys-(Boc)$_2$ and base in DMF; v. Reaction of BHALys [Lys]$_2$ [α-Fmoc]$_2$ [ε-Lys]$_2$ [Boc]$_4$ with excess piperidine in DMF.

Figure 13:
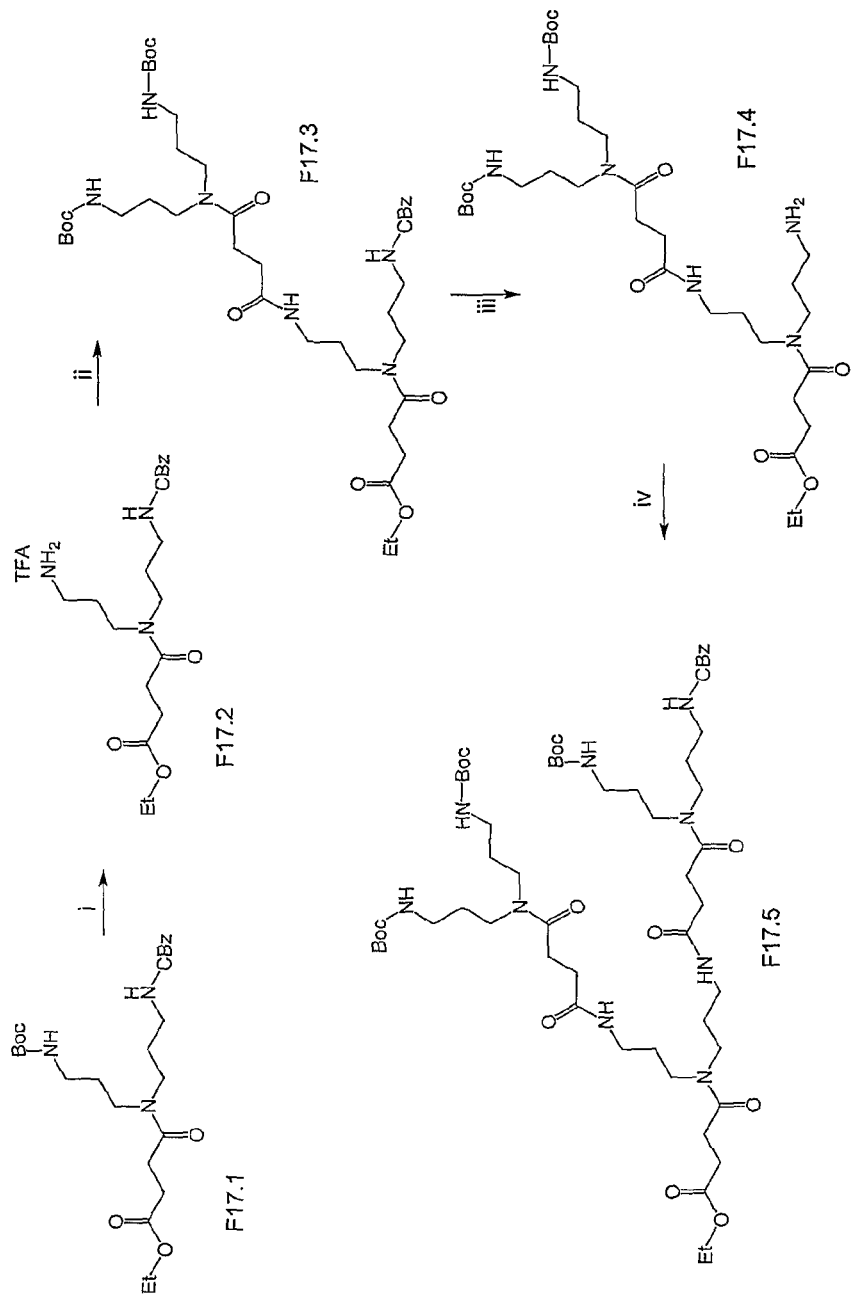

FIG. 13 is a schematic illustration of the synthesis of Example 18 (Scheme 2).

In Scheme 2: i. Reaction of EtOSu[NPN]$_2$ [Boc] [CBz] with a mixture of TFA and Acetic acid; ii. Reaction of EtOSu [NPN]$_2$ [NH$_2$.TFA] [CBz] with PNPOSu[NPN]$_2$ [Boc]$_2$ in DMF and TEA; iii. Reaction of EtOSu[NPN]$_2$ [CBz] [Su [NPN]$_2$] [Boc]$_2$ with ammonium formate and Pd on C in DMF/Water; iv Reaction of EtOSu[NPN]$_2$ [NH$_2$] [Su[NPN]$_2$] [Boc]$_2$ with PNPOSu[NPN]$_2$ [Boc] [CBz] in DMF and TEA provided EtOSu[NPN]$_2$ [Su[NPN]$_2$]$_2$ [CBz] [Boc]$_3$.

Figure 14A:
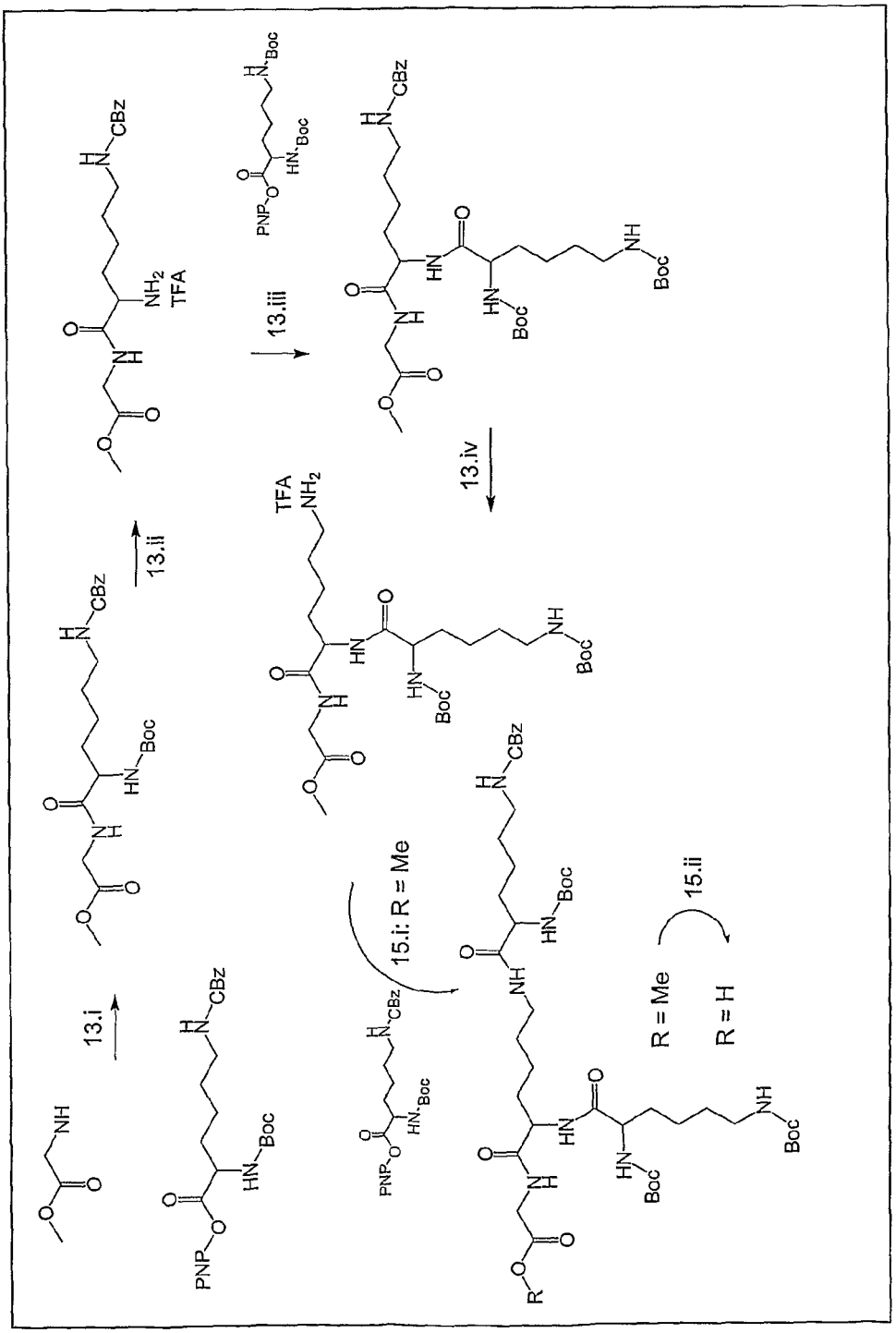
Figure 14B:
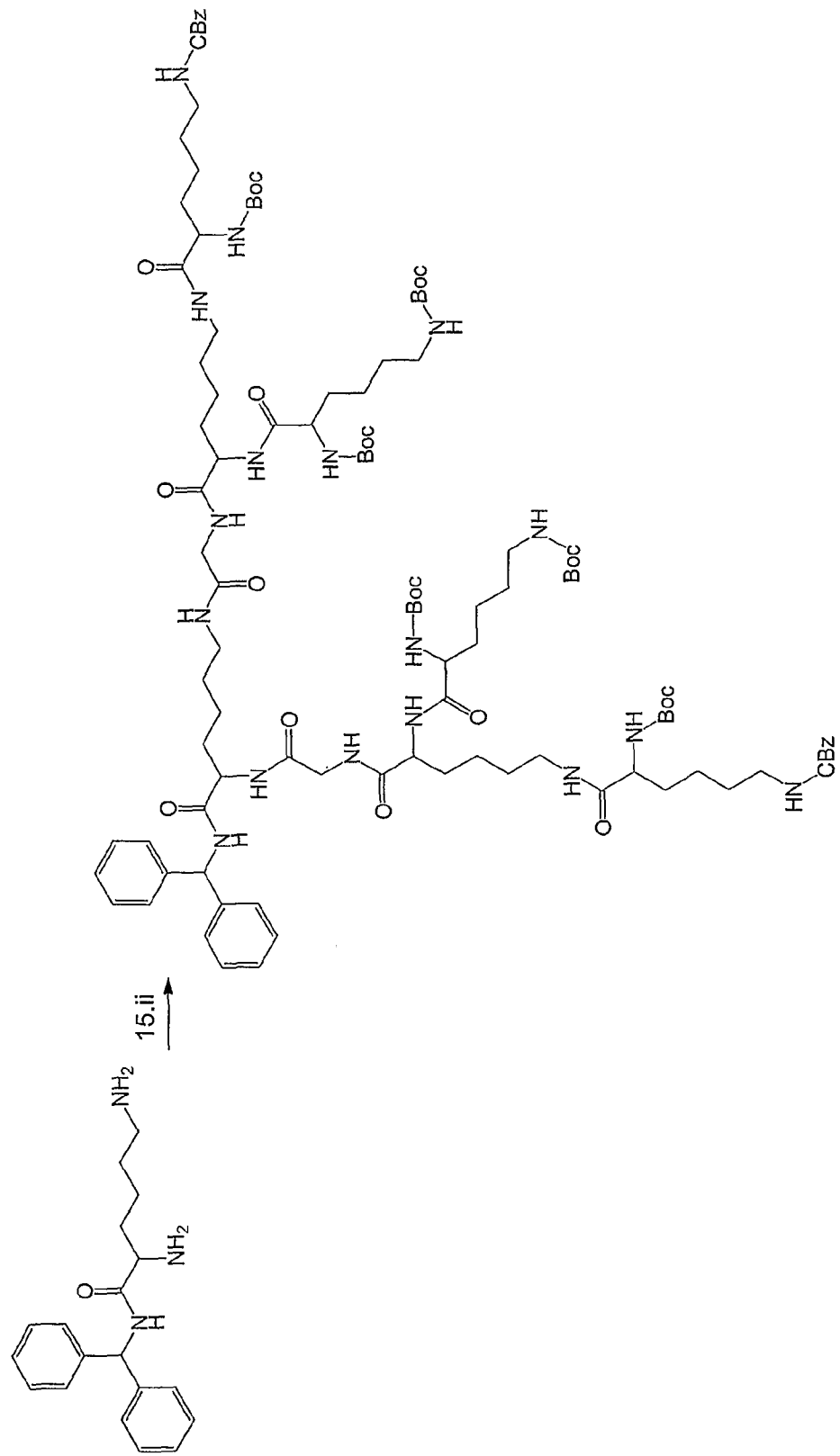

FIGS. 14A and 14B are schematic illustrations of the synthesis of a macromolecule (Example 15) that makes use of a dendritic motif prepared in Example 13.

In Scheme 3: 13.i. Reaction of methyl glycinate with PNPO-Lys-α-Boc-ε-CBz in DMF and TEA; 13.ii. Reaction of MeO-GlyLys [α-Boc] [ε-CBz] with TFA and Acetic acid; 13.iii. Reaction of MeO-GlyLys [α-NH$_2$.TFA] [ε-CBz] with PNPO-Lys(Boc)$_2$ in DMF and TEA; 13.iv. Reaction of MeO-GlyLys [ε-CBz] [α-Lys] [Boc]$_2$ with H$_2$ and Pd on Carbon in Methanol with TFA; 15.i. Reaction of GlyLys [ε-NH$_2$.TFA] [α-Lys] [Boc]$_2$ with PNPO-Lys-α-Boc-ε-CBz in DMF and TEA; 15.ii. Reaction of MeOGlyLys [Lys]$_2$ [Boc]$_3$ [ε,ε-CBz] with NaOH in Methanol/Water to give HO-GlyLys [Lys]$_2$ [Boc]$_3$ [ε,ε-CBz].

In Scheme 4: 15.ii. Reaction of BHALys [NH$_2$.TFA]$_2$ with HO-GlyLys [Lys]$_2$ [Boc]$_3$ [ε,ε-CBz], DCC and DMAP in DMF and TEA to give BHALys [GlyLys]$_2$ [Lys]$_4$ [Boc]$_6$ [ε,ε-CBz]$_2$.

Figure 15A:
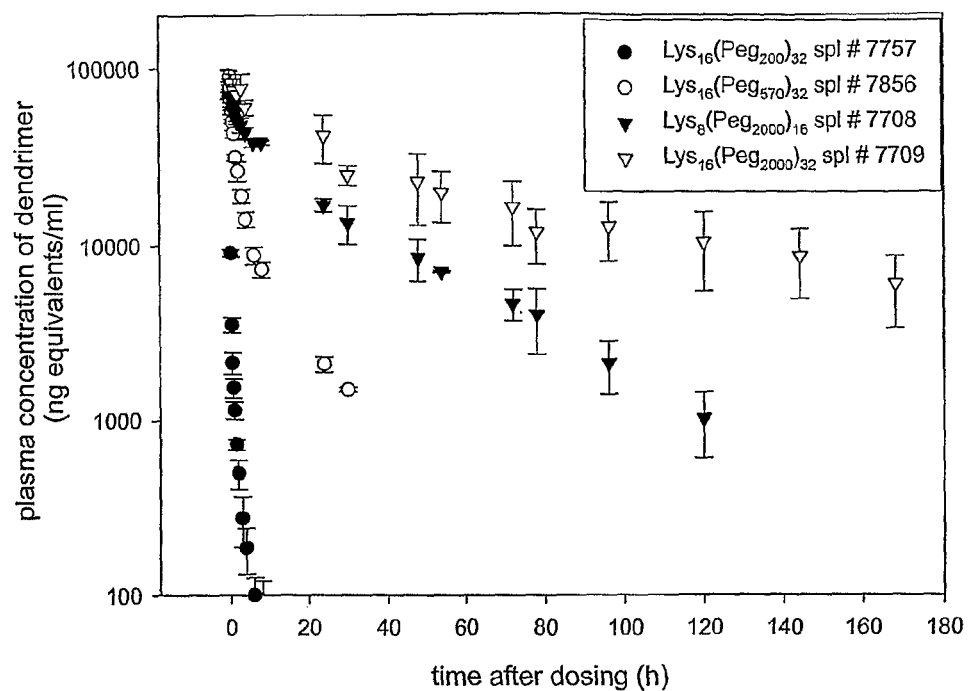

FIG. 15A is a graph showing plasma concentration levels over time of various macromolecules identified in Table 6, Example 64.

Figure 15B:
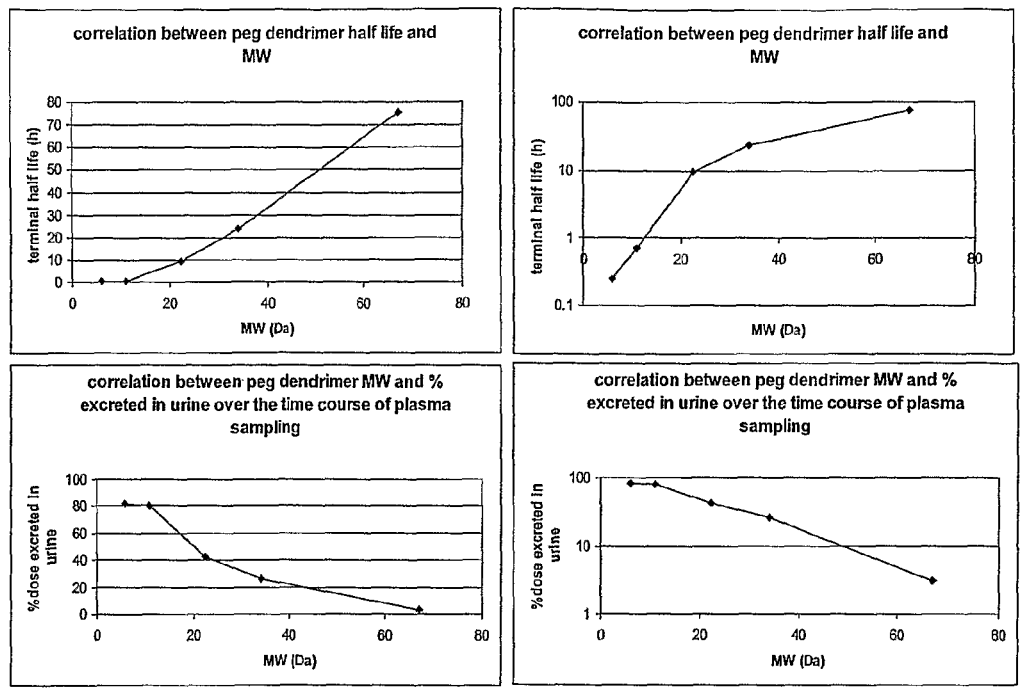

FIG. 15B is a series of graphs illustrating the correlation between PEG macromolecule half-life and molecular weight, on a linear and logarithmic scale and the correlation between PEG macromolecule molecular weight and a % excreted in urea over time, on a linear and logarithmic scale.

FIG. 16 shows the set of five topological isomers of the asymmetric macromolecule structures in a 2D representation as described in Example 65. The diagrams show the locations of the labelled functional moieties A and B for the five different types of topological isomers that were compared in Example 65.

FIG. 17 provides 3D graphical representations which derive from the computer modelling simulations conducted in Example 65 and demonstrate the distributions of the A and B functional moieties for five types of topological isomers of the macromolecules according to the present invention.

Figure 18:
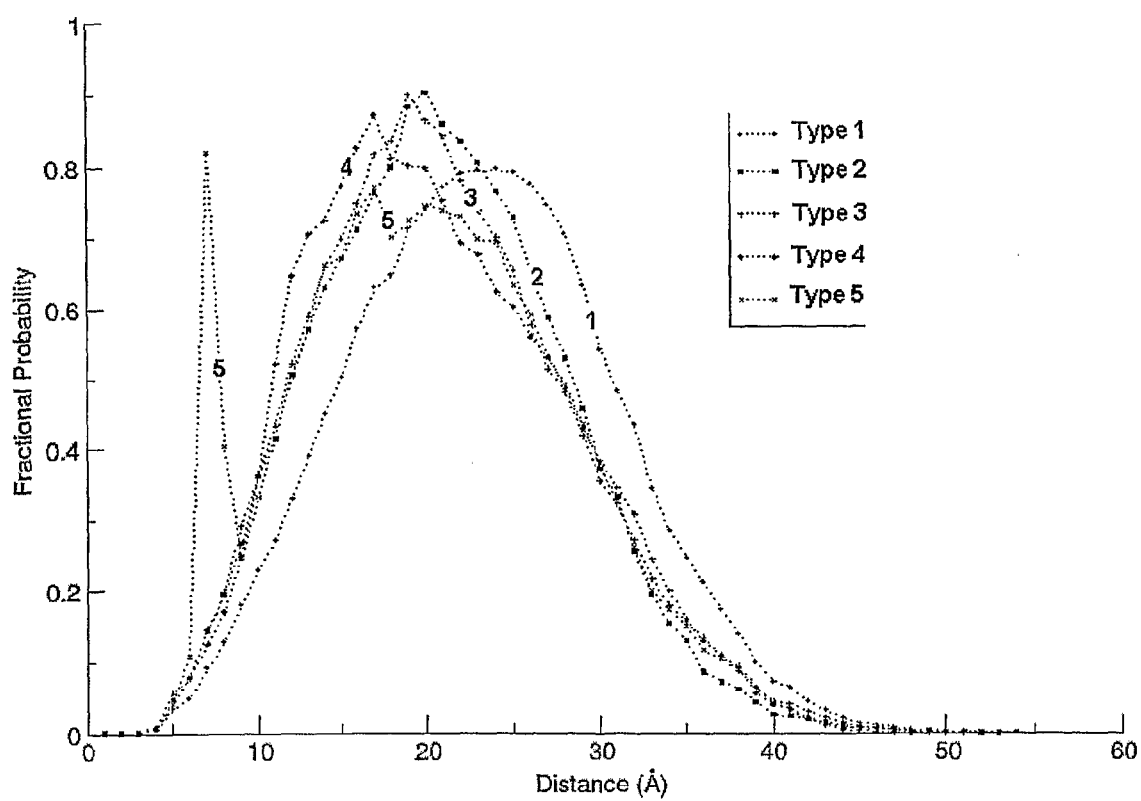

FIG. 18. The distributions of all distances from functional moieties A to functional moieties B, and the variation with clustering type from Example 65: asymmetric building units (see text). Results are shown as the fractional probability, that is, the chance of finding a functional moiety of the different type within 0.5 Å of the indicated distance.

Figure 19:
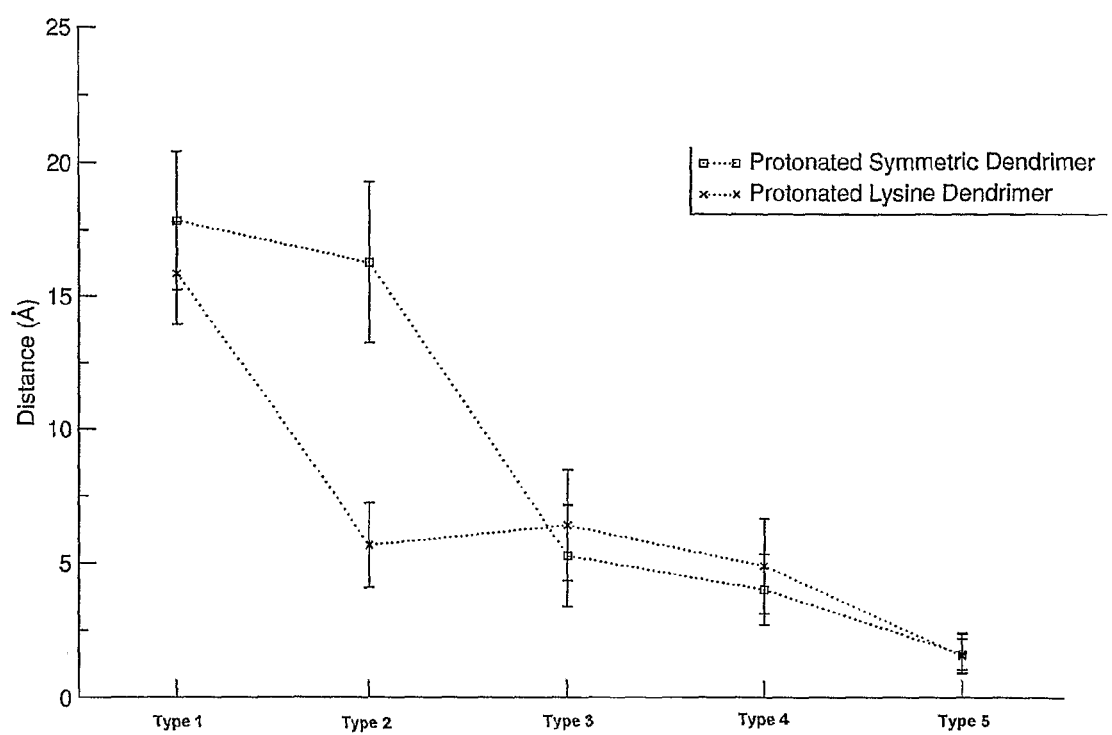

FIG. 19 is a graph of the distances between the centre of mass of the functional moieties A and the centre of mass of the functional moieties A for each of the cluster types from Example 65: asymmetric. The error bars represent ±1 standard deviation.

Figure 20:
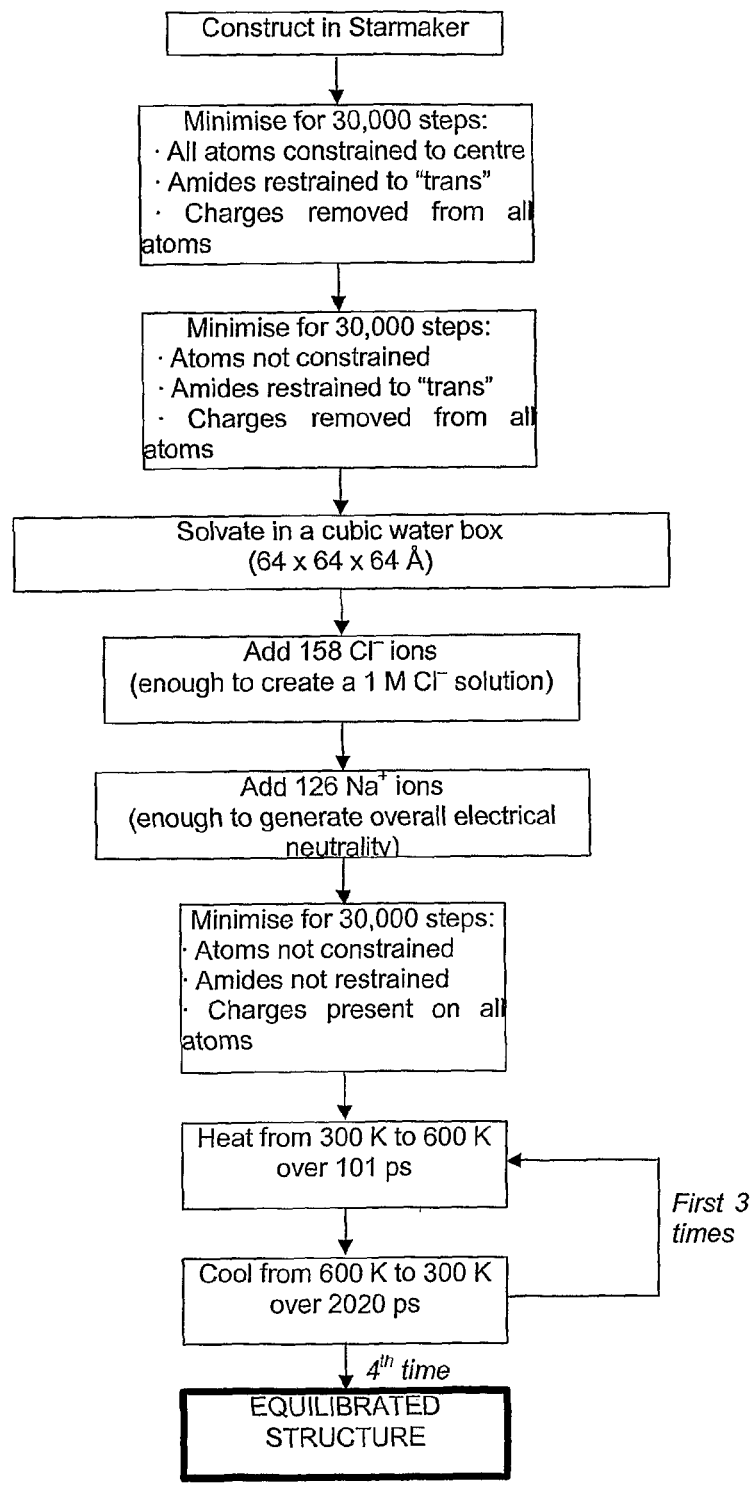

FIG. 20 is a schematic diagram of the protocol used to obtain an equilibrated macromolecule structure in Example 65.

Figure 21:
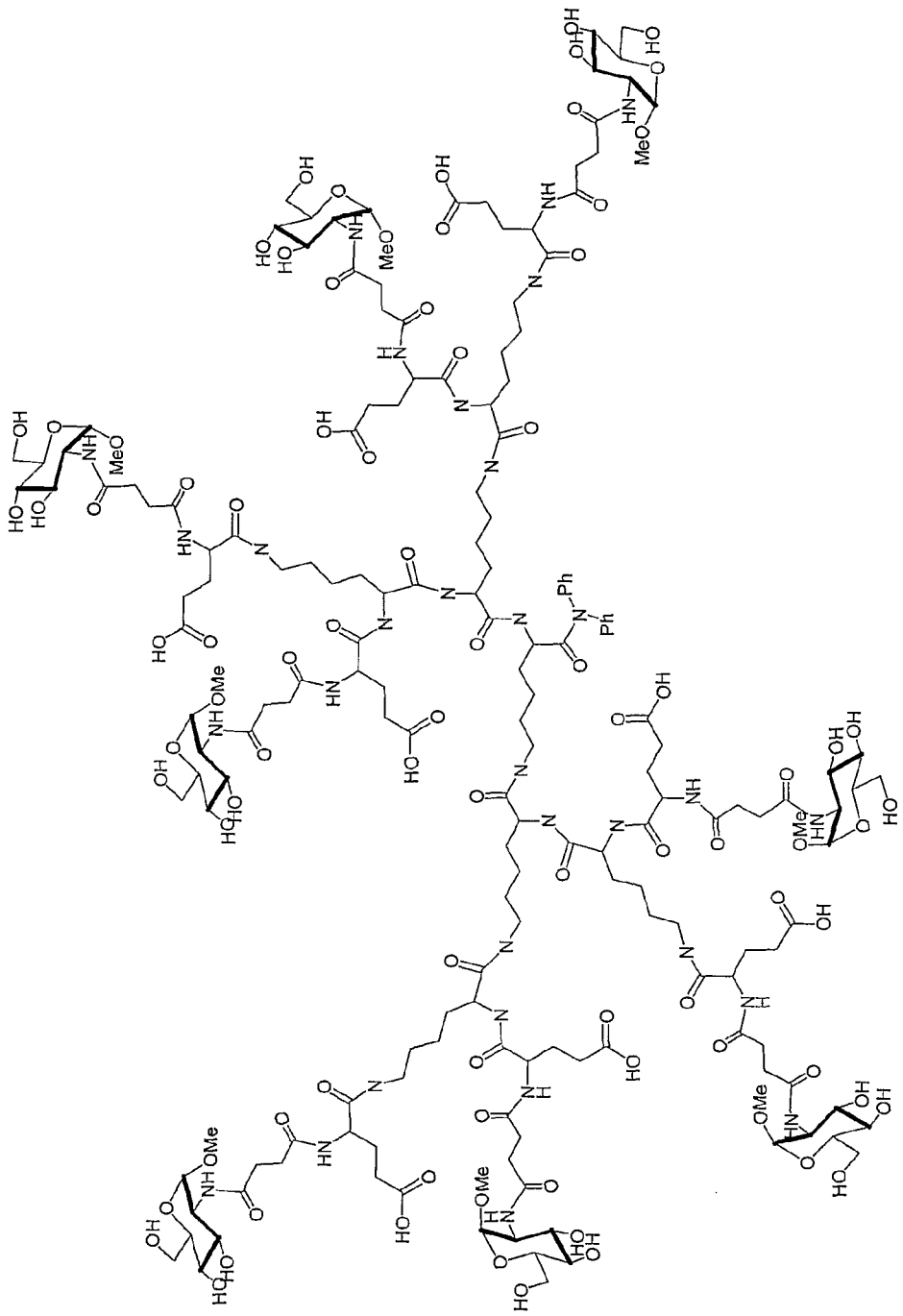

FIG. 21 is BHALys [Lys]$_2$ [Glu]$_4$ [α-COC2-α-S-GlcNAc]$_4$ [γ-CO$_2$H]$_4$ which is described in Example 66; this is an anti-inflammatory macromolecule according to a preferred embodiment of the invention, bearing surface carbohydrate groups and carboxylate moieties in a 1:1 stoichiometry.

EXAMPLES

The following examples serve to illustrate the invention. The examples are based on lysine building units, but are not limited to such. Examples 1 to 28 are structural examples which demonstrate the synthesis of the macromolecules and dendritic motifs of this invention. Included in the Structural section is a demonstration (Example 28) of the Chromatographic behaviour of different topological isomers which have a common surface group stoichiometry. This example shows that the topological isomers interact with the stationary phase differently, yielding different retention times which are recorded in Table 23.

In the Antimicrobial section, Examples 29 to 50 describe a number of macromolecules with two different functional moieties which have anti-HIV activity. The anti-HIV data is collected in Table 24 of Example 50. Again, a set of comparative data provides evidence that topological isomers with a common surface group stoichiometry can provide different biological activities. It is particularly important to note the potent anti-microbial activity achieved with Examples 46 and 48, which are significantly more active than SPL7013, a homogenous surface dendrimer. This demonstrates the usefulness of being able to provide a macromolecule with controlled stoichiometry/topology that includes two different functional moieties.

In the ADME section, Examples 51 to 64 provide a series of macromolecules with surfaces comprised of both pharmaceutical active agents and modifier compounds. The data provided by Example 64: see Table 25 and FIGS. 15A and 15B, serves to demonstrate how the pharmacokinetic behaviour of macromolecules can 14 controlled through the appropriate tuning of the type and size of modifying functional moiety used on the surface in conjunction with the pharmaceutically active moiety. An important feature of these macromolecules is the controlled stoichiometry and topology of the pharmaceutically active moiety or residue thereof to surface modifier (PEG).

In the Anti-Inflammatory section, it has been demonstrated by the data provided in Example 73, Table 27 that macromolecules with a homogenous surface of anionic functional moieties, 73.11 and 73.12 have anti-inflammatory activity. It has also been observed that one of the macromolecules, 73.8 with a homogenous surface of the glucosamine moiety: COC2CO-2-N-α-OMe-Glc functional moiety has anti-inflammatory activity. It is anticipated that macromolecules which combine anionic functional moieties with functional moieties that include the Glucosamine residue, such as Examples 66 through 71, with defined stoichiometries of 1:1, 1:2, 1:3, 1:4, 1:5, 1:6 and 1:7 of saccharide to anionic functional moiety, will have therapeutic anti-inflammatory activity on the basis that these molecules provide a controlled stoichiometry/topology of the two Functional Moieties which contribute to the anti-inflammatory activity of the homogenous surface compounds.

A system of nomenclature has been developed for the purposes of identifying the individual compounds described in this patent. The macromolecule nomenclature makes use of the abbreviations in the following table.

TABLE 21

Macromolecule Nomenclature Abbreviations and Structures

| Abbreviation | Function | Name | Structure[1] |
|---|---|---|---|
| BHALys | Core | Benzhydrylamidolysine | |
| DAH | Core | Diaminohexane | |
| EDA | Core | Ethylenediamine | |
| TETA | Core | Triethyltetraamine | |
| NEOEOENLys | Core | | |

TABLE 21-continued

Macromolecule Nomenclature Abbreviations and Structures

| Abbreviation | Function | Name | Structure[1] |
|---|---|---|---|
| Su(NPN)$_2$ | Building unit | | (structure shown) |
| Lys | Building unit | Lysine | (structure shown) |
| GlyLys | Building unit | | (structure shown) |
| NH$_2$•TFA | | | Represents the surface amine groups of the building units, here shown as the TFA salt, and is treated as a "functional moiety" for the purposes of the nomenclature. |
| Glu | Surface building unit | Glutamate | (structure shown) |
| CO$_2$H | | | Represents the surface carboxylate groups of the surface building units and is treated as a "functional moiety" for the purposes of the nomenclature. |
| Boc | Functional moiety | t-butyloxycarbonyl | 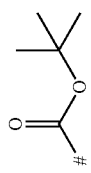 |

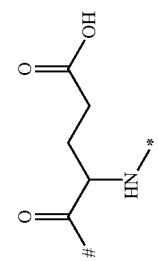

TABLE 21-continued

Macromolecule Nomenclature Abbreviations and Structures

| Abbreviation | Function | Name | Structure[1] |
|---|---|---|---|
| Fmoc | Functional moiety | Fluorenylmethoxy-carbonyl | |
| CBz | Functional moiety | Benzyloxycarbonyl | |
| 4-Nitro-CBz | Functional moiety | 4-Nitro-benzyloxycarbonyl | |
| COCH$_2$O-3,6-Napht(SO$_3$Na)$_2$ | Functional moiety | 1-carboxy-3,6-naphthyldisulfonic acid di-sodium salt | |

TABLE 21-continued

Macromolecule Nomenclature Abbreviations and Structures

| Abbreviation | Function | Name | Structure[1] |
|---|---|---|---|
| CO-3,5-Ph(SO$_3$Na)$_2$ | Functional moiety | 1-carboxy-3,5-phenyldisulfonic acid di-sodium salt | |
| CO-4-Ph(SO3Na) | Functional moiety | 1-carboxy-4-phenylsulfonic acid di-sodium salt | |
| CO$_2$(EtO)$_3$CH$_3$ | Functional moiety | | |
| PEG$_{200}$ | Functional moiety | | |
| COPEG$_{12}$ | Functional moiety | | |
| PEG$_{1100}$ | Functional moiety | | |

TABLE 21-continued

Macromolecule Nomenclature Abbreviations and Structures

| Abbreviation | Function | Name | Structure[1] |
|---|---|---|---|
| PEG$_{2KD}$ | Functional moiety | | |
| PEG$_{1716}$ | Functional moiety | | |
| PEG$_{2845}$ | Functional moiety | | |
| PEG$_{3974}$ | Functional moiety | | |
| α-t-Bu-MTX | Functional moiety | α-t-Butyl-N-[4-[[2,4-diamino-6-pteridinyl]methyl]methylamino]benzoyl]-L-glutamate | |

TABLE 21-continued

Macromolecule Nomenclature Abbreviations and Structures

| Abbreviation | Function | Name | Structure[1] |
|---|---|---|---|
| MTX | Functional moiety | N-[4-[[(2,4-diamino-6-pteridinyl)methyl]methylamino]benzoyl]-L-glutamate | 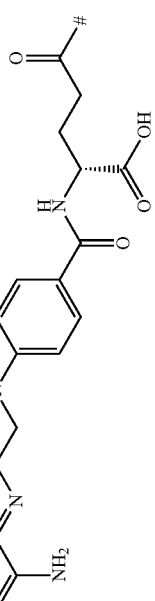 |
| COCH$_2$CH$_2$CO-Taxol | Functional moiety | | 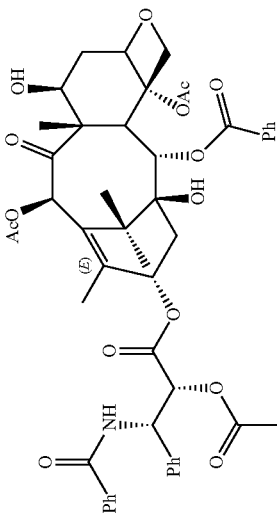 |
| COCH$_3$ | Functional moiety | Acetamide | 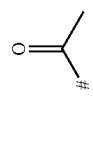 |
| COC2-α-S-GlcNAc | Functional moiety | | 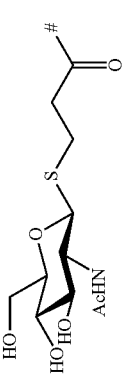 |

[1] Asterisk indicates amine group bonded as amide to carboxyl group of lysine building unit, surface building unit or functional moiety. Hash indicates carboxyl group bonded as amide to amine of core or building unit The dendrimer nomenclature in the following examples makes use of the following formula:

Core[Last Complete Layer; Building Unit]$_n$–[functional moiety]$_m$[Incomplete Outer Layer; Building Unit]$_p$[functional moiety]$_q$ Where:
  Core is the molecule to which the lysine building units are attached and will include at least one amine moiety to which the first layer of lysine building units is added; where a dendritic motif is described, the building unit which includes the apex carboxylate moiety is treated as the core,
  n is the number of lysine building units on the outermost complete layer of the macromolecule, p is the number of lysine building units on the incomplete outer layer of the macromolecule,
  m is the number of functional moieties for example pharmaceutical active moieties or protecting groups, on the outermost complete layer of building units; q is the number of functional moieties on the incomplete outer layer of building units, Optionally, a functional moiety, with or without building units may be appended to the core; these are then denoted as [functional moiety]$_r$ [building unit]$_s$ Core [Last Complete Layer; Building Unit]$_n$–[functional moiety]$_m$ [Incomplete Outer Layer; Building Unit]$_p$ [functional moiety]$_q$.

Where:
  r is the number of functional moieties appended, and
  s is the number of lysine building units on the outer layer of the motif appended to the core.

These Formulae are able to completely describe the size of a macromolecule through provision of the core and the outer layer(s) since sufficient information is provided about the building units and functional moieties used in the construction of these macromolecule structures and the valency of the core is known.

All lysine macromolecules prepared as the fully Boc protected forms were synthesised and purified according to the procedures described in patent WO95/34595. Removal of the Boc protecting group was conducted according to the procedures described in same patent.

Further chemical abbreviations are listed in Table 22.

TABLE 22

Chemical Names and Abbreviations.

| Abbreviation | Full Name |
|---|---|
| PyBop | Benzotriazole-1-yl-oxy-tris-pyrrolidino-phosphonium hexafluorophosphate |
| DMF | Dimethylformamide |
| DCM | Dichloromethane |
| TFA | Trifluoroacetic acid |
| DIPEA | Diisopropyl amine |
| TEA | triethylamine |
| Ether | Diethyl ether |
| EtOAc | ethyl acetate |
| DMSO | Dimethylsulfoxide |
| can | Acetonitrile |
| Rt | room temperature |
| Ca | Circa |
| Ppt | Precipitate |
| HPLC | High Performance Liquid Chromatography |
| MS | Mass Spectrometry |
| CE | Capillary Electrophoresis |
| PFP-Lys-α-Fmoc-ε-Boc | Pentafluorophenol active ester of α-Fmoc-ε-Boc-Lysine |
| PFP-Lys-α-Boc-ε-Fmoc | Pentafluorophenol active ester of α-Boc-ε-Fmoc-Lysine |
| HO-Lys-α-Fmoc-ε-Boc | α-Fmoc-ε-Boc-Lysine |
| PNPO-Lys-α-NH$_2$-ε-Boc | α-NH$_2$-ε-Boc-Lysine |
| PNPO-Lys-α,ε-(Boc)$_2$ | p-Nitrophenol active ester of α,ε-(Boc)$_2$-Lysine |
| PNPO-Lys(CBz)$_2$ | p-Nitrophenol active ester of α,ε-(CBz)$_2$-Lysine |
| PNPO-α-Boc-ε-CBz-Lys | p-Nitrophenol active ester of α-Boc-ε-CBz-Lysine |
| PNPO-α-CBz-ε-Boc-Lys | p-Nitrophenol active ester of α-CBz-ε-Boc-Lysine |

| Abbreviation | Full Name | Structure |
|---|---|---|
| BHA | Benzhydrylamine | 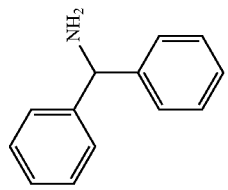 |
| [NPN]$_2$ [Boc] [CBz] | | 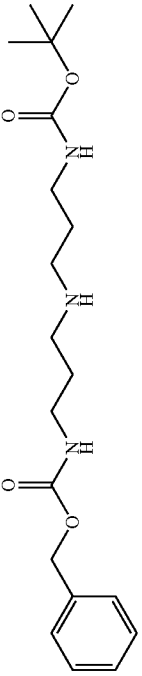 |

TABLE 22-continued
| 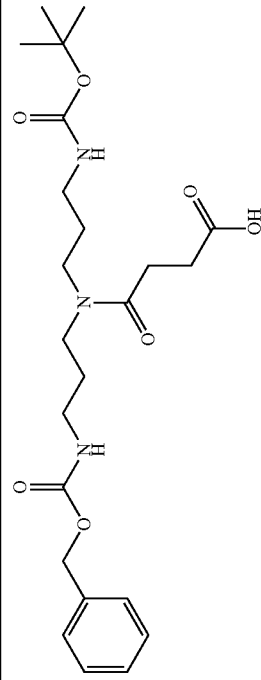 | 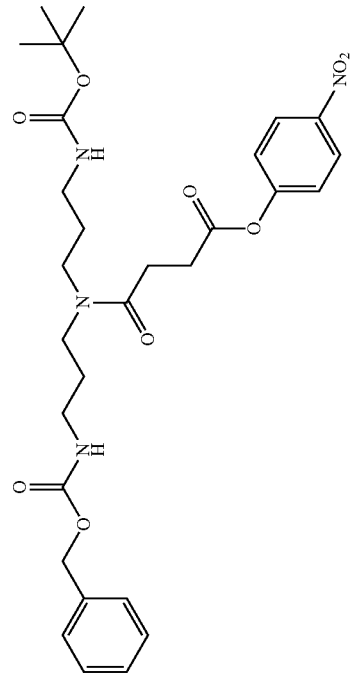 | 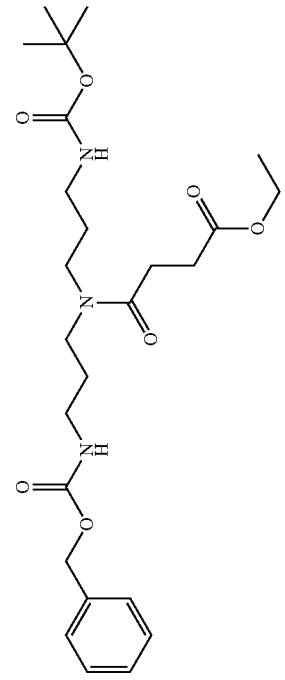 |
| --- | --- | --- |
| HO-Su[NPN]₂ [Boc][CBz] | PNPO-Su[NPN]₂ [Boc][CBz] | [BOC][CBz][NPN]₂SuOEt |

TABLE 22-continued
| | |
|---|---|
| [BOC][NH₂][NPN]₂SuOEt | 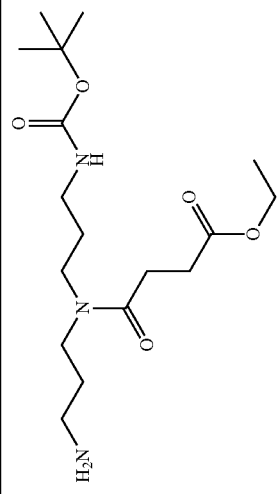 |
| MeO-GlyLys [α-Boc] [ε-CBz] | 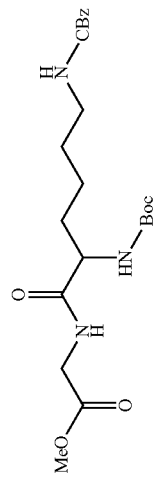 |
| HO-GlyLys [α-Boc] [ε-CBz] | 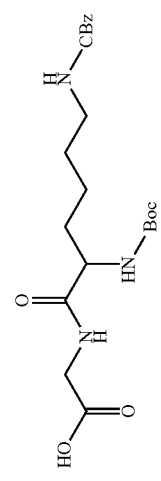 |
| PNPO-CO₂PEG₃ | |
| HO-Lys-α-CO₂PEG₃-ε-Boc | 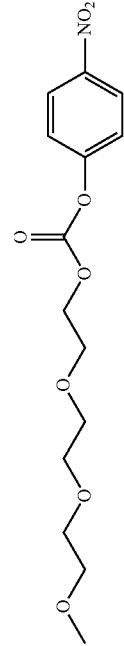 |

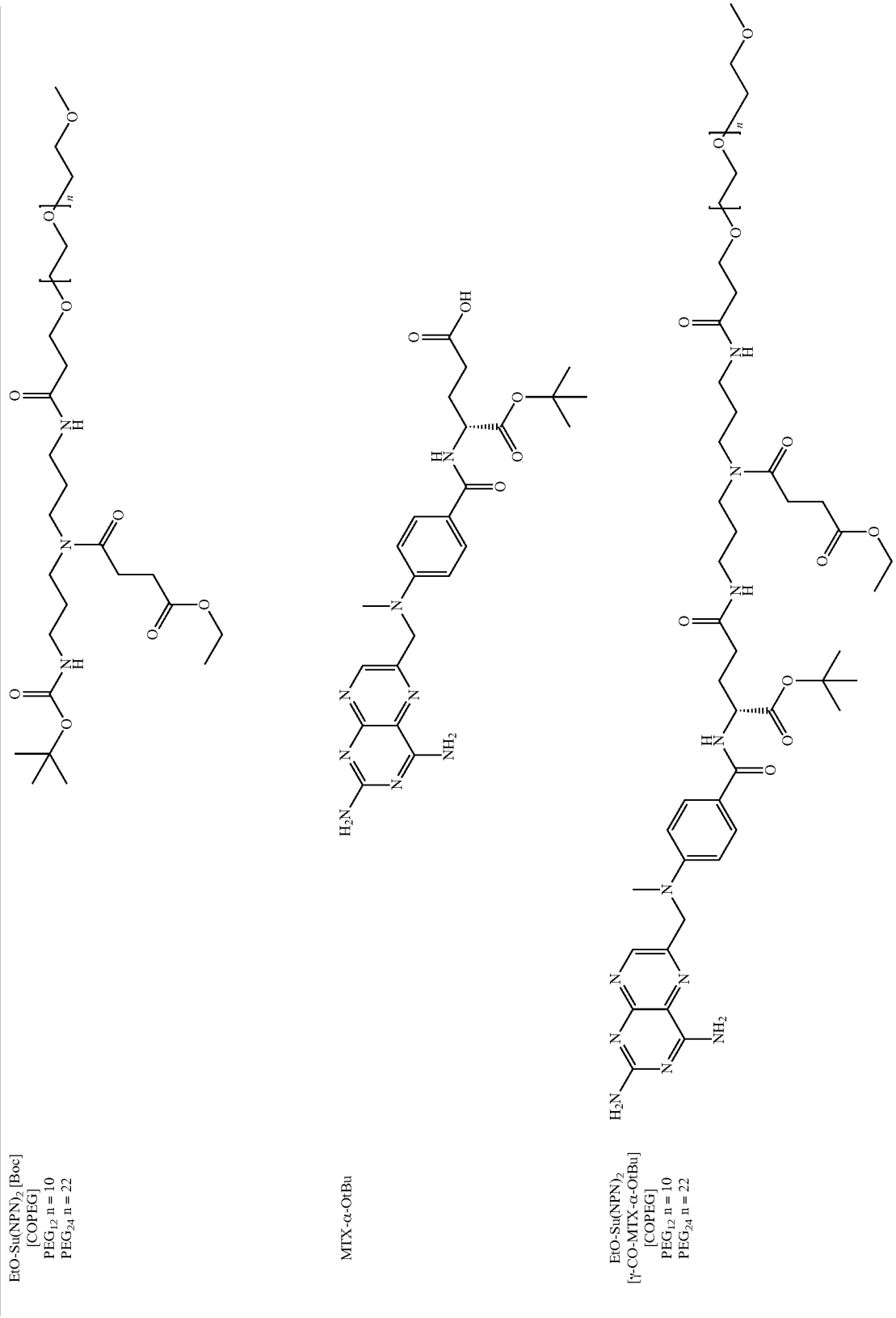

TABLE 22-continued

| | |
|---|---|
| HO-Su(NPN)₂[γ-CO-MTX-α-OtBu][COPEG] PEG₁₂ n = 10 PEG₂₄ n = 22 | |
| NHS-COC2-(perAc)-α-S-GlcNAc | (−) 2-Carboxyethyl 2-deoxy-2-acetamido-3,4,6-tetra-O-acetyl-1-thio-β-D-glucopyranoside. |
| HO-COC2-α-S-GlcNAc | (−) 2-carboxyethyl 2-deoxy-2-acetamido-1-thio-α-D-glucopyranoside |
| HO-COC2CO-2-N-α-OMe-Glc | Methyl 2-deoxy-2-[3-(methoxycarbonyl)propanamido]-α-D-glucopyranoside |
| PNPO-COC5-α-S-(perAc)-GlcNAc | 5-{[(4-nitrophenyl)oxy]carbonyl} pentyl 2-acetamido-3,4,6-tri-O-acetyl-2-deoxy-1-thio-β-d-glucopyranoside |

TABLE 22-continued

| | |
|---|---|
| PNPO-Glu-α-Boc-δ-OBn | p-Nitrophenol active ester of α-Boc-δ-Bn-Glutamate |
| PNPO-Glu-α-Boc-δ-OMe | p-Nitrophenol active ester of α-Boc-δ-Me-Glutamate |
| PNPO-Glu-α-Boc-δ-OFm | p-Nitrophenol active ester of α-Boc-δ-Fluorenylmethyl-Glutamate |
| HO-Lys-α-CBz-ε-Alloc | Lysine-α-CBz-ε-Allyloxycarbonyl |
| NHS-COPEG$_{12}$ | N-hydroxysuccinimide ester of MeO—(CH$_2$CH$_2$O)$_{11}$CH$_2$CH$_2$CO$_2$H |
| HO-COPEG$_{24}$ | |
| NHS-COPEG$_{24}$ | |

TABLE 22-continued
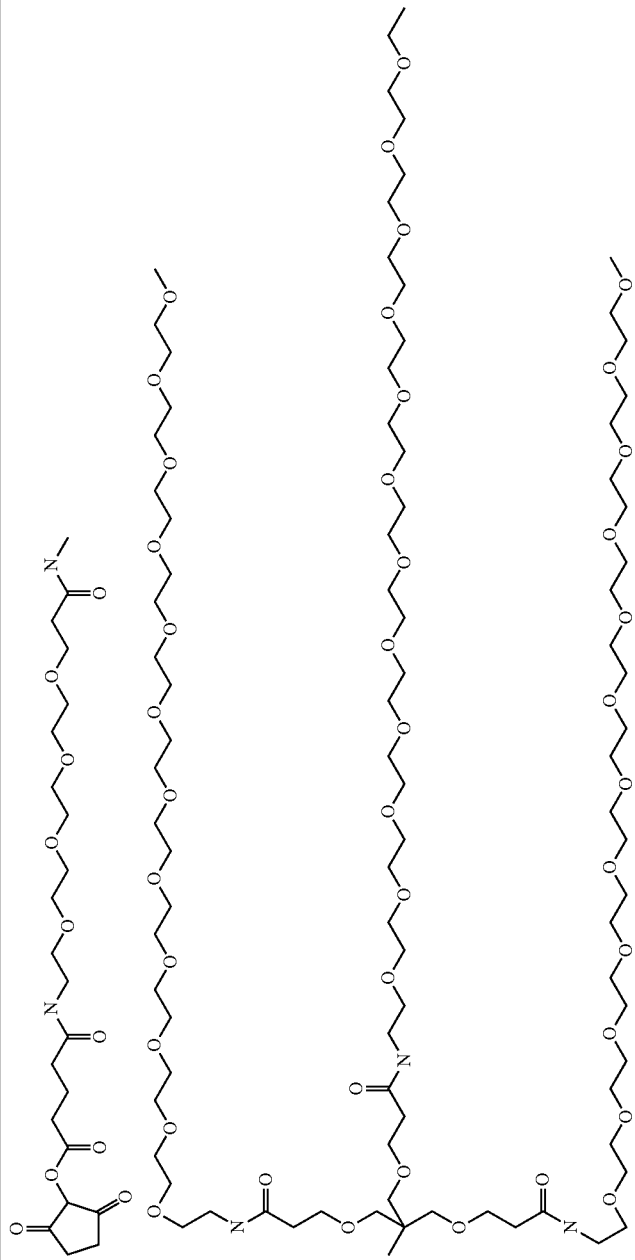
NHS-COPEG$_{2300}$
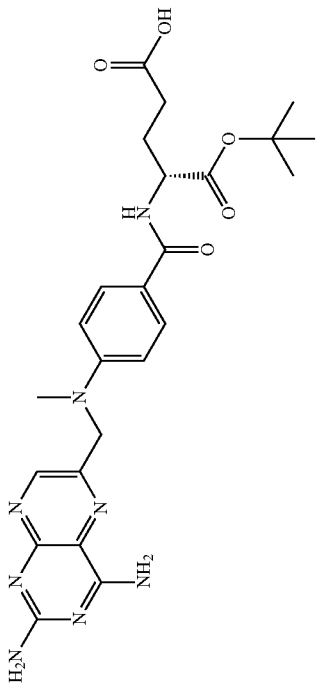
α-t-Butyl-N-[4-[[2,4-diamino-6-pteridinyl)methyl]methylamino]benzoyl]-L-glutamate
α-tBu-γ-MTX-OH Centramate Details:

Pall Filtron Centramate™ 3 gauge system (part #FS011K10) with 3K Centramate Cassette with Omega Membrane—Medium Screen (part #OS003C12).

Operating with a back-pressure of 20-30 psi.

NMR Equipment Details:

Bruker 300 UltraShield™ 300 MHz NMR instrument.

HPLC and MS Equipment Details

HPLC—Waters 2795 with 2996 Diode Array Detector (DAD)

MS—Waters ZQ4000 with ESI probe, inlet flow split to give around 50 pt/min to the MS.

Mass Spectra data was acquired in negative electrospray ionisation mode. The raw data was deconvoluted using a Maximum Entropy algorithm (MaxEnt) as implemented in MassLynx software v4.0, supplied by Waters Corporation. The data reported in the experimental details corresponds to the observed value after deconvolution to a theoretical zero charge state.

CE Equipment

Beckman P/ACE MDQ with diode array detector

Capillary is underivatised fused silica, 75 μm i.d.×40 cm to detector

Preparation of:

Preparation of BHALys [Lys]$_{16}$ [COCH$_2$O-3,6-Naph(SO$_3$Na)$_2$]$_{32}$ SPL7013 as per International patent application no PCT/AU02/00407 (WO 02/079299).

Structural Examples

Example 1

BHALys [Lys]$_2$ [α-Boc]$_2$ [ε-NH$_2$]$_2$ i. BHALys [Lys]$_2$[α-Boc]$_2$ [ε-CBz]$_2$

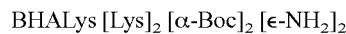

| Surface Topology | Surface Stoichiometry | |
|---|---|---|
| ((Boc CBz)(Boc CBz))$^4$ | 2 | Boc |
| | 2 | CBz |

BHALys [NH$_2$.TFA] (200 mg, 0.371 mmol) was dissolved in DMF (2.0 ml) and treated with TEA (258 μl, 1.85 mmol), stirring at ambient temperature and resulting in a clear solution. PNPO-α-Boc-ε-CBz-Lys (446 mg, 0.890 mmol) was added in one portion and the reaction mixture immediately turned bright yellow, and after five minutes all solid matter had dissolved. Stirring was continued for 24 h, then the reaction mixture was poured onto iced water and stirred. This suspension was filtered and the resulting solid pellet was rinsed repeatedly with water. The solid pellet was air-dried, resuspended in ACN, filtered and air-dried to give BHALys [Lys]$_2$ [α-Boc]$_2$ [ε-CBz]$_2$ (343 mg, 89%) as an off-white solid.

LC/MS (Hydrophobic/TFA): ESI (+ve) m/z=1037.19 [M+H]+; calculated (C57H77N7O11) 1036.29 g/mol. Rf (min)=13.8.

ii. BHALys [Lys]$_2$ [α-Boc]$_2$ [ε-NH$_2$]$_2$

| Surface Topology | Surface Stoichiometry | |
|---|---|---|
| ((Boc NH$_2$)(Boc NH$_2$))$^4$ | 2 | Boc |
| | 2 | NH$_2$ |

BHALys [Lys]$_2$ [α-Boc]$_2$ [ε-CBz]$_2$ (170 mg, 0.164 mmol) was suspended in 9:1 DMF/H$_2$O (5.0 ml) and ammonium formate (41 mg, 0.656 mmol) was added. The solution was stirred at ambient temperature for 10 min then Pd/C (10% w/w, 87 mg) was added and stirring was continued for 2 h. The reaction was terminated by filtering off the catalyst and the filter was rinsed with 9:1 DMF/H$_2$O (5.0 ml). The combined filtrates were pale yellow and clear, and concentrated in vacuo to give a pale yellow syrup. The syrup was treated with water (15 ml) which was removed in vacuo, then freeze-dried in water (10 ml) to give BHALys [Lys]$_2$ [α-Boc]$_2$ [ε-NH$_2$]$_2$ as a fine white lyophilate (120 mg, 96%).

LC/MS (Hydrophilic/TFA): ESI (+ve) m/z=882.12 [M+H+TFA]+, 769.08 [M+H]+, 384.66 [M+2H]/2+; calculated (C41H65N7O7) 768.01 g/mol. Rf (min)=15.9.

Example 2

BHALys [Lys]$_4$ [α-NH$_2$]$_4$ [ε-Boc]$_4$ i. BHALys [Lys]$_4$ [α-CBz]$_4$ [ε-Boc]$_4$

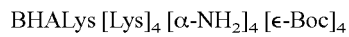

| Surface Topology | Surface Stoichiometry | |
|---|---|---|
| (((Boc CBz)(Boc CBz))$^4$((Boc CBz)(Boc CBz))$^4$)$^8$ | 4 | Boc |
| | 4 | CBz |

A solution of BHALys [Lys]$_2$ [NH$_2$.TFA]$_4$ (501 mg, 0.98 mmol), TEA (0.7 ml, 5.02 mmol) and DMF (10 ml) was treated with PNPO-α-CBz-ε-Boc-Lys (1.18 g, 2.35 mmol) following the method described in Example 1.i. The product BHALys [Lys]$_4$ [α-CBz]$_4$ [ε-Boc]$_4$ (830 mg, 84%) was obtained as a colourless solid.

LC/MS (Phobic/TFA): ESI (+ve) m/z=1009.71 [M+2H]/2+; calculated C107H153N15O23 2017.48 g/mol. Rf (min)= 7.58.

ii. BHALys [Lys]$_4$[α-NH$_2$]$_4$ [ε-Boc]$_4$

| Surface Topology | Surface Stoichiometry | |
|---|---|---|
| (((Boc NH$_2$)(Boc NH$_2$))$^4$((Boc NH$_2$)(Boc NH$_2$))$^4$)$^8$ | 4 | Boc |
| | 4 | NH$_2$ |

To a magnetically stirred solution of BHALys [Lys]$_4$ [α-CBz]$_4$ [ε-Boc]$_4$ (400 mg, 0.3 mmol) and 2,2,2-trifluoroethanol (8 ml) was added 10% Pd/C (203 mg). The black suspension was hydrogenated under standard conditions (Rt, atmospheric pressure) for 19 h. After this time, the suspension was filtered through a 0.45 micron filter disk. The filtrate was concentrated under reduced pressure to give the product BHALys [Lys]$_4$ [α-NH$_2$]$_4$ [ε-Boc]$_4$ (285 mg, 96%) as a light fawn coloured oil.

LC/MS (Hydrophilic/TFA): ESI (+ve) m/z=1481.32 [M+H]+, 741.10 [M+2H]/2+; calculated C75H129N15O15 1480.94 g/mol. Rf (min)=8.40.

Example 3

BHALys [Lys]$_4$ [α-Boc]$_4$ [ε-NH$_2$]$_4$ i. BHALys [Lys]$_4$ [α-Boc]$_4$ [ε-CBz]$_4$

| Surface Topology | Surface Stoichiometry | |
|---|---|---|
| (((Boc CBz)(Boc CBz))$^4$((Boc CBz)(Boc CBz))$^4$)$^8$ | 4 | Boc |
| | 4 | CBz |

A solution of BHALys [Lys]$_2$ [NH$_2$.TFA]$_4$ (503 mg, 0.49 mmol), TEA (0.7 ml, 5.02 mmol) and DMF (10 ml) was treated with PNPO-α-Boc-ε-CBz-Lys (1.18 g, 2.35 mmol). The reaction and product isolation were carried out according to the method described in Example 1.i. The product BHALys [Lys]$_4$ [α-Boc]$_4$ [ε-CBz]$_4$ (875 mg, 88%) was isolated as a colourless solid.

LC/MS (Phobic/TFA): ESI (+ve) m/z=1009.71 [M+2H]/2+; calculated C107H153N15O23 2017.48 g/mol. Rf (min)=7.40.

ii. BHALys [Lys]$_4$[α-Boc]$_4$ [ε-NH$_2$]$_4$

| Surface Topology | Surface Stoichiometry | |
|---|---|---|
| (((Boc NH$_2$)(Boc NH$_2$))$^4$((Boc NH$_2$)(Boc NH$_2$))$^4$)$^8$ | 4 | Boc |
| | 4 | NH$_2$ |

A solution of BHALys [Lys]$_4$ [α-Boc]$_4$ [ε-CBz]$_4$ (400 mg, 0.2 mmol) and 2,2,2-trifluoroethanol (8 ml) was added 10% Pd/C (205 mg). The reaction and product isolation were carried out according to the method described in Example 2.ii to give the product BHALys [Lys]$_4$ [α-Boc]$_4$ [ε-NH$_2$]$_4$ (288 mg, 98%) as a glassy oil.

LC/MS (Phobic/TFA): ESI (+ve) m/z=741.1 [M+2H]/2+, 494.6 [M+3H]/3+; calculated C75H129N15O15 1480.94 g/mol. Data deconvoluted using transform calculation to give mw=1480.52. Rf (min)=1.04.

Example 4

BHALys [Lys]$_8$ [α-Boc]$_8$ [ε-NH2]$_8$ i. BHALys [Lys]$_8$ [α-Boc]$_8$ [ε-CBz]$_8$

| Surface Topology | Surface Stoichiometry | |
|---|---|---|
| ((((Boc CBz)(Boc CBz))$^4$((Boc CBz)(Boc CBz))$^4$)$^8$(((Boc CBz)(Boc CBz))$^4$((Boc CBz)(Boc CBz))$^4$)$^8$)$^{16}$ | 8 | Boc |
| | 8 | CBz |

A solution of BHALys [Lys]$_4$ [NH$_2$.TFA]$_8$ (1.59 mmol), TEA (4.50 ml, 32.30 mmol) and DMF (30 ml) was treated with PNPO-α-Boc-ε-CBz-Lys (7.75 g, 15.45 mmol) as a solid. The reaction and product isolation were carried out according to the method described in Example 1.i to give BHALys [Lys]$_8$ [α-Boc]$_8$ [ε-CBz]$_8$t (5.52 g, 87%) as a colourless solid.

LC/MS (Phobic/TFA): ESI (+ve) observed [M+H/3]+ m/z=1328; calculated for C207H305N31O47 3979.9; Rf (min)=20.22 mins.

ii. BHALys [Lys]$_8$ [α-Boc]$_8$ [ε-NH$_2$]$_8$

| Surface Topology | Surface Stoichiometry | |
|---|---|---|
| ((((Boc NH$_2$)(Boc NH$_2$))$^4$((Boc NH$_2$)(Boc NH$_2$))$^4$)$^8$(((Boc NH$_2$)(Boc NH$_2$))$^4$((Boc NH$_2$)(Boc NH$_2$))$^4$)$^8$)$^{16}$ | 8 | Boc |
| | 8 | NH$_2$ |

BHALys [Lys]$_8$ [α-Boc]$_8$ [ε-CBz]$_8$ (500 mg, 0.126 mmol) was suspended in 9:1 DMF/H$_2$O (12.5 ml) and ammonium formate (127 mg, 2.01 mmol) and Pd/C (10% w/w, 266 mg) were added. The reaction and product isolation were carried out according to the method described in Example 1.ii to give BHALys [Lys]$_8$ [α-Boc]$_8$ [ε-NH$_2$]$_8$ as a fine white lyophilate (155 mg, 42%).

LC/MS (Hydrophilic/TFA): ESI (+ve) m/z=969.83 [M+3H]/3+, 727.67 [M+4H]/4+, 582.39 [M+5H]/5+; calculated (C143H257N31O31) 2906.8 g/mol. Data deconvoluted using transform calculation to give mw=2906.5. Rf (min)=14.7.

Example 5

BHALys [Lys]$_8$ [α-NH$_2$.TFA]$_8$ [ε-CBz]$_8$

| Surface Topology | Surface Stoichiometry | |
|---|---|---|
| ((((NH$_2$ CBz)(NH$_2$ CBz))$^4$((NH$_2$ CBz)(NH$_2$ CBz))$^4$)$^8$(((NH$_2$ CBz)(NH$_2$ CBz))$^4$((NH$_2$ CBz)(NH$_2$ CBz))$^4$)$^8$)$^{16}$ | 8 | NH$_2$ |
| | 8 | CBz |

BHALys [Lys]$_8$ [α-Boc]$_8$ [ε-CBz]$_8$ (1000 mg, 0.251 mmol) was suspended in acetic acid (5.5 ml) and stirred at 0° C. while TFA (5.5 ml) was added drop wise. The reaction mixture was allowed to warm to Rt and left to stir for 17 h, at which point the reaction mixture was triturated in Ether The resulting suspension was stirred for 10 min, and liquids were removed by centrifugation and decanting. The remaining precipitate was washed by stirring for 10 min with Ether, which was again removed by centrifugation and decanting, then the precipitate was dried in vacuo, dissolved in water and freeze-dried to give BHALys [Lys]$_8$ [α-NH$_2$. TFA]$_8$ [ε-CBz]$_8$ as a white powder (840 mg, 105%).

LC/MS (Hydrophilic/TFA): ESI (+ve) m/z=1060.70 [M+3H]/3+, 795.51 [M+4H]/4+, 636.30 [M+5H]/5+; calculated (C167H241N31O31) 3178.95 g/mol. Data deconvoluted using transform calculation to give mw=3178.0. Rf (min)=19.1.

Example 6

BHALys [Lys]$_8$ [α-NH$_2$]$_8$ [ε-Boc]$_8$ i. BHALys [Lys]$_8$ [α-CBz]$_8$ [ε-Boc]$_8$

| Surface Topology | Surface Stoichiometry | |
|---|---|---|
| ((((Boc CBz)(Boc CBz))$^4$((Boc CBz)(Boc CBz))$^4$)$^8$(((Boc CBz)(Boc CBz))$^4$((Boc CBz)(Boc CBz))$^4$)$^8$)$^{16}$ | 8<br>8 | Boc<br>CBz |

To a magnetically stirred solution of BHALys [Lys]$_4$ [NH$_2$.TFA]$_8$ (1.59 mmol), TEA (4.40 ml, 31.57 mmol) and DMF (32 ml) was added PNPO-α-CBz-ε-Boc-Lys (7.69 g, 15.33 mmol) as a solid and in one portion at Rt. The reaction and product isolation were carried out according to the method described in Example 1.i to give BHALys [Lys]$_8$ [α-CBz]$_8$ [ε-Boc]$_8$ (5.41 g, 85%) as an off-white solid.

LC/MS (Phobic/TFA/Speedy Ramp): ESI (+ve) observed [M+H/3]+ m/z=1328; calculated for C207H305N31O47 3979.9; Rf (min)=12.98 mins ii. BHALys [Lys]$_8$ [α-NH$_2$]$_8$ [ε-Boc]$_8$

| Surface Topology | Surface Stoichiometry | |
|---|---|---|
| ((((Boc NH$_2$)(Boc NH$_2$))$^4$((Boc NH$_2$)(Boc NH$_2$))$^4$)$^8$(((Boc NH$_2$)(Boc NH$_2$))$^4$((Boc NH$_2$)(Boc NH$_2$))$^4$)$^8$)$^{16}$ | 8<br>8 | Boc<br>NH$_2$ |

To a magnetically stirred solution of BHALys [Lys]$_8$ [α-CBz]$_8$ [ε-Boc]$_8$ (200 mg, 0.05 mmol) and 2,2,2-trifluoroethanol (2 ml) was added 10% Pd/C (198 mg). The reaction and product isolation were carried out according to the method described in Example 2.ii to give the product BHALys [Lys]$_8$ [α-NH$_2$]$_8$ [ε-Boc]$_8$ (140 mg, 96%) as a near colourless oil.

LC/MS (Phobic/TFA): ESI (+ve) m/z=1454.45 [M+2H]/2+, 969.74 [M+3H]/3+, 727.56 [M+4H]/4; calculated C143H257N31O31 2906.80 g/mol. Data deconvoluted using transform calculation to give mw=2906.68. Rf (min)=1.25.

Example 7

BHALys [Lys]$_8$ [α-CBz]$_8$ [ε-NH$_2$.TFA]$_8$

| Surface Topology | Surface Stoichiometry | |
|---|---|---|
| ((((NH$_2$ CBz)(NH$_2$ CBz))$^4$((NH$_2$ CBz)(NH$_2$ CBz))$^4$)$^8$(((NH$_2$ CBz)(NH$_2$ CBz))$^4$((NH$_2$ CBz)(NH$_2$ CBz))$^4$)$^8$)$^{16}$ | 8<br>8 | NH$_2$<br>CBz |

BHALys [Lys]$_8$ [α-CBz]$_8$ [ε-Boc]$_8$ (20.0 mg, 0.005 mmol) was suspended in acetic acid (109 μl) and stirred in water bath. TFA (109 μl) was added carefully. The reaction and product isolation were carried out according to the method described in Example 5.i to give BHALys [Lys]$_8$ [α-CBz]$_8$ [ε-NH$_2$.TFA]$_8$ (12.1 mg, 76%) as a white solid.

LC/MS (Hydrophilic/TFA): ESI (+ve) m/z=1060.43 [M+3H]/3+, 795.63 [M+4H]/4+, 636.79 [M+5H]/5+; calculated (C167H241N31O31) 3178.95 g/mol. Data deconvoluted using transform calculation to give mw=3179.25. Rf (min)=16.6.

Example 8

BHALys [Lys]$_4$ [Su[NPN]$_2$]$_8$ [NH$_2$.TFA]$_8$ [CBz]$_8$ i. N-(Benzyloxycarbonyl)-3-bromopropylamine TEA (6.91 g, 68.5 mmol) was added drop wise to an ice-cooled mixture of 3-bromopropylamine.hydrobromide (10.0 g, 45.6 mmol) and N-(Benzyloxycarbonyloxy)-succinimide (11.22 g, 47.9 mmol) in DCM (200 mL). The stirred mixture was allowed to warm to Rt overnight, then washed with water, brine, dried (MgSO$_4$), filtered and concentrated, providing 11.43 g (92%) of N-(Benzyloxycarbonyl)-3-bromopropylamine, as a pale yellow oil. $^1$H NMR (CDCl3): 7.35 (m, 5H), 5.10 (s, 2H), 4.89 (br s, 1H), 3.44 (t, J=6.6 Hz), 3.35 (dd, J=12.9, 6.3 Hz, 2H), m (2.06, 2H). LCMS (LC: Hydrophobic/TFA, RT=6.4 min; MS: 294, 296 ([M+NH4]+, 22%), 272, 274 ([M+H]+, 100%).

ii. [NPN]$_2$ [Boc] [CBz]

TEA (17.1 mL, 123.5 mmol) was added drop wise to a stirred mixture of N-(Benzyloxycarbonyl)-3-bromopropylamine (11.20 g, 41.2 mmol) and N-Boc diaminopropane (7.16 g, 41.2 mmol) in DMF (150 mL) at Rt. The mixture was heated to 70° C. for one hour, then ca. ⅔rds of the solvent was removed in vacuo. The concentrated DMF mixture was then diluted with water and washed with ether. The DMF/aqueous mixture was then basified (1.0M NaOH), and extracted with ether. The combined ether extracts were then washed with water, dried (MgSO$_4$), filtered and concentrated to provide 7.13 g (47%) of [NPN]$_2$ [Boc] [CBz] as a clear colourless oil. LCMS (LC: Hydrophobic/TFA, RT=14.0 min; MS: 366 ([M+H]+, 100%), 310 ([M-tBu]+, 94%), 266 ([M-Boc]+, 94%).

iii. HO-Su[NPN]$_2$ [Boc] [CBz]

| Surface Topology | Surface Stoichiometry | |
|---|---|---|
| HO—CO (Boc CBz) | 1<br>1<br>1 | CO$_2$H<br>Boc<br>CBz |

To a stirred mixture of [NPN]$_2$ [Boc] [CBz] (6.55 g, 17.9 mmol) in toluene (60 mL) at Rt was added succinic anhydride (1.79 g, 17.9 mmol). The mixture was heated to 70° C. for one hour, then concentrated. The residue was then dissolved in EtOAc/ether (5:1) and washed with NaOH. The base washes were then washed with ether, then acidified (HCl, 1.0 M, 250 mL). The aqueous mixture was then washed with EtOAc (3×250 mL), dried (MgSO$_4$), filtered, and concentrated, providing 6.97 g (84%) of HO-Su[NPN]$_2$ [Boc] [CBz] as a colourless viscous oil. $^1$H NMR (CDCl$_3$): δ 7.36 (m, 5H), 5.65 (br s, 1H), 5.08, 5.10 (2s, 2H), 4.74 (br s, 1H), 3.00-3.45 (m, 8H), 2.54-2.72 (m, 4H), 1.60-1.89 (m, 4H), 1.43, 1.45 (2s, 9H). LCMS (LC: hydrophilic/TFA RT=15.0 min; MS: 466 ([M+H]+, 15%), 366 ([M−Boc]+, 100%).

iv. PNPO-Su[NPN]$_2$ [Boc] [CBz]

| Surface Topology | Surface Stoichiometry | |
|---|---|---|
| PNPO—CO (Boc CBz) | 1 | CO—OPNP |
| | 1 | Boc |
| | 1 | CBz |

To a stirred mixture of 4-nitrophenol (1.91 g, 13.7 mmol) and HO-Su[NPN]$_2$ [Boc] [CBz] (6.39 g, 13.7 mmol) in EtOAc (150 mL) at Rt was added DCC (2.97 g, 14.4 mmol), dissolved in EtOAc (50 mL). The mixture was left to stir at Rt overnight, then filtered. The mixture was then washed with K$_2$CO$_3$ (1.0 M)/Brine 1:1, brine, dried (MgSO$_4$), filtered and concentrated, providing 7.80 g of crude material. The crude was then purified by fcc (2% MeOH in DCM), providing 7.07 g (88%) of PNPO-Su[NPN]$_2$ [Boc] [CBz]. 1H NMR (CDCl$_3$): δ 8.24 (d, J=9.0 Hz, 1H), 8.20 (d, J=9.0 Hz, 1H), 7.13-7.39 (m, 8H), 5.63 (br s, 1H), 5.12 (br s, 1H), 5.09, (s, 2H), 4.95 (br s, 1H), 4.62 (br s, 1H), 2.98-3.48 (m, 8H), 2.86-2.94 (m, 2H), 2.66-2.74 (m, 2H), 1.58-1.89 (m, 4H), 1.43 (s, 9H). LCMS (LC: Hydrophilic/formate, RT=21.0 min; MS: 604 ([M+NH$_4$]+, 36%), 587 ([M+H]+, 100%), 531 ([M−tBu]+, 19%), 487 ([M−Boc]+, 12%).

v. BHALys [Lys]$_4$ [Su[NPN]$_2$]$_8$ [Boc]$_8$ [CBz]$_8$

| Surface Topology | Surface Stoichiometry | |
|---|---|---|
| ((((Boc CBz)(Boc CBz))$^4$((Boc CBz)(Boc CBz))$^4$)$^8$(((Boc CBz)(Boc CBz))$^4$((Boc CBz)(Boc CBz))$^4$)$^8$)$^{16}$ | 8 | CBz |
| | 8 | Boc |

To a stirred mixture of PNPO-Su[NPN]$_2$ [Boc] [CBz] (564 mg, 0.96 mmol, 9.6 eq.) and BHALys [Lys]$_4$ [NH$_2$.TFA]$_8$ (200 mg, 0.10 mmol, 1.0 eq.) in DMF (17 mL) was added TEA (0.28 mL, 2.0 mmol, 20.0 eq.). The mixture was stirred at Rt overnight, the solvent removed in vacuo, and the residue purified by flash chromatography (residue preadsorbed onto silica; impurities eluted with 5% MeOH in DCM, product eluted in 10-15% MeOH) to provide BHALys [Lys]$_4$ [Su [NPN]$_2$]$_8$ [Boc]$_8$ [CBz]$_8$ (455 mg, 95%) as a viscous yellow oil.

LCMS (LC: Hydrophilic/TFA, RT=17.05 min; MS: (transform) 4660 ([M+H]+, 10%), 4561 ([M−Boc+H]+, 8%), 4460 ([M−2Boc+H]+, 7%), 4360 ([M−3Boc+H]+, 10%), 4260 ([M−4Boc+H]+, 100%).

vi. BHALys [Lys]$_4$ [Su[NPN]$_2$]$_8$ [NH$_2$.TFA]$_8$ [CBz]$_8$

| Surface Topology | Surface Stoichiometry | |
|---|---|---|
| ((((NH$_2$ CBz)(NH$_2$ CBz))$^4$((NH$_2$ CBz)(NH$_2$ CBz))$^4$)$^8$(((NH$_2$ CBz)(NH$_2$ CBz))$^4$((NH$_2$ CBz)(NH$_2$ CBz))$^4$)$^8$)$^{16}$ | 8 | CBz |
| | 8 | NH$_2$ |

BHALys [Lys]$_4$ [Su[NPN]$_2$]$_8$ [Boc]$_8$ [CBz]$_8$ (93 mg, 19.9 μmol) was dissolved in acetic acid (2 mL) and cooled. To this stirred mixture was then added TFA (2 mL), drop wise, then the mixture was allowed to warm to Rt. After stirring overnight, the mixture was poured into cold water, then concentrated. The residue was taken up in water and concentrated again (2×), then freeze-dried, providing 103 mg of white solid material (108% if calculate as TFA salt). LCMS (LC: Hydrophilic/formic acid, RT=12.57 min; MS: (transform) 3858 ([M+H]+, 100%), 3724 ([M−CBz+H]+, 20%), 3589 ([M−2CBz+H]+, 7%).

Example 9

BHALys [Lys]$_{16}$ [α-Boc]$_{16}$ [ε-NH$_2$]$_{16}$ i. BHALys [Lys]$_{16}$ [α-Boc]$_{16}$ [ε-CBz]$_{16}$

| Surface Topology | Surface Stoichiometry | |
|---|---|---|
| ((((Boc CBz)(Boc CBz))$^4$((Boc CBz)(Boc CBz))$^4$)$^8$(((Boc CBz)(Boc CBz))$^4$((Boc CBz)(Boc CBz))$^4$)$^8$)$^{16}$ | 16 | Boc |
| | 16 | Boc |
| | 16 | CBz |

To a stirred solution of BHALys [Lys]$_8$ [NH$_2$.TFA]$_{16}$ (0.81 mmol), TEA (4.50 ml, 32.30 mmol) and DMF (30 ml) was added PNPO-α-Boc-ε-CBz-Lys (7.94 g, 15.83 mmol) as a solid and in one portion at Rt. The reaction and product isolation were carried out according to the method described in Example 1.i to give BHALys [Lys]$_{16}$ [α-Boc]$_{16}$ [ε-CBz]$_{16}$ (5.79 g, 91%) as a colourless solid.

LC/MS (Phobic/TFA): ESI (+ve) observed [M+H/4]+ m/z=1977; [M+H/5]+ m/z=1582; calculated for C407H609N63O95 7904.9; Rf (min)=23.51 mins.

ii. BHALys [Lys]$_{16}$ [α-Boc]$_{16}$ [ε-NH$_2$]$_{16}$

| Surface Topology | Surface Stoichiometry | |
|---|---|---|
| ((((Boc NH$_2$)(Boc NH$_2$))$^4$((Boc NH$_2$)(Boc NH$_2$))$^4$)$^8$(((Boc NH$_2$)(Boc NH$_2$))$^4$((Boc NH$_2$)(Boc NH$_2$))$^4$)$^8$)$^{16}$ | 16 | Boc |
| | 16 | NH$_2$ |
| ((((Boc NH$_2$)(Boc NH$_2$))$^4$((Boc NH$_2$)(Boc NH$_2$))$^4$)$^8$(((Boc NH$_2$)(Boc NH$_2$))$^4$((Boc NH$_2$)(Boc NH$_2$))$^4$)$^8$)$^{16}$ | | |

A suspension of BHALys [Lys]$_{16}$ [α-Boc]$_{16}$ [ε-CBz]$_{16}$ (50 mg, 0.006 mmol), 10% Pd/C (53 mg) and acetic acid (2 ml) was vigorously stirred under hydrogen at Rt for 16 h. The black suspension was filtered. Concentration of the filtrate in vacuo afforded the product (26 mg, 71%) a straw coloured oil.

LC/MS (Phobic/TFA): ESI (+ve) observed [M+H/5]+ m/z=1152; [M+H/6]+ m/z=961; [M+H/7]+ m/z=824; [M+H/

8]+ m/z=721; [M+H/9]+ m/z=641; calculated for C279H513N63O63 5758.53; Rf (min)=2.37 mins.

Example 10

BHALys [Lys]$_{16}$ [α-NH$_2$.TFA]$_{16}$ [ε-CBz]$_{16}$

| Surface Topology | Surface Stoichiometry | |
|---|---|---|
| ((((NH$_2$ CBz)(NH$_2$ CBz))$^4$((NH$_2$ CBz)(NH$_2$ CBz))$^4)^8$(((NH$_2$ CBz)(NH$_2$ CBz))$^4$((NH$_2$ CBz)(NH$_2$ CBz))$^4)^8)^{16}$ | 16 | NH$_2$ |
| ((((NH$_2$ CBz)(NH$_2$ CBz))$^4$((NH$_2$ CBz)(NH$_2$ CBz))$^4)^8$(((NH$_2$ CBz)(NH$_2$ CBz))$^4$((NH$_2$ CBz)(NH$_2$ CBz))$^4)^8)^{16}$ | 16 | CBz |

BHALys [Lys]$_{16}$ [α-Boc]$_{16}$ [ε-CBz]$_{16}$ (1000 mg, 0.127 mmol) was suspended in acetic acid (5.5 ml) and stirred at 0° C. while TFA (5.5 ml) was added drop wise. The reaction and product isolation were carried out according to the method described in Example 5.i to give BHALys [Lys]$_{16}$ [α-NH$_2$.TFA]$_{16}$ [ε-CBz]$_{16}$ as a white powder (832 mg, 114%).

LC/MS (Hydrophilic/TFA): ESI (+ve) m/z=1576.85 [M+4H]/4+, 1261.34 [M+5H]/5+, 1051.27 [M+6H]/6+, 901.15 [M+7H]/7+; calculated (C327H481N63O63) 6302.83 g/mol. Data deconvoluted using transform calculation to give mw=6301.5. Rf (min)=19.0.

Example 11

BHALys [Lys]$_{16}$[α-NH$_2$]$_{16}$[ε-Boc]$_{16}$ i. BHALys [Lys]$_{16}$[α-4-Nitro-CBz]$_{16}$[ε-Boc]$_{16}$

| Surface Topology | Surface Stoichiometry | |
|---|---|---|
| ((((Boc 4-Nitro-CBz)(Boc 4-Nitro-CBz))$^4$((Boc 4-Nitro-CBz)(Boc 4-Nitro-CBz))$^4)^8$(((Boc 4-Nitro-CBz)(Boc 4-Nitro-CBz))$^4$((Boc 4-Nitro-CBz)(Boc 4-Nitro-CBz))$^4)^8)^{16}$ | 16 | Boc |
| ((((Boc 4-Nitro-CBz)(Boc 4-Nitro-CBz))$^4$((Boc 4-Nitro-CBz)(Boc 4-Nitro-CBz))$^4)^8$(((Boc 4-Nitro-CBz)(Boc 4-Nitro-CBz))$^4$((Boc 4-Nitro-CBz)(Boc 4-Nitro-CBz))$^4)^8)^{16}$ | 16 | 4-Nitro-CBz |

To a magnetically stirred solution of BHALys [Lys]$_8$ [NH$_2$.TFA]$_{16}$ (59 mg, 0.015 mmol) and DMF (5 ml) was added pyBOP (248 mg, 0.48 mmol). To this solution was added a mixture of HO-α-4-Nitro-CBz-ε-Boc-Lys (194 mg, 046 mmol), DIPEA (0.35 ml, 2.00 mmol) and DMF (3 ml) at Rt. Stirring was continued for 24 hrs at Rt. After this time, the clear but now brown coloured solution was transferred to a conical flask containing ACN (500 ml). A fine precipitate was observed to have formed which was subsequently collected by filtration. This was allowed to air dry under suction overnight thereby affording the product BHALys [Lys]$_{16}$ [α-4-nitro-CBz]$_{16}$ [ε-Boc]$_{16}$ (98 mg, 76%) as an orange/brown coloured glass like solid.

ii. BHALys [Lys]$_{16}$ [α-NH$_2$]$_{16}$ [ε-Boc]$_{16}$

| Surface Topology | Surface Stoichiometry | |
|---|---|---|
| ((((Boc NH$_2$)(Boc NH$_2$))$^4$((Boc NH$_2$)(Boc NH$_2$))$^4)^8$(((Boc NH$_2$)(Boc NH$_2$))$^4$((Boc NH$_2$)(Boc NH$_2$))$^4)^8)^{16}$ | 16 | Boc |
| ((((Boc NH$_2$)(Boc NH$_2$))$^4$((Boc NH$_2$)(Boc NH$_2$))$^4)^8$(((Boc NH$_2$)(Boc NH$_2$))$^4$((Boc NH$_2$)(Boc NH$_2$))$^4)^8)^{16}$ | 16 | NH$_2$ |

To a magnetically stirred solution of BHALys [Lys]$_{16}$ [α-4-nitro-CBz]$_{16}$ [ε-Boc]$_{16}$ (10 mg, 0.0012 mmol) and 2,2,2-trifluoroethanol (1 ml) was added 10% Pd/C (12 mg). The reaction and product isolation were carried out according to the method described in Example 2.ii to give the product BHALys [Lys]$_{16}$ [α-NH$_2$]$_{16}$ [ε-Boc]$_{16}$ (5.4 mg, 81%) as a fawn coloured glassy solid.

LC/MS (Hydrophilic/TFA): ESI (+ve) m/z=1440.49 [M+4H]/4+, 1152.45 [M+5H]/5+; calculated C279H513N63O63 5758.53 g/mol. Data deconvoluted using transform calculation to give mw=5757.88. Rf (min)=8.22.

Example 12

BHALys [Lys]$_{16}$[α-Boc]$_{16}$[ε-NH$_2$]$_{16}$ i. BHALys [Lys]$_{16}$[α-Boc]$_{16}$[ε-4-nitro-CBz]$_{16}$

| Surface Topology | Surface Stoichiometry | |
|---|---|---|
| ((((Boc 4-Nitro-CBz)(Boc 4-Nitro-CBz))$^4$((Boc 4-Nitro-CBz)(Boc 4-Nitro-CBz))$^4)^8$(((Boc 4-Nitro-CBz)(Boc 4-Nitro-CBz))$^4$((Boc 4-Nitro-CBz)(Boc 4-Nitro-CBz))$^4)^8)^{16}$ | 16 | Boc |
| ((((Boc 4-Nitro-CBz)(Boc 4-Nitro-CBz))$^4$((Boc 4-Nitro-CBz)(Boc 4-Nitro-CBz))$^4)^8$(((Boc 4-Nitro-CBz)(Boc 4-Nitro-CBz))$^4$((Boc 4-Nitro-CBz)(Boc 4-Nitro-CBz))$^4)^8)^{16}$ | 16 | 4-Nitro-CBz |

To a magnetically stirred solution of BHALys [Lys]$_8$ [NH$_2$.TFA]$_{16}$ (0.25 g, 0.13 mmol), TEA (0.35 ml, 2.51 mmol) and DMF (4 ml) was added PNPO-α-Boc-ε-4-nitro-CBz-Lys (0.67 g, 1.23 mmol) as a solid and in one portion at Rt. The reaction and product isolation were carried out according to the method described in Example 1.i and ultimately provided BHALys [Lys]$_{16}$[α-Boc]$_{16}$[ε-4-nitro-CBz]$_{16}$ (500 mg, 91%) as an off white solid.

LC/MS (Phobic/TFA): ESI (+ve) m/z=1725.94 [M+5H]/5+; calculated C407H593N79O127 8624.64 g/mol. Rf (min)= 8.60.

ii. BHALys [Lys]$_{16}$[α-Boc]$_{16}$ [ε-NH$_2$]$_{16}$

| Surface Topology | Surface Stoichiometry | |
|---|---|---|
| ((((Boc NH$_2$)(Boc NH$_2$))$^4$((Boc NH$_2$)(Boc NH$_2$))$^4)^8$(((Boc NH$_2$)(Boc NH$_2$))$^4$((Boc NH$_2$)(Boc NH$_2$))$^4)^8)^{16}$ | 16 | Boc |
| | 16 | NH$_2$ |

-continued

| Surface Topology | Surface Stoichiometry |
|---|---|
| ((((Boc NH$_2$)(Boc NH$_2$))$^4$((Boc NH$_2$)(Boc NH$_2$))$^4$)$^8$(((Boc NH$_2$)(Boc NH$_2$))$^4$((Boc NH$_2$)(Boc NH$_2$))$^4$)$^8$)$^{16}$ | |

To a magnetically stirred solution of BHALys [Lys]$_{16}$[α-Boc]$_{16}$[ε-4-nitro-CBz]$_{16}$ (103 mg, 0.023 mmol) and 2,2,2-trifluoroethanol (2 ml) was added 10% Pd/C (106 mg). The reaction and product isolation were carried out according to the method described in Example 2.ii to give the product BHALys [Lys]$_{16}$[α-Boc]$_{16}$[ε-NH$_2$]$_{16}$ (68 mg, 98%) as a fawn coloured glassy solid.

LC/MS (Hydrophilic/TFA): ESI (+ve) m/z=1152.51 [M+5H]/5+, 960.59 [M+6H]/6+, 823.70 [M+7H]/7+; calculated C279H513N63O63 5758.53 g/mol. Data deconvoluted using transform calculation to give mw=5757.94. Rf (min)= 7.06.

Example 13

BHALys [GlyLys]$_2$ [Lys]$_4$ [α,α-Boc]$_2$ [α,ε-Boc]$_2$ [ε,α-NH$_2$]$_2$ [ε,ε-NH$_2$]$_2$

Part of this example is described in FIG. 14A (Scheme 3).

i. MeO-GlyLys [α-Boc] [ε-CBz]

| Surface Topology | Surface Stoichiometry | |
|---|---|---|
| MeO—CO (Boc CBz) | 1 | CO$_2$Me |
| | 1 | Boc |
| | 1 | CBz |

To a magnetically stirred suspension of MeOGly.HCl (12.56 g, 0.11 mol) and DMF (200 ml) was slowly added TEA (42 ml, 0.3 mol) at Rt. The active ester, PNPO-α-Boc-ε-CBz-Lys (50.15 g, 0.1 mol), was added to the suspension in 2-3 g portions. The now bright yellow coloured reaction mixture was allowed to stir at Rt for 18 h. The volatiles were removed in vacuo and the resulting residue was partitioned between EtOAc (200 ml), 10% aq. Na$_2$CO$_3$ solution (100 ml) and water (175 ml). The separated organic layer was washed sequentially with 5% aq. Na$_2$CO$_3$ (4×200 ml), 0.25M aq. HCl (3×50 ml) and brine (1×50 ml) before being dried (MgSO$_4$), filtered and concentrated under reduced pressure to give MeO-GlyLys [α-Boc] [ε-CBz] (44.39 g, 98%) of a colourless oil.

LC/MS (Phobic/Formate): ESI (+ve) m/z=452.02 [M+H]+; calculated C22H33N3O7 451.52 g/mol. Rf (min)= 5.22.

ii. MeO-GlyLys [α-NH$_2$.TFA] [ε-CBz]

| Surface Topology | Surface Stoichiometry | |
|---|---|---|
| MeO—CO (NH$_2$ CBz) | 1 | CO$_2$Me |
| | 1 | NH$_2$ |
| | 1 | CBz |

To a chilled (ice water bath) and magnetically stirred solution of MeO-GlyLys [α-Boc] [ε-CBz] (43.4 g, 96.03 mmol) in acetic acid (150 ml) was added neat TFA in 1 ml portions (total volume of acid added=150 ml). The cooling bath was removed and the reaction mixture was allowed to stir at Rt for 4 h. After this time, another 20 ml of TFA was added to the reaction mixture and stirring was continued for a further 1 h at Rt. The volatiles were subsequently removed by rotary evaporation. The final traces of acid were removed from the crude product via azeoptroping with methanol (5×200 ml). The product, MeO-GlyLys [α-NH$_2$.TFA] [ε-CBz] (46.04 g, 103%), was obtained as a pale yellow oil.

LC/MS (Hydrophilic/Formate): ESI (+ve) m/z=352 [M+H]+; calculated C17H25N3O5 351.40 g/mol. Rf (min)= 12.33.

iii. MeO-GlyLys [ε-CBz] [α-Lys] [Boc]$_2$

| Surface Topology | Surface Stoichiometry | |
|---|---|---|
| MeO—CO ((CBz Ø)(Boc Boc))$^4$ | 1 | CO$_2$Me |
| | 2 | Boc |
| | 1 | CBz |

To a magnetically stirred solution of MeO-GlyLys [α-NH$_2$.TFA] [ε-CBz] (96.0 mmol) and DMF (200 ml) was added TEA (33.5 ml, 0.24 mol) followed by PNPO-Lys (Boc)$_2$ (49.37 g, 0.106 mol). The homogenous solution was allowed to stir at Rt for 17 h. A solution of glycine (3.98 g, 53 mmol) in water (50 ml) was added to the crude reaction mixture and stirring was continued for a further 18 h. Water (200 ml) was added to the reaction flask which induced precipitation of a yellow solid. This material was collected by filtration and then re-suspended in 5% aq. Na$_2$CO$_3$ (200 ml). This suspension was left to stir for 1.5 h at Rt. The crude product was collected by filtration and re-suspended in water a further 3 times (3×200 ml). The solids collected by filtration for the final time were left to air dry under suction for 17 h and final traces of moisture were removed under high vacuum (oil pump). The desired compound, MeO-GlyLys [s-CBz] [α-Lys] [Boc]$_2$ (61.07 g, 94%), was ultimately obtained as a pale, fine yellow coloured powder.

LC/MS (Phobic/Formate): ESI (+ve) m/z=680.15 [M+H]+; calculated C33H53N5O10 679.82 g/mol. Rf (min)= 7.90.

iv. MeO-GlyLys [ε-NH$_2$.TFA] [α-Lys] [Boc]$_2$

| Surface Topology | Surface Stoichiometry | |
|---|---|---|
| MeO—CO ((NH$_2$ Ø)(Boc Boc))$^4$ | 1 | CO$_2$Me |
| | 2 | Boc |
| | 1 | NH$_2$ |

To a magnetically stirred solution of MeO-GlyLys [ε-CBz] [α-Lys] [Boc]$_2$ (2.00 g, 2.94 mmol), TFA (0.23 ml, 2.99 mmol) and methanol (60 ml) was carefully added 10% Pd/C (322 mg). The black suspension was hydrogenated under standard conditions (Rt, atmospheric pressure) for 4 h. After this time, the suspension was filtered through a 0.45 micron filter disk. The filtrate was concentrated under reduced pressure to give the product MeO-GlyLys [ε-NH$_2$.TFA] [α-Lys] [Boc]$_2$ (1.93 g, 99%) as a colourless foam.

LC/MS (Phobic/TFA): ESI (+ve) m/z=546.45 [M+H]+; calculated C25H47N5O8 545.68 g/mol. Rf (min)=1.27.

v. MeO-GlyLys [Lys]$_2$ [α,α-Boc] [α,ε-Boc] [ε,α-CBz] [ε,ε-CBz]

| Surface Topology | Surface Stoichiometry | |
|---|---|---|
| MeO—CO ((CBz CBz)(Boc Boc))$^4$ | 1 | CO$_2$Me |
| | 2 | Boc |
| | 2 | CBz |

To a magnetically stirred solution of MeO-GlyLys [ε-NH$_2$.TFA] [α-Lys] [Boc]$_2$ (922 mg, 1.40 mmol), TEA (0.5 ml, 3.59 mmol) and DMF (25 ml) was added PNPO-α-CBz-ε-Boc-Lys (822 mg, 1.65 mmol) as a solid. The reaction and product isolation were carried out according to the method described in Example 1.i and ultimately provided MeO-GlyLys [Lys]$_2$ [α,α-Boc] [α,ε-Boc] [ε,α-CBz] [ε,ε-CBz] (452 mg, 34%) as an off white solid.

LC/MS (Phobic/TFA): ESI (+ve) m/z=942.53 [M+H]+; calculated C47H71N7O13 942.13 g/mol. Rf (min)=5.28.

vi. HO-GlyLys [Lys]$_2$ [α,α-Boc] [α,ε-Boc] [ε,α-CBz] [ε,ε-CBz]

| Surface Topology | Surface Stoichiometry | |
|---|---|---|
| HO—CO ((CBz CBz)(Boc Boc))$^4$ | 1 | CO$_2$H |
| | 2 | Boc |
| | 2 | CBz |

To a magnetically stirred solution of MeO-GlyLys [Lys]$_2$ [α,α-Boc] [α,ε-Boc] [ε,α-CBz] [ε,ε-CBz] (452 mg, 0.48 mmol), methanol (6 ml) and water (3 ml) was added 1M aq. NaOH solution (1 ml) at Rt. Stirring was continued at Rt for 3.5 h. The now clear but yellow coloured reaction mixture was concentrated to dryness under reduced pressure and the resulting gel like residue was treated with water (20 ml) and Ether (20 ml). To the biphasic mixture was added 1M aq. KHSO$_4$ solution (3 ml) and immediately a white precipitate formed. The precipitate was collected by filtration and left to air dry under suction for 48 h. The product, HO-GlyLys [Lys]$_2$ [α,α-Boc] [α,ε-Boc] [ε,α-CBz] [ε,ε-CBz] (343 mg, 77%), was obtained as a colourless solid.

LC/MS (Phobic/TFA): ESI (+ve) m/z=928.54 [M+H]+; calculated C46H69N7O13 928.10 g/mol. Rf (min)=4.73.

vii. BHALys [GlyLys]$_2$ [Lys]$_4$ [α,α-Boc]$_2$ [α,ε-Boc]$_2$ [ε,α-CBz]$_2$ [ε,ε-CBz]$_2$

| Surface Topology | Surface Stoichiometry | |
|---|---|---|
| ((((CBz CBz)(Boc Boc))$^4$((CBz CBz)(Boc Boc))$^4$)$^8$ | 4 | Boc |
| | 4 | CBz |

To a magnetically stirred solution of BHALys [NH$_2$.TFA]$_2$ (21 mg, 0.039 mmol) and DMF (1.5 ml) was added pyBOP (82 mg, 0.16 mmol). To this solution was added a mixture of HO-GlyLys [Lys]$_2$ [α,α-Boc] [α,ε-Boc] [ε,α-CBz] [ε,ε-CBz] (138 mg, 0.15 mmol), DIPEA (0.1 ml, 0.60 mmol) and DMF (1 ml) at Rt. Stirring was continued for 48 h at Rt. After this time, the crude reaction mixture was transferred to a beaker containing ACN (300 ml). The solution was stirred at Rt for 2 h during which time a fine precipitate formed. This material was collected by filtration and air dried under suction overnight. This process afforded the product BHALys [GlyLys]$_2$ [Lys]$_4$ [α,α-Boc]$_2$ [α,ε-Boc]$_2$ [ε,α-CBz]$_2$ [ε,ε-CBz]$_2$ (66 mg, 83%) as an off white coloured solid.

LC/MS (Phobic/TFA): ESI (+ve) m/z=1066.52 [M+2H]/2+; calculated C111H159N17O25 2131.58 g/mol. Rf (min) =7.07.

viii. BHALys [GlyLys]$_2$ [Lys]$_4$ [α,α-Boc]$_2$ [α,ε-Boc]$_2$ [ε,α-NH$_2$]$_2$ [ε,ε-NH$_2$]$_2$

| Surface Topology | Surface Stoichiometry | |
|---|---|---|
| (((NH$_2$ NH$_2$)(Boc Boc))$^4$((NH$_2$ NH$_2$)(Boc Boc))$^4$)$^8$ | 4 | Boc |
| | 4 | NH$_2$ |

To a magnetically stirred solution of BHALys [GlyLys (Boc)$_2$(CBz)$_2$]$_2$ (60 mg, 0.028 mmol) and 2,2,2-trifluoroethanol (3 ml) was added 10% Pd/C (59 mg). The black suspension was hydrogenated under standard conditions (Rt, atmospheric pressure) for 17 h. After this time, the suspension was filtered through a 0.45 micron filter disk. The filtrate was concentrated under reduced pressure to give the product BHALys [GlyLys]$_2$ [Lys]$_4$ [α,α-Boc]$_2$ [α,ε-Boc]$_2$ [ε,α-NH$_2$]$_2$ [ε,ε-NH$_2$]$_2$ (42 mg, 95%) as a fawn coloured glassy solid.

LC/MS (Phobic/TFA): ESI (+ve) m/z=1595.71 [M+H]α, 798.20 [M+2H]/2+; calculated C79H135N17O17 1595.05 g/mol. Rf (min)=8.69.

Example 14

BHALys [Lys]$_2$ [GlyLys]$_4$ [Lys]$_8$ [α,α-Boc]$_4$ [ε,α-NH$_2$]$_4$ [ε,ε-NH$_2$]$_4$ i. BHALys [Lys]$_2$ [GlyLys]$_4$ [Lys]$_8$ [α,α-Boc]$_4$ [α,ε-Boc]$_4$ [ε,α-CBz]$_4$ [ε,ε-CBz]$_4$

| Surface Topology | Surface Stoichiotnetry | |
|---|---|---|
| (((((CBz CBz)(Boc Boc))$^4$((CBz CBz)(Boc Boc))$^4$)$^8$(((CBz CBz)(Boc Boc))$^4$((CBz CBz)(Boc Boc))$^4$)$^8$)$^{16}$ | 8 | Boc |
| | 8 | CBz |

To a magnetically stirred solution of BHALys [Lys]$_2$ [NH$_2$.TFA]$_4$ (21 mg, 0.021 mmol) and DMF (1.5 ml) was added pyBOP (88 mg, 0.17 mmol). To this solution was added a mixture of HO-GlyLys [Lys]$_2$ [α,α-Boc] [α,ε-Boc] [ε,α-CBz] [ε,ε-CBz] (148 mg, 0.16 mmol), DIPEA (0.11 ml, 0.63 mmol) and DMF (1 ml) at Rt. The reaction and product isolation were carried out according to the method described in Example 11.i to provide the product BHALys [Lys]$_2$ [GlyLys]$_4$ [Lys]$_8$ [α,α-Boc]$_4$ [α,ε-Boc]$_4$ [ε,α-CBz]$_4$ [ε,ε-CBz]$_4$ (78 mg, 70%) as an off white coloured solid.

LC/MS (Phobic/TFA): ESI (+ve) m/z=1403.39 [M+3H]/3+, calculated C215H317N35O51 4208.09 g/mol. Rf (min)=8.10.

ii. BHALys [Lys]$_2$ [GlyLys]$_4$ [Lys]$_8$ [α,α-Boc]$_4$ [α,ε-Boc]$_4$ [ε,α-NH$_2$]$_4$ [ε,ε-NH$_2$]$_4$

| Surface Topology | Surface Stoichiometry | |
|---|---|---|
| (((NH$_2$ NH$_2$)(Boc Boc))$^4$((NH$_2$ NH$_2$)(Boc Boc))$^4$)$^8$(((NH$_2$ NH$_2$)(Boc Boc))$^4$((NH$_2$ NH$_2$)(Boc Boc))$^4$)$^8$)$^{16}$ | 8 | Boc |
| | 8 | NH$_2$ |

To a magnetically stirred solution of BHALys [Lys]$_2$ [GlyLys(Boc)$_2$(CBz)$_2$]$_4$ (64 mg, 0.015 mmol) and 2,2,2-trifluoroethanol (3 ml) was added 10% Pd/C (65 mg). The black suspension was hydrogenated under standard conditions (Rt, atmospheric pressure) for 17 h. After this time, the suspension was filtered through a 0.45 micron filter disk. The filtrate was concentrated under reduced pressure to give the product BHALys [Lys]$_2$ [GlyLys]$_4$ [Lys]$_8$ [α,α-Boc]$_4$ [α,ε-Boc]$_4$ [ε,α-NH$_2$]$_4$ [ε,ε-NH$_2$]$_4$ (43 mg, 90%) as a fawn coloured glassy solid.

LC/MS (Philic/TFA): ESI (+ve) m/z=1568.12 [M+2H]/2+, 1045.70 [M+3H]/3+, 784.54 [M+4H]/4+; calculated C151H269N35O35 3135.01 g/mol. Data deconvoluted using transform calculation to give mw=3134.15. Rf (min)=8.75.

Example 15

HOGlyLys [Lys]$_2$ [Boc]$_3$ [ε,ε-CBz]

This synthesis is depicted in FIGS. 14A and 14B as Schemes 3 and 4.

i. MeO-GlyLys [Lys]$_2$ [Boc]$_3$ [ε,ε-CBz]

| Surface Topology | Surface Stoichiometry | |
|---|---|---|
| MeO—CO ((CBz Boc)(Boc Boc))$^4$ | 1 | CO$_2$Me |
| | 3 | Boc |
| | 1 | CBz |

PNPO-Lys-α-Boc-ε-CBz (535 mg, 1.07 mmol) was added to a stirred solution of MeO-GlyLys [ε-NH$_2$.TFA] [α-Lys][Boc]$_2$ (640 mg, 0.97 mmol) in dimethylformamide (10 ml). TEA (340 μl, 2.43 mmol) was added and the reaction and product isolation were carried out according to the method described in Example 1.i to give MeOGlyLys [Lys]$_2$ [Boc]$_3$ [ε,ε-CBz] (818 mg, 93%) as a brittle white foam.

$^1$H nmr (300 MHz, CD$_3$OD) δ (ppm): 1.2-2.0 (m, 45H); 3.03 (t, J=6.6 Hz, 2H); 3.12 (t, J=6.6 Hz, 2H); 3.19 (m, 2H); 3.71 (s, 3H); 3.88 (d, J=17.4 Hz, 1H); 3.93-4.06 (m, 2H); 4.00 (d, J=17.7 Hz, 1H); 4.38 (dd, J 5.4, 8.4 Hz, 1H); 5.07 (s, 2H); 7.25-7.45 (m, 5H).

LC/MS (Hydrophobic/Formate): ESI (+ve) observed [M+H]$^+$ m/z=908.4; calculated for C$_{44}$H$_{74}$N$_7$O$_{13}$ 908.5; observed [M+NH$_4$]$^+$ m/z=925.4; calculated for C$_{44}$H$_{77}$N$_8$O$_{13}$ 925.5. Rf (min)=9.5.

ii. HO-GlyLys [Lys]$_2$ [Boc]$_3$ [ε,ε-CBz]

| Surface Topology | Surface Stoichiometry | |
|---|---|---|
| HO—CO ((CBz Boc)(Boc Boc))4 | 1 | CO2H |
| | 3 | Boc |
| | 1 | CBz |

MeOGlyLys [Lys]$_2$ [Boc]$_3$ [ε,ε-CBz] (500 mg, 0.55 mmol) was dissolved in a solution of sodium hydroxide (44 mg, 1.10 mmol) in methanol (8 ml) and water (4 ml). The reaction and product isolation were carried out according to the method described in Example 13.vi to give HO-GlyLys [Lys]$_2$ [Boc]$_3$ [ε,ε-CBz] (481 mg, 96%) as an amorphous white solid.

$^1$H nmr (300 MHz, CD$_3$OD) δ (ppm): 1.2-2.0 (m, 45H); 3.03 (t, J=6.6 Hz, 2H); 3.12 (t, J=6.6 Hz, 2H); 3.19 (m, 2H); 3.84 (d, J=18.0 Hz, 1H); 3.95-4.07 (m, 2H); 3.97 (d, J=17.7 Hz, 1H); 4.39 (dd, J 5.4, 8.4 Hz, 1H); 5.07 (s, 2H); 7.25-7.38 (m, 5H).

LC/MS (Hydrophobic/TFA): ESI (+ve) observed [M+H]$^+$ m/z=894.3; calculated for C$_{43}$H$_{72}$N$_7$O$_{13}$ 894.5. Rf (min)=8.4.

iii. BHALys [GlyLys]$_2$ [Lys]$_4$ [Boc]$_6$ [ε,ε-CBz]$_2$ (C$_{105}$H$_{163}$N$_{17}$O$_{25}$ MW 2063.5)

| Surface Topology | Surface Stoichiometry | |
|---|---|---|
| (((CBz Boc)(Boc Boc))$^4$((CBz Boc)(Boc Boc))$^4$)$^8$ | 6 | Boc |
| | 2 | CBz |

N,N'-Dicyclohexylcarbodiimide (186 mg 0.90 mmol) was added to a solution of HOGlyLys [Lys]$_2$ [Boc]$_3$ [ε,ε-CBz] (536 mg, 0.60 mmol), BHALys [NH$_2$.TFA]$_2$ (135 mg, 0.250 mmol), 4,4-dimethylaminopyridine (7.3 mg, 60 μmol) and TEA (210 μl, 1.50 mmol) in dimethylformamide (10 ml): The solution was stirred at Rt for 15 h and the volatile components were then removed in vacuo. Silica gel chromatography (methanol/DCM gradient) gave BHALys [GlyLys]$_2$ [Lys]$_4$ [Boc]$_6$ [ε,ε-CBz]$_2$ (245 mg, 47%). A small sample (20 mg) was treated with acetic acid/TFA in the usual way to provide analytical data.

LC/MS (Philic/TFA): ESI (+ve) observed [M+H]$^+$ m/z=1463.2; calculated for C$_{75}$H$_{116}$N$_{17}$O$_{13}$ 1462.9.

iv. BHALys [GlyLys]$_2$ [Lys]$_4$ [Boc]$_6$ [ε,ε-NH$_2$]$_2$

| Surface Topology | Surface Stoichiometry | |
|---|---|---|
| (((NH$_2$ Boc)(Boc Boc))$^4$((NH$_2$ Boc)(Boc Boc))$^4$)$^8$ | 2 | NH$_2$ |
| | 6 | Boc |

To a magnetically stirred solution of BHALys [GlyLys (Boc)$_3$(CBz)]$_2$ (95 mg, 0.046 mmol) and 2,2,2-trifluoroethanol (2 ml) was added 10% Pd/C (16.4 mg). The black suspension was hydrogenated under standard conditions (Rt, atmospheric pressure) for 19 h. After this time, the suspension was filtered through a 0.45 micron filter disk. The filtrate was concentrated under reduced pressure to give the product BHALys[GlyLys]$_2$[Lys]$_4$[Boc]$_6$[ε,ε-NH$_2$]$_2$ (83 mg, 93%) as a glass like solid.

LC/MS (Phobic/Formate): ESI (+ve) m/z=898.50 [M+2H]/2+; calculated C89H151N17O21 1795.23 g/mol. Rf (min)=4.34.

Example 16

BHALys [Lys]$_{16}$ [α,α-Boc]$_8$ [α,ε-Boc]$_8$ [ε,α-Boc]$_8$ [ε,ε-CBz]$_8$ i. BHALys [Lys]$_8$ [ε-CBz]$_8$ [α-Lys]$_8$ [Boc]$_{16}$

| Surface Topology | Surface Stoichiometry | |
|---|---|---|
| (((((CBz Ø)(Boc Boc))4((CBz Ø)(Boc Boc))4)8(((CBz Ø)(Boc Boc))4((CBz Ø)(Boc Boc))4)8)16 | 16 | Boc |
| | 8 | CBz |
| (((((CBz Ø)(Boc Boc))4((CBz Ø)(Boc Boc))4)8(((CBz Ø)(Boc Boc))4((CBz Ø)(Boc Boc))4)8)16 | | |

PNPO-Lys(Boc)$_2$ (3.6 g, 7.2 mmol) and TEA (2.1 mL, 15 mmol) were added to a stirred solution of BHALys [Lys]$_8$ [ε-CBz]$_8$ [α-NH$_2$.TFA]$_8$ (3 g, 0.75 mmol) in DMF (30 mL). The reaction and product isolation were carried out according to the method described in Example 1.i to provide BHALys [Lys]$_8$ [ε-CBz]$_8$ [α-Lys]$_8$ [Boc]$_{16}$ as a white powder (4.2 g, 98%).

LC/MS (Fast Hydrophobic/TFA): Rf (min)=–13.70; ESI (+ve) m/z=1936 ([M+3]/3), 1452 ([M+4]/4), 1062 ([M+5-Boc]/5); Calc. C295H465N47O71. M+1. 5083.4 ii. BHALys [Lys]$_8$ [ε-NH$_2$]$_8$ [α-Lys]$_8$ [Boc]$_{16}$

| Surface Topology | Surface Stoichiometry | |
|---|---|---|
| ((((NH$_2$ Ø)(Boc Boc))4((NH$_2$ Ø)(Boc Boc))4)8(((NH$_2$ Ø)(Boc Boc))4((NH$_2$ Ø)(Boc Boc))4)8)16 | 16 | Boc |
| | 8 | NH$_2$ |
| ((((NH$_2$ Ø)(Boc Boc))4((NH$_2$ Ø)(Boc Boc))4)8(((NH$_2$ Ø)(Boc Boc))4((NH$_2$ Ø)(Boc Boc))4)8)16 | | |

To a stirred solution of BHALys [Lys]$_8$ [ε-CBz]$_8$ [α-Lys]$_8$ [Boc]$_{16}$ (2.2 g, 0.38 mmol) in acetic acid (30 mL), was added 10% Pd/C (101 mg, 0.095 mmol). The resulting homogeneous mixture was at Rt for 16 h under hydrogen. The solution was filtered and concentrated in vacuo. The resulting sticky residue was redissolved in water and freeze dried to provide BHALys [Lys]$_8$ [ε-NH$_2$]$_8$ [α-Lys]$_8$ [Boc]$_{16}$ (1.97 g, 0.38 mmol) which contained some acetic acid residue.

LC/MS (Hydrophilic/TFA): Rf (min)=18.53; ESI (+ve) m/z=1184 ([M+4]/4), 947 ([M+5]/5), 790 ([M+6]/6); Calc. C231H417N47O55. M+1. 4731.1 iii. BHALys [Lys]$_{16}$ [α,α-Boc]$_8$ [α,ε-Boc]$_8$ [ε,α-Boc]$_8$ [ε,ε-CBz]$_8$

| Surface Topology | Surface Stoichiometry | |
|---|---|---|
| ((((CBz Boc)(Boc Boc))4((CBz Boc)(Boc Boc))4)8(((CBz Boc)(Boc Boc))4((CBz Boc)(Boc Boc))4)8)16 | 24 | Boc |
| | 8 | CBz |
| ((((CBz Boc)(Boc Boc))4((CBz Boc)(Boc Boc))4)8(((CBz Boc)(Boc Boc))4((CBz Boc)(Boc Boc))4)8)16 | | |

PNPO-α-Boc-ε-CBz-Lys (90 mg, 0.18 mmol) and TEA (0.05 mL, 0.35 mmol) were added to a stirred solution of BHALys [Lys]$_8$ [ε-NH$_2$]$_8$ [α-Lys]$_8$ [Boc]$_{16}$ (90 mg, 0.019 mmol) in DMF (10 mL). The reaction and product isolation were carried out according to the method described in Example 1.i to provide BHALys [Lys]$_{16}$ [α,α-Boc]$_8$ [α,ε-Boc]$_8$[ε,α-Boc]$_8$ [ε,ε-CBz]$_8$ (51 mg, 35%)

LC/MS (Phobic TFA Speedy Rp): Rf (min)=14.32; ESI (+ve) m/z=2544 ([M+3]/3), 1909 ([M+4]/4), 1527 ([M+5]/5); Calc. C383H625N63O95. M+1. 7629

Example 17

BHALys [Lys]$_{16}$ [α,α-Boc]$_8$ [α,ε-Boc]$_8$ [ε,α-Boc]$_8$ [ε,ε-Fmoc]$_8$

| Surface Topology | Surface Stoichiometry | |
|---|---|---|
| ((((Fmoc Boc)(Boc Boc))4((Fmoc Boc)(Boc Boc))4)8(((Fmoc Boc)(Boc Boc))4((Fmoc Boc)(Boc Boc))4)8)16 | 24 | Boc |
| | 8 | Fmoc |
| ((((Fmoc Boc)(Boc Boc))4((Fmoc Boc)(Boc Boc))4)8(((Fmoc Boc)(Boc Boc))4((Fmoc Boc)(Boc Boc))4)8)16 | | |

PFP-Lys-α-Boc-ε-Fmoc (96 mg, 0.15 mmol) and TEA (0.04 mL, 0.27 mmol) were added to a stirred solution of BHALys [Lys]$_8$ [ε-NH$_2$]$_8$ [α-Lys]$_8$ [Boc]$_{16}$ (100 mg, 0.017 mmol) in DMF (10 mL). The solution was stirred at Rt for 16 h. The reaction mixture was then added to ACN (100 ml) producing a clear gelatinous precipitate. This precipitate was collected by filtration and washed with ACN. The precipitated was dried at Rt to provide BHALys [Lys]$_{16}$ [α,α-Boc]$_8$ [α,ε-Boc]$_8$ [ε,α-Boc]$_8$ [ε,ε-Fmoc]$_8$ (30 mg, 21%)

LC/MS (Hydrophobic/TFA): Rf (min)=7.72; ESI (+ve) m/z=1667 ([M+5]/5), 1389 ([M+6]/6), 1191 ([M+7]/7); Calc. C439H657N63O95. M+1 8332

Example 18

HO Su(NPN)$_2$ [Su(NPN)$_2$]$_2$ [CBz] [Boc]$_3$

Part of this synthesis is schematically illustrated in FIG. 13 (Scheme 2).

i. EtO-Su[NPN]$_2$ [Boc] [CBz]

| Surface Topology | Surface Stoichiometry | |
|---|---|---|
| EtO—CO (Boc CBz) | 1 | CO—OEt |
| | 1 | Boc |
| | 1 | CBz |

A stirred mixture of PNPO-Su[NPN]$_2$ [Boc] [CBz] (1.0 g, 1.7 mmol) and TEA (0.5 g, 4.95 mmol) in EtOH (80 mL) was heated at 70° C. for 16 h, concentrated, then purified by flash chromatography (PNPOH removed with hexane/EtOAc 1:1, ethyl ester with EtOAc only) to give EtO-Su[NPN]$_2$ [Boc] [CBz] as an oil. LCMS (LC: Hydrophilic/formate, RT=17.8 min; MS: 511 ([M+NH4]+, 10%), 494 ([M+H]+, 100%).

ii. EtO-Su[NPN]$_2$ [NH$_2$.TFA] [CBz]

| Surface Topology | Surface Stoichiometry | |
|---|---|---|
| EtO—CO (NH$_2$ CBz) | 1 | CO—OEt |
| | 1 | NH$_2$ |
| | 1 | CBz |

EtO-Su[NPN]$_2$ [Boc] [CBz] (720 mg, 1.46 mmol) was dissolved in acetic acid (10 mL) and cooled slightly. To this stirred mixture was then added TFA (10 mL), drop wise. After 30 min. the ice-bath was removed, and after 5 hours the mixture was concentrated in vacuo. The residue was taken up in water, then concentrated to remove excess acid. This was repeated (2×), then the sample was taken up in water and freeze-dried, providing EtO-Su[NPN]$_2$ [NH$_2$.TFA] [CBz] as a colourless oil, 715 mg (97% if calc. TFA salt). LCMS (LC: Hydrophilic/TFA, RT=12.47 min; MS: 394 ([M+H]+, 100%).

iii. EtO-Su[NPN]$_2$ [CBz] [Su[NPN]$_2$] [Boc]$_2$

| Surface Topology | Surface Stoichiometry | |
|---|---|---|
| EtO—CO ((CBz Ø)(Boc Boc))$^4$ | 1 | CO—OEt |
| | 2 | Boc |
| | 1 | CBz |

To a stirred mixture of EtO-Su[NPN]$_2$ [NH$_2$.TFA] [CBz] (715 mg, 1.41 mmol) in DMF (20 mL) was added PNPOSu[NPN]$_2$ [Boc]$_2$ (778 mg, 1.41 mmol) and TEA (0.49 mL, 3.52 mmol). The mixture was stirred at Rt overnight, the solvent removed in vacuo, and the residue taken up in EtOAc (100 mL). This mixture was washed with a K$_2$CO$_3$ solution (5%), dried (MgSO$_4$), filtered and concentrated. The crude was purified by flash chromatography (10% MeOH in DCM), providing 0.95 g (84%) of EtO-Su[NPN]$_2$ [CBz] [Su[NPN]$_2$] [Boc]$_2$ as a viscous oil. LCMS (LC: Hydrophobic/formate, RT=6.91 min; MS: 807 ([M+H]+, 100%), 824 ([M+NH$_4$]+, 32%).

iv. EtO-Su[NPN]$_2$ [NH$_2$] [Su[NPN]$_2$] [Boc]$_2$

| Surface Topology | Surface Stoichiometry | |
|---|---|---|
| EtO—CO ((NH$_2$ Ø)(Boc Boc))$^4$ | 1 | CO—OEt |
| | 2 | Boc |
| | 1 | NH$_2$ |

To a stirred mixture of EtO-Su[NPN]$_2$ [CBz] [Su[NPN]$_2$] [Boc]$_2$ (865 mg, 1.07 mmol) in DMF/H$_2$O (9:1, 19 mL) was added ammonium formate (135 mg, 1.07 mmol) and 10% Pd/C (288 mg, 0.25 equiv. Pd). The mixture was stirred for 2 h. at Rt, filtered, and concentrated. The residue was taken up in water, then concentrated to remove excess acid. This was repeated (2×), then the sample was taken up in water and freeze-dried, providing 672 mg (93%) of EtO-Su[NPN]$_2$ [NH$_2$] [Su[NPN]$_2$] [Boc]$_2$ as a colourless oil. LCMS (LC: Hydrophilic/TFA, RT=13.9 min; MS: 673 ([M+H]+, 37%), 259 (100%).

v. EtO-Su[NPN]$_2$ [Su[NPN]$_2$]$_2$ [CBz] [Boc]$_3$

| Surface Topology | Surface Stoichiometry | |
|---|---|---|
| EtO—CO ((CBz Boc)(Boc Boc))$^4$ | 1 | CO—OEt |
| | 3 | Boc |
| | 1 | CBz |

To a stirred mixture of EtO-Su[NPN]$_2$ [NH$_2$] [Su[NPN]$_2$] [Boc]$_2$ (739 mg, 1.1 mmol) in DMF (20 mL) was added PNPOSu[NPN]$_2$ [Boc] [CBz] (644 mg, 1.1 mmol) and TEA (0.38 mL, 2.7 mmol). The mixture was stirred at Rt overnight, the solvent removed in vacuo, and the residue taken up in EtOAc (150 mL). This mixture was washed with a K$_2$CO$_3$ solution (5%), dried (MgSO$_4$), filtered and concentrated, providing 1.30 g (106%) of crude material, EtO-Su[NPN]$_2$ [Su[NPN]$_2$]$_2$ [CBz] [Boc]$_3$ as a pale yellow oil. LCMS (LC: Hydrophobic/formate, RT=3.3 min; MS: 1138 ([M+NH4]+, 2%), 1121 ([M+H]+, 3%), 561 ([M+2H/2]+, 100%).

vi. HO-Su[NPN]$_2$ [Su[NPN]$_2$]$_2$ [CBz] [Boc]$_3$

| Surface Topology | Surface Stoichiometry | |
|---|---|---|
| HO—CO ((CBz Boc)(Boc Boc))$^4$ | 1 | CO$_2$H |
| | 3 | Boc |
| | 1 | CBz |

To a stirred mixture of EtOSu[NPN]$_2$ [Su[NPN]$_2$]$_2$ [CBz] [Boc]$_3$ (0.6 g, 0.6 mmol) in THF (10 mL) was added NaOH solution (H$_2$O 4 mL, NaOH 127 mg, 3.0 mmol). The mixture was stirred for 2 d at Rt, concentrated, the diluted with dilute HCl (50 mL). The aqueous phase was then washed with EtOAc, the organics combined, dried (MgSO$_4$), filtered and concentrated to provide 0.8 g of white solid.

Example 19

BHALys [α-GlyLys] [Lys]$_2$ [Boc]$_4$ [ε-GlyLys] [Lys]$_2$ [NH$_2$]$_4$ i. MeO-GlyLys [Lys]$_2$ [Boc]$_4$

| Surface Topology | Surface Stoichiometry | |
|---|---|---|
| MeO—CO ((Boc Boc)(Boc Boc))$^4$ | 1 | CO$_2$Me |
| | 4 | Boc |

To a magnetically stirred solution of MeO-GlyLys [ε-NH$_2$.TFA] [α-Lys] [Boc]$_2$ (968 mg, 1.47 mmol), TEA (0.51 ml, 3.66 mmol) and DMF (25 ml) was added PNPO-α-Boc-ε-Boc-Lys (1.38 g, 2.95 mmol) as a solid and in one portion at Rt. The reaction and product isolation were carried out according to the method described in Example 13.iii to give MeO-GlyLys [Lys]$_2$ [Boc]$_4$ (1.19 g, 93%) as a near colourless solid.

LC/MS (Phobic/TFA): ESI (+ve) m/z=874.40 [M+H]+; calculated C41H75N7O13 874.09 g/mol. Rf (min)=4.83.

ii. MeO-GlyLys [Lys]$_2$ [NH$_2$.TFA]$_4$

| Surface Topology | Surface Stoichiometry | |
|---|---|---|
| MeO—CO ((NH$_2$ NH$_2$)(NH$_2$ NH$_2$))$^4$ | 1 | CO$_2$Me |
| | 4 | Boc |

To a chilled (ice-water bath) and magnetically stirred suspension of MeO-GlyLys [Lys]$_2$ [Boc]$_4$ (1.19 g, 1.36 mmol) and DCM (60 ml) was added neat TFA (4.2 ml, 54.5 mmol) in a drop wise manner. The reaction and product isolation were carried out according to the method described in Example 12. The product MeO-GlyLys [Lys]$_2$ [NH$_2$.TFA]$_4$ (1.15 g, 91%) was obtained as a glassy solid.

LC/MS (Philic/TFA): ESI (+ve) m/z=474.23 [M+H]+; calculated C21H43N7O5 473.62 g/mol. Rf (min)=0.59.

iii. MeO-GlyLys [Lys]$_2$ [4-Nitro-CBz]$_4$

| Surface Topology | Surface Stoichiometry | |
|---|---|---|
| MeO—CO ((4-Nitro-CBz 4-Nitro-CBz)(4-Nitro-CBz 4-Nitro-CBz))$^4$ | 1 | CO$_2$Me |
| | 4 | 4-Nitro-CBz |

To a magnetically stirred mixture of MeO-GlyLys [Lys]$_2$ [NH$_2$.TFA]$_4$ (606 mg, 0.65 mmol), THF (12 ml) and DIPEA (1.4 ml, 8.03 mmol) was added, in one portion and as a solid, 4-nitrobenzylchloroformate (853 mg, 3.96 mmol). The suspension was allowed to stir at Rt for a further 19 h. The crude reaction mixture was transferred to a beaker containing a 1:1 mixture of ACN and water (200 ml).The suspension was stirred for 2 h before being filtered and the solids collected left to dry overnight under suction. The desired product MeO-GlyLys [Lys]$_2$ [4-Nitro-CBz]$_4$ (367 mg, 47%) was obtained as a pale yellow coloured solid.

LC/MS (Phobic/TFA): ESI (+ve) m/z=1190.35 [M+H]+; calculated C53H63N11O21 1190.15 g/mol. RF (min)=5.17.

iv. HO-GlyLys [Lys]$_2$ [4-Nitro-CBz]$_4$

| Surface Topology | Surface Stoichiometry | |
|---|---|---|
| HO—CO ((4-Nitro-CBz 4-Nitro-CBz)(4-Nitro-CBz 4-Nitro-CBz))$^4$ | 1 | CO$_2$H |
| | 4 | 4-Nitro-CBz |

To a magnetically stirred suspension of MeO-GlyLys [Lys]$_2$ [4-Nitro-CBz]$_4$ (297 mg, 0.25 mmol), methanol (3 ml), and water (1.5 ml) was added 1M aq. NaOH solution (1 ml). The suspension was stirred at 60° C. for ca. 5 h after which time, LCMS analysis of the crude reaction mixture deemed the reaction complete. To the mixture was added 1M aq. KHSO4 solution (2 ml). After stirring at room temperature for approximately 10 mins, the suspension was filtered. The solids retained were allowed to air dry under suction overnight. The product, HO-GlyLys [Lys]$_2$ [4-Nitro-CBz]$_4$ (41 mg, 14%) was obtained as a light grey coloured solid.

LC/MS (Phobic/TFA): ESI (+ve) m/z=1176.35 [M+H]+; calculated C52H61N11O21 1176.13 g/mol. Rf (min)=4.85.

v. HO-GlyLys [Lys]$_2$ [Boc]$_4$

| Surface Topology | Surface Stoichiometry | |
|---|---|---|
| HO—CO ((Boc Boc)(Boc Boc))$^4$ | 1 | CO$_2$H |
| | 4 | Boc |

To a magnetically stirred solution of MeO-GlyLys [Lys]$_2$ [Boc]$_4$ (1.0 g, 1.14 mmol), methanol (12 ml) and water (6 ml) was added 1M aq. NaOH solution (2.2 ml) at Rt. The reaction mixture was stirred at Rt for 18 h. The reaction and product isolation were carried out according to the method described in Example 13.vi to afford HO-GlyLys [Lys]$_2$ [Boc]$_4$ (1.05 g, 107%) as a colourless solid.

LC/MS (Phobic/TFA): ESI (+ve) m/z=860.62 [M+H]+; calculated C40H73N7O13 860.07 g/mol. Rf (min)=4.41.

vi. PNPO-GlyLys [Lys]$_2$ [Boc]$_4$

| Surface Topology | Surface Stoichiometry | |
|---|---|---|
| PNPO—CO ((Boc Boc)(Boc Boc))$^4$ | 1 | CO—OPNP |
| | 4 | Boc |

To a magnetically stirred solution of HOGlyLys [Lys]$_2$ [Boc]$_4$ (983 mg, 1.14 mmol) and EtOAc (20 ml) was added, in the following order, p-nitrophenol (175 mg, 1.26 mmol) and DCC (260 mg, 1.26 mmol). After stirring at Rt for ca. 5 mins, the reaction mixture became a slurry due to the formation of a gel like precipitate. Stirring was continued at Rt for a further 22 h. The crude reaction mixture was diluted upon the addition of EtOAc (10 ml) then filtered. The filtrate was concentrated under reduced pressure to give PNPO-GlyLys [Lys]$_2$ [Boc]$_4$ as an orange/yellow coloured solid.

LC/MS (Phobic/TFA): ESI (+ve) m/z=981.71 [M+H]+; calculated C46H76N8O15 981.16 g/mol. Rf (min)=5.65.

vii. BHALys [α-Boc] [ε-Fmoc]

| Surface Topology | Surface Stoichiometry | |
|---|---|---|
| (Boc Fmoc) | 1 | Boc |
| | 1 | Fmoc |

HO-Lys-α-Boc-ε-Fmoc (10.34 g, 22.1 mmol) was dissolved in dry DMF (100 mL) and chilled. DCC (4.74, 23.0 mmol) was added followed by HOBt (3.12 g, 23.1 mmol). BHA (5 mL, 28.9 mol) was dissolved in dry DMF (25 mL) and added drop wise to the reaction under argon. Reaction stirred at Rt overnight. DCU was filtered and the filtrate was partitioned between EtOAc and water. Organic layer was washed with 0.3M Na$_2$CO$_3$, then with brine, followed by 0.1M KHSO$_4$ and then brine. EtOAc solution was dried over MgSO$_4$, filtered and concentrated under reduced pressure to give BHALys [α-Boc] [ε-Fmoc] as a pale yellow solid. Material was subjected to, high vacuum overnight (14.36 g, 22.6 mmol, 103%) EtOAc, $^1$H-nmr (300 MHz, D$_6$DMSO) λ 1-1.7 (15H); 2.9 (2H); 4.15-4.4 (3H) 6.1 (1H) 7.1-8 (18H) HPLC (Hydrophobic) Rt 12.92 min ESI MS (+ve) 634.16 (M+H)$^+$; Calc. MF C$_{39}$H$_{43}$N$_3$O$_5$ M+H, 633.79.

viii. BHALys [ε-Fmoc] [α-NH$_2$.TFA]

| Surface Topology | Surface Stoichiometry | |
|---|---|---|
| (Boc NH$_2$) | 1 | NH$_2$ |
| | 1 | Fmoc |

BHALys [α-Boc] [ε-Fmoc] (14.26 g, 22.5 mmol) was suspended in DCM (40 mL) and chilled, forming a gel. TFA (30 mL, 43.2 mmol) was added slowly via a dropping funnel which dissolved the gel and the homogeneous solution was stirred for 4 hours at Rt and then concentrated to give BHALys [s-Fmoc] [α-NH$_2$.TFA] as a yellow oil. HPLC (Hydrophobic) Rt=8.59 min; ESI MS (+ve) 534.19 (M+H)$^+$; Calc MF: C$_{34}$H$_{35}$N$_3$O$_3$; M+H, 533.68 $^1$H-nmr (MG-036-110-04) (300 MHz, D$_6$DMSO) λ (ppm) 1.0-1.8 (30H); 2.8-3.0 (4H); 3.9 (1H); 4.2-4.5 (4H); 6.1 (1H); 7.2-7.9 (18H)

ix. BHALys [ε-Fmoc] [α-GlyLys] [Lys]$_2$ [Boc]$_4$

| Surface Topology | Surface Stoichiometry | |
|---|---|---|
| (((4-Nitro-CBz Ø)(ØØ))$^4$((Boc Boc)(Boc Boc))$^4$)$^8$ | 1 | 4-Nitro-CBz |
| | 4 | Boc |

To a magnetically stirred solution of BHALys [α-NH$_2$.TFA]$_4$ [ε-Fmoc] (75 mg, 0.12 mmol) and DMF (2 ml) was added PNPO-GlyLys [Lys]$_2$ [Boc]$_4$ (230 mg, 0.23 mmol), followed by triethylamine (22 μL, 0.16 mmol). The reaction and product isolation were carried out according to the method described in Example 13.iii to afford BHALys [ε-Fmoc] [α-GlyLys] [Lys]$_2$ [Boc]$_4$, in crude form, (314 mg) as a light yellow coloured gum like residue.

LC/MS (Phobic/TFA): ESI (+ve) m/z=1375.69 [MαH]+; calculated C74H106N10O15 1375.73 g/mol. Rf (min)=7.14.

x. BHALys [ε-NH$_2$] [α-GlyLys] [Lys]$_2$ [Boc]$_4$

| Surface Topology | Surface Stoichiometry | |
|---|---|---|
| (((NH$_2$ Ø)(ØØ))$^4$((Boc Boc)(Boc Boc))$^4$)$^8$ | 1 | NH$_2$ |
| | 4 | Boc |

Piperidine (1 ml) was added to a magnetically stirred mixture of BHALys[α-GlyLys(Boc)4][ε-Fmoc] (0.12 mmol) and DMF (4 ml). Stirring was continued at room temperature for 50 mins. The volatiles were removed under reduced pressure and the residue treated with ethyl acetate (ca. 100 ml). The precipitate which formed was collected and left to air dry under suction for 2 h. The product, BHALys [ε-NH$_2$] [α-GlyLys] [Lys]$_2$ [Boc]$_4$ (33 mg, 24%) was obtained as a light yellow coloured solid.

LC/MS (Philic/TFA): ESI (+ve) m/z=1153.70 [M+H]+; calculated C595H96N10O13 1153.47 g/mol. Rf (min)= 10.51.

xi. BHALys [α-GlyLys] [Lys]$_2$ [Boc]$_4$ [ε-GlyLys] [Lys]$_2$ [4-NitroCBz]$_4$

| Surface Topology | Surface Stoichiometry | |
|---|---|---|
| (((4-Nitro-CBz 4-Nitro-CBz)(4-Nitro-CBz 4-Nitro-CBz))$^4$((Boc Boc)(Boc Boc))$^4$)$^8$ | 4 | 4-Nitro-CBz |
| | 4 | Boc |

To a magnetically stirred solution BHALys [ε-NH$_2$] [α-GlyLys] [Lys]$_2$ [Boc]$_4$ (26 mg, 0.02 mmol) and DMF (1 ml) was added pyBOP (23 mg, 0.044 mmol). To this solution was added a mixture of HO-GlyLys [Lys]$_2$ [4-Nitro-CBz]$_4$ (40 mg, 0.034 mmol), DIPEA (25 μL, 0.14 mmol) and DMF (0.5 ml) at room temperature. The reaction and product isolation were carried out according to the method described in Example 11.i. The product BHALys [α-GlyLys] [Lys]$_2$ [Boc]$_4$ [ε-GlyLys] [Lys]$_2$ [4-NitroCBZ]$_4$ (7.8 mg, 15%) was obtained as a grey coloured solid.

LC/MS (Phobic/TFA): ESI (+ve) m/z=1156.63 [M+2H]/ 2+, calculated C111H155N21O33 2311.59 g/mol. Rf (min)= 7.02 xii. BHALys [α-GlyLys] [Lys]$_2$ [Boc]$_4$ [ε-GlyLys] [Lys]$_2$ [NH$_2$]$_4$

| Surface Topology | Surface Stoichiometry | |
|---|---|---|
| (((4-Nitro-CBz 4-Nitro-CBz)(4-Nitro-CBz 4-Nitro-CBz))$^4$((NH$_2$ NH$_2$)(NH$_2$ NH$_2$))$^4$)$^8$ | 4 | 4-Nitro-CBz |
| | 4 | NH$_2$ |

A suspension of BHALys [α-GlyLys] [Lys]$_2$ [Boc]$_4$ [ε-GlyLys] [Lys]$_2$ [4-NitroCBz]$_4$, 2,2,2-trifluoroethanol (3 ml) and 10% Pd/C was subjected to high pressure hydrogenation conditions (room temperature, 50 PSI) for 1.5 h. After this time, the black suspension was filtered and the filtrate collected was concentrated under reduced pressure. The product BHALys [α-GlyLys] [Lys]$_2$ [Boc]$_4$ [ε-GlyLys] [Lys]$_2$ [NH$_2$]$_4$ (4.1 mg, 76%) was obtained as a clear, colourless oily smear.

LC/MS (Phobic/TFA): ESI (+ve) m/z=798.08 [M+2H]/2+; calculated C795H135N17O17 1595.06 g/mol. Rf (min)= 3.33.

Example 20

BHALys [Lys]$_2$ [α-NH$_2$]$_2$ [ε-Lys]$_2$ [Boc]$_4$

Figure 12:
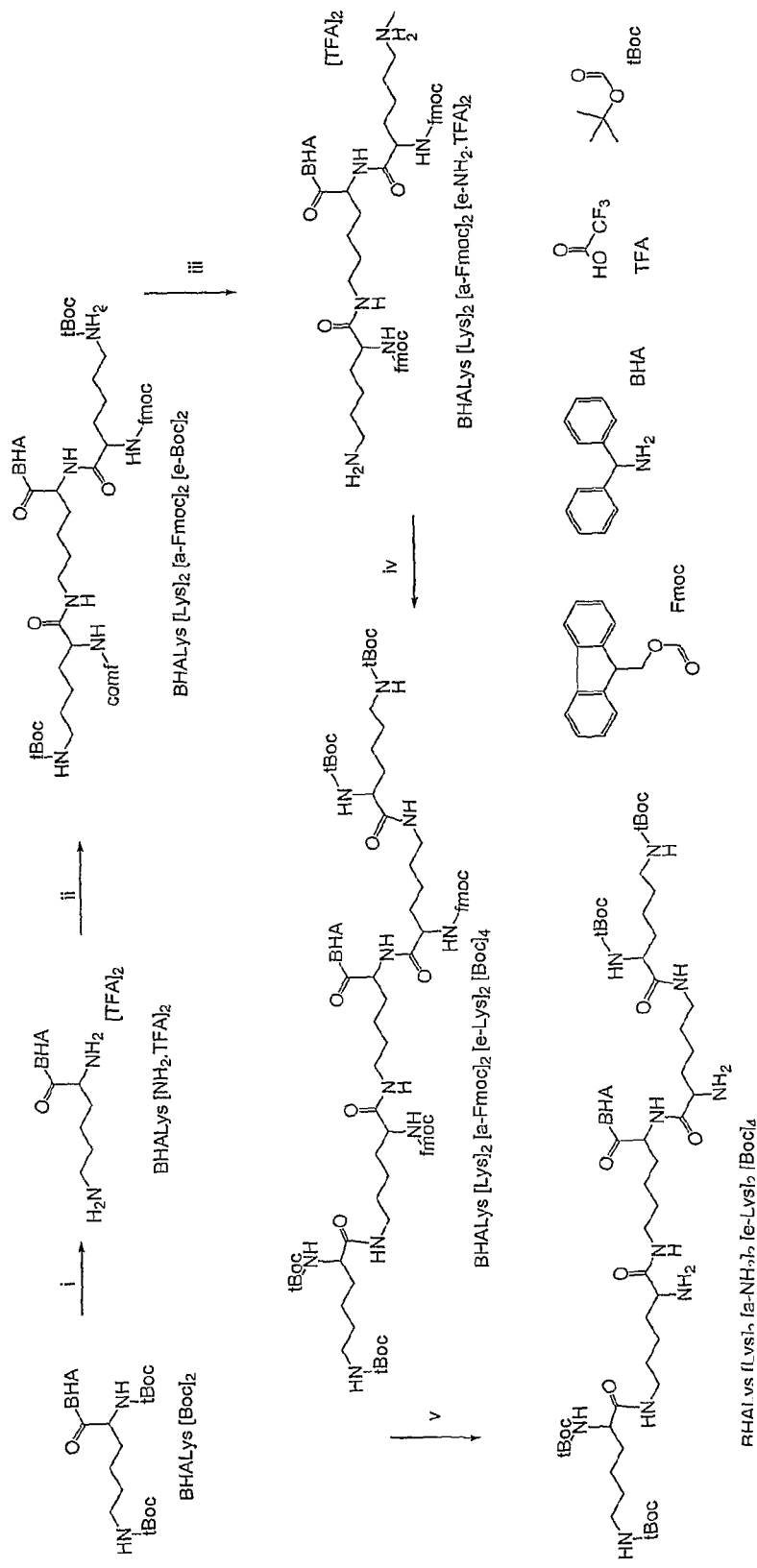
FIG. 12 is a schematic illustration of the synthesis of Example 20 (Scheme 1).

The synthesis is schematically illustrated in FIG. 12 (Scheme 1).

i. BHALys [NH$_2$.TFA]$_2$

| Surface Topology | Surface Stoichiometry | |
|---|---|---|
| (NH$_2$ NH$_2$) | 2 | NH$_2$ |

BHALys [Boc]$_2$ (10.014 g, 19.6 mmol) was suspended in DCM (30 mL) and chilled, forming a gel. TFA (30 mL, 43.2 mmol) was added slowly via a dropping funnel which dissolved the gel and the homogeneous solution was stirred overnight at Rt. Reaction mixture was slowly added to ice cold Ether (300 mL) with stirring, to form of a fine white precipitate. Suspended solid was collected by filtration, washed with Ether (50 mL×2) dissolved in water and freeze dried to give BHALys [Lys]$_2$ [NH$_2$.TFA]$_2$ (10.2 g, 18.9 mmol, 97%).

HPLC (hydrophilic/formate) Rt=11.8 min; ESI MS (+ve) 311.83 (M+H)$^+$; Calc MF: C$_{19}$H$_{25}$N$_3$O; M+H, 311.43.

ii. BHALys [Lys]$_2$ [α-Fmoc]$_2$ [ε-Boc]$_2$

| Surface Topology | Surface Stoichiometry | |
|---|---|---|
| ((Fmoc Boc)(Fmoc Boc))$^4$ | 1 | Fmoc |
| | 3 | Boc |

DIPEA (6.8 mL, 39.0 mmol) and BHALys [NH$_2$.TFA]$_2$ (10.2 g, 18.9 mmol) were dissolved in dry DMF (30 mL) and were added drop wise under argon to a solution of PFP-Lys-α-Fmoc-ε-Boc (37.4 g, 38.9 mmol) in dry DMF (70 mL). The reaction and product isolation were carried out according to the method described in Example 1.i to provide BHALys [Lys]$_2$ [α-Fmoc]$_2$ [ε-Boc]$_2$ as a white precipitate (18.9 g, 15.6 mmol, 79.5%).

iii. BHALys [Lys]$_2$ [α-Fmoc]$_2$ [ε-NH$_2$.TFA]$_2$

| Surface Topology | Surface Stoichiometry | |
|---|---|---|
| ((NH$_2$ Boc)(Fmoc Boc))$^4$ | 1 | NH$_2$ |
| | 3 | Boc |

BHALys [Lys]$_2$ [α-Fmoc]$_2$ [ε-Boc]$_2$ (18.4 g, 15.2 mmol) was suspended in DCM (75 mL) and chilled, forming a gel.

TFA (75 mL, 1.08 mol) was added slowly. The reaction and product isolation were carried out according to the method described in Example 19.ii to give BHALys [Lys]$_2$ [ε-Fmoc]$_2$ [α-NH$_2$.TFA]$_2$ in quantitative yield. (19.2 g, 15.8 mmol)—residual TFA present.

HPLC (Hydrophobic) Rt=10.4 min; ESI MS (+ve) 1012.15 (M+H)$^+$; Calc MF: C$_{61}$H$_{69}$N$_7$O$_7$; M+H, 1013.27 iv. BHALys [Lys]$_2$ [α-Fmoc]$_2$ [ε-Lys]$_2$ [Boc]$_4$

| Surface Topology | Surface Stoichiometry | |
|---|---|---|
| (((Fmoc Ø)(Boc Boc))$^4$((Fmoc Ø)(Boc Boc))$^4$)$^8$ | 2 | Fmoc |
| | 4 | Boc |

BHALys [Lys]$_2$ [α-Fmoc]$_2$ [ε-NH$_2$.TFA]$_2$ (19.2 g, 15.5 mmol) dissolved in dry DMF (90 mL) was added drop wise under of argon to a solution of PNPO-Lys(Boc)$_2$ (17.4 g, 37.2 mmol) and DIPEA (8.5 mL, 48.8 mmol) in dry DMF (250 mL) on ice. Once addition was complete the reaction was stirred overnight at Rt. Reaction mixture was slowly added to ACN (2 L) with vigorous stirring to form a white precipitate. Suspension was stirred for 30 minutes after which the precipitate was collected. Filtered solid was washed with ACN and dried giving a white solid (20.42 g), which was insoluble in a suitable HPLC solvent. 23 mg was deprotected for LCMS analysis using the standard Boc deprotection method and the data showed incomplete reaction. PNPO-Lys(Boc)$_2$ (7.1 g, 15.2 mmol) was added to a solution of the partially reacted material (20.4 g) dissolved in DMF (315 mL), followed by DIPEA (2.6 mL, 15.2 mmol) and stirred overnight at Rt. Reaction mixture was poured into ACN (2 L) and the precipitate collected. Filtered solid was washed with ACN (250 mL×3) and dried overnight at 40° C. to give BHALys [Lys]$_2$ [α-Fmoc]$_2$ [Lys]$_2$ [Boc]$_4$ as a white solid (19.6 g, 11.7 mmol, 72%)

HPLC (Hydrophobic): rf 8.2 min. ESI MS (+ve) 1268.72 (M+H)$^+$; 634.97 ((M+2H$^+$)/2). Calc. MF C$_{93}$H$_{125}$N$_{11}$O$_{17}$; M+H$^+$. 1669.1 v. BHALys [Lys]$_2$ [α-NH$_2$]$_2$ [ε-Lys]$_2$ [Boc]$_4$

| Surface Topology | Surface Stoichiometry | |
|---|---|---|
| (((NH2 Ø)(Boc Boc))4((NH2 Ø)(Boc Boc))4)8 | 2 | NH2 |
| | 4 | Boc |

A solution of piperidine (11.6 mL, 145 mmol) in DMF (120 mL) was added to BHALys [Lys]$_2$ [α-Fmoc]$_2$ [ε-Lys]$_2$ [Boc]$_4$ (19.6 g) at Rt forming a yellow solution. Reaction was stirred at Rt for 3 hours after which a slight cloudiness developed. The suspension was concentrated to approximately 70 mL and added to a slurry of ice water with stirring. A fine, faintly yellow precipitate was formed and this was collected. Methanol was added to dissolve the solid. Filtrate was concentrated (10.2 g) and solid purified by flash chromatography using 50:1:1 Isopropanol:water:concentrated Ammonia giving BHALys [Lys]$_2$ [α-NH$_2$]$_2$ [ε-Lys]$_2$ [Boc]$_4$ as a white solid (7.83 g, 6.4 mmol, 54%)

HPLC (Hydrophobic) Rt=8.75 min. ESI MS (+ve) 1224.81 (M+H)$^+$; 612.85 ((M+2H$^+$)/2) Calc MF: C$_{63}$H$_{105}$N$_{11}$O$_{13}$;

M+H, 1224.61. $^1$H-nmr (300 MHz, MeOD) λ (ppm) 1.2-1.8 (66H); 2.9-3.35 (5H); 3.85-4.0 (3H); 4.45 (1H); 6.2 (1H); 7.2-7.4 (10H)

Example 21

Demonstration of Orthogonal Protecting Group Removal

BHALys [Lys]$_8$ [ε-CBz]$_8$ [α-Lys]$_8$ [α-NH$_2$]$_8$ [ε-Boc]$_8$ i. BHALys [Lys]$_8$ [ε-CBz]$_8$ [α-Lys]$_8$ [α-Fmoc]$_8$ [ε-Boc]$_8$

| Surface Topology | Surface Stoichiometry | |
|---|---|---|
| (((((CBz Ø)(Fmoc Boc))$^4$((CBz Ø)(Fmoc Boc))$^4$)$^8$(((CBz Ø)(Fmoc Boc))$^4$((CBz Ø)(Fmoc Boc))$^4$)$^8$)$^{16}$ | 8 | CBz |
| | 8 | Fmoc |
| | 8 | Boc |
| (((((CBz Ø)(Fmoc Boc))$^4$((CBz Ø)(Fmoc Boc))$^4$)$^8$(((CBz Ø)(Fmoc Boc))$^4$((CBz Ø)(Fmoc Boc))$^4$)$^8$)$^{16}$ | | |

To a mixture of BHALys [Lys]$_8$ [α-NH$_2$]$_8$ [ε-CBz]$_8$ (0.025 mmol), TFA and DMF was added N,N-diisopropylethylamine (0.105 ml, 0.60 mmol) and PFP-Lys-α-Fmoc-ε-Boc (154 mg, 0.24 mmol) at Rt. The clear, colourless reaction mixture was stirred for a further 16 h at Rt. After this time, the reaction solution was transferred to a beaker containing ACN (ca. 150 ml) and immediately, a colourless precipitate formed. This precipitate, after being collected via filtration and washed with ACN, was air dried under suction overnight. BHALys [Lys]$_8$ [ε-CBz]$_8$ [α-Lys]$_8$ [α-Fmoc]$_8$ [ε-Boc]$_8$ (157 mg, 92%) was obtained as a colourless solid.

The protecting groups may then be removed by one of the following three processes:

ii. BHALys [Lys]$_8$ [ε-CBz]$_8$ [α-Lys]$_8$ [α-NH$_2$]$_8$ [ε-Boc]$_8$

| Surface Topology | Surface Stoichiometry | |
|---|---|---|
| (((((CBz Ø)(NH$_2$ Boc))$^4$((CBz Ø)(NH$_2$ Boc))$^4$)$^8$(((CBz Ø)(NH$_2$ Boc))$^4$((CBz Ø)(NH$_2$ Boc))$^4$)$^8$)$^{16}$ | 8 | CBz |
| | 8 | NH$_2$ |
| | 8 | Boc |
| (((((CBz Ø)(NH$_2$ Boc))$^4$((CBz Ø)(NH$_2$ Boc))$^4$)$^8$(((CBz Ø)(NH$_2$ Boc))$^4$((CBz Ø)(NH$_2$ Boc))$^4$)$^8$)$^{16}$ | | |

A suspension of BHALys [ε-CBz]$_8$ [α-Lys]$_8$ [α-Fmoc]$_8$ [ε-Boc]$_8$ (20 mg, 0.0029 mmol) and DMF was treated with piperidine at Rt. Stirring was continued at Rt for a further 18 h. After this time, the reaction mixture was diluted with DMF (ca. 2 ml), and concentrated under reduced pressure. The product was obtained as a colourless solid residue.

LC/MS (Phobic/TFA): ESI (+ve) observed [M+H/3]+ m/z=1670; [M+H/4]+ m/z=1252; [M+H/5]+ m/z=1002; [M+H/6]+ m/z=825; calculated for C255H401N47O55 5005.27; Rf (min)=10.10 mins.

iii. BHALys [Lys]$_8$ [ε-CBz]$_8$ [α-Lys]$_8$ [α-Fmoc]$_8$ [ε-NH$_2$.TFA]$_8$

| Surface Topology | Surface Stoichiometry | |
|---|---|---|
| (((((CBz Ø)(Fmoc NH$_2$))$^4$((CBz Ø)(Fmoc NH$_2$))$^4$)$^8$(((CBz Ø)(Fmoc NH$_2$))$^4$((CBz Ø)(Fmoc NH$_2$))$^4$)$^8$)$^{16}$ | 8 | CBz |
| | 8 | Fmoc |
| | 8 | NH$_2$ |
| (((((CBz Ø)(Fmoc NH$_2$))$^4$((CBz Ø)(Fmoc NH$_2$))$^4$)$^8$(((CBz Ø)(Fmoc NH$_2$))$^4$((CBz Ø)(Fmoc NH$_2$))$^4$)$^8$)$^{16}$ | | |

A suspension of BHALys [Lys]$_8$ [ε-CBz]$_8$ [α-Lys]$_8$ [α-Fmoc]$_8$ [ε-Boc]$_8$ (20 mg, 0.0029 mmol) and AcOH was treated with neat TFA at Rt. Stirring was continued at Rt for a further 16 h. After this time, the reaction mixture was diluted with AcOH (ca. 2 ml), and concentrated under reduced pressure. BHALys [Lys]$_8$ [ε-CBz]$_8$ [α-Lys]$_8$ [α-Fmoc]$_8$ [ε-NH$_2$.TFA]$_8$ was obtained as a colourless oily residue.

LC/MS (Phobic/TFA): ESI (+ve) observed [M+H/4]+ m/z=1496; [M+H/5]+ m/z=1197; [M+H/6]+ m/z=998; [M+H/7]+ m/z=855; calculated for C355H417N47O55 5982.28; Rf (min)=13.86 mins.

iv. BHALys [Lys]$_8$ [ε-NH$_2$]$_8$ [α-Lys]$_8$ [α-Fmoc]$_8$ [ε-Boc]$_8$

| Surface Topology | Surface Stoichiometry | |
|---|---|---|
| ((((NH$_2$ Ø)(Fmoc Boc))$^4$((NH$_2$ Ø)(Fmoc Boc))$^4$)$^8$(((NH$_2$ Ø)(Fmoc Boc))$^4$((NH$_2$ Ø)(Fmoc Boc))$^4$)$^8$)$^{16}$ | 8 | NH$_2$ |
| | 8 | Fmoc |
| | 8 | Boc |
| ((((NH$_2$ Ø)(Fmoc Boc))$^4$((NH$_2$ Ø)(Fmoc Boc))$^4$)$^8$(((NH$_2$ Ø)(Fmoc Boc))$^4$((NH$_2$ Ø)(Fmoc Boc))$^4$)$^8$)$^{16}$ | | |

A suspension of BHALys [Lys]$_8$ [ε-CBz]$_8$ [α-Lys]$_8$ [α-Fmoc]$_8$ [ε-Boc]$_8$ (19.6 mg, 0.0029 mmol), 10% Pd/C (22 mg) and AcOH was stirred vigorously under hydrogen at Rt for 18 h. The black suspension was diluted with AcOH (ca. 5 ml) and filtered. Concentration of the clear and colourless filtrate under reduced pressure gave BHALys [Lys]$_8$ [ε-NH$_2$]$_8$ [α-Lys]$_8$ [α-Fmoc]$_8$ [ε-Boc]$_8$ as a clear oil.

LC/MS (Phobic/TFA): ESI (+ve) observed [M+H/4]+ m/z=1429; [M+H/5]+ m/z 1143; calculated for C311H433N47O55 5710.14; Rf (min)=14.67 mins.

Example 22

BHALys [Lys]$_2$ [GlyLys]$_4$ [ε-NH$_2$]$_4$ [α-Lys] [Boc]$_8$ i. HO-GlyLys [ε-CBz] [α-Lys] [Boc]$_2$

| Surface Topology | Surface Stoichiometry | |
|---|---|---|
| HO—CO ((CBz Ø)(Boc Boc))$^4$ | 1 | CO$_2$H |
| | 1 | CBz |
| | 2 | Boc |

To a magnetically stirred solution of MeO-GlyLys [ε-CBz] [α-Lys] [Boc]$_2$ (1.0 g, 1.47 mmol), methanol (32 ml) and water (16 ml) was added 1M aq. NaOH solution (3 ml) at Rt. The reaction and product isolation were carried out according to the method described in Example 13.vi to afford HO-GlyLys [ε-CBz] [α-Lys] [Boc]$_2$ (942 mg, 96%) as a colourless foam.

LC/MS (Phobic/TFA): ESI (+ve) m/z=666.40 [M+H]+; calculated C33H54N5O9 664.83 g/mol. Rf (min)=3.53.

ii. PNPO-GlyLys [ε-CBz] [α-Lys] [Boc]$_2$

| Surface Topology | Surface Stoichiometry | |
|---|---|---|
| PNPO—CO ((CBz Ø)(Boc Boc))$^4$ | 1 | CO—OPNP |
| | 1 | CBz |
| | 2 | Boc |

To a magnetically stirred solution of HO-GlyLys [ε-CBz] [α-Lys] [Boc]$_2$ (430 mg, 0.65 mmol) and EtOAc (10 ml) was added, in the following order, p-nitrophenol (99 mg, 0.71 mmol) and DCC (147 mg, 0.71 mmol). After stirring at Rt for ca. 5 mins, the reaction mixture became a slurry due to the formation of a gel like precipitate. Stirring was continued at Rt for a further 22 h. The crude reaction mixture was diluted upon the addition of EtOAc (15 ml) then filtered. The filtrate was concentrated under reduced pressure to give an orange/yellow coloured solid. After subjection of the crude material to silica gel flash chromatography (EtOAc), the product PNPO-GlyLys [ε-CBz] [α-Lys] [Boc]$_2$ (Rf 0.4) (344 mg, 66%) was obtained as an off white solid.

LC/MS (Phobic/TFA): ESI (+ve) m/z=787.31 [M+H]+; calculated C38H54N6O12 786.89 g/mol. Rf (Min)=5.24.

iii. BHALys [Lys]$_2$ [GlyLys]$_4$ [ε-CBz]$_4$ [α-Lys] [Boc]$_8$

| Surface Topology | Surface Stoichiometry | |
|---|---|---|
| (((((CBz Ø)(Boc Boc))$^4$((CBz Ø)(Boc Boc))$^4$)$^8$(((CBz Ø)(Boc Boc))$^4$((CBz Ø)(Boc Boc))$^4$)$^8$)$^{16}$ | 4 | CBz |
| | 8 | Boc |

To a magnetically stirred solution of BHALys [Lys]$_2$ [NH$_2$.TFA]$_4$ (30 mg, 0.029 mmol), TEA (0.06 ml, 0.43 mmol) and DMF (0.5 ml) was added a solution of PNPOGlyLys(α-DBL)(ε-CBz) (172 mg, 0.22 mmol dissolved in 2 ml DMF) at Rt. The reaction and product isolation were carried out according to the method described in Example 1.i. The product, BHALys [Lys]$_2$[GlyLys(Boc)$_2$(CBz)]$_4$ (87 mg, 94%), was obtained as an off white solid.

LC/MS (Phobic/TFA): ESI (+ve) m/z=1580.31 [M+2H]/2+, 1053.90 [M+3H]/3+; calculated C159H245N27O39 3158.85 g/mol. Data deconvoluted using transform calculation to give mw=3158.29. Rf (min)=7.75.

iv. BHALys [Lys]$_2$ [GlyLys]$_4$ [ε-NH$_2$]$_4$ [α-Lys] [Boc]$_8$

| Surface Topology | Surface Stoichiometry | |
|---|---|---|
| (((((NH$_2$ Ø)(Boc Boc))$^4$((NH$_2$ Ø)(Boc Boc))$^4$)$^8$(((NH$_2$ Ø)(Boc Boc))$^4$((NH$_2$ Ø)(Boc Boc))$^4$)$^8$)$^{16}$ | 4 | NH$_2$ |
| | 8 | Boc |

To a magnetically stirred solution of BHALys [Lys]$_2$ [GlyLys(Boc)$_2$(CBz)]$_4$ (82 mg, 0.026 mmol) and 2,2,2-trifluoroethanol (2 ml) was added 10% Pd/C (55 mg). The black suspension was hydrogenated under standard conditions (rt, atmospheric pressure) for 17 h. After this time, the suspension was filtered through a 0.45 micron filter disk. The filtrate was concentrated under reduced pressure to give the product BHALys [Lys]$_2$[GlyLys(Boc)$_2$(NH$_2$)]$_4$ (68 mg, 99%) as a light brown coloured glassy solid.

LC/MS (Philic/TFA): ESI (+ve) m/z=1311.90 [M+2H]/2+, 874.92 [M+3H]/3+, 656.46 [M+4H]/4+; calculated C127H221N27O31 2622.32 g/mol. Data deconvoluted using transform calculation to give mw=2621.78. Rf (min)=9.55.

Example 23

BHALys [Lys]$_4$ [ε,α-Boc] [ε,ε-NH$_2$] [Boc]$_6$ i. BHALys [α-Fmoc] [ε-Boc]

| Surface Topology | Surface Stoichiometry | |
|---|---|---|
| (Boc Fmoc) | 1 | Boc |
| | 1 | Fmoc |

HO-Lys-α-Fmoc-ε-Boc (13.6 g, 29.1 mmol) was dissolved in dry DMF (110 mL) and chilled. DCC (6.3 g, 30.6 mmol) was added followed by HOBt (4.1 g, 30.6 mmol). Benzhydrylamine (5 mL, 28.9 mol) was dissolved in dry DMF (40 mL) and added drop wise to the reaction under argon. The reaction and product isolation were carried out according to the method described in Example 19.vii to give BHALys [α-Fmoc] [ε-Boc] as a pale yellow solid. Material was dried at 40° C. for 2 hours (17.36 g, 27.3 mmol, 94%).

HPLC (Hydrophobic) rf 12.92 min. ESI MS (+ve) 634.12 (M+H)$^+$: Calc. MF C$_{39}$H$_{43}$N$_3$O$_5$ M+H, 633.79.

ii. BHALys [α-Fmoc] [ε-NH$_2$.TFA]

| Surface Topology | Surface Stoichiometry | |
|---|---|---|
| (NH$_2$ Fmoc) | 1 | NH$_2$ |
| | 1 | Fmoc |

BHALys [α-Fmoc] [s-Boc] (17.3 g, 27.3 mmol) was deprotected with in DCM (60 mL) TFA (100 mL, 1.43 mol) and DCM (40 mL) in the method of Example 19.ii to give BHALys [α-Fmoc] [s-NH$_2$.TFA] as a white solid.

HPLC (Hydrophobic) Rt=6.59 min; ESI MS (+ve) 533.9 (M+H)$^+$; Calc MF: $C_{34}H_{35}N_3O_3$; M+H, 533.68.

$^1$H-nmr (300 MHz, D$_6$DMSO) λ (ppm) 1.15-1.75 (6H); 2.65-2.85 (2H); 4.05-4.45 (3H); 6.1 (1H); 7.0-8.0 (18H)

$^{13}$Cnmr (300 MHz, D$_6$DMSO) λ (ppm) 22.47 (1CH$_2$); 26.55 (1CH$_2$); 31.39 (1CH$_2$); 46.65 (1CH$_2$); 54.38 (1CH); 55.90 (1C); 65.59 (1C); 119.06-143.87 16 peaks (24 Ar—C); 155.98 (1C-Carbamate); 171.28 (1C-Amide)

iii. BHALys [α-Fmoc] [ε-Lys] [Boc]$_2$

| Surface Topology | Surface Stoichiometry | |
|---|---|---|
| ((Fmoc Ø)(Boc Boc))$^4$ | 2 | Boc |
| | 1 | Fmoc |

BHALys [α-Fmoc] [ε-NH$_2$.TFA] (14.64 g, 22.6 mmol) was reacted with PNPO-Lys(Boc)$_2$ (13.4 g, 28.7 mmol) in dry DMF (80 mL) and DIPEA (7.2 mL, 37.3 mmol) in DMF (145 mL), in the same manner as in Example 1.i. The solid was collected and washed repetitively with Ether to give BHALys [α-Fmoc] [ε-Lys] [Boc]$_2$ as a white solid (13.8 g, 16.0 mmol, 60%)

HPLC (Hydrophobic) rf 13.59 min. ESI MS (+ve) 862.17 (M+H)$^+$; 879.27 (M+NH$_4^+$); Calc. MF $C_{50}H_{63}N_5O_8$ M+H, 862.09.

$^1$H-nmr (300 MHz, D$_6$DMSO) λ (ppm) 1.15-1.75 (30H); 2.8-3.2 (4H); 4.3 (1H); 4.1-4.3 (3H); 7.2-7.95 (18H)

iv. BHALys [α-NH$_2$] [ε-Lys] [Boc]$_2$

| Surface Topology | Surface Stoichiometry | |
|---|---|---|
| ((NH$_2$ Ø)(Boc Boc))$^4$ | 2 | Boc |
| | 1 | NH$_2$ |

The Fmoc protecting group was removed from BHALys [α-Fmoc] [ε-Lys] [Boc]$_2$ (13.8 g, 16.0 mmol) using piperidine (20 mL, 25.0 mmol) in DMF (80 mL) in similar manner to Example 1.v. Material was purified by flash chromatography (EtOAc:PM 17:2 (PM=Isopropanol:waterconcentrated Ammonia 20:1:1). to give BHALys [α-NH$_2$][ε-Lys] [Boc]$_2$ as a white solid (8.04 g, 12.5 mmol, 79%) rf product=0.35.

$^1$H-nmr (300 MHz, MeOD) λ 1.2-1.9 (30H); 3.0-3.3 (4H); 3.4 (1H); 3.95 (1H); 6.2 (1H); 7.2-7.4 (10H)

HPLC (Hydrophobic) Rt=7.15 min. ESI MS (+ve) 640.5 (M+H)$^+$; Calc MF: $C_{35}H_{53}N_5O_6$; M+H, 639.84.

v. BHALys [Lys]$_2$ [α,ε-Fmoc] [Boc]$_3$

| Surface Topology | Surface Stoichiometry | |
|---|---|---|
| ((Fmoc Boc)(Boc Boc))$^4$ | 3 | Boc |
| | 1 | Fmoc |

HO-Lys-α-Boc-δ-Fmoc (2.94 g, 6.3 mmol) was dissolved in dry DMF (10 mL) and chilled. DCC (1.36 g, 6.60 mmol) in DMF (5 mL) was added followed by HOBt (893 mg, 6.60 mmol) in DMF (5 mL). BHALys [α-NH$_2$][ε-Lys] [Boc]$_2$ (4.02 g, 6.3 mol) was dissolved in dry DMF (12 mL) and added drop wise to the reaction under argon. Reaction stirred at Rt overnight. DCU was filtered and the filtrate concentrated under reduced pressure. The residue was triturated with Ether, filtered and washed with EtOAc to give BHALys [Lys]$_2$ [α,ε-Fmoc] [Boc]$_3$ as a white solid (5.33 g, 4.88 mmol, 78%.)

HPLC (Hydrophobic) rf 14.58 min. ESI MS (+ve) 1090.31 (M+H)$^+$; 1107.39 (M+NH$_4^+$); Calc. MF $C_{61}H_{83}N_7O_{11}$ M+H, 1090.38.

vi. BHALys [Lys]$_2$ [α,ε-Fmoc] [NH$_2$.TFA]$_3$

| Surface Topology | Surface Stoichiometry | |
|---|---|---|
| ((Fmoc NH$_2$)(NH$_2$ NH$_2$))$^4$ | 3 | NH$_2$ |
| | 1 | Fmoc |

BHALys [Lys]$_2$ [α,ε-Fmoc] [Boc]$_3$ (92 mg, 84.4 mmol) was deprotected using TFA and DCM as for the method of Example 19.ii. Reaction concentrated under reduced pressure and the residue washed with ether to give BHALys [Lys]$_2$ [α,ε-Fmoc] [NH$_2$.TFA]$_3$ as a solid (85 mg, 82%)

HPLC (Hydrophobic) rf 15.77 min. ESI MS (+ve) 790.09 (M+H)$^+$; 395.71 (M+2H$^+$)/2; Calc. MF $C_{46}H_{59}N_7O_5$ M+H, 790.03.

$^1$H-nmr (300 MHz, MeOD) λ (ppm); 1.25 (18H); 2.8-3.0 (4H); 3.8 (1H); 4.0-4.5 (5H); 6.2 (1H); 7.2-7.8 (18H)

vii. BHALys [Lys]$_2$ [α,ε-Fmoc] [Lys]$_3$ [Boc]$_6$

| Surface Topology | Surface Stoichiometry | |
|---|---|---|
| (((Fmoc Ø)(Boc Boc))$^4$((Boc Boc)(Boc Boc))$^4$)$^8$ | 6 | Boc |
| | 1 | Fmoc |

BHALys [Lys]$_2$ [α,ε-Fmoc] [NH$_2$.TFA]$_3$ (75 mg, 66.3 umol) was dissolved in dry DMF (1 mL) and added drop wise to a solution of PNPO-Lys(Boc)$_2$ (120 mg, 0.25 mmol) and DIPEA (50 μL, 1.5 eq/NH$_2$) in dry DMF (1 ml) under argon. Once addition complete, the reaction was stirred at Rt overnight. Reaction was filtered, concentrated under reduced pressure and the residue triturated with Ether, filtered and then washed with EtOAc repetitively to give BHALys [Lys]$_2$ [α,ε-Fmoc] [Lys]$_3$ [Boc]$_6$ as a solid (113 mg, 63.6 umol, 96%)

HPLC (Hydrophobic) rf 16.52 min. ESI MS (+ve) 888 (M+2H$^+$)/2; Calc. MF $C_{61}H_{83}N_7O_{11}$ M+H, 1775.26.

viii. BHALys [Lys]$_2$ [α,ε-NH$_2$] [Lys]$_3$ [Boc]$_6$

| Surface Topology | Surface Stoichiometry | |
|---|---|---|
| (((Fmoc Ø)(Boc Boc))$^4$((Boc Boc)(Boc Boc))$^4$)$^8$ | 6 | Boc |
| | 1 | Fmoc |

BHALys [Lys]$_2$ [α,ε-Fmoc] [Lys]$_3$ [Boc]$_6$ (113 mg, 63.6 umol) was dissolved in dry DMF (1 mL) using piperidine (0.2 mL) in similar manner to Example 1.v. Material was purified by flash chromatography to give BHALys [Lys]$_2$ [α,ε-NH$_2$] [Lys]$_3$ [Boc]$_6$ as an oil (50 mg, 30 umol).

ix. BHALys [Lys]$_4$ [α,ε,α-Boc] [α,ε,ε-4-Nitro-CBz] [Boc]$_6$

| Surface Topology | Surface Stoichiometry | |
|---|---|---|
| (((4-Nitro-CBz Boc)(Boc Boc))$^4$((Boc Boc)(Boc Boc))$^4$)$^8$ | 7 | Boc |
| | 1 | 4-Nitro-CBz |

To a magnetically stirred solution of BHALys [Lys]$_2$ [α,ε-NH$_2$] [Lys]$_3$ [Boc]$_6$ (99.5 mg, 0.064 mmol), DMF (2 ml) and TEA (25 μl, 0.18 mmol) was added PNPO-Lys-α-Boc-ε-4-Nitro-CBz (45.2 mg, 0.083 mmol) in one portion at Rt. The bright yellow coloured solution was allowed to stir at Rt for 22 h. The reaction and product isolation were carried out according to the method described in Example 1.i. The product, BHALys [Lys]$_4$ [α,ε,α-Boc] [α,ε,ε-4-Nitro-CBz] [Boc]$_6$ (105 mg, 83%) was obtained as an off-white solid.

LC/MS (Phobic/TFA): ESI (+ve) m/z=1961.39 [M+H]+, 981.00 [M+2H]/2+; calculated C98H158N16O25 1960.44 g/mol. Data deconvoluted using transform calculation to give mw=1959.99. Rf (min): 7.37.

x. BHALys [Lys]$_4$ [α,ε,α-Boc] [α,ε,ε-NH$_2$] [Boc]$_6$

| Surface Topology | Surface Stoichiometry | |
|---|---|---|
| (((NH$_2$ Boc)(Boc Boc))$^4$((Boc Boc)(Boc Boc))$^4$)$^8$ | 7 | Boc |
| | 1 | NH$_2$ |

To a magnetically stirred solution of BHALys [Lys]$_4$ [ε,α-Boc] [ε,ε-4-Nitro-CBz] [Boc]$_6$ (100 mg, 0.051 mmol) and TFE (2 ml) was added 10% Pd/C (27.2 mg). The black suspension was hydrogenated at Rt and pressure for 5 h. The suspension was filtered through a silica plug and concentration of the filtrate afforded BHALys [Lys]$_4$ [α,ε,α-Boc] [α,ε,ε-NH$_2$] [Boc]$_6$ (68.6 mg, 75%) as a fawn coloured, glass like solid.

LC/MS (Phobic/TFA): ESI (+ve) m/z=1781.34 [M+H]+, 891.63 [M+2H]/2+; calculated C90H153N15O21 1781.31 g/mol. Rf (min): 6.05.

Example 24

BHALys [Lys]$_2$ [α,ε-Lys][NH$_2$]$_2$ [Lys]$_3$ [Boc]$_6$ i. BHALys [Lys]$_2$ [α,ε-Lys] [CBz]$_2$ [Lys]$_3$ [Boc]$_6$

| Surface Topology | Surface Stoichiometry | |
|---|---|---|
| (((CBz CBz)(Boc Boc))$^4$((Boc Boc)(Boc Boc))$^4$)$^8$ | 6 | Boc |
| | 2 | CBz |

To a magnetically stirred solution of BHALys [Lys]$_2$ [α,ε-NH$_2$] [Lys]$_3$ [Boc]$_6$ (50 mg, 0.032 mmol), DMF (1 ml) and TEA (11 μl, 0.08 mmol) was added PNPO-Lys(CBz)$_2$ (35 mg, 0.064 mmol) in one portion at room temperature. The reaction and product isolation were carried out according to the method described in Example 1.i to give BHALys [Lys]$_2$ [α,ε-Lys] [CBz]$_2$ [Lys]$_3$ [Boc]$_6$ (48.2 mg, 77%) as an off-white solid.

LC/MS (Phobic/TFA): ESI (+ve) m/z=1950.01 [M+H]+, 975.50 [M+2H]/2+; calculated C101H157N15O23 1949.46 g/mol. Data deconvoluted using transform calculation to give mw=1948.94. Rf (min): 7.61.

ii. BHALys [Lys]$_2$ [α,ε-Lys] [NH$_2$]$_2$ [Lys]$_3$[Boc]$_6$

| Surface Topology | Surface Stoichiometry | |
|---|---|---|
| (((NH$_2$ NH$_2$)(Boc Boc))$^4$((Boc Boc)(Boc Boc))$^4$)$^8$ | 6 | Boc |
| | 2 | NH$_2$ |

To a magnetically stirred solution of BHALys [Lys]$_2$ [α,ε-Lys] [CBz]$_2$ [Lys]$_3$ [Boc]$_6$ (13.4 mg, 7 μmol) and TFE (2 ml) was added 10% Pd/C (15.9 mg). The black suspension was hydrogenated at room temperature and under pressure (50 PSI) for ca. 10 h. The suspension was filtered and concentration of the filtrate afforded BHALys [Lys]$_2$ [α,ε-Lys] [NH$_2$]$_2$ [Lys]$_3$ [Boc]$_6$ (7.6 mg, 66%) as a light brown coloured oil.

LC/MS (Phobic/TFA): ESI (+ve) m/z=1680.93 [M+H]+, 841.14 [M+2H]/2+; calculated C85H145N15O19 1681.19 g/mol. Rf (min): 5.53.

Example 25

BHALys [Lys]$_2$ [Lys]$_4$ [α,ε,α-CBz] [α,ε,ε-Alloc] [Boc]$_6$

| Surface Topology | Surface Stoichiometry | |
|---|---|---|
| (((CBz Alloc)(Boc Boc))$^4$((Boc Boc)(Boc Boc))$^4$)$^8$ | 6 | Boc |
| | 1 | CBz |
| | 1 | Alloc |

To a magnetically stirred solution of BHALys [Lys]$_2$ [α,ε-NH$_2$] [Lys]$_3$ [Boc]$_6$ (46.7 mg, 0.03 mmol) and DMF (0.5 ml) was added pyBOP (43 mg, 0.083 mmol) in one portion at room temperature. To this mixture was added a solution of HO-Lys-α-CBz-ε-Alloc dicyclohexylamine salt (39 mg, 0.071 mmol), DIPEA (45 μl, 0.26 mmol) and DMF (0.5 ml). The flask containing the capping group was rinsed with DMF (0.5 ml) which was also added to the reaction mix. The clear and near colourless reaction mixture was allowed to stir at room temperature for 44 h. The crude reaction mixture was transferred to a beaker containing acetonitrile (250 ml) and the flocculant precipitate which formed was collected by filtration and allowed to dry overnight under suction. The product, BHALys [Lys]$_2$ [Lys]$_4$ [α,ε,α-CBz] [α,ε,ε-Alloc] [Boc]$_6$ (33 mg, 58%) was obtained as an off-white solid.

LC/MS (Phobic/TFA): ESI (+ve) m/z=1899.80 [M+H]+, 950.83 [M+2H]/2+; calculated C97H155N15O23 1899.40 g/mol. Data deconvoluted using transform calculation to give mw=1898.91. Rf (min): 7.39.

Example 26

BHALys [Lys]$_2$ [ε-NH$_2$]$_2$ [α-Lys]$_2$ [Boc]$_4$ i. BHALys [Lys]$_2$ [α-Boc]$_2$ [ε-Fmoc]$_2$

| Surface Topology | Surface Stoichiometry | |
|---|---|---|
| ((Boc Fmoc)(Boc Fmoc))$^4$ | 2 | Boc |
| | 2 | Fmoc |

To a solution of HO-Lys-α-Boc-ε-Fmoc (18.3 g, 39.1 mmol) in DMF (150 mL) on ice, was added DCC (8.47 g, 41.1 mmol) and HOBt (41.1 mmol). BHALys [NH$_2$.TFA]$_2$ (10.23 g, 19.6 mmol) was added drop wise as a solution in DMF (50 mL) with DIPEA (9 mL, 52 mmol). Once addition complete, reaction stirred at Rt overnight. DCU formed was filtered and the filtrate was added to Ether (2 L) with stirring. The precipitate was collected and washed with Ether. Filtered solid was then suspended in 20% MeOH in EtOAc and sonicated for 20 minutes. A fine white suspension was filtered and the process repeated using 20% MeOH in EtOAc (100 mL) to provide BHALys [Lys]$_2$ [α-Boc]$_2$ [ε-Fmoc]$_2$ as a white solid (18.6 g, 15.3 mmol, 78%).

ii. BHALys [Lys]$_2$ [ε-Fmoc]$_2$ [α-NH$_2$.TFA]$_2$

| Surface Topology | Surface Stoichiometry | |
|---|---|---|
| ((NH$_2$ Fmoc)(NH$_2$ Fmoc))$^4$ | 2 | NH$_2$ |
| | 2 | Fmoc |

BHALys [Lys]$_2$ [ε-Fmoc]$_2$ [α-Boc]$_2$ (18.9 g, 15.6 mmol) was suspended in DCM (75 mL) and chilled. TFA (75 mL, 1.08 mol) was added slowly. The reaction and product isolation were carried out according to the method described in Example 19.ii to give BHALys [Lys]$_2$ [ε-Fmoc]$_2$ [α-NH$_2$.TFA]$_2$ in quantitative yield. (19.6 g, 15.8 mmol)—some excess TFA present.

HPLC (Hydrophobic) Rt=10.4 min; ESI MS (+ve) 1012.15 (M+H)$^+$; Calc MF: C$_{61}$H$_{69}$N$_7$O$_7$; M+H, 1013.27.

iii. BHALys [Lys]$_2$ [ε-Fmoc]$_2$ [α-Lys]$_2$ [Boc]$_4$

| Surface Topology | Surface Stoichiometry | |
|---|---|---|
| (((Fmoc Ø)(Boc Boc))$^4$((Fmoc Ø)(Boc Boc))$^4$)$^8$ | 4 | Boc |
| | 2 | Fmoc |

BHALys [Lys]$_2$ [ε-Fmoc]$_2$ [α-NH$_2$.TFA]$_2$ (19.6 g, 15.8 mmol) dissolved in dry DMF (80 mL) was added drop wise under argon to a solution of PNPO-Lys(Boc)$_2$ (18.4 g, 39.4 mmol) and DIPEA (7.88 mL, 45.2 mmol) in dry DMF (200 mL) on ice. The reaction and product isolation were carried out according to the method described in Example 1.i. to give the product BHALys [Lys]$_2$ [ε-Fmoc]$_2$ [α-Lys]$_2$ [Boc]$_4$ in 85% yield (22.3 g, 13.4 mmol).

HPLC (Hydrophobic) RT=6.8 min. ESI MS (+ve) 1269 (M+H)$^+$; Calc. MF C$_{73}$H$_{93}$N$_{11}$O$_9$; M+H, 1269.1.

$^1$H-nmr (300 MHz, D$_6$DMSO) λ (ppm) 1.4-2.3 (66H); 3.2-3.5 (10H); 4.3 (2H); 4.5-4.9 (9H); 6.5 (1H); 7.6-7.9 (28H)

iv. BHALys [Lys]$_2$ [ε-NH$_2$]$_2$ [α-Lys]$_2$ [Boc]$_4$

| Surface Topology | Surface Stoichiometry | |
|---|---|---|
| (((NH$_2$ Ø)(Boc Boc))$^4$((NH$_2$ Ø)(Boc Boc))$^4$)$^8$ | 4 | Boc |
| | 2 | NH$_2$ |

BHALys [Lys]$_2$ [ε-Fmoc]$_2$ [α-Lys]$_2$ [Boc]$_4$ (22.3 g, 13.4 mmol) was suspended in dry DMF (120 mL) and piperidine (32 mL, 402 mmol) in DMF (40 mL) was slowly added to the mixture with stirring. Reaction became homogeneous after 15 minutes and was stirred for a further 45 minutes at Rt and then cooled overnight. DMF was removed under reduced pressure. Material was purified by flash chromatography with solvent system 13:1:1 Isopropanol:Water:Concentrated Ammonia to give a white solid BHALys [Lys]$_2$ [ε-NH$_2$]$_2$ [α-Lys]$_2$ [Boc]$_4$; 9.28 g, 7.58 mmol, 58%). HPLC (Hydrophobic): Rt=6.84 min. ESI MS (+ve) 1224.57 (M+H)$^+$; 612.96 ((M+2H$^+$)/2) Calc MF: C$_{63}$H$_{105}$NH$_{11}$O$_{13}$; M+H, 1224.61

$^1$H-nmr (300 MHz, D$_6$DMSO) λ (ppm) 1.2-1.8 (66H); 2.9-3.35 (5H); 3.85-4.0 (3H); 4.45 (1H); 6.2 (1H); 7.2-7.4 (10H)

Example 27

BHALys [Lys]$_4$ [GlyLys]$_8$ [ε-NH$_2$]$_8$ [α-Lys]$_8$ [Boc]$_{16}$ i. HO-GlyLys [ε-CBz] [α-Lys] [Boc]$_2$

| Surface Topology | Surface Stoichiometry | |
|---|---|---|
| HO—CO ((CBz Ø)(Boc Boc))$^4$ | 1 | CO$_2$H |
| | 2 | Boc |
| | 1 | CBz |

To a magnetically stirred solution of MeO-GlyLys [ε-CBz] [α-Lys] [Boc]$_2$ (1.0 g, 1.47 mmol), methanol (32 ml) and water (16 ml) was added 1M aq. NaOH solution (3 ml) at room temperature. The reaction and product isolation were carried out according to the method described in Example 13.vi to afford HO-GlyLys [ε-CBz] [α-Lys] [Boc]$_2$ (942 mg, 96%) as a colourless foam.

LC/MS (Phobic/TFA): ESI (+ve) m/z=666.40 [M+H]+; calculated C33H54N5O9 664.83 g/mol. Rf (min)=3.53.

ii. PNPO-GlyLys [ε-CBz] [α-Lys] [Boc]$_2$

| Surface Topology | Surface Stoichiometry | |
|---|---|---|
| PNPO—CO ((CBz Ø)(Boc Boc))$^4$ | 1 | CO$_2$PNP |
| | 2 | Boc |
| | 1 | CBz |

To a magnetically stirred solution of HO-GlyLys [ε-CBz] [α-Lys] [Boc]$_2$ (430 mg, 0.65 mmol) and EtOAc (10 ml) was added, in the following order, p-nitrophenol (99 mg, 0.71 mmol) and DCC (147 mg, 0.71 mmol). The reaction and product isolation were carried out according to the method described in Example 19.vi Silica gel flash chromatography (EtOAc) provided PNPO-GlyLys [ε-CBz] [α-Lys] [Boc]$_2$ (Rf 0.4) (344 mg, 66%) as an off white solid.

LC/MS (Phobic/TFA): ESI (+ve) m/z=787.31 [M+H]+; calculated C38H54N6O12 786.89 g/mol. Rf (min)=5.24.

iii. BHALys [Lys]$_4$ [GlyLys]$_8$ [ε-CBz]$_8$ [α-Lys]$_8$ [Boc]$_{16}$

| Surface Topology | Surface Stoichiometry | |
|---|---|---|
| (((CBz Ø)(Boc Boc))$^4$((CBz Ø)(Boc Boc))$^4$)$^8$(((CBz Ø)(Boc Boc))$^4$((CBz Ø)(Boc Boc))$^4$)$^8$)$^{16}$ | 16 | Boc |
| (((CBz Ø)(Boc Boc))$^4$((CBz Ø)(Boc Boc))$^4$)$^8$(((CBz Ø)(Boc Boc))$^4$((CBz Ø)(Boc Boc))$^4$)$^8$)$^{16}$ | 8 | CBz |

To a stirred solution of BHALys [Lys]$_4$ [NH$_2$.TFA]$_8$ (30 mg, 0.015 mmol), TEA (0.06 ml, 0.43 mmol) and DMF (0.5 ml) was added a solution of PNPO-GlyLys [ε-CBz] [α-Lys] [Boc]$_2$ (172 mg, 0.22 mmol) in DMF (2 ml) at Rt. The reaction and product isolation were carried out according to the method described in Example 1.i to provide BHALys [Lys]$_4$ [GlyLys]$_8$ [ε-CBz]$_8$ [α-Lys]$_8$ [Boc]$_{16}$ (80 mg, 85%) as an off white solid.

LC/MS (Phobic/TFA): ESI (+ve) m/z=1566.46 [M+4H]/4+; calculated C311H489N55O79 6262.63 g/mol. Rf (min)=8.95.

iv. BHALys [Lys]$_4$ [GlyLys]$_8$ [ε-NH$_2$]$_8$ [α-Lys]$_8$ [Boc]$_{16}$

| Surface Topology | Surface Stoichiometry | |
|---|---|---|
| (((NH$_2$ Ø)(Boc Boc))$^4$((NH$_2$ Ø)(Boc Boc))$^4$)$^8$(((NH$_2$ Ø)(Boc Boc))$^4$((NH$_2$ Ø)(Boc Boc))$^4$)$^8$)$^{16}$ | 16 | Boc |
| (((NH$_2$ Ø)(Boc Boc))$^4$((NH$_2$ Ø)(Boc Boc))$^4$)$^8$(((NH$_2$ Ø)(Boc Boc))$^4$((NH$_2$ Ø)(Boc Boc))$^4$)$^8$)$^{16}$ | 8 | NH$_2$ |

To a stirred solution of BHALys [Lys]$_4$ [GlyLys]$_8$ [ε-CBz]$_8$ [α-Lys]$_8$ [Boc]$_{16}$ (73.5 mg, 0.012 mmol) and 2,2,2-trifluoroethanol (3 ml) was added 10% Pd/C (44 mg). The black suspension was hydrogenated under standard conditions (room temperature, atmospheric pressure) for 17 h. LCMS analysis of an aliquot taken from the crude reaction mixture indicated that the reaction was incomplete. A further portion of catalyst was added (44 mg) and the crude reaction suspension was re-subjected to hydrogenolysis under high pressure (50 PSI) at room temperature for 48 h. After this time, the suspension was filtered through a 0.45 micron filter disk. The filtrate was concentrated under reduced pressure to give the product BHALys [Lys]$_4$ [GlyLys]$_8$ [ε-NH$_2$]$_8$ [α-Lys]$_8$ [Boc]$_{16}$ (52 mg, 85%) as a brown coloured glassy solid.

LC/MS (Phobic/TFA): ESI (+ve) m/z=1298.13 [M+4H]/4+, 1038.76 [M+5H]/5+, 865.61 [M+6H]/6+; calculated C247H441N55O63 5189.55 g/mol. Data deconvoluted using transform calculation to give mw=5188.51. Rf (min)=3.99.

Example 28

Chromatographic Behaviour of Topological Isomers

HPLC—Waters 2795 with 2996 Diode Array Detector (DAD)

Solvent A: 1% TFA in water; Solvent B: Acetonitrile; Solvent C: Water.

Column: Waters Xterra MS-C8, 3.5 um, 3 mm×50 mm at 0.4 ml/min

Gradient: Starting eluent A (10%) B (40%) C (50%) isocratic for 1 min; linear gradient to A (10%) B (90%) C (0%) over 6 min; isocratic for 2 min; linear gradient to Starting eluent over 2 min; condition column at Starting eluent for 4 min (Total run 15 min).

TABLE 23

HPLC retention times for sets of Topological Isomers

| Set | Topology | A:B | A + B | Example: Name | Rt*(UV) (mins) |
|---|---|---|---|---|---|
| 1 | (((AB)(AB))$^4$((AB)(AB))$^4$)$^8$ | 1:1 | 8 | 3.ii: BHALys [Lys]4 [α-Boc]4 [ε-NH2]4 | 0.87 |
| 1 | (((AB)(AB))$^4$((AB)(AB))$^4$)$^8$ | 1:1 | 8 | 2.ii: BHALys [Lys]4 [α-CBz]4 [ε-Boc]4 | 1.55 |
| 1 | (((AA)(BB))$^4$((AA)(BB))$^4$)$^8$ | 1:1 | 8 | 13.viii: BHALys [GlyLys]2 [Lys]4 [α,α-Boc]2 [α,ε-Boc]2 [ε,α-NH2]2 [ε,ε-NH2]2 | 1.73 |
| 1 | (((AA)(AA))$^4$((BB)(BB))$^4$)$^8$ | 1:1 | 8 | 19.xii: BHALys [a-GlyLys] [Lys]2 [Boc]4 [e-GlyLys] [Lys]2 [NH2]4 | 3.37 |
| 2 | (((AB)(AB))$^4$((AB)(AB))$^4$)$^8$ × 2 | 1:1 | 16 | 4.ii: BHALys [Lys]8 [α-Boc]8 [ε-NH2]8 | 1.01 |
| 2 | (((AB)(AB))$^4$((AB)(AB))$^4$)$^8$ × 2 | 1:1 | 16 | 6.ii: BHALys [Lys]8 [α-NH2]8 [ε-Boc]8 | 1.02 |
| 2 | (((AA)(BB))$^4$((AA)(BB))$^4$)$^8$ × 2 | 1:1 | 16 | 14.ii BHALys [Lys]2 [GlyLys]4 [Lys]8 [α,α-Boc]4 [α,ε-Boc]4 [ε,α-NH2]4 [ε,ε-NH2]4 | 1.01 |
| 3 | (((AB)(BB))$^4$((AB)(BB))$^4$)$^8$ | 1:3 | 8 | 15.iv: BHALys [GlyLys]2 [Lys]4 [Boc]6 [ε,ε-NH2]2 | 4.5 |
| 3 | (((AA)(BB))$^4$((BB)(BB))$^4$)$^8$ | 1:3 | 8 | 24.ii: BHALys [Lys]2 [α,ε-Lys] [NH2]2 [Lys]3 [Boc]6 | 5.46 |
| 4 | (((AB)(BB))$^4$((AB)(BB))$^4$)$^8$ | 1:3 | 8 | 15.iii: BHALys [GlyLys]2 [Lys]4 [Boc]6 [ε,ε-CBz]2 | 7.14 |

TABLE 23-continued

HPLC retention times for sets of Topological Isomers

| Set | Topology | A:B | A + B | Example: Name | Rt*(UV) (mins) |
|---|---|---|---|---|---|
| 4 | $(((AA)(BB))^4((BB)(BB))^4)^8$ | 1:3 | 8 | 24.i: BHALys [Lys]$_2$ [α,ε-Lys] [CBz]$_2$ [Lys]$_3$ [Boc]$_6$ | 7.56 |

*Rt = Retention time of topological isomer.

This data serves to demonstrate that macromolecules which have different topologies of the same surface functional moiety stoichiometry behave differently when interacting with a physico-chemical environment.

Antimicrobial Examples

Example 29

BHALys [Lys]$_4$ [α-COCH$_2$O-3,6-Naph(SO$_3$Na)$_2$]$_4$ [ε-COC$_5$H$_{12}$]$_4$

| Surface Topology | Surface Stoichiometry | |
|---|---|---|
| $(((Hex\ B)(Hex\ B))^4((Hex\ B)(Hex\ B))^4)^8$ | 4 | COC$_5$H$_{12}$ = Hex |
| | 4 | COCH$_2$O-3,6-Naph[SO3Na]$_2$ = B | i. BHALys [Lys]$_4$ [α-Boc]$_4$ [ε-COC$_5$H$_{12}$]$_4$ SPL8059

PyBOP (0.20 g, 0.38 mmol) was added to a stirred solution of BHALys [Lys]$_4$ [α-Boc]$_4$[ε-NH$_2$.TFA]$_4$ (60 mg, 0.032 mmol) in DMF/DMSO (1:1) (6 mL). A solution of hexanoic acid (42 mg, 0.36 mmol) and diisopropylethylamine (0.3 mL, 1.72 mmol) in DMF/DMSO (1:1) (3 mL) was added gradually. The mixture was stirred at Rt for 16 h. Reaction mixture was poured into ACN (0.3 L) and filtered. The precipitate was dried in vacuo to give BHALys [Lys]$_4$ [α-Boc]$_4$[ε-COC$_5$H$_{12}$]$_4$ as a white solid (53 mg, 70%).

LC/MS (phobic) ESI (+ve) m/z=1873.32 (M+); 937.54 ((M+2H)$^{2+}$). Calculated (C$_{99}$H$_{169}$N$_{15}$O$_{19}$) 1873.49 (M+). Rf (min)=7.27 ii. BHALys [Lys]$_4$ [α-NH$_2$.TFA]$_4$ [ε-COC$_5$H$_{12}$]$_4$

A solution of TFA/DCM (1:1) (2 mL) was added slowly to BHALys [Lys]$_4$ [α-Boc]$_4$[ε-COC$_5$H$_{12}$]$_4$ (25 mg, 0.013 mmol) dispersed in DCM (3 mL). The mixture was stirred at Rt for 16 h. The solvent was removed in vacuo and the residue triturated with Ether. The residue was washed with Ether (3×10 mL), dried in vacuo to give BHALys [Lys]$_4$ [α-NH$_2$.TFA]$_8$[ε-COC$_5$H$_{12}$]$_4$ as a white solid (28 mg, 108%).

LC/MS (philic) ESI (+ve) m/z=1473.12 (M+); 737.21 ((M+2H)$^{2+}$); 491.93 ((M+3H)$^{3+}$). Calculated (C$_{79}$H$_{137}$N$_{15}$O$_{11}$) 1473.03 (NH$_2$ form). Rf (min)=8.75 iii. BHALys [Lys]$_4$ [α-COCH$_2$O-3,6-Naph(SO$_3$Na)$_2$]$_4$ [ε-COC$_5$H$_{12}$]$_4$ PyBOP (0.07 g, 0.13 mmol) was added to a stirred solution of BHALys [Lys]$_4$ [α-NH$_2$.TFA]$_4$ [ε-COC$_5$H$_{12}$]$_4$ (24 mg, 0.012 mmol) in DMF/DMSO (1:1) (3 mL). A solution of HOCOCH$_2$O-3,6-Naph(SO$_3$Na)$_2$ (0.05 g, 0.12 mmol) and diisopropylethylamine (0.1 mL, 0.57 mmol) in DMF/DMSO (1:1) (2 mL) was added gradually. The mixture was stirred at Rt for 16 h. Reaction mixture was poured into water (0.3 L) and filtered. Purification was performed by tangential flow filtration on a Centramate (2K membrane, 0.5 L sample reservoir). After an initial wash with Milli-Q water (5 L) the retentate was washed with two aliquots of 1M sodium carbonate (100 mL) separated by a Milli-Q water wash (1 L), then filtration was continued until filtrate pH was neutral (approx. 5 L). Retentate was conc. in vacuo, and freeze dried to give BHALys [Lys]$_4$ [α-COCH$_2$O-3,6-Naph(SO$_3$Na)$_2$]$_4$ [ε-COC$_5$H$_{12}$]$_4$ as a white solid (26 mg, 69%).

1H nmr (300 MHz, D$_2$O) λ (ppm): 0.5-0.7 (12H); 0.8-1.8 (68H); 1.9-2.1 (8H); 2.9-3.3 (14H); 4.0-4.3 (7H); 5.9 (1H); 7.0-7.3, 7.8-8.1, 8.2-8.5 (30H). Note the CH$_2$O protons are obscured by the water peak (4.4-4.9 ppm).

LC/MS (Ion Pairing): ESI (-ve) m/z=1424.09 ((M-2H)$^{2-}$); 948.86 ((M-3H)$^{3-}$); 711.49 ((M-4H)$^{4-}$); 569.04 ((M-5H)$^{5-}$); 473.98 ((M-6H)$^{6-}$). Data deconvoluted using maximum entropy calculation to give MW=2850.00 (M-, in H form) Calculated (H form) (C$_{127}$H$_{169}$N$_{15}$O$_{43}$S$_5$) 2850.30 (M-). Rf (min)=9.46

CE (pH 9): 76.0% purity Rf (min)=7.63

Example 30

BHALys [Lys]$_4$ [α-COC$_5$H$_{12}$]$_4$[ε-COCH$_2$O-3,6-Naph(SO$_3$Na)$_2$]$_4$ SPL8018

| Surface Topology | Surface Stoichiometry | |
|---|---|---|
| $(((Hex\ B)(Hex\ B))^4((Hex\ B)(Hex\ B))^4)^8$ | 4 | COC$_5$H$_{12}$ = Hex |
| | 4 | COCH$_2$O-3,6-Naph[SO3Na] = B | i. BHALys [Lys]$_4$ [α-COC$_5$H$_{12}$]$_4$[ε-Boc]$_4$

Prepared from BHALys [Lys]$_4$ [α-NH$_2$.TFA]$_4$ [ε-Boc]$_4$ (81 mg, 0.055 mmol) in similar manner to Example 29.i. The precipitate was dried in vacuo to give BHALys [Lys]$_4$ [α-COC$_5$H$_{12}$]$_4$[ε-Boc]$_4$ as a white solid (0.07 g, 69%).

LC/MS (phobic) ESI (+ve) m/z=1873.32 (M+); 937.61 ((M+2H)$^{2+}$). Calculated (C$_{99}$H$_{169}$N$_{15}$O$_{19}$) 1873.49 (M+). Rf (min)=7.95 ii. BHALys [Lys]$_4$ [α-COC$_5$H$_{12}$]$_4$[ε-NH$_2$.TFA]$_4$

BHALys [Lys]$_4$ [α-COC$_5$H$_{12}$]$_4$[ε-Boc]$_4$ (35 mg, 0.019 mmol) deprotected as for 29.ii to give BHALys [Lys]$_4$ [α-Hexyl]$_4$[ε-NH$_2$.TFA]$_4$ as a white solid (38 mg, 105%).

LC/MS (philic) ESI (+ve) m/z=1473.12 (M+); 737.21 ((M+2H)$^{2+}$); 491.87 ((M+3H)$^{3+}$). Calculated (C$_{79}$H$_{137}$N$_{15}$O$_{11}$) 1473.03 (NH$_2$ form). Rf (min)=8.23 iii. BHALys [Lys]$_4$ [α-COC$_5$H$_{12}$]$_4$[ε-COCH$_2$O-3,6-Naph(SO$_3$Na)$_2$]$_4$ Prepared from BHALys [Lys]$_4$ [α-COC$_5$H$_{12}$]$_4$[ε-NH$_2$.TFA]$_4$ (36 mg, 0.019 mmol) and HOCOCH$_2$O-3,6-Naph(SO$_3$Na)$_2$ (0.07 g, 0.16 mmol) in similar manner to Example 29.iii to give BHALys [Lys]$_4$ [α-COC$_5$H$_{12}$]$_4$[ε-COCH$_2$O-3,6-Naph(SO$_3$Na)$_2$]$_4$ as a white solid (0.04 g, 78%).

LC/MS (Ion Pairing): ESI (−ve) m/z=1423.62 ((M−2H)$^{2-}$); 949.13 ((M−3H)$^{3-}$); 711.49 ((M−4H)$^{4-}$); 568.98 ((M−5H)$^{5-}$); 473.98 ((M−6H)$^{6-}$). Data deconvoluted using maximum entropy calculation to give MW=2850.00 (M−, in H form) Calculated (H form) (C$_{127}$H$_{169}$N$_{15}$O$_{43}$S$_8$) 2850.30 (M−). Rf (min)=9.26

CE (pH 9): 85.9% purity Rf (min)=7.61

Example 31

BHALys [Lys]$_4$ [α-CO-4-PhSO$_3$Na]$_4$[ε-COC$_5$H$_{12}$]$_4$

| Surface Topology | Surface Stoichiometry | |
|---|---|---|
| (((Hex B)(Hex B))$^4$((Hex B)(Hex B))$^4$)$^8$ | 4 | COC$_5$H$_{12}$ = Hex |
| | 4 | CO-4-PhSO$_3$Na = B |

Prepared from BHALys [Lys]$_4$ [α-NH$_2$.TFA]$_4$[ε-COC$_5$H$_{12}$]$_4$ (26 mg, 0.013 mmol) and 4-sulfobenzoic acid (0.03 g, 0.15 mmol) in a similar way to Example 29.iii to give BHALys [Lys]$_4$ [α-CO-4-PhSO$_3$Na]$_4$[ε-COC$_5$H$_{12}$]$_4$ as a white solid (25 m g, 80%).

LC/MS (Ion Pairing): ESI (−ve) m/z=1103.74 ((M−2H)$^{2-}$); 735.25 ((M−3H)$^{3-}$); 551.36 ((M−4H)$^{4-}$). Data deconvoluted using maximum entropy calculation to give MW=2209.54 (M−, in H form) Calculated (H form) (C$_{107}$H$_{153}$N$_{15}$O$_{27}$S$_4$) 2209.70 (M−). Rf (min)=10.30

CE (pH 9): 85.7% purity Rf (min)=5.24

Example 32

DAH [Lys]$_8$ [α-CO-3,5-Ph(SO$_3$Na)$_2$]$_8$[ε-COC$_5$H$_{12}$]$_8$ SPL7919 i. DAH [Lys]$_2$ [Boc]$_4$

A suspension of PNPO-Lys(Boc)$_2$ (44.3 g, 94.9 mmol) in DMF (124 mL) and a solution of 1,6-diaminohexane (4.95 g, 42.6 mmol) and TEA (13.2 mL, 94.7 mmol) in DMF (160 mL) were reacted and a product isolated as for Example 1.i to give DAH [Lys]$_2$ [Boc]$_4$ as a colourless solid (19.3 g, 59% yield, 95.6% purity by LCMS, [R$_f$=5.85 mins]). Second and third crops of product were obtained (3.68 g and 4.47 g respectively) from concentration of the washing solvents. Total mass of product obtained=27.5 g (84% yield). ESMS m/z 796 (20, M+Na); 674 (100, [M-Boc]+1); 574 (12, [M-Boc]+1.

ii. DAH [Lys]$_2$ [NH$_2$.TFA]$_4$

DAH [Lys]$_2$ [Boc]$_4$ (20.0 g, 25.9 mmol) was deprotected using DCM (110 mL) was added TFA (280 mL, 3.63 mol) according to the method of Example 19.ii. The resulting solid was dissolved in the minimum amount of water then lyophilized to give DAH [Lys]$_2$ [NH$_2$.TFA]$_4$ as a flocculant, colourless solid. The bulk of this material was used in the next reaction without further purification.

iii. DAH [Lys]$_4$ [Boc]$_8$

A suspension of PNPO-Lys(Boc)$_2$ (55.2 g, 118 mmol) in DMF (190 mL) was reacted with a solution of DAH [Lys]$_2$ [NH$_2$.TFA]$_4$ (24.6 mmol), TEA (TEA) (35.0 mL, 251 mmol) and DMF (180 mL) was reacted and a product isolated according to the method of Example 1.i. The product, DAH [Lys]$_4$ [Boc]$_8$ was obtained as a colourless solid (34.9 g, 84% yield, >99.5% purity by LCMS, [R$_f$=13.6 mins]). ESMS m/z 1587 (8, [M-Boc]+1); 744 (100, ½[M−2Boc]+1); 644 (60, ½[M−4Boc]+1); 544 (10, ½[M−6Boc]+1).

iv. DAH [Lys]$_4$ [NH$_2$.TFA]$_8$

DAH [Lys]$_4$ [Boc]$_8$ (1.0 g, 0.60 mmol) was deprotected using DCM (12.8 mL) and TFA (12.8 mL, 166 mmol) according to the method of Example 19.ii. The resulting solid was dissolved in the minimum amount of water then lyophilized to give DAH [Lys]$_4$ [NH$_2$.TFA]$_8$ as a flocculant, colourless solid.

v. DAH [Lys]$_8$ [α-Boc]$_8$ [ε-CBz]$_8$

A solution of DAH [NH$_2$.TFA]$_8$ (0.59 mmol), TEA (TEA) (1.65 mL, 11.84 mmol) and DMF (12 mL) and solid PNPO-Lys-α-Boc-ε-CBz (2.84 g, 5.66 mmol) were reacted, and a product isolated, according to the method of Example 1.i. The product, DAH [Lys]$_8$ [α-Boc]$_8$ [ε-CBz]$_8$, was obtained as a colourless solid (1.94 g, 87%).

vi. DAH [Lys]$_8$ [α-Boc]$_8$ [ε-NH$_2$]$_8$

DAH [Lys]$_8$ [α-Boc]$_8$ [ε-CBz]$_8$ (994 mg, 0.26 mmol) was added, as a solid and in one portion, to a chilled (−78° C.) and magnetically stirred solution of liquid ammonia (ca. 90 mL) and sodium metal (ca. 200 mg) maintained under an atmosphere of argon. The cold bath was removed and the blue coloured reaction mixture was left to reflux at ambient temperatures for 40 mins. After this time, the reaction flask was re-chilled to −78° C. and dry methanol (3 mL) was slowly added to the reaction mixture. The now white coloured mixture was opened to the atmosphere and left to warm to Rt overnight. The resulting grey coloured solid residue was treated with methanol (ca. 200 mL). The suspension was filtered and the filtrate was concentrated under reduced pressure to afford DAH [Lys]$_8$ [α-Boc]$_8$ [ε-NH$_2$]$_8$ (0.53 g, 73%) as a colourless foam.

LC/MS (Hydrophilic/TFA) ESI (+ve) m/z=1356 [M+2H]/2+, 905 [M+3H]/3+; calculated C130H248N30O30 2711.58 g/mol. Data deconvoluted using transform calculation to give mw=2711.17. Rf (min)=13.1 vii. DAH [Lys]$_8$ [α-Boc]$_8$ [ε-COC$_5$H$_{12}$]$_8$

PyBOP (0.53 g, 1.01 mmol) was added to a stirred solution of DAH [Lys]$_8$ [α-Boc]$_8$ [ε-NH$_2$]$_8$ (152 mg, 0.056 mmol) in DMF/DMSO (1:1) (10 mL). A solution of hexanoic acid (0.10 g, 0.89 mmol) and diisopropylethylamine (0.7 mL, 4.02 mmol) in DMF/DMSO (1:1) (5 mL) was added gradually. The mixture was stirred at Rt for 16 h. Reaction mixture was poured into ACN (0.4 L) and filtered. The precipitate was dried in vacuo to give DAH [Lys]$_8$ [α-Boc]$_8$[ε-COC$_5$H$_{12}$]$_8$ as an off-white solid (0.16 g, 66%).

LC/MS (phobic) ESI (+ve) m/z=1166.47 ((M+3H)$^{3+}$); 874.96 ((M+4H)$^{4+}$). Data deconvoluted using maximum entropy calculation to give MW=3496.50 (M+) Calculated (C$_{178}$H$_{328}$N$_{30}$O$_{38}$) 3496.74 (M+). Rf (min)=18.59 viii. DAH [Lys]$_8$ [α-NH$_2$.TFA]$_8$ [ε-COC$_5$H$_{12}$]$_8$

DAH [Lys]$_8$ [α-Boc]$_8$ [ε-COC$_5$H$_{12}$]$_8$ (126 mg, 0.036 mmol) dispersed in DCM (3 mL) was deprotected with a solution of TFA/DCM (1:1) (3 mL) as for Example 29.ii to give DAH [Lys]$_8$ [α-NH$_2$.TFA]$_8$[ε-COC$_5$H$_{12}$]$_8$ as a sticky white solid (0.15 g, 117%).

LC/MS (philic) ESI (+ve) m/z=899.38 ((M+3H)$^{3+}$); 674.76 ((M+4H)$^{4+}$). Data deconvoluted using maximum entropy calculation to give MW=2695.50 (M+, in the NH$_2$ form) Calculated (C$_{138}$H$_{264}$N$_{30}$O$_{22}$) 2695.80 (NH$_2$ form). Rf (min)=15.87 ix. DAH [Lys]$_8$ [α-CO-3,5-Ph(SO$_3$Na)$_2$]$_8$[ε-COC$_5$H$_{12}$]$_8$

AH [Lys]$_8$ [α-NH$_2$.TFA]$_8$ [ε-COC$_5$H$_1$]$_8$ (76 mg, 0.021 mmol) in DMF/DMSO (1:1) (4 mL) and PyBOP (0.25 g, 0.48 mmol) were reacted with solution of 3,5-disulfobenzoic acid (0.16 g, 0.56 mmol) and diisopropylethylamine (0.3 mL, 1.72 mmol) in DMF/DMSO (1:1) (5 mL) according to the method of Example 29.iii to give DAH [Lys]$_8$ [α-CO-3,5-Ph(SO$_3$Na)$_2$]$_8$[ε-COC$_5$H$_{12}$]$_8$ as a white solid (0.11 g, 75%).

LC/MS (Ion Pairing): ESI (−ve) m/z=686.05 ((M−7H)$^{7-}$); 600.21 ((M−8H)$^{8-}$); 533.51 ((M−9H)$^{9-}$); 480.14 ((M−10H)$^{10-}$); 436.43 ((M−11H)$^{11-}$). Data deconvoluted using maximum entropy calculation to give MW=4809.50 (M−, in H form) Calculated (H form) (C$_{194}$H$_{296}$N$_{30}$O$_{78}$S$_{16}$) 4809.70 (M−). Rf (min)=9.30

CE (pH 9): 76.4% purity Rf (min)=19.56

Example 33

DAH [Lys]$_8$ [α-COCH$_2$O-3,6-Naph(SO$_3$Na)$_2$]$_8$ [ε-COC$_5$H$_{12}$]$_8$

Figure 1:
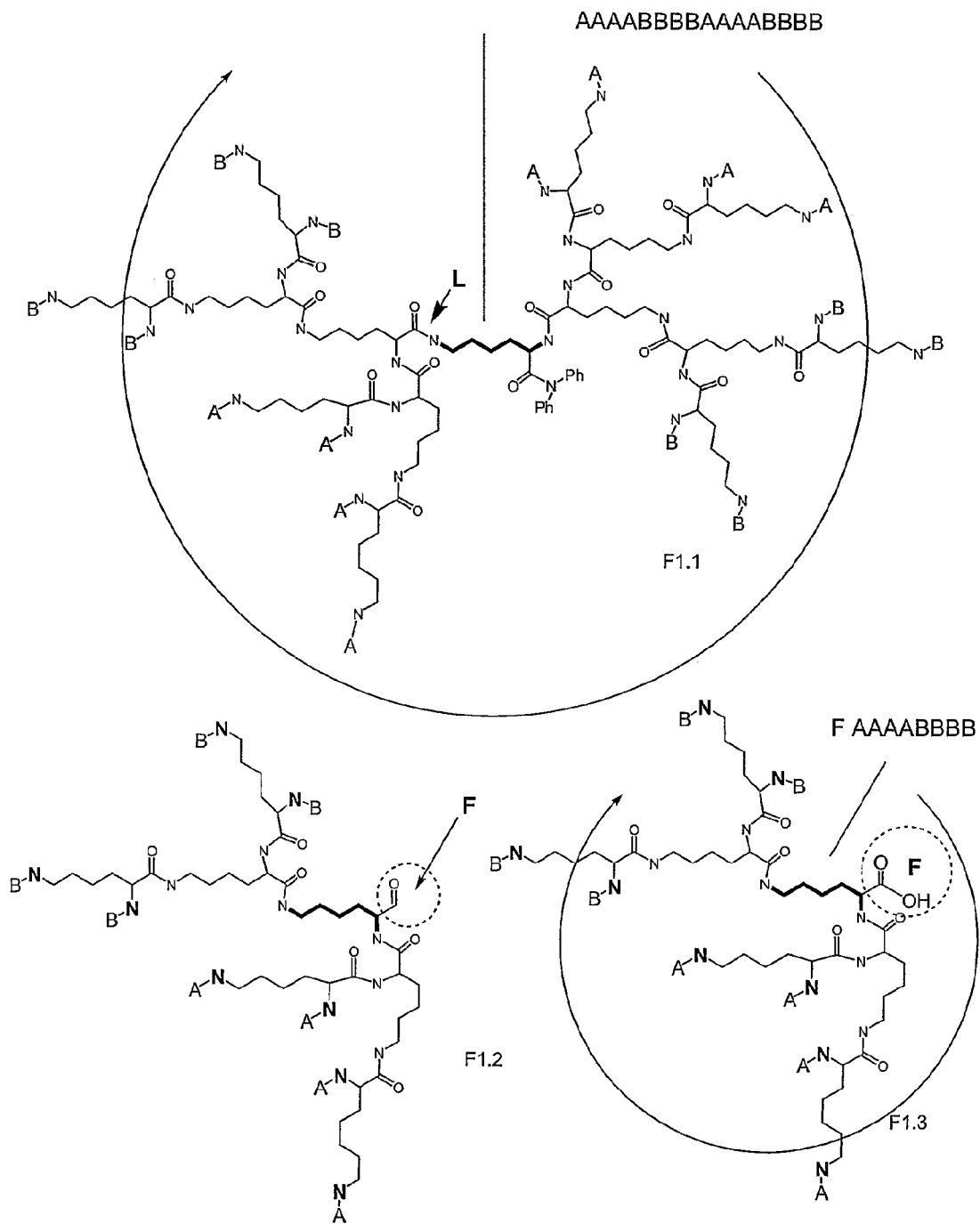
Figure 10:
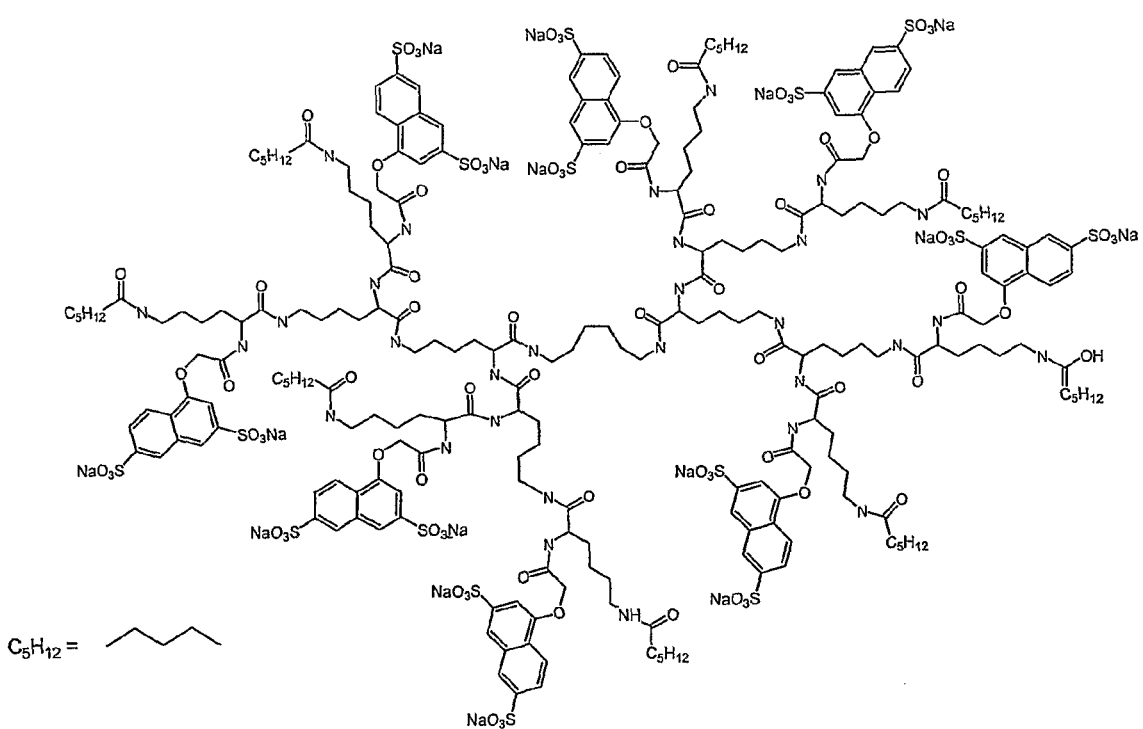
FIG. 10 is DAH [Lys]$_8$ [α-COCH$_2$O-3,6-Naph(SO$_3$Na)$_2$]$_8$ [ε-COC$_5$H$_{12}$]$_8$ which is described in Example 33, as an antisexually transmitted microbial macromolecule according to a preferred embodiment of the invention, with polyanionic surface molecules and lipophilic modifiers having activity against sexually transmitted infections such as HIV.

Example 33 is depicted in FIG. 10.

| Surface Topology | Surface Stoichiometry | |
|---|---|---|
| ((((Hex B)(Hex B))$^4$((Hex B)(Hex B))$^4$)$^8$(((Hex B)(Hex B))$^4$((Hex B)(Hex B))$^4$)$^8$)$^{16}$ | 8 | COC$_5$H$_{12}$ = Hex |
| | 8 | COCH$_2$O-3,6-Naph[SO3Na]$_2$ = B |

DAH [Lys]$_8$ [α-NH$_2$.TFA]$_8$ [ε-COC$_5$H$_{12}$]$_8$ (76 mg, 0.021 mmol) in DMF/DMSO (1:1) (4 mL) and PyBOP (0.30 g, 0.57 mmol) were reacted with a solution of HOCOCH$_2$O-3,6-Naph(SO$_3$Na)$_2$ (0.21 g, 0.51 mmol) and diisopropylethylamine (0.3 mL, 1.72 mmol) in DMF/DMSO (1:1) (5 mL) according to the method of Example 29.iii to give DAH [Lys]$_8$ [α-COCH$_2$O-3,6-Naph(SO$_3$Na)$_2$]$_8$ [ε-COC$_5$H$_{12}$]$_8$ as a white solid (0.16 g, 130%).

LC/MS (Ion Pairing): ESI (−ve) m/z=907.50 ((M−6H)$^{6-}$); 777.73 ((M−7H)$^{7-}$); 680.68 ((M−8H)$^{8-}$); 604.44 ((M−9H)$^{9-}$); 543.88 ((M−10H)$^{10-}$); 494.54 ((M−11H)$^{11-}$); 453.32 ((M−12H)$^{12-}$). Data deconvoluted using transform calculation to give MW=5450.95 (M−, in H form) Calculated (H form) (C$_{234}$H$_{328}$N$_{30}$O$_{86}$S$_{16}$) 5450.38 (M−). Rf (min)=9.27

CE (pH 9): 79.2% purity Rf (min)=17.03

Example 34

BHALys [Lys]$_8$ [α-CO$_2$PEG$_3$]$_8$ [ε-CO-3,5-Ph(SO$_3$Na)$_2$]$_8$

| Surface Topology | Surface Stoichiometry | |
|---|---|---|
| ((((PEG B)(PEG B))$^4$((PEG B)(PEG B))$^4$)$^8$(((PEG B)(PEG B))$^4$((PEG B)(PEG B))$^4$)$^8$)$^{16}$ | 8 | CO$_2$PEG$_3$ = PEG |
| | 8 | CO-3,5-Ph[SO$_3$Na]$_2$ = B | i. PNPO—CO$_2$PEG$_3$

To an ice-cooled stirred mixture of triethyleneglycol monomethyl ether (2.5 g, 15.2 mmol), N-methylmorpholine (2.08 g, 20.6 mmol) and DMAP (93 mg, 0.76 mmol) in DCM was added 4-nitrophenylchloroformate (3.38 g, 16.75 mmol) in one portion. The mixture was left to warm to Rt overnight, then concentrated. The residue was taken up in EtOAc (120 mL) and washed with dil. HCl (2×100 mL, 1.0 M), saturated NaHCO$_3$ (100 mL), K$_2$CO$_3$ (5%, 4×100 mL) and brine. The organic phase was then dried (MgSO$_4$), filtered, and concentrated, providing 3.90 g (78%) of PNPO—CO$_2$PEG$_3$ as a pale yellow oil. LCMS (LC: phobic, TFA, RT=3.8 min.; MS (M$_{calc}$. C$_{14}$H$_{19}$NO$_8$=329.31): 352 ([M+Na]$^+$, 70%), 330 ([M+H]$^+$, 48%). $^1$H (CDCl$_3$): δ 8.27 (d, J=9.3 Hz, 2H), 7.38 (d, J=9.3 Hz, 2H), 4.42-4.45 (m, 2H), 3.79-3.82 (m, 2H), 3.64-3.74 (m, 6H), 3.55-3.58 (m, 2H), 3.37 (s, 3H).

i. HO-Lys-α-CO$_2$PEG$_3$-ε-Boc

| Surface Topology | Surface Stoichiometry | |
|---|---|---|
| HO—CO (CO$_2$PEG$_3$ Boc) | 1 | CO$_2$H |
| | 1 | CO$_2$PEG$_3$ |
| | 1 | Boc |

To a stirred mixture of PNPO—CO$_2$PEG$_3$ (3.90 g, 11.84 mmol) in DMF (60 mL) was added HO-Lys-α-NH$_2$-ε-Boc (2.78 g, 11.28 mmol). The suspension was stirred at 60° C. overnight, then cooled and poured into NaHCO$_3$ solution (5%, 150 mL). The aqueous solution was then washed with EtOAc (2×150 mL), then acidified (HCl, 1.0 M, 180 mL). The aqueous phase was then washed with EtOAc (3×200 mL) again, and the last 3 extracts combined, dried (MgSO$_4$), filtered and concentrated. The residue was then purified by silica gel chromatography (10% MeOH/90% DCM), providing HO-Lys-α-CO$_2$PEG$_3$-ε-Boc as a viscous oil (2.50 g, 51%).

LCMS (LC: philic, TFA, RT=11.0 min; MS (M$_{calc}$ C$_{19}$H$_{36}$N$_2$O$_9$=436.51): 459 ([M+Na], 20%), 337 ([M−BOC+H]$^+$, 100%).

$^1$H (CDCl$_3$): δ 5.64 (br d, 1H), 4.03-4.41 (m, 3H), 3.52-3.71 (m, 9H), 3.37 (s, 3H), 3.01-3.20 (m, 4H), 1.81-1.95 (m, 2H), 1.64-1.80 (m, 2H), 1.42 (s, 9H).

ii. BHALys [Lys]$_8$ [α-CO$_2$PEG$_3$]$_8$ [ε-Boc]$_8$

A solution of BHALys [Lys]$_4$ [NH$_2$.TFA]$_8$ and (0.095 g, 0.048 mmol) and PyBOP (0.30 g, 0.57 mmol) in DMF/

DMSO (1:1) (10 mL) was reacted with a solution of HO-Lys-α-CO$_2$PEG$_3$-ε-Boc (0.20 g, 0.45 mmol) and diisopropylethylamine (0.4 mL, 2.30 mmol) in DMF/DMSO (1:1) (5 mL). The mixture was stirred at Rt for 16 h. Solvent was removed in vacuo and the residue triturated with ACN. The precipitate, BHALys [Lys]$_8$ [α-CO$_2$PEG$_3$]$_8$ [ε-Boc]$_8$ was collected by filtration. (0.15 g, 68%).

LC/MS (Hydrophobic): ESI (+ve) m/z=1377.1 ((M−3Boc)+H$^{3+}$); 1008.2 ((M−4Boc)+H$^{4−}$). Calculated MW=4431 (M+) Calculated (C$_{207}$H$_{369}$N$_{63}$O$_{71}$) 4428 (M+). Rf (min)=14.30 iii. BHALys [Lys]$_8$ [α-CO$_2$PEG$_3$]$_8$ [ε-NH$_2$.TFA]$_8$

BHALys [Lys]$_8$ [α-CO$_2$PEG$_3$]$_8$ [ε-Boc]$_8$ (0.15 g, 0.034 mmol) suspended in DCM (4 mL). A solution of TFA/DCM (1:1) (4 mL) was added and the mixture stirred at Rt for 16 h. The solvent was removed in vacuo and the residue triturated with Ether. Solvent was removed from the crude product, BHALys [Lys]$_8$ [α-CO$_2$PEG$_3$]$_8$ [ε-NH$_2$.TFA]$_8$ by decanting and the trituration repeated thrice.

LC/MS (Hydrophilic): ESI (+ve) m/z=1210.10 ((M$^{3+}$+1H); 907.82 ((M$^{4+}$+1H); 726.32 ((M$^{5+}$+1H). Data deconvoluted using maximum entropy calculation to give MW=3627 (M+, free base form) Calculated (free base form) (C$_{167}$H$_{305}$N$_{31}$O$_{55}$) 3627 (M+). Rf (min)=11.84 iv. BHALys [Lys]$_8$ [α-CO$_2$PEG$_2$]$_8$ [ε-CO-3,5-Ph(SO$_3$Na)$_2$]$_8$

A solution of BHALys [Lys]$_8$ [α-CO$_2$PEG$_3$]$_8$ [ε-NH$_2$.TFA]$_s$ (0.086 g, 0.019 mmol) and PyBOP (0.19 g, 0.37 mmol) in DMF/DMSO (1:1) (4 mL) was reacted with a solution of 3,5-disulfobenzoic acid (0.10 g, 0.34 mmol) and diisopropylethylamine (0.3 mL, 1.72 mmol) in DMF/DMSO (1:1) (3 mL) according to the method of Example 29.iii to give BHALys [Lys]$_8$ [α-CO$_2$PEG$_3$]$_8$ [ε-CO-3,5-Ph(SO$_3$Na)$_2$]$_8$ as white solid (0.15 g, 130%).

1H nmr (300 MHz, D$_2$O) λ (ppm): 1.0-1.8 (90H); 2.9-3.2, 3.2-3.4, 3.4-3.7, and 3.9-4.3 (165H); 6.0 (1H); 7.1-7.3 (10H); 8.2-8.4 (24H).

LC/MS (Ion Pairing): ESI (−ve) m/z=1912.76 ((M−3H)$^{3−}$); 1434.27 ((M−4H)$^{4−}$); 1147.39 ((M−5H)$^{5−}$); 955.63 ((M−6H)$^{6−}$). Data deconvoluted using maximum entropy calculation to give MW=5742 (M−, in the H form) Calculated (H form) (C$_{223}$H$_{337}$N$_{31}$O$_{111}$S$_{16}$) 5741 (M−). Rf (min)=6.54
CE (pH 9 method): 87.5% purity Rf (min)=11.09

Example 35

BHALys [Lys]$_8$ [α-CO$_2$PEG$_3$]$_8$ [ε-CO-4-PhSO$_3$Na]$_8$

| Surface Topology | Surface Stoichiometry |
| --- | --- |
| ((((PEG B)(PEG B))$^4$((PEG B)(PEG B))$^4$)$^8$(((PEG B)(PEG CO-4-Ph[SO$_3$Na]))$^4$((PEG B)(PEG B))$^4$)$^8$)$^{16}$ | 8 CO$_2$PEG$_3$ = PEG<br>8 CO-4-Ph[SO$_3$Na] = B |

A solution of BHALys [Lys]$_8$ [α-CO$_2$PEG$_3$]$_8$ [ε-NH$_2$.TFA]$_8$ (0.086 g, 0.019 mmol) and PyBOP (0.17 g, 0.33 mmol) in DMF/DMSO (1:1) (4 mL) was reacted with a solution of 4-sulfobenzoic acid (0.07 g, 0.35 mmol) and diisopropylethylamine (0.3 mL, 1.75 mmol) in DMF/DMSO (1:1) as for the method of Example 29.iii to give BHALys [Lys]$_8$ [α-CO$_2$PEG$_3$]$_8$ [ε-CO-4-PhSO$_3$Na]$_8$ as white solid (0.12 g, 120%).

1H nmr (300 MHz, D$_2$O) λ (ppm): 1.0-1.8 (90H); 2.9-3.1, 3.2-3.3, 3.4-3.6, and 3.9-4.3 (165H); 6.0 (1H); 7.1-7.3 (10H); 7.7-7.9 (32H).

LC/MS (Ion Pairing): ESI (−ve) m/z=1274.17 ((M−4H)$^{4−}$); 1019.09 ((M−5H)$^{5−}$); 849.10 ((M−6H)$^{6−}$); 727.71 ((M−7H)$^{7−}$); 636.78 ((M−8H)$^{8−}$). Data deconvoluted using maximum entropy calculation to give MW=5100 (M−, in the H form) Calculated (H form) (C$_{223}$H$_{337}$N$_{31}$O$_{87}$S$_8$) 5101 (M−). Rf (min)=7.25
CE (pH 9): 93.11% Rf (min)=7.31

Example 36

BHALys [Lys]$_8$ [α-COCH$_2$O-3,6-Naph(SO$_3$Na)$_2$]$_8$ [ε-CBz]$_8$ SPL7966

| Surface Topology | Surface Stoichiometry |
| --- | --- |
| ((((A CBz)(A CBz))$^4$((A CBz)(A CBz))$^4$)$^8$(((A CBz) (A CBz))$^4$((A CBz)(A CBz))$^4$)$^8$)$^{16}$ | 8 COCH$_2$O-3,6-Naph[SO3Na]$_2$ = A<br>8 CBz |

A solution of BHALys [Lys]$_8$ [α-NH$_2$.TFA]$_8$ [ε-CBz]$_8$ (35 mg, 0.009 mmol) and PyBOP (79 mg, 0.15 mmol) in DMF/DMSO (1:1) (2 mL) was reacted with a solution of HOCOCH$_2$O-3,6-Naph(SO$_3$Na)$_2$ (59 mg, 0.15 mmol) and diisopropylethylamine (0.1 mL, 0.57 mmol) in DMF/DMSO (1:1) (2 mL) according to the method of Example 29.iii to give BHALys [Lys]$_8$ [α-COCH$_2$O-3,6-Naph(SO$_3$Na)$_2$]$_8$ [ε-CBz]$_8$ as a white solid (18 mg, 33%).

1H nmr (300 MHz, D$_2$O) λ (ppm): 0.9-1.8 (90H); 2.7-3.1 (30H); 4.0-4.4 (15H); 5.9 (1H); 6.8-7.2 and 7.7-8.3 (90H). Note the CH$_2$O protons are obscured by the water peak (4.5-4.9 ppm).

LC/MS (Ion Pairing): ESI (−ve) m/z=1185.65 ((M−5H)$^{6−}$); 987.78 ((M−6H)$^{6−}$); 846.66 ((M−7H)$^{7−}$); 740.78 ((M−8H)$^{8−}$); 658.32 ((M−9H)$^{9−}$). Data deconvoluted using transformation calculation to give MW=5934.40 (M−, in the H form) Calculated (H form) (C$_{263}$H$_{305}$N$_{31}$O$_{95}$S$_{16}$) 5933.43 (M−). Rf (min)=8.43
CE (pH 9): 72.8% purity Rf (min)=13.67

Example 37

BHALys [Lys]$_8$ [α-CO-3,5-Ph(SO$_3$Na)$_2$]$_8$ [ε-CBz]$_8$ SPL7862

| Surface Topology | Surface Stoichiometry |
| --- | --- |
| ((((A CBz)(A CBz))$^4$((A CBz)(A CBz))$^4$)$^8$(((A CBz)(A CBz))$^4$((A CBz)(A CBz))$^4$)$^8$)$^{16}$ | 8 CO-3,5-Ph[SO3Na]$_2$ = A<br>8 CBz |

A solution of (BHALys [Lys]$_8$ [α-NH$_2$.TFA]$_8$ [ε-CBz]$_8$) (0.102 g, 0.025 mmol) and PyBOP (0.29 g, 0.55 mmol) in DMF/DMSO (1:1) (7 mL) was reacted with a solution of 3,5-disulfobenzoic acid (0.16 g, 0.55 mmol) and diisopropylethylamine (0.4 mL, 2.30 mmol) in DMF/DMSO (1:1) (3 mL) according to the method of Example 29.iii to give BHALys [Lys]$_8$ [α-CO-3,5-Ph(SO$_3$Na)$_2$]$_8$ [ε-CBz]$_8$ as white solid (0.17 g, 124%). 1H nmr (300 MHz, D$_2$O) λ (ppm): 1.0-1.8 (90H); 2.8-3.3 (30H); 4.0-4.4 (15H); 6.0 (1H); 7.0-7.3 and 8.1-8.4 (74H). Note the CH$_2$O protons are obscured by the water peak (4.6-5.0 ppm).

LC/MS (Ion Pairing): ESI (-ve) m/z=1762.92 ((M-3H)$^{3-}$); 1321.95 ((M-4H)$^{4-}$); 1057.38 ((M-5H)$^{5-}$); Data deconvoluted using maximum entropy calculation to give MW=5295 (M-, in the H form) Calculated (H form) (C$_{273}$H$_{273}$N$_{31}$O$_{87}$S$_{16}$) 5293 (M-). Rf (min)=8.04

CE (pH 9 method): 83.7% purity Rf (min)=19.62

Example 38

BHALys [Lys]$_8$ [α-CO-4-Ph(SO$_3$Na)]$_8$ [ε-CBz]$_8$

| Surface Topology | Surface Stoichiometry | |
|---|---|---|
| ((((A CBz)(A CBz))$^4$((A CBz)(A CBz))$^4$)$^8$(((A CBz)(A CBz))$^4$((A CBz)(A CBz))$^4$)$^8$)$^{16}$ | 8 | CO-4-Ph[SO3Na] = A |
| | 8 | CBz |

A solution of BHALys [Lys]$_8$ [α-NH$_2$.TFA]$_8$ [ε-CBz]$_8$ (0.104 g, 0.025 mmol) and PyBOP (0.30 g, 0.57 mmol) in DMF/DMSO (1:1) (7 mL) was reacted with a solution of 4-sulfobenzoic acid (0.12 g, 0.60 mmol) and diisopropylethylamine (0.4 mL, 2.30 mmol) in DMF/DMSO (1:1) (3 mL) according to the method of Example 29.iii to give BHALys [Lys]$_8$ [α-CO-4-Ph(SO$_3$Na)]$_8$ [ε-CBz]$_8$ as white solid (0.17 g, 108%). 1H nmr indicated 4-sulfobenzoic acid was present. Product was recrystallised from methanol/water (1:1) to give a white solid (15 mg, 9%).

1H nmr (300 MHz, D$_2$O) λ (ppm): 1.0-1.8 (90H); 2.8-3.2 (30H); 4.0-4.4 (15H); 5.9 (1H); 7.0-7.3 and 7.6-7.8 (82H). Note the CH$_2$O protons are obscured by the water peak (4.5-5.0 ppm).

LC/MS (Ion Pairing): ESI (-ve) m/z=929.31 ((M-5H)$^{5-}$); 774.48 ((M-6H)$^{6-}$); 663.69 ((M-7H)$^{7-}$); 580.67 ((M-8H)$^{8-}$). Data deconvoluted using maximum entropy calculation to give MW=4654 (M-, in the H form) Calculated (H form) (C$_{223}$H$_{273}$N$_{31}$O$_{63}$S$_8$) 4652 (M-). Rf (min)=9.65

CE (pH 9 method): 86.7% purity Rf (min)=14.3

Example 39

BHALys [Lys]$_{16}$ [α-COCH$_2$O-3,6-Naph(SO$_3$Na)$_2$]$_{16}$ [ε-CBz]$_{16}$

| Surface Topology | Surface Stoichiometry | |
|---|---|---|
| ((((A CBz)(A CBz))$^4$((A CBz)(A CBz))$^4$)$^8$(((A CBz) (A CBz))$^4$((A CBz)(A CBz))$^4$)$^8$)$^{16}$ | 16 | COCH$_2$O-3,6-Naph[SO3Na]$_2$ = A |
| ((((A CBz)(A CBz))$^4$((A CBz)(A CBz))$^4$)$^8$(((A CBz) (A CBz))$^4$((A CBz)(A CBz))$^4$)$^8$)$^{16}$ | 16 | CBz |

A solution of BHALys [Lys]$_{16}$ [α-NH$_2$.TFA]$_{16}$ [ε-CBz]$_{16}$ (0.102 g, 0.013 mmol) and PyBOP (0.29 g, 0.56 mmol) in DMF/DMSO (1:1) (10 mL) was reacted with a solution of HOCOCH$_2$O-3,6-Naph(SO$_3$Na)$_2$ (0.21 g, 0.51 mmol) and diisopropylethylamine (0.5 mL, 2.87 mmol) in DMF/DMSO (1:1) (5 mL) according to the method of Example 29.iii to give BHALys [Lys]$_{16}$ [α-COCH$_2$O-3,6-Naph(SO$_3$Na)$_2$]$_{16}$ [ε-CBz]$_{16}$ as white solid (0.21 g, 136%).

1H nmr (300 MHz, D$_2$O) λ (ppm): 1.0-1.8 (186H); 2.73.1 (62H); 4.0-4.5 (31H); 6.0 (1H); 6.7-7.1 and 7.7-8.5 (170H). Note the CH$_2$O protons are obscured by the water peak (4.6-5.0 ppm).

LC/MS (Ion Pairing): ESI (-ve) m/z=1180.00 ((M-10H)$^{10-}$); 1073.00 ((M-11H)$^{11-}$); 983.46 ((M-12H)$^{12-}$); 907.69 ((M-13H)$^{13-}$); 842.85 ((M-14H)$^{14-}$); 786.53 ((M-15H)$^{15-}$); 737.25 ((M-16H)$^{16-}$); 693.72 ((M-17H)$^{17-}$); 655.26 ((M-18H)$^{18-}$). Data deconvoluted using maximum entropy calculation to give MW=11813 (M-, in the H form) Calculated (H form) (C$_{439}$H$_{545}$N$_{63}$O$_{175}$S$_{32}$) 11812 (M-). Rf (min)=7.34

CE (pH 9): 55.3% purity Rf (min)=20.23

Example 40

BHALys [Lys]$_{16}$ [α-CO-3,5-Ph(SO$_3$Na)$_2$]$_{16}$ [ε-CBz]$_{16}$

| Surface Topology | Surface Stoichiometry | |
|---|---|---|
| ((((A CBz)(A CBz))$^4$((A CBz)(A CBz))$^4$)$^8$(((A CBz)(A CBz))$^4$((A CBz)(A CBz))$^4$)$^8$)$^{16}$ | 16 | CO-3,5-Ph[SO3Na]$_2$ = A |
| ((((A CBz)(A CBz))$^4$((A CBz)(A CBz))$^4$)$^8$(((A CBz)(A CBz))$^4$((A CBz)(A CBz))$^4$)$^8$)$^{16}$ | 16 | CBz |

A solution of BHALys [Lys]$_{16}$ [α-NH$_2$.TFA]$_{16}$ [ε-CBz]$_{16}$ (0.108 g, 0.013 mmol) and PyBOP (0.31 g, 0.59 mmol) in DMF/DMSO (1:1) (7 mL) was reacted with a solution of 3,5-disulfobenzoic acid (0.17 g, 0.62 mmol) and diisopropylethylamine (0.4 mL, 2.30 mmol) in DMF/DMSO (1:1) (3 mL) according to the method of Example 29.iii to give BHALys [Lys]$_{16}$ [α-CO-3,5-Ph(SO$_3$Na)$_2$]$_{16}$ [ε-CBz]$_{16}$ as white solid (0.20 g, 134%).

1H nmr (300 MHz, D$_2$O) λ (ppm): 1.0-1.8 (186H); 2.8-3.3 (62H); 4.0-4.4 (31H); 6.0 (1H); 7.0-7.2 and 8.2-8.4 (138H). Note the CH$_2$O protons are obscured by the water peak (4.6-5.0 ppm).

LC/MS (Ion Pairing): ESI (-ve) m/z=876.84 ((M-12H)$^{12-}$); 808.99 ((M-13H)$^{13-}$); 751.20 ((M-14H)$^{14-}$); 701.27 ((M-15H)$^{15-}$); 657.37 ((M-16H)$^{16-}$); 618.52 ((M-17H)$^{17-}$); 584.21 ((M-18H)$^{18-}$). Data deconvoluted using maximum entropy calculation to give MW=10533 (M-, in the H form) Calculated (H form) (C$_{439}$H$_{545}$N$_{63}$O$_{175}$S$_{32}$) 10531 (M-). Rf (min)=8.06

CE (pH 9 method): 69.5% purity Rf (min)=20.39

Example 41

BHALys [Lys]$_{16}$ [α-CO-4-Ph(SO$_3$Na)]$_{16}$ [ε-CBz]$_{16}$

| Surface Topology | Surface Stoichiometry | |
|---|---|---|
| ((((A CBz)(A CBz))$^4$((A CBz)(A CBz))$^4$)$^8$(((A CBz)(CBz))$^4$((A CBz)(A CBz))$^4$)$^8$)$^{16}$ | 16 | CO-4-Ph(SO3Na) = A |
| ((((A CBz)(A CBz))$^4$((A CBz)(A CBz))$^4$)$^8$(((A CBz)(A CBz))$^4$((A CBz)(A CBz))$^4$)$^8$)$^{16}$ | 16 | CBz |

A solution of (BHALys [Lys]$_{16}$ [α-NH$_2$.TFA]$_{16}$ [ε-CBz]$_{16}$) (0.117 g, 0.014 mmol) and PyBOP (0.33 g, 0.63 mmol) in DMF/DMSO (1:1) (7 mL) was reacted with a solution of 4-sulfobenzoic acid (0.14 g, 0.67 mmol) and diisopropylethylamine (0.4 mL, 2.30 mmol) in DMF/DMSO (1:1) (3 mL) according to the method of Example 29.iii to give BHALys [Lys]$_{16}$ [α-CO-4-Ph(SO$_3$Na)]$_{16}$ [ε-CBz]$_{16}$ as a white solid (0.17 g, 121%).

1H nmr (300 MHz, D$_2$O) λ (ppm): 1.0-1.9 (186H); 2.7-3.2 (62H); 4.0-4.4 (31H); 6.0 (1H); 6.9-7.2 and 7.6-7.8 (154H). Note the CH$_2$O protons are obscured by the water peak (4.6-5.0 ppm).

LC/MS (Ion Pairing): ESI (−ve) m/z=924.00 ((M−10H)$^{10-}$); 840.02 ((M−11H)$^{11-}$); 769.81 ((M−12H)$^{12-}$); 710.61 ((M−13H)$^{13-}$); 659.78 ((M−14H)$^{14-}$); 615.74 ((M−15H)$^{15-}$); 577.34 ((M−16H)$^{16-}$). Data deconvoluted using maximum entropy calculation to give MW=9252 (M−, in the H form) Calculated (H form) (C$_{439}$H$_{545}$N$_{63}$O$_{127}$S$_{16}$) 9250 (M−). Rf (min)=9.08

CE (pH 9 method): 78.0% purity Rf (min)=18.07

Example 42

BHALys [GlyLys]$_2$ [Lys]$_4$ [α,α-Boc]$_2$ [α,ε-Boc]$_2$ [ε,α-COCH$_2$O-3,6-Naph(SO$_3$Na)$_2$]$_2$ [ε,ε-COCH$_2$O-3,6-Naph(SO$_3$Na)$_2$]$_2$

| Surface Topology | Surface Stoichiometry | |
|---|---|---|
| (((A A)(Boc Boc))$^4$((A A)(Boc Boc))$^4$)$^8$ | 4 | COCH$_2$O-3,6-Naph(SO$_3$Na)$_2$ = A |
| | 4 | Boc |

A solution of BHALys [GlyLys$_2$(Boc)$_2$(NH$_2$)$_2$]$_2$ (34 mg, 0.021 mmol) and PyBOP (0.11 g, 0.21 mmol) in DMF/DMSO (1:1) (2 mL) was reacted with a solution of HOCOCH$_2$O-3,6-Naph(SO$_3$Na)$_2$ (0.07 g, 0.13 mmol) and DIPEA (0.2 mL, 1.15 mmol) in DMF/DMSO (1:1) (1 mL) was added gradually. The mixture was stirred at room temperature for 16 h. Solvent was removed in vacuo and the residue triturated with acetonitrile. The precipitate was collected by filtration and purified on a desalting column (PD-10). Eluent was freeze dried to give BHALys [GlyLys$_2$(Boc)$_2$(COCH$_2$O-3,6-Naph(SO$_3$Na)$_2$)$_2$]$_2$ as a white solid (15 mg, 27%).

LC/MS (Ion Pairing): ESI (−ve) m/z=989.89 ((M−3H)$^{3-}$); 741.94 ((M−4H)$^{4-}$); 593.56 ((M−5H)$^{5-}$). Data deconvoluted using maximum entropy calculation to give MW=2972.50 (M−, in H form) Calculated (H form) (C$_{127}$H$_{167}$N$_{17}$O$_{49}$S$_8$) 2972.29 (M−). Rf (min)=9.57

Example 43

BHALys [GlyLys]$_2$ [Lys]$_4$ [α,α-COCH$_2$O-3,6-Naph(SO$_3$Na)$_2$]$_2$ [α,ε-COCH$_2$O-3,6-Naph(SO$_3$Na)$_2$]$_2$ [ε,α-COC$_5$H$_{12}$]$_2$ [ε,ε-COC$_5$H$_{12}$]$_2$

| Surface Topology | Surface Stoichiometry | |
|---|---|---|
| (((Hex Hex)(B B))$^4$((Hex Hex)(B B))$^4$)$^8$ | 4 | COC$_5$H$_{12}$ = Hex |
| | 4 | COCH$_2$O-3,6-Naph(SO$_3$Na)$_2$ = B | i. BHALys [GlyLys]$_2$ [Lys]$_4$ [α,α-Boc]$_2$ [α,ε-Boc]$_2$ [ε,α-COC$_5$H$_{12}$]$_2$ [ε,ε-COC$_5$H$_{12}$]$_2$

A solution of BHALys [GlyLys]$_2$ [Lys]$_4$ [α,α-Boc]$_2$ [α,ε-Boc]$_2$ [ε,α-NH$_2$]$_2$ [ε,ε-NH$_2$]$_2$ (42 mg, 0.026 mmol) and PyBOP (0.13 g, 0.25 mmol) in DMF/DMSO (1:1) (2 mL) was reacted with a solution of hexanoic acid (27 mg, 0.23 mmol) and DIPEA (0.2 mL, 1.15 mmol) in DMF/DMSO (1:1) (1 mL) according to the method of Example 29.i to give BHALys [GlyLys]$_2$ [Lys]$_4$ [α,α-Boc]$_2$ [α,ε-Boc]$_2$ [ε,α-COC$_5$H$_{12}$]$_2$ [ε,ε-COC$_5$H$_{12}$]$_2$ as a greyish solid which was used directly for the next step.

ii. BHALys [GlyLys]$_2$ [Lys]$_4$ [α,α-NH$_2$.TFA]$_2$ [α,ε-NH$_2$.TFA]$_2$ [ε,α-COC$_5$H$_{12}$]$_2$ [ε,ε-COC$_5$H$_{12}$]$_2$

BHALys [GlyLys]$_2$ [Lys]$_4$ [α,α-Boc]$_2$ [α,ε-Boc]$_2$ [ε,α-COC$_5$H$_{12}$]$_2$ [ε,ε-COC$_5$H$_{12}$]$_2$ dispersed in DCM (1 mL) was deprotected with a solution of TFA/DCM (1:1) (2 mL) according to the method of Example 29.ii to give BHALys [GlyLys]$_2$ [Lys]$_4$ [α,α-NH$_2$.TFA]$_2$ [α,ε-NH$_2$.TFA]$_2$ [ε,α-COC$_5$H$_{12}$]$_2$ [ε,ε-COC$_5$H$_{12}$]$_2$ as a white solid (28 mg, 47% for two steps). LC/MS (philic) ESI (+ve) m/z=1587.22 (M+); 794.51 ((M+2H)$^{2+}$); 529.93 ((M+3H)$^{3+}$). Calculated (C$_{83}$H$_{143}$N$_{17}$O$_{13}$) 1587.13 (NH$_2$ form). Rf (min)=8.94 iii. BHALys [GlyLys]$_2$ [Lys]$_4$ [α,α-COCH$_2$O-3,6-Naph(SO$_3$Na)$_2$]$_2$ [α,ε-COCH$_2$O-3,6-Naph(SO$_3$Na)$_2$]$_2$ [ε,α-COC$_5$H$_{12}$]$_2$ [ε,ε-COC$_5$H$_{12}$]$_2$ A solution of BHALys [GlyLys]$_2$ [Lys]$_4$ [α,α-NH$_2$.TFA]$_2$ [α,ε-NH$_2$.TFA]$_2$ [ε,α-COC$_5$H$_{12}$]$_2$ [ε,ε-COC$_5$H$_{12}$]$_2$ (21 mg, 0.010 mmol) and PyBOP (0.07 g, 0.13 mmol) in DMF/DMSO (1:1) (1 mL) was reacted with a solution of HOCOCH$_2$O-3,6-Naph(SO$_3$Na)$_2$ (0.03 g, 0.08 mmol) and DIPEA (0.5 mL, 2.87 mmol) in DMF/DMSO (1:1) (1 mL) was added gradually. The mixture was stirred at Rt for 16 h. Solvent was removed in vacuo and the residue dissolved in water and purified by size exclusion chromatography (Sephadex LH-20). Dendrimer containing fractions were freeze dried to give BHALys [GlyLys$_2$ (COCH$_2$O-3,6-Naph(SO$_3$Na)$_2$)$_2$(hexyl)$_2$]$_2$ as a white solid (11 mg, 34%).

LC/MS (Ion Pairing): ESI (−ve) m/z=1480.87 ((M−2H)$^{2-}$); 986.96 ((M−3H)$^{3-}$); 740.14 ((M−4H)$^{4-}$); 592.10 ((M−5H)$^{5-}$); 493.54 ((M−6H)$^{6-}$); 423.39 ((M−7H)$^{7-}$). Data deconvoluted using maximum entropy calculation to give MW=2965.00 (M+1, in H form) Calculated (H form) (C$_{131}$H$_{175}$N$_{17}$O$_{45}$S$_8$) 2964.40 (M−). Rf (min)=9.26

Example 44

| Surface Topology | Surface Stoichiometry | |
|---|---|---|
| | 8 | COCH$_2$O-3,6-Naph(SO$_3$Na)$_2$ = B |

BHALys [Lys]$_2$ [GlyLys]$_4$ [Lys]$_8$ [α,α-Boc]$_4$ [α,ε-Boc]$_4$ [ε,α-COCH$_2$O-3,6-Naph(SO$_3$Na)$_2$]$_4$ [ε,ε-COCH$_2$O-3,6-Naph(SO$_3$Na)$_2$]$_4$ A solution of BHALys$_2$ [GlyLys$_2$(Boc)$_2$(NH$_2$)$_2$]$_4$ (33 mg, 0.011 mmol) and PyBOP (0.12 g, 0.24 mmol) in DMF/DMSO (1:1) (2 mL) was reacted with a solution of HOCOCH$_2$O-3,6-Naph(SO$_3$Na)$_2$ (0.07 g, 0.13 mmol) and DIPEA (0.2 mL, 1.15 mmol) in DMF/DMSO (1:1) (1 mL). The mixture was stirred at room temperature for 16 h. Solvent was removed in vacuo and the residue triturated with acetonitrile. The precipitate was collected by filtration purified on a desalting column (PD-10). Eluent was freeze dried to give BHALys [Lys]$_2$ [GlyLys]$_4$ [Lys]$_8$ [α,α-Boc]$_4$ [α,ε-Boc]$_4$ [ε,α-COCH$_2$O-3,6-Naph(SO$_3$Na)$_2$]$_4$ [ε,ε-COCH$_2$O-3,6-Naph(SO$_3$Na)$_2$]$_4$
as a white solid (25 mg, 38%).

LC/MS (Ion Pairing): ESI (−ve) m/z=1471.44 ((M−4H)$^{4-}$); 1177.16 ((M−5H)$^{5-}$); 980.55 ((M−6H)$^{6-}$); 840.35 ((M−7H)$^{7-}$); 735.26 ((M−8H)$^{8-}$); 653.40 ((M−9H)$^{9-}$). Data deconvoluted using maximum entropy calculation to give MW=5890.00 (M−, in H form) Calculated (H form) (C$_{247}$H$_{333}$N$_{35}$O$_{99}$S$_{16}$) 5889.50 (M−). Rf (min)=9.55

Example 45

BHALys [Lys]$_2$ [GlyLys]$_4$ [Lys]$_8$ [α,α-COCH$_2$O-3,6-Naph(SO$_3$Na)$_2$]$_4$ [α,ε-COCH$_2$O-3,6-Naph(SO$_3$Na)$_2$]$_4$ [ε,α-COC$_5$H$_{12}$]$_4$ [ε,ε-COC$_5$H$_{12}$]$_4$

| Surface Topology | Surface Stoichiometry | |
|---|---|---|
| (((((Hex Hex)(B B))$^4$((Hex Hex)(B B))$^4$)$^8$(((Hex Hex) (B B))$^4$((Hex Hex)(B B))$^4$)$^8$)$^{16}$ | 8 | COC$_5$H$_{12}$ = Hex |
| | 8 | COCH$_2$O-3,6-Naph(SO$_3$Na)$_2$ = B | i. BHALys [Lys]$_2$ [GlyLys]$_4$ [Lys]$_8$ [α,α-Boc]$_4$ [α,ε-Boc]$_4$ [ε,α-COC$_5$H$_{12}$]$_4$ [ε,ε-COC$_5$H$_{12}$]$_4$

A solution of BHALys [Lys]$_2$ [GlyLys]$_4$ [Lys]$_8$ [α,α-Boc]$_4$ [α,ε-Boc]$_4$ [ε,α-NH$_2$]$_4$ [ε,ε-NH$_2$]$_4$ (43 mg, 0.014 mmol) and PyBOP (0.13 g, 0.25 mmol) in DMF/DMSO (1:1) (2 mL) was reacted with a solution of hexanoic acid (27 mg, 0.23 mmol) and DIPEA (0.2 mL, 1.15 mmol) in DMF/DMSO (1:1) (1 mL) according to the method of Example 29.i to give BHALys [Lys]$_2$ [GlyLys]$_4$ [Lys]$_8$ [α,α-Boc]$_4$ [α,ε-Boc]$_4$ [ε,α-COC$_5$H$_{12}$]$_4$ [ε,ε-COC$_5$H$_{12}$]$_4$ as a greyish solid which was used directly for the next step.

ii. BHALys [Lys]$_2$ [GlyLys]$_4$ [Lys]$_8$ [α,α-NH$_2$.TFA]$_4$ [α,ε-NH$_2$.TFA]$_4$ [ε,α-COC$_5$H$_{12}$]$_4$ [ε,ε-COC$_5$H$_{12}$]$_4$

BHALys [Lys]$_2$ [GlyLys]$_4$ [Lys]$_8$ [α,α-Boc]$_4$ [α,ε-Boc]$_4$ [ε,α-COC$_5$H$_{12}$]$_4$ [ε,ε-COC$_5$H$_{12}$]$_4$ dispersed in DCM (1 mL) was deprotected with a solution of TFA/DCM (1:1) (2 mL) according to the method of Example 29.ii to give BHALys [Lys]$_2$ [GlyLys]$_4$ [Lys]$_8$ [α,α-NH$_2$.TFA]$_4$ [α,ε-NH$_2$.TFA]$_4$ [ε,α-COC$_5$H$_{12}$]$_4$ [ε,ε-COC$_5$H$_{12}$]$_4$ as a white solid (44 mg, 80% for two steps).

LC/MS (philic) ESI (+ve) m/z=1560.69 ((M+2H)$^{2+}$); 1040.77 ((M+3H)$^{3+}$); 780.72 ((M+4H)$^{4+}$); 624.85 ((M+5H)$^{5+}$). Calculated (C$_{189}$H$_{285}$N$_{35}$O$_{27}$) 3119.18 (NH$_2$ form). Rf (min)=9.29 iii. BHALys [Lys]$_2$ [GlyLys]$_4$ [Lys]$_8$ [α,α-COCH$_2$O-3,6-Naph(SO$_3$Na)$_2$]$_4$ [α,ε-COCH$_2$O-3,6-Naph(SO$_3$Na)$_2$]$_4$ [ε,α-COC$_5$H$_{12}$]$_4$ [ε,ε-COC$_5$H$_{12}$]$_4$ PyBOP (0.06 g, 0.12 mmol) was added to a stirred solution of BHALys$_2$ [GlyLys$_2$ (NH$_2$.TFA)$_2$(hexyl)$_2$]$_4$ (21 mg, 0.005 mmol) in DMF/DMSO (1:1) (1 mL). A solution of HOCOCH$_2$O-3,6-Naph(SO$_3$Na)$_2$ (0.04 g, 0.09 mmol) and DIPEA (0.6 mL, 3.44 mmol) in DMF/DMSO (1:1) (1 mL) was added gradually. The mixture was stirred at Rt for 16 h. Solvent was removed in vacuo and the residue dissolved in water and purified by size exclusion chromatography (Sephadex LH-20). Dendrimer containing fractions were freeze dried to give BHALys$_2$ [GlyLys$_2$ (COCH$_2$O-3,6-Naph(SO$_3$Na)$_2$)$_2$(hexyl)$_2$]$_4$ as a white solid (6 mg, 18%).

LC/MS (Ion Pairing): ESI (−ve) m/z=1467.17 ((M−4H)$^{4-}$); 1173.62 ((M−5H)$^{5-}$); 978.28 ((M−6H)$^{6-}$); 838.08 ((M−7H)$^{7-}$); 733.26 ((M−8H)$^{8-}$); 651.74 ((M−9H)$^{9-}$); 586.64 ((M−10H)$^{10-}$). Data deconvoluted using maximum entropy calculation to give MW=5875.00 (M+1, in H form) Calculated (H form) (C$_{255}$H$_{349}$N$_{35}$O$_{91}$S$_{16}$) 5873.72 (M−). Rf (min)=10.12

Example 46

BHALys [Lys]$_2$[α,ε-Lys] [CBz]$_2$ [Lys]$_3$ [COCH$_2$O-3,6-Naph(SO$_3$Na)$_2$]$_6$

| Surface Topology | Surface Stoichiometry | |
|---|---|---|
| ((((CBzCBz)(B B))$^4$((B B)(B B))$^4$)$^8$ | 2 | CBz |
| | 6 | COCH$_2$O-3,6-Naph(SO$_3$Na)$_2$ = B | i. BHALys [Lys]$_2$ [α,ε-Lys] [CBz]$_2$ [Lys]$_3$ [NH$_2$.TFA]$_6$

A solution of TFA (0.5 mL) was added slowly to BHALys [Lys]$_2$ [α,ε-Lys] [CBz]$_2$ [Lys]$_3$ [Boc]$_6$ (30 mg, 0.015 mmol) dispersed in acetic acid (0.5 mL). The mixture was stirred at room temperature for 16 h. The solvent was removed in vacuo to give BHALys [Lys]$_2$ [α,ε-Lys] [CBz]$_2$ [Lys]$_3$ [NH$_2$.TFA]$_6$ as a pale yellow oil (31 mg, 99%).

LC/MS (philic) ESI (+ve) m/z=1348.67 ((M$^+$)); 675.09 ((M+2H)$^{2+}$). Calculated (C$_{71}$H$_{109}$N$_{15}$O$_{11}$) 1348.72 (NH$_2$ form). Rf (min)=7.54 ii. BHALys [Lys]$_2$ [α,ε-Lys] [CBz]$_2$ [Lys]$_3$ [COCH$_2$O-3,6-Naph(SO$_3$Na)$_2$]$_6$ PyBOP (0.15 g, 0.29 mmol) was added to a stirred solution of BHALys [Lys]$_2$ [α,ε-Lys] [CBz]$_2$ [Lys]$_3$ [NH$_2$.TFA]$_6$ (31 mg, 0.015 mmol) in DMF/DMSO (1:1) (2 mL). A solution of HOCOCH$_2$O-3,6-Naph(SO$_3$Na)$_2$ (0.11 g, 0.28 mmol) and DIPEA (0.2 mL, 1.15 mmol) in DMF/DMSO (1:1) (2 mL) was added gradually. The mixture was stirred at room temperature for 16 h. Solvent was removed in vacuo and the residue dissolved in water and purified by size exclusion chromatography (Sephadex LH-20). Dendrimer containing fractions were freeze dried to give BHALys [Lys]$_2$ [α,ε-Lys] [CBz]$_2$ [Lys]$_3$ [COCH$_2$O-3,6-Naph(SO$_3$Na)$_2$]$_6$ as a white solid (4 mg, 7%).

LC/MS (Ion Pairing): ESI (−ve) m/z=1706.45 ((M−2H)$^{2-}$); 1137.01 ((M−3H)$^{3-}$); 852.50 ((M−4H)$^{4-}$); 681.88 ((M−5H)$^{5-}$); 568.40 ((M−6H)$^{6-}$). Data deconvoluted using maximum entropy calculation to give MW=3415.00 (M−, in H form) Calculated (H form) (C$_{143}$H$_{157}$N$_{15}$O$_{59}$S$_{12}$) 3414.62 (M−). Rf (min)=10.55

Example 47

| Surface Topology | Surface Stoichiometry | |
|---|---|---|
| (((A A)(Boc Boc))$^4$((Boc Boc)(Boc Boc))$^4$)$^8$ | 2 | COCH$_2$O-3,6-Naph(SO$_3$Na)$_2$ = A |
| | 6 | Boc |

BHALys [Lys]$_2$ [α,ε-Lys] [COCH$_2$O-3,6-Naph(SO$_3$Na$_2$]$_2$ [Lys]$_3$ [Boc]$_6$ PyBOP (0.02 g, 0.03 mmol) was added to a stirred solution of BHALys$_4$ [Boc]$_6$ [NH$_2$]$_2$ (4 mg, 0.002 mmol) in DMF/DMSO (1:1) (1 mL). A solution of HOCOCH$_2$O-3,6-Naph (SO-$_3$Na)$_2$ (0.01 g, 0.02 mmol) and diisopropylethylamine (50 μL, 0.29 mmol) in DMF/DMSO (1:1) (1 mL) was added gradually. The mixture was stirred at room temperature for 16 h. Solvent was removed in vacuo and the residue triturated with acetonitrile. The crude product was collected by filtration and triturated with water. The precipitate was dried in vacuo to give BHALys$_4$ [Boc]$_6$ [COCH$_2$O-3,6-Naph(SO$_3$Na)$_2$]$_2$ as a greyish solid (3 mg, 53%).

Example 48

BHALys [GlyLys]$_2$ [Lys]$_4$ [COCH$_2$O-3,6-Naph(SO$_3$Na)$_2$]$_6$ [ε,ε-CBz]$_2$

| Surface Topology | Surface Stoichiometry | |
|---|---|---|
| ((((CBz CBz)(B B))$^4$((B B)(B B))$^4$)$^8$ | 2 | CBz |
| | 6 | COCH$_2$O-3,6-Naph(SO$_3$Na)$_2$ = B | i. BHALys [GlyLys]$_2$ [Lys]$_4$ [NH$_2$.TFA]$_6$ [ε,ε-CBz]$_2$

A solution of TFA (0.5 mL) was added slowly to BHALys [GlyLys]$_2$ [Lys]$_4$ [Boc]$_6$ [ε,ε-CBz]$_2$ (25 mg, 0.012 mmol) dispersed in acetic acid (0.5 mL). The mixture was stirred at room temperature for 16 h. The solvent was removed in vacuo to give BHALys [GlyLys]$_2$ [Lys]$_4$ [NH$_2$.TFA]$_6$ [ε,ε-CBz]$_2$ as a pale yellow oil (24 mg, 92%).

LC/MS (philic) ESI (+ve) m/z=1463.88 ((M+1)$^+$); 732.29 ((M+2H)$^{2+}$); 488.55 ((M+3H)$^{3+}$). Calculated (C$_{75}$H$_{115}$N$_{17}$O$_{13}$) 1462.82 (NH$_2$ form). Rf (min)=7.25 ii. BHALys [GlyLys]$_2$ [Lys]$_4$ [COCH$_2$O-3,6-Naph(SO$_3$Na)$_2$]$_6$ [ε,ε-CBz]$_2$ PyBOP (0.11 g, 0.21 mmol) was added to a stirred solution of BHALys [GlyLys$_2$(NH$_2$.TFA)$_3$(CBz)]$_2$ (24 mg, 0.011 mmol) in DMF/DMSO (1:1) (2 mL). A solution of HOCOCH$_2$O-3,6-Naph(SO$_3$Na)$_2$ (0.08 g, 0.20 mmol) and DIPEA (0.5 mL, 2.87 mmol) in DMF/DMSO (1:1) (2 mL) was added gradually. The mixture was stirred at room temperature for 16 h. Solvent was removed in vacuo and the residue triturated with acetonitrile. The precipitate was collected by filtration purified on a desalting column (PD-10). Eluent was freeze dried to give BHALys [GlyLys]$_2$ [Lys]$_4$ [COCH$_2$O-3,6-Naph(SO$_3$Na)$_2$]$_6$ [ε,ε-CBz]$_2$ as a white solid (18 mg, 42%).

LC/MS (Ion Pairing): ESI (−ve) m/z=1175.22 ((M−3H)$^{3−}$); 881.14 ((M−4H)$^{4−}$); 704.63 ((M−5H)$^{5−}$); 587.24 ((M−6H)$^{6−}$); 503.50 ((M−7H)$^{7−}$). Data deconvoluted using maximum entropy calculation to give MW=3529.00 (M−, in H form) Calculated (H form) (C$_{147}$H$_{163}$N$_{17}$O$_{61}$S$_{12}$) 3528.72 (M−). Rf (rein)=10.34

Example 49

BHALys [GlyLys]$_2$ [Lys]$_4$ [Boc]$_6$ [ε,ε-COCH$_2$O-3,6-Naph(SO$_3$Na)$_2$]$_2$

| Surface Topology | Surface Stoichiometry | |
|---|---|---|
| (((A A)(Boc Boc))$^4$((Boc Boc)(Boc Boc))$^4$)$^8$ | 2 | COCH$_2$O-3,6-Naph(SO$_3$Na)$_2$ = A |
| | 6 | Boc |

PyBOP (0.08 g, 0.14 mmol) was added to a stirred solution of BHALys [GlyLys$_2$(Boc)$_3$(NH$_2$)]$_2$ (19 mg, 0.011 mmol) in DMF/DMSO (1:1) (2 mL). A solution of HOCOCH$_2$O-3,6-Naph(SO$_3$Na)$_2$ (0.05 g, 0.12 mmol) and DIPEA (0.1 mL, 0.57 mmol) in DMF/DMSO (1:1) (1 mL) was added gradually. The mixture was stirred at room temperature for 16 h. Solvent was removed in vacuo and the residue triturated with acetonitrile. The precipitate was collected by filtration purified on a desalting column (PD-10). Eluent was freeze dried to give BHALys [GlyLys$_2$(Boc)$_3$(COCH$_2$O-3,6-Naph(SO$_3$Na)$_2$)]$_2$ as a white solid (10 mg, 37%).

LC/MS (Ion Pairing): ESI (−ve) m/z=1240.91 ((M−2H)$^{2−}$); 826.99 ((M−3H)$^{3−}$); 620.01 ((M−4H)$^{4−}$). Data deconvoluted using transform calculation to give MW=2484.00 (M−, in H form) Calculated (H form) (C$_{113}$H$_{167}$N$_{17}$O$_{37}$S$_4$) 2483.89 (M−). Rf (min)=10.55

Example 50

Antiviral Efficacy of Macromolecules with Controlled Surface Topology

MT-2 cells are infected with the T cell tropic NL4.3 strain of HIV-1 in the presence of 6, 5-fold serial concentrations of compound in triplicate wells of a 96 well plate. In the same plate, cells are exposed to the same drug concentrations in the absence of virus to determine the cytotoxic concentrations of the compound. The prototype macromolecule, SPL7103, which inhibits HIV replication, is tested in each assay as a positive control [see Dezzutti C S, James V N, Ramos A, Sullivan S T, Siddig A, Bush T J, Grohskopf L A, Paxton L, Subbarao S, Hart C E. In vitro comparison of topical microbicides for prevention of human immunodeficiency virus type 1 transmission. Antimicrob Agents Chemother. 2004; 48: 3834-44].

After 6 days incubation at 37° C. in a CO$_2$ incubator, cell viability of both virus-infected and uninfected cells is determined by incubating cells for 3-4 hours with 3-(4,5-dimethylthiazol-2-yl)-5-(3-carboxymethoxyphenyl)-2-(4-sulfophenyl)-2H-tetrazolium (MTS) according to manufacturer's instructions (CellTiter 96 AQueous One Solution Cell Proliferation assay (Promega, Madison Wis.)). The 50% cytotoxic concentration (CC$_{50}$) and 50% inhibitory concentration (IC$_{50}$) is calculated for each drug from dose response curves using XLfit 4.1 software (ID Business Solutions Ltd, Guildford, Surrey, UK). Data from this assay is tabulated in Table 5.

TABLE 24

Antiviral activities for macromolecules with controlled surface stoichiometry

| Ex. # | Topology | A + B | A:B | A | B | $EC_{50}$* (ug/ml) | Set# |
|---|---|---|---|---|---|---|---|
| 29 | ABABABAB | 8 | 1:1 | $COCH_2O$-3,6-Naph$(SO_{-3}Na)_2$ | $COC_5H_{12}$ | 23.8 | 1 |
| 30 | ABABABAB | 8 | 1:1 | $COC_5H_{12}$ | $COCH_2O$-3,6-Naph$(SO_3Na)_2$ | 58.3 | 1 |
| 31 | ABABABAB | 8 | 1:1 | CO-4-PhSO$_3$Na | $COC_5H_{12}$ | 344 | |
| 32 | ABABABAB × 2 | 16 | 1:1 | CO-3,5-Ph$(SO_3Na)_2$ | $COC_5H_{12}$ | 5.8 | |
| 33 | ABABABAB × 2 | 16 | 1:1 | $COCH_2O$-3,6-Naph$(SO_{-3}Na)_2$ | $COC_5H_{12}$ | 0.71 | 3 |
| 34 | ABABABAB × 2 | 16 | 1:1 | $CO_2PEG_3$ | CO-3,5-Ph$(SO_3Na)_2$ | 84.5 | |
| 35 | ABABABAB × 2 | 16 | 1:1 | $CO_2PEG_3$ | CO-4-PhSO$_3$Na | >500 | |
| 36 | ABABABAB × 2 | 16 | 1:1 | $COCH_2O$-3,6-Naph$(SO_{-3}Na)_2$ | CBz | 3.2 | |
| 37 | ABABABAB × 2 | 16 | 1:1 | CO-3,5-Ph$(SO_3Na)_2$ | CBz | 2 | |
| 38 | ABABABAB × 2 | 16 | 1:1 | CO-4-PhSO$_3$Na | CBz | 2.2 | |
| 39 | ABABABAB × 4 | 32 | 1:1 | $COCH_2O$-3,6-Naph$(SO_{-3}Na)_2$ | CBz | 2.4 | |
| 40 | ABABABAB × 4 | 32 | 1:1 | CO-3,5-Ph$(SO_3Na)_2$ | CBz | 3.2 | |
| 41 | ABABABAB × 4 | 32 | 1:1 | CO-4-PhSO$_3$Na | CBz | 4.2 | |
| 42 | AABB AABB | 8 | 1:1 | $COCH_2O$-3,6-Naph$(SO_{-3}Na)_2$ | Boc | 10.6 | |
| 43 | AABB AABB | 8 | 1:1 | $COCH_2O$-3,6-Naph$(SO_{-3}Na)_2$ | $COC_5H_{12}$ | 0.24 | 1 |
| 44 | AABB AABB × 2 | 16 | 1:1 | $COCH_2O$-3,6-Naph$(SO_{-3}Na)_2$ | Boc | 0.33 | |
| 45 | AABB AABB × 2 | 16 | 1:1 | $COCH_2O$-3,6-Naph$(SO_{-3}Na)_2$ | $COC_5H_{12}$ | 0.37 | 3 |
| 46 | AABB BBBB | 8 | 1:3 | CBz | $COCH_2O$-3,6-Naph$(SO_3Na)_2$ | 0.14 | |
| 47 | AABB BBBB | 8 | 1:3 | $COCH_2O$-3,6-Naph$(SO_{-3}Na)_2$ | Boc | >50 | 2 |
| 48 | AABB BBBB | 8 | 1:3 | CBz | $COCH_2O$-3,6-Naph$(SO_3Na)_2$ | 0.13 | |
| 49 | ABBB ABBB | 8 | 1:3 | $COCH_2O$-3,6-Naph$(SO_{-3}Na)_2$ | Boc | 2.2 | 2 |
| | SPL7013 | 32 | — | $COCH_2O$-3,6-Naph$(SO_{-3}Na)_2$ | — | 1.5 | |

*All compounds showed $CC_{50}$ values >250 ug/ml
Sets of compounds in which the surface stoichiometry of functional moieties is the same, but for which the topology is different.

This data serves to demonstrate that macromolecules which have different topologies of the same surface functional moiety stoichiometry behave differently when interacting with a physico-chemical environment. It is important also to highlight the potent anti-HIV activity of Examples 46 and 48, which can be seen to be considerably more active than SPL7013 which is a macromolecule with only a single type of Functional moiety on the surface.

ADME Examples

Example 51

BHALys [Lys]$_8$ [PEG$_{200}$]$_{16}$

To a stirred solution of BHA[Lys]$_8$TFA$_{16}$ (125 mg, 0.03 mmol) in DMF (8 mL) was added PyBOP (556 mg, 1.0 mmol), followed by a solution of PEG 200 (240 mg, 1.0 mmol), N,N-diisopropylethylamine (709 µL, 4.0 mmol) in DMF (16 mL) and DMSO (2 mL). The solution was stirred at Rt for 16 h. The reaction mixture was poured into water (180 mL) and filtered and washed with water. The aqueous solution was transferred to a 3K stirred cell and water was passed through the cell, remaining water was removed by freeze drying to give a free flowing white solid (20 mg, 11%)

LC/MS (Philic TFA): Rf (min)=16.72. ESI (+ve) z=5598 (M+H$^+$).

Example 52

BHALys [Lys]$_{16}$ [PEG$_{200}$]$_{32}$

To a stirred solution of BHA[Lys]$_{16}$TFA$_{32}$ (30 mg, 0.004 mmol) in DMF (3 mL) under argon was added PyBOP (142 mg, 0.271 mmol), followed by a solution of PEG 200 (62 mg, 0.263 mmol), N,N-diisopropylethylamine (182 µL, 1.04 mmol) in DMF (3 mL). The solution was stirred at Rt for 16 h. The solvents were removed under reduced pressure and the resulting crude mixture was dissolved in a minimum volume of water. Purification by sephadex column (LH-20) using water as the eluent gave the desired product as a white solid (20 mg, 44%) after removing the water by freeze drying.

LC/MS (Philic TFA): Rf (min)=16.74 ESI (+ve) m/z=11,141 (M+H$^+$).

Example 53

BHALys [Lys]$_{16}$ [PEG$_{570}$]$_{32}$

To a stirred solution of BHA[Lys]$_{16}$TFA$_{32}$ (20 mg, 0.003 mmol) in dry DMF (2 mL) under nitrogen was added TEA (36 µL, 0.261 mmol) and PEG 685.75, NHS ester (119 mg, 0.174 mmol). The reaction mixture was stirred at Rt for 16 h. The solution was poured into a 5K stirred cell and water (600 mL) was passed through the cell, remaining water was removed by freeze drying (×2) to give a glassy solid (50 mg, 88%). LC (Philic TFA): Rf (min) 12.42.

Example 54

BHALys [Lys]$_8$ [PEG$_{2KD}$]$_{16}$

To a stirred solution of BHA[Lys]$_8$TFA$_{16}$ (30 mg, 0.008 mmol) in dry DMF (2 mL) under nitrogen was added PyBOP (141 mg, 0.271 mmol), followed by a solution of PEG 2000, NHS ester (612 mg, 0.306 mmol), N,N-diisopropylethylamine (180 µL, 1.04 mmol) in DMF (1.4 mL) and DMSO (0.6 mL). The solution was stirred at Rt for 16 h. The reaction mixture was poured into a 10K stirred cell and water (800 mL) was passed through the cell, remaining water was removed by freeze drying to give a free flowing white solid (149 mg, 54%).

Example 55

BHALys [Lys]$_{16}$ [PEG$_{2KD}$]$_{32}$ SPL 7709

To a stirred solution of BHA[Lys]$_{16}$TFA$_{32}$ (30 mg, 0.004 mmol) in dry DMF (2 mL) under argon was added PyBOP (142 mg, 0.272 mmol), followed by a solution of PEG 2000, NHS ester (522 mg, 0.261 mmol), N,N-diisopropylethylamine (182 µL, 1.04 mmol) in DMF (3 mL) and DMSO (1 mL). The solution was stirred at Rt for 16 h. The reaction mixture was poured into water and filtered and washed with water. Purification was performed by tangential flow filtration on a Mini-mate (10K membrane, 2 L of water). Solvent was removed by freeze drying to give a free flowing white solid (210 mg, 76%)

LC/MS (Philic TFA): Rf (min)=16.29 ESI (+ve) m/z=67, 696 (M+H$^+$)

i. EtO-Su(NPN)$_2$ [Boc] [NH$_2$]

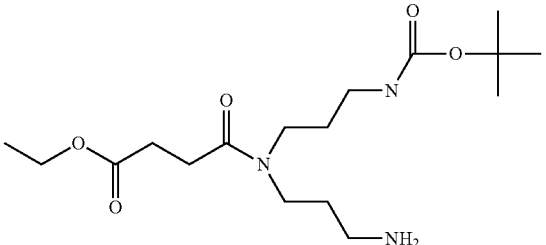

To a stirred mixture of EtO-Su(NPN)$_2$ [Boc] [CBz] (0.88 g, 1.77 mmol) in DMF/H$_2$O (9:1, 20 mL) was added ammonium formate (224 mg, 3.55 mmol) and Pd/C (10%, 470 mg). The mixture was stirred for 2 h at room temperature, then filtered (0.2 µm PALL filter disc) and concentrated. The residue was taken up in water and concentrated (2×). This was then repeated with MeOH and DCM, providing 0.54 g (84%) of EtO-Su(NPN)$_2$ [Boc] [NH$_2$] as a clear colourless oil. LCMS (LC: philic, TFA, RT=6.2 min; MS (M$_{calc}$ C$_{17}$H$_{33}$N$_3$O$_5$=359.47): 360 ([M+H]$^+$, 100%). $^1$H (CDCl$_3$): δ 5.30 (br s, 1H), 4.80 (br s, 1H), 4.12 (q, J=9.0 Hz, 2H), 3.29-3.46 (m, 4H), 3.14 (m, 1H), 3.07 (m, 1H), 2.56-2.80 (m, 6H), 1.60-1.90 (m, 4H), 1.42, 1.43 (2s, 9H), 1.25 (t, J=9.0 Hz, 3H).

ii. EtO-Su(NPN)$_2$ [Boc] [COPEG$_{12}$]

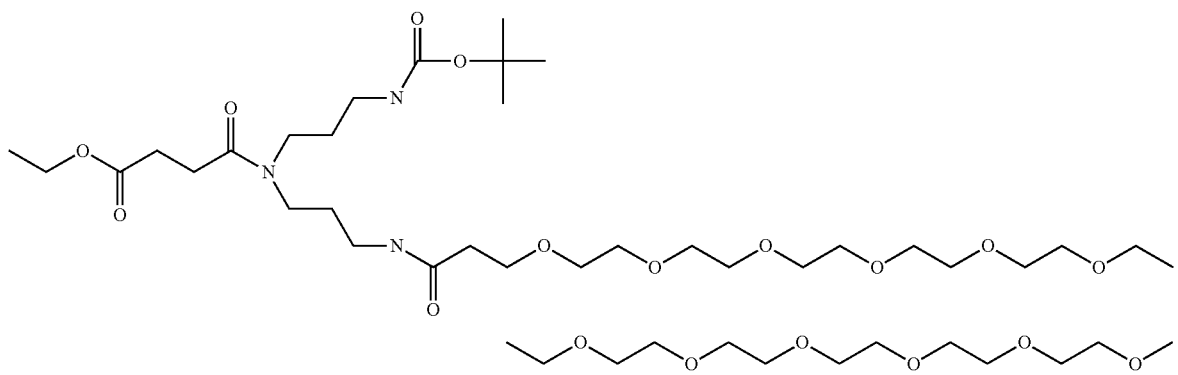

Example 56

BHALys [Lys]$_2$ [Su(NPN)$_2$]$_4$ [γ-CO-MTX-α-OtBu]$_4$ [COPEG$_{12}$]$_4$

Figure 11:
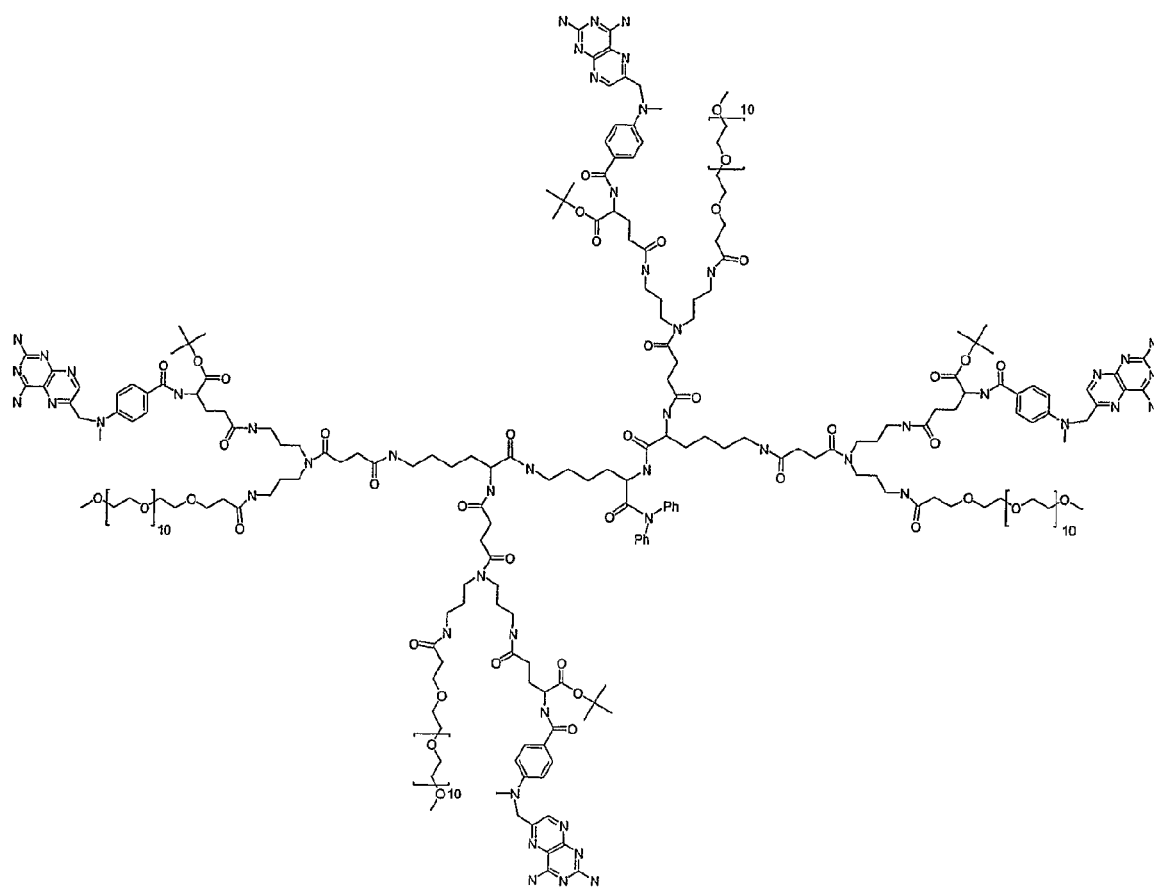
FIG. 11 is BHALys [Lys]$_2$ [Su(NPN)$_2$]$_4$ [MTX- -OtBu]$_4$ [PEG$_{24}$]$_4$ which is described in Example 56, and which is a drug sustenance macromolecule according to a preferred embodiment of the invention, bearing surface PEG groups and to which a drug of interest is covalently attached.

This example is depicted graphically in FIG. 11.

| Surface Topology | Surface Stoichiometry |
|---|---|
| (((Drug PEG)(Drug PEG))$^4$((Drug PEG)(Drug PEG))$^4$)$^8$ | 16 COPEG$_{12}$ = PEG<br>16 γ-CO-MTX-α-OtBu = Drug |

To a stirred mixture of EtO-Su(NPN)$_2$ [Boc] [NH$_2$] (157 mg, 0.44 mmol) in DCM (2 mL) was added TEA (121 µl, 0.87 mmol) and NHS-COPEG$_{12}$ (300 mg, 0.44 mmol) as a DCM (2 mL) solution. The mixture was stirred at room temperature overnight, concentrated, then purified by flash column chromatography (2-10% MeOH/DCM, providing 331 mg (82%) of EtO-Su(NPN)$_2$ [Boc] [COPEG$_{12}$] as a clear colourless oil. LCMS (LC: philic, TFA, RT=8.2 min; MS (M$_{calc}$ C$_{43}$H$_{83}$N$_3$O$_{16}$=930.15): 948 ([M+NH$_4$]$^+$, 12%), 931 ([M+H]$^+$, 2%), 416 (½[M–BOC+2H$^+$], 100%). $^1$H (CDCl$_3$): δ 7.10 (br s, 1H), 7.03 (br s, 1H), 4.16 (q, J=9.0 Hz, 2H), 3.72 (m, 2H), 3.58-3.66 (m, 36H), 3.52-3.56 (m, 2H), 3.47 (s, 2H), 2.96-3.42 (m, 7H), 3.37 (s, 4H), 2.70 (s, 4H), 2.60 (m, 4H), 2.47 (m, 2H), 1.60-1.90 (m, 4H), 1.41, 1.43 (2s, 9H), 1.24 (t, J=9.0 Hz, 3H).

iii. EtO-Su(NPN)₂ [NH₂.TFA] [COPEG₁₂]

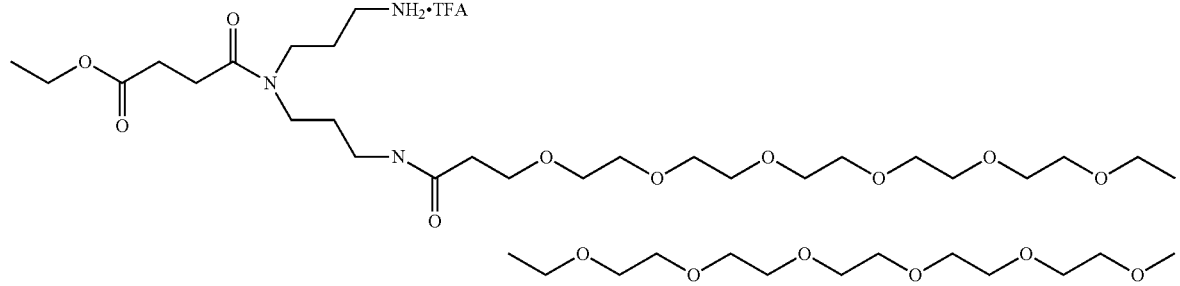

To a stirred mixture of EtO-Su(NPN)₂ [Boc] [COPEG₁₂] (180 mg, 0.19 mmol) in DCM (2 mL) was added TFA (0.50 mL). The mixture was stirred at room temperature for 6 h, concentrated, H₂O added and concentrated (2×). The residue was then taken up in H₂O again (20 mL), filtered (0.2 μm PALL filter disc) then freeze-dried, providing 0.17 g (93%) of EtO-Su(NPN)₂ [NH₂.TFA] [COPEG₁₂] as a clear colourless oil. LCMS (LC: philic, TFA, RT=5.9 min; MS ($M_{calc}$ $C_{38}H_{75}N_3O_{16}$=830.03): 831 ([M+H]⁺, 7%), 425 (½[M+Na⁺+H⁺], 30%), 416 (½[M+2H⁺], 100%). ¹H (D₂O): δ 4.17 (q, J=9.0 Hz, 2H), 3.80 (t, J=6.0 Hz, 2H), 3.62-3.75 (m, 43H), 3.38-3.53 (m, 4H), 3.40 (s, 3H), 2:90-3.31 (m, 4H), 2.77 (s, 4H), 2.64-2.89 (m, 4H), 2.52-2.58 (m, 2H), 1.72-2.11 (m, 4H), 1.13 (t, J=9.0 Hz, 3H).

iv. EtO-Su(NPN)₂ [γ-CO-MTX-α-OtBu] [COPEG₁₂]

55, 635} in DMF (0.5 mL) at 0° C. was added PyBOP (18 mg, 34.8 μmol) and DIPEA (23 μL, 0.127 mmol). The mixture was stirred at 0° C. for 30 min, then room temperature for 3 h. The DMF was removed, and the residue purified by preparative TLC (7% MeOH, 93% DCM, Rf=0.3) providing 23 mgs (55%) of EtO-Su(NPN)₂ [γ-CO-MTX-α-OtBu] [COPEG₁₂] as an orange oil. LCMS (LC: philic, TFA, RT=8.0 min; MS ($M_{calc}$ $C_{62}H_{103}N_{11}O_{20}$=1322.57): 1323 ([M+H]⁺, 2%), 662 (½[M+2H⁺], 17%), 634 (½[M–tBu+2H⁺], 82%). ¹H (CD₃OD): δ 8.60 (s, 1H), 8.28 (t, J=9.0 Hz, 1H), 7.95-8.05 (m, 1H), 7.72-7.80 (m, 1H), 7.75 (d, J=7.8 Hz, 2H), 6.87 (d, J=7.8 Hz, 2H), 4.88 (s, 2H), 4.36-4.47 (m, 1H), 4.07 (4, J=7.2 Hz, 2H), 3.51-3.78 (m, 50H), 3.18-3.38 (m, 12H), 2.54-2.64 (m, 4H), 2.31-2.48 (m, 4H), 1.75-1.85 (m, 2H), 1.59-1.70 (m, 2H), 1.47 (s, 9H), 1.21 (t, J=7.8 Hz, 3H).

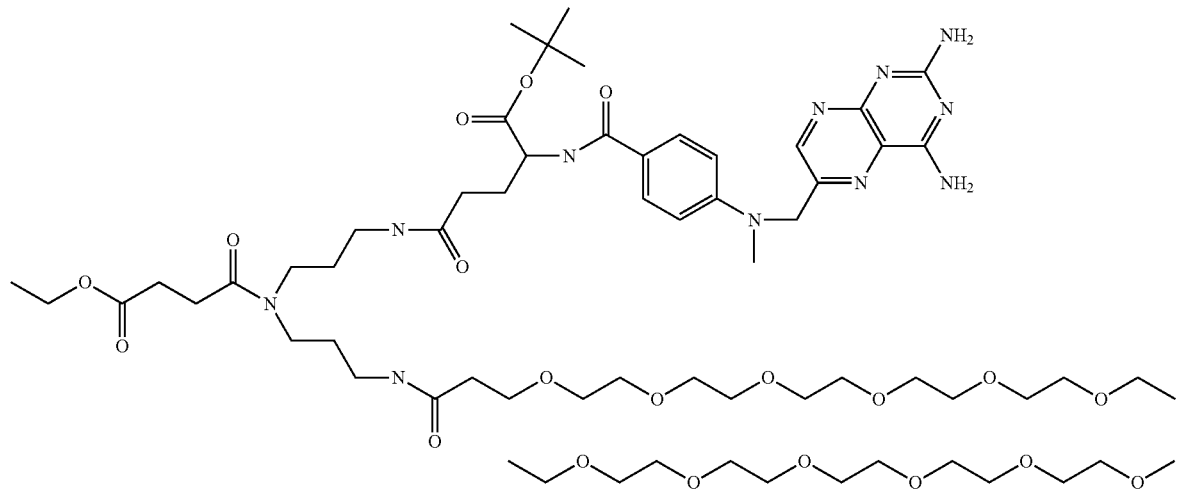

To a stirred mixture of EtO-Su(NPN)₂ [NH₂.TFA] [COPEG₁₂] (30 mg, 31.7 μmol) and MTX-α-OtBu (16.2 mg, 31.7 μmol) {C. L. Francis, Q. Yang, N. K. Hart, F. Widmer, M. K. Manthey and H. Ming He-Williams, *Aust. J. Chem.* 2002, v. HO-Su(NPN)$_2$ [γ-CO-MTX-α-OtBu] [COPEG$_{12}$]

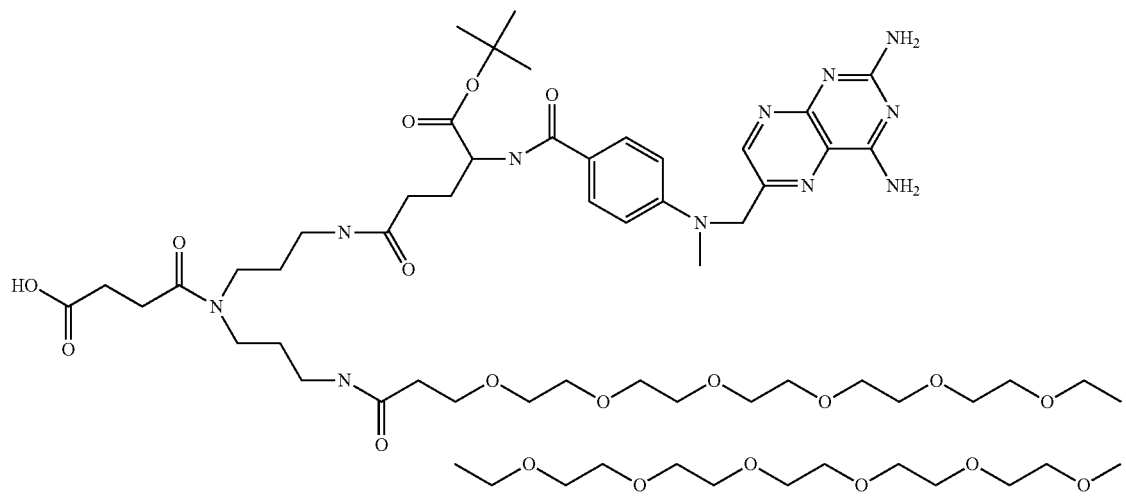

To a stirred mixture of EtO-Su(NPN)$_2$ [γ-CO-MTX-α-OtBu] [COPEG$_{12}$] (109 mg, 82.4 μmol) in THF/H$_2$O (2:1, 9 mL) was added NaOH (0.16 mL, 1.0M). The reaction was left to stir for 16 h at room temperature, and additional NaOH added if required (reaction judged by tlc). After the reaction was complete the pH was adjusted to neutral with HCl (1.0M). The solvent was then removed, the residue taken up in MeOH, and filtered to remove salt. The residue was then purified by preparative TLC (18% MeOH, 82% DCM, Rf=0.4) providing 52 mgs (49%) of HO-Su(NPN)$_2$ [γ-CO-MTX-α-OtBu] [COPEG$_{12}$] as an orange oil. LCMS (LC: philic, TFA, RT=6.8 min; MS (M$_{calc}$ C$_{60}$H$_{99}$N$_{11}$O$_{20}$=1294.52): 1317 ([M+Na], 3%), 1295 ([M+H]$^+$, 2%), 648 (½[M+2H$^+$], 10%), 620 (½[M−tBu+2H$^+$], 74%), 419 (100%).

vi. BHALys[Lys]$_2$[Su(NPN)$_2$(MTX-☐-OtBu)(PEG$_{12}$Me)]$_4$

To a stirred mixture of HO-Su(NPN)$_2$ [γ-CO-MTX-α-OtBu] [COPEG$_{12}$] (10 mg, 7.7 μmol) and BHALys [Lys]$_2$ [NH$_2$.TFA]$_4$ (1.43 mg, 1.4 μmol) in DMF (1.2 mL) at 0° C. was added PyBOP (4.0 mg, 7.7 μmol) and DIPEA (3.9 μL, 22.4 μmol). The mixture was stirred at 0° C. for 30 min, then it for 3 h. The DMF was removed, and the residue purified by PREP HPLC (Waters Xterra MS C$_{18}$, 10 μm, 19×250 mm, 30-60% ACN, 0.1% TFA, 8 mL/min, RT=34 min), providing 2 mg (25%) of the desired dendrimer. LCMS (LC: philic, TFA, RT=8.0 min; MS: 1136 (⅕[M+5H$^+$], 18%), 946 (⅙[M+6H$^+$], 100%), 812 (⅐[M+7H$^+$], 22%) Transforms to 5,673.34. (M$_{calc}$ C$_{271}$H$_{437}$N$_{51}$O$_{79}$=5673.80).

Example 57

BHALys [Lys]$_4$ [Su(NPN)$_2$]$_8$ [γ-CO-MTX-α-OtBu]$_8$ [COPEG$_{12}$]$_8$

| Surface Topology | Surface Stoichiometry |
|---|---|
| ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ | 8 COPEG$_{12}$ = PEG<br>8 γ-CO-MTX-α-OtBu = Drug |

The reaction of HO-Su(NPN)$_2$ [γ-CO-MTX-α-OtBu] [COPEG$_{12}$] with BHALys [Lys]$_4$ [NH$_2$.TFA]$_8$ was carried out according to the method of Example 56.vi to provide BHALys [Lys]$_4$ [Su(NPN)$_2$]$_8$ [γ-CO-MTX-α-OtBu]$_8$ [COPEG$_{12}$]$_8$: 25 mg (63%, 1.32 mCi/g) PREP HPLC (5-60% ACN, 90 min, RT 54 min).

LCMS (LC: philic, TFA, RT=9.0 min; MS: 1614 (⅐[M+7H$^+$], 26%), 1413 (⅛[M+8H$^+$], 73%), 1256 (⅑[M+9H$^+$], 100%) Transforms to 11,294.54. (M$_{calc}$ C$_{535}$H$_{873}$N$_{103}$O$_{159}$=11,292.52).

Example 58

BHALys [Lys]$_8$ [Su(NPN)$_2$]$_{16}$ [γ-CO-MTX-α-OtBu]$_{16}$ [COPEG$_{12}$]$_{16}$

| Surface Topology | Surface Stoichiometry |
|---|---|
| ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$<br>((((Drug PEG)(Drug PEG))$^4$((Drug | 16 COPEG$_{12}$ = PEG<br>16 γ-CO-MTX-α-OtBu = Drug |

-continued

| Surface Topology | Surface Stoichiometry |
|---|---|
| PEG)(Drug PEG))$^4$)$^8$(((Drug PEG)(Drug PEG))$^4$((Drug PEG)(Drug PEG))$^4$)$^8$)$^{16}$ | |

The reaction of HO-Su(NPN)$_2$ [γ-CO-MTX-α-OtBu] [COPEG$_{12}$] with BHALys [Lys]$_8$ [NH$_2$.TFA]$_{16}$ was carried out according to the method of Example 56.vi to provide BHALys [Lys]$_8$ [Su(NPN)$_2$]$_{16}$ [γ-CO-MTX-α-OtBu]$_{16}$ [COPEG$_{12}$]$_{16}$ 15 mg (65%, 1.27 mCi/g) PREP HPLC (5-60% ACN, 90 min, RT 66 min). LCMS (LC: philic, TFA, RT=9.0 min; MS: 2254 ($\frac{1}{10}$[M+10H$^+$], 24%), 2049 ($\frac{1}{11}$[M+11H$^+$], 56%), 1879 ($\frac{1}{12}$[M+12H$^+$], 100%), 1734 ($\frac{1}{13}$[M+13H$^+$], 55%) Transforms to 22,531.91 (M$_{calc}$ C$_{1063}$H$_{1745}$N$_{207}$O$_{319}$=22,529.73).

Example 59

BHALys [Lys]$_{16}$ [Su(NPN)$_2$]$_{32}$ [γ-CO-MTX-α-OtBu]$_{32}$ [COPEG$_{12}$]$_{32}$

| Surface Topology | Surface Stoichiometry |
|---|---|
| ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ | 32 COPEG$_{12}$ = PEG 32 γ-CO-MTX-α-OtBu = Drug |

The reaction of HO-Su(NPN)$_2$ [γ-CO-MTX-α-OtBu] [COPEG$_{12}$] with BHALys [Lys]$_{16}$ [NH$_2$.TFA]$_{32}$ was carried out according to the method of Example 56.vi to provide BHALys [Lys]$_{16}$ [Su(NPN)$_2$]$_{32}$ [γ-CO-MTX-α-OtBu]$_{32}$ [COPEG$_{12}$]$_{32}$: 21 mg (45%, 1.31 mCi/g) PREP HPLC (5-60% ACN, 90 min, RT 71 min). LCMS (LC: philic, TFA, RT=9.2 min; MS: (M$_{calc}$ C$_{2119}$H$_{3489}$N$_{415}$O$_{639}$=45,004.27), MALDI; 40,697 (broad hump).

Example 60

BHALys [Lys]$_4$ [Su(NPN)$_2$]$_8$ [γ-CO-MTX-α-OtBu]$_8$ [COPEG$_{24}$]$_8$

| Surface Topology | Surface Stoichiometry |
|---|---|
| ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ | 8 COPEG$_{24}$ = PEG 8 γ-CO-MTX-α-OtBu = Drug | i. HO-Su(NPN)$_2$ [γ-CO-MTX-α-OtBu] [COPEG$_{24}$]

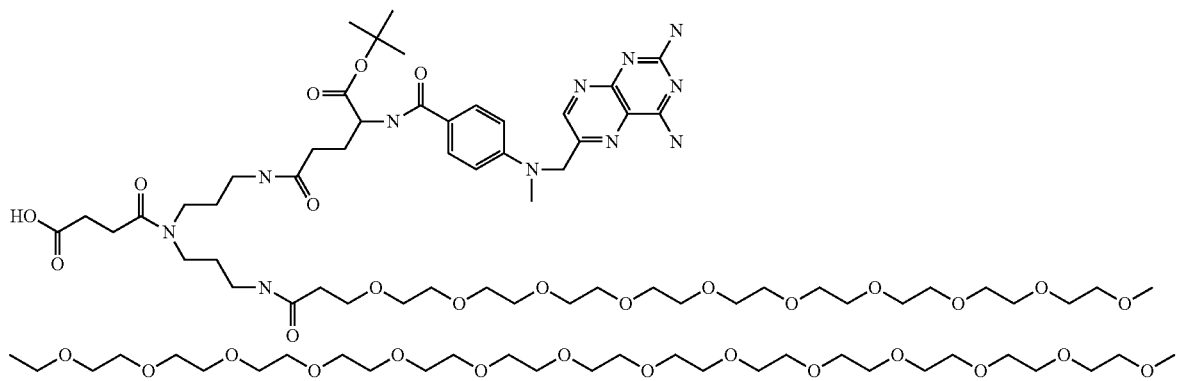

This material was prepared in stepwise fashion from EtO-Su(NPN)$_2$ [Boc] [NH$_2$] and NHS-COPEG$_{24}$ by way of the method for Example 56.ii to provide EtO-Su(NPN)$_2$ [Boc] [COPEG$_{24}$]; the Boc group was removed by way of the method for Example 56.iii to provide EtO-Su(NPN)$_2$ [NH$_2$.TFA] [COPEG$_{24}$]; the MTX-α-OtBu was added by way of the method for 56.iv to provide EtO-Su(NPN)$_2$ [γ-CO-MTX-α-OtBu] [COPEG$_{24}$] and the ester was hydrolysed by way of the method for 56.v to provide HO-Su(NPN)$_2$ [γ-CO-MTX-α-OtBu] [COPEG$_{24}$].

LCMS (LC: philic, TFA, RT=7.3 min; MS (M$_{calc}$ C$_{84}$H$_{147}$N$_{11}$O$_{32}$=1823.10): 921 ($\frac{1}{2}$[M+NH$_4$H]$^+$, 9%), 912 ($\frac{1}{2}$[M+2H$^+$], 12%), 608 ($\frac{1}{3}$[M+3H$^+$], 100%), 461 ($\frac{1}{4}$[M+NH$_4$+3H]$^+$, 35%.

ii. BHALys [Lys]$_4$ [Su(NPN)$_2$]$_8$ [γ-CO-MTX-α-OtBu]$_8$ [COPEG$_{24}$]$_8$

The reaction of HO-Su(NPN)$_2$ [γ-CO-MTX-α-OtBu] [COPEG$_{24}$] with BHALys [Lys]$_4$ [NH$_2$.TFA]$_8$ was carried out according to the method of Example 56.vi to provide BHALys [Lys]$_4$ [Su(NPN)$_2$]$_8$ [γ-CO-MTX-α-OtBu]$_8$ [COPEG$_{24}$]$_8$ 25 mg (62%, 0.96 mCi/g) PREP HPLC (5-60% ACN, 90 min, RT 66 min).

LCMS (LC: philic, TFA, RT=9.2 min; MS: 1726 ($\frac{1}{9}$[M+9H$^+$], 25%), 1553 ($\frac{1}{10}$[M+10H$^+$], 63%), 1412 ($\frac{1}{11}$[M+11H$^+$], 77%), 1294 ($\frac{1}{12}$[M+12H$^+$], 100%), 1195 ($\frac{1}{13}$[M+

13H+], 83%) Transforms to 15,521.12. ($M_{calc}$ $C_{727}H_{1257}N_{103}O_{255}$=15,521.15).

Example 61

BHALys [Lys]$_8$ [Su(NPN)$_2$]$_{16}$
[γ-CO-MTX-α-OtBu]$_{16}$ [COPEG$_{24}$]$_{16}$

| Surface Topology | Surface Stoichiometry |
|---|---|
| ((((Drug PEG)(Drug PEG))$^4$((Drug PEG) (Drug PEG))$^4$)$^8$(((Drug PEG)(Drug PEG))$^4$((Drug PEG) (Drug PEG))$^4$)$^8$)$^{16}$ ((((Drug PEG)(Drug PEG))$^4$((Drug PEG) (Drug PEG))$^4$)$^8$(((Drug PEG)(Drug PEG))$^4$((Drug PEG) (Drug PEG))$^4$)$^8$)$^{16}$ | 16 COPEG$_{24}$ = PEG<br>16 γ-CO-MTX-α-OtBu = Drug |

The reaction of HO-Su(NPN)$_2$ [γ-CO-MTX-α-OtBu] [COPEG$_{24}$] with BHALys [Lys]$_8$ [NH$_2$.TFA]$_8$ was carried out according to the method of Example 56.vi to provide BHALys [Lys]$_8$ [Su(NPN)$_2$]$_{16}$ [γ-CO-MTX-α-OtBu]$_{16}$ [COPEG$_{24}$]$_{16}$: 39 mg (66%, 0.93 mCi/g) PREP HPLC (5-60% ACN, 90 min, RT 70 min). LCMS (LC: philic, TFA, RT=9.4 min; MS: Deconvoluted with Max Ent to 31,033 ($M_{calc}$ $C_{1447}H_{2513}N_{207}O_{511}$=30,987.22).

Example 62

BHALys [Lys]$_{16}$ [Su(NPN)$_2$]$_{32}$
[γ-CO-MTX-α-OtBu]$_{32}$ [COPEG$_{24}$]$_{32}$

| Surface Topology | Surface Stoichiometry |
|---|---|
| ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ | 32 COPEG24 = PEG<br>32 γ-CO-MTX-α-OtBu = Drug |

The reaction of HO-Su(NPN)$_2$ [γ-CO-MTX-α-OtBu] [COPEG$_{24}$] with BHALys [Lys]$_{16}$ [NH$_2$.TFA]$_8$ was carried out according to the method of Example 56.vi to provide BHALys [Lys]$_{16}$ [Su(NPN)$_2$]$_{32}$ [γ-CO-MTX-α-OtBu]$_{32}$ [COPEG$_{24}$]$_{32}$: 38 mg (49%, 0.95 mCi/g) PREP HPLC (5-60% ACN, 90 min, RT 70 min). LCMS (LC: philic, TFA, RT=9.5 min; MS: ($M_{calc}$ $C_{2887}H_{5025}N_{415}O_{1023}$=61, 919.36)

Example 63

BHALys [Lys]$_{16}$ [Su(NPN)$_2$]$_{32}$
[γ-CO-MTX-α-OtBu]$_{32}$ [COPEG$_{24}$]$_{32}$

| Surface Topology | Surface Stoichiometry |
|---|---|
| ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ ((((Drug PEG)(Drug PEG))$^4$((Drug PEG)(Drug PEG))$^4$)$^8$(((Drug PEG)(Drug PEG))$^4$((Drug PEG)(Drug PEG))$^4$)$^8$)$^{16}$ | 16 COPEG$_{24}$ = PEG<br>16 γ-CO-MTX-α-OtBu = Drug | i. HO-Su(NPN)$_2$ [γ-CO-MTX-α-OtBu] [COPEG$_{2300}$]

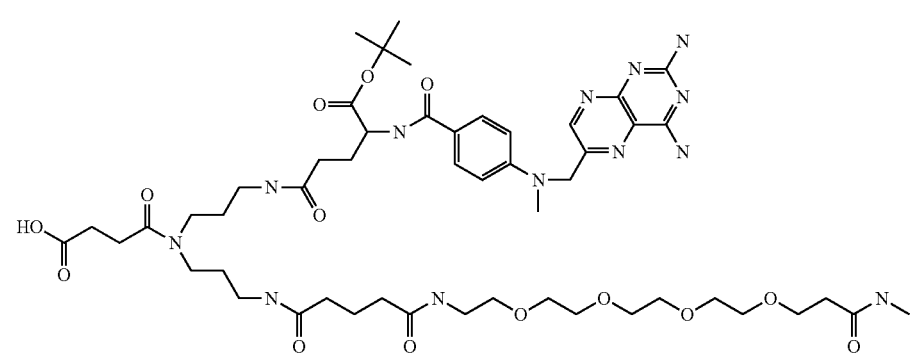

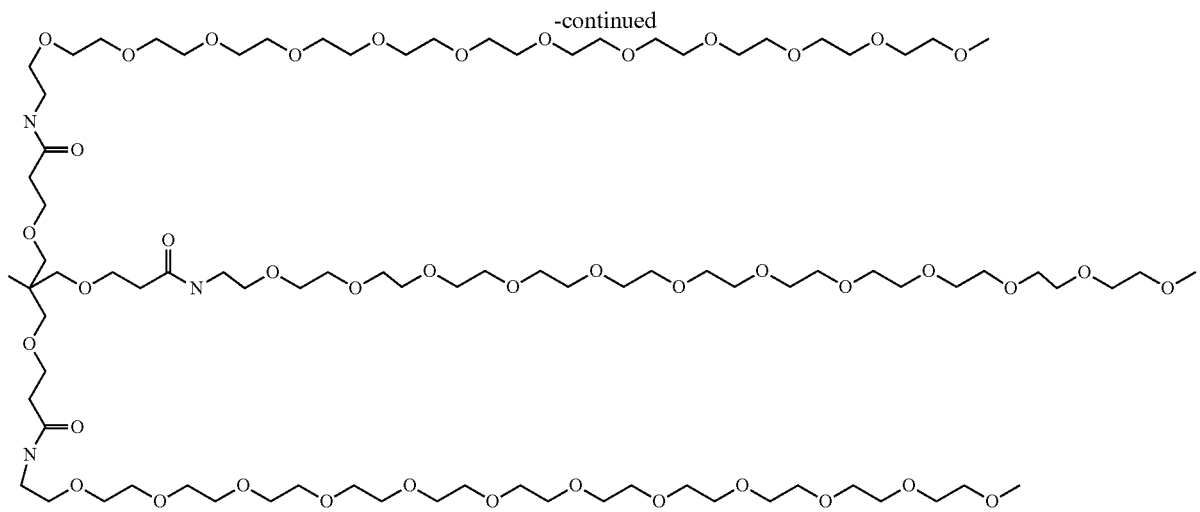

This material was prepared in stepwise fashion from EtO-Su(NPN)$_2$ [Boc] [NH$_2$] and NHS-COPEG$_{2300}$ by way of the method for Example 56.ii to provide EtO-Su(NPN)$_2$ [Boc] [COPEG$_{2300}$]; the Boc group was removed by way of the method for Example 56.iii to provide EtO-Su(NPN)$_2$ [NH$_2$.TFA][COPEG$_{2300}$]; the MTX-α-OtBu was added by way of the method for 56.iv to provide EtO-Su(NPN)$_2$ [γ-CO-MTX-α-OtBu] [COPEG$_{2300}$] and the ester was hydrolysed by way of the method for 56.v to provide HO-Su(NPN)$_2$ [γ-CO-MTX-α-OtBu] [COPEG$_{2300}$].

LCMS (LC: philic, TFA, RT=7.8 min; MS (M$_{calc}$ C$_{138}$H$_{250}$N$_{16}$O$_{56}$=3029.6): 758 (¼[M+4H$^+$], 100%), 607 (⅕[M+5H$^+$], 67%), 506 (⅙[M+6H$^+$], 22%), Transforms to 3,029.2. (M$_{calc}$ C$_{138}$H$_{250}$N$_{16}$O$_{56}$=3029.6). $^1$H (CDCl$_3$): δ 8.4.9 (s, 1H), 7.71 (m, 1H), 7.20-7.52 (m, 2H), 6.64-7.14 (m, 8H), 6.20 (m, 1H), 4.75 (s, 1H), 4.42-4.58 (m, 1H), 3.51-3.78 (m, 170H), 3.38-3.46 (m, 10H), 3.14-3.28 (m, 6H), 2.65-3.12 (m, 10H), 2.50-2.60 (m, 4H), 2.31-2.49 (m, 10H), 2.14-2.28 (m, 4H), 2.02-2.13 (m, 2H), 1.85-1.97 (m, 2H), 1.67-1.83. (m, 2H) 1.50-1.63 (m, 2H), 1.46 (s, 9H), 1.36-1.44 (m, 2H).

ii. BHALys [Lys]$_8$ [Su(NPN)$_2$]$_{16}$ [γ-CO-MTX-α-OtBu]$_{16}$ [COPEG$_{2300}$]$_{16}$

The reaction of HO-Su(NPN)$_2$ [γ-CO-MTX-α-OtBu] [COPEG$_{2300}$] with BHALys [Lys]$_8$ [NH$_2$.TFA]$_{16}$ was carried out according to the method of Example 56.vi to provide BHALys [Lys]$_8$ [Su(NPN)$_2$]$_{16}$ [γ-CO-MTX-α-OtBu]$_{16}$ [COPEG$_{2300}$]$_{16}$: 7 mg (23%, 0.57 mCi/g) PREP HPLC (5-60% ACN, 80 min, RT 62 min). LCMS (LC: philic, TFA, RT=9.8 min; MS: (M$_{calc}$ C$_{2311}$H$_{4161}$N$_{287}$O$_{895}$=50,291.22).

Example 64

Plasma Clearance Studies for Radiolabelled Macromolecules

Tritiated poly-lysine macromolecules were dissolved in phosphate buffered saline (PBS), pH 7.4) and frozen until required. Rats were intravenously administered 5 mg/kg of macromolecule via an indwelling cannula (implanted in the jugular vein) over 2 min.

Immediately following dosing, a blood sample (t=0) was collected via an indwelling carotid artery cannula and placed in a heparinised eppendorf tube.

Blood samples were then collected at predetermined intervals for the following 30 hr, and the plasma separated. In addition, urine and faeces were collected at 0-8 hr, 8-24 hr and 24-30 hr. At sacrifice (30 hr after the intravenous dose) the major organs (liver, kidneys, spleen, pancreas, heart, lung and brain) were collected and weighed. The tritium content of plasma, urine, faeces and the various tissue samples were determined using validated scintillation assays.

Data from Example 64 is tabulated in Table 25, and shown in FIGS. 15A and 15B.

TABLE 25

Pharmacokinetic Parameters for Radiolabelled Macromolecules

| Macromolecule | Example | MW (kDa) | plasma T½ (h) | % of $^3$H dose excreted in total urine |
|---|---|---|---|---|
| (PEG$_{200}$)$_{16}$ | 51 | 6 | 0.25 ± 0.04 | 82.2 ± 6.4 |
| (PEG$_{200}$)$_{32}$ | 52 | 11.1 | 0.72 ± 0.03 | 80.4 ± 13.6 |
| (PEG$_{12}$)$_{32}$ | 53 | 22.4 | 9.45 ± 0.42 | 42.9 ± 2.7 |
| (PEG$_{2KD}$)$_{16}$ | 54 | 34.1 | 23.90 ± 2.56 | 26.0 ± 4.6 |
| (PEG$_{2KD}$)$_{32}$ | 55 | 67 | 75.35 ± 9.3 | 3.1 ± 1.9 |
| (PEG$_{12}$)$_4$(MTX)$_4$ | 56 | — | — | — |
| (PEG$_{12}$)$_8$(MTX)$_8$ | 57 | 11.3 | 4.0 ± 1.8$^a$ | 56.1 ± 8.7 |
| (PEG$_{12}$)$_{16}$(MTX)$_{16}$ | 58 | 22.5 | 9.0 ± 0.2$^a$ | 29.0 ± 3.4 |
| (PEG$_{12}$)$_{32}$(MTX)$_{32}$ | 59 | 45.0 | 23.7 ± 5.0 | 2.4 ± 0.5 |
| (PEG$_{24}$)$_8$(MTX)$_8$ | 60 | 15.5 | 3.9 ± 0.1$^a$ | 64.2 ± 4.6 |
| (PEG$_{24}$)$_{16}$(MTX)$_{16}$ | 61 | 31.0 | 21.0 ± 1.7 | — |
| (PEG$_{24}$)$_{32}$(MTX)$_{32}$ | 62 | 61.9 | 51.4 ± 2.7 | 1.2 ± 0.1 |
| (PEG$_{2300}$)$_{16}$(MTX)$_{16}$ | 63 | 50.3 | 34.1 ± 1.1 | 8.7 ± 1.6 |

Molecular Modelling

Example 65

Simulation of a 4$^{th}$ Generation BHALys-Polylysine Macromolecule

Simulation of 5 types of a BHA substituted (L)-lysine core macromolecule consisting of 4 layers of lysine building units was undertaken.

The asymmetric sets contained the following topological isomers:

| Macro-molecule | Topological description |
|---|---|
| Type 1:<br>16-tet<br>cluster | $((((AA)(AA))^4((AA)(AA))^4)^8(((AA)(AA))^4((AA)(AA))^4)^8)^{16}$<br>$((((BB)(BB))^4((BB)(BB))^4)^8(((BB)(BB))^4((BB)(BB))^4)^8)^{16}$ |
| Type 2:<br>Octet<br>cluster | $((((AA)(AA))^4((AA)(AA))^4)^8(((BB)(BB))^4((BB)(BB))^4)^8)^{16}$<br>$((((AA)(AA))^4((AA)(AA))^4)^8(((BB)(BB))^4((BB)(BB))^4)^8)^{16}$ |
| Type 3:<br>Quartet<br>cluster | $((((AA)(AA))^4((BB)(BB))^4)^8(((AA)(AA))^4((BB)(BB))^4)^8)^{16}$<br>$((((AA)(AA))^4((BB)(BB))^4)^8(((AA)(AA))^4((BB)(BB))^4)^8)^{16}$ |
| Type 4:<br>Couplet<br>cluster | $((((AA)(BB))^4((AA)(BB))^4)^8(((AA)(BB))^4((AA)(BB))^4)^8)^{16}$<br>$((((AA)(BB))^4((AA)(BB))^4)^8(((AA)(BB))^4((AA)(BB))^4)^8)^{16}$ |
| Type 5:<br>No<br>cluster | $((((AB)(AB))^4((AB)(AB))^4)^8(((AB)(AB))^4((AB)(AB))^4)^8)^{16}$<br>$((((AB)(AB))^4((AB)(AB))^4)^8(((AB)(AB))^4((AB)(AB))^4)^8)^{16}$ |

The initial structure was constructed using a computer program which uses stochastic searching to build an extended structure and minimise the number of close contacts. This structure was then placed in a water box and equilibrated according to the protocol shown in FIG. 20. The composition of the entire system is shown in Table 26.

TABLE 26

Composition of the polylysine macromolecule used in the simulation.

| Component | Number of molecules | Number of atoms per molecule | Total number of atoms |
|---|---|---|---|
| Dendrimer | 1 | 710 | 710 |
| Water | 8254 | 3 | 24762 |
| Na$^+$ | 126 | 1 | 126 |
| Cl$^-$ | 158 | 1 | 158 |
| | | Total | 25756 |

The equilibrated macromolecule thus obtained was simulated for a further 12 ns. During this simulation, temperature was maintained at 300 K using Langevin temperature coupling, while pressure was maintained at 1 atm using Nose-Hoover pressure coupling.

Simulations were carried out using the OPLS-AA force field (Jorgensen, W. L et al. (1996). J. Am. Chem. Soc 118, 11225-11236) and the molecular dynamics software NAMD. (Kalé, L. et at (1999) J. Comp. Phys. 151, 283-312). Where necessary, additional torsional parameters were obtained by adopting related torsional parameters already present in the force field. Water molecules were treated explicitly using the TIP3P water model, an implementation of which was present in the OPLS-AA force field. (Jorgensen, W. L et al. (1983). J. Chem. Phys. 79, 926-935).

The resulting simulation trajectories were visually inspected using the trajectory visualisation software, VMD, and the program Sybyl. In addition, two types of distances were calculated. The first is the distance distribution (1), the set of all A-B distances. The second distance is the separation between the centres of mass of the two sets of atoms (2); this distance acts as a quantitative measure of polarisation, and is computed in a similar manner as electric and magnetic dipole moments.

$$s = \sqrt{(x_B - x_A)^2 + (y_B - y_A)^2 + (z_B - z_A)^2} \quad (1)$$

$$\bar{n}_B(k \leq s \leq l) = \frac{\int_k^l F(s)ds}{N_f}$$

$$P_B(k \leq s \leq l) = \frac{\bar{n}_B(k \leq s \leq l)}{N_A}$$

$$S = \sqrt{\left(\frac{1}{N_B}\sum_{j=1}^{N_B} x_B - \frac{1}{N_A}\sum_{i=1}^{N_A} x_A\right)^2 + \left(\frac{1}{N_B}\sum_{j=1}^{N_B} y_B - \frac{1}{N_A}\sum_{i=1}^{N_A} y_A\right)^2 + \left(\frac{1}{N_B}\sum_{j=1}^{N_B} z_B - \frac{1}{N_A}\sum_{i=1}^{N_A} z_A\right)^2} \quad (2)$$

where $(x_A, y_A, z_A)$ and $(x_B, y_B, z_B)$ are the Cartesian coordinates of any atom in a set of atoms A and in another set of atoms B respectively; $N_A$ and $N_B$ are the total numbers of atoms in the sets A and B; $N_f$ is the total number of frames considered; s is the distance between an atom in set A and an atom in set B; S is the distance, in a single frame, between the centre of mass of set A and the centre of mass of set B; F(s) is the total number of times (across all $N_f$ frames) any atom in set B is separated from an atom in set A by the distance s; $\bar{n}_B(k \leq s \leq l)$ is the average, over all frames, of the number of atoms of set B lying between the distances k and l from any atom in set A; and $P_B(k \leq s \leq l)$ is the probability of any one atom in set B lying between the distances k and l from an atom in set A. In the present work, 1 Å shells were used, i.e., l=k+1.

The final frame of the simulation of the simplified 2-dimensional structural drawings in FIG. 16 is shown in FIG. 17, where the functional moieties A and B are represented as light and dark balls respectively.

Inflammation Examples

Example 66

BHALys [Lys]$_2$ [Glu]$_4$ [α-COC2-α-S-GlcNAc]$_4$ [γ-CO$_2$H]$_4$ i. BHALys [Lys]$_2$ [Glu]$_4$ [α-Boc]$_4$ [γ-CO$_2$Me]$_4$

To a magnetically stirred solution of BHALys [Lys]$_2$ [NH$_2$.TFA]$_4$ (400 mg, 0.391 mmol), TEA (0.218 ml, 1.56 mmol) and DMF (10 ml) was added PNPO-Glu-α-Boc-δ-OMe (0.717 g, 1.88 mmol) as a solid and in one portion at room temperature. The reaction suspension immediately turned bright yellow in colour and after stirring for ca. 2 mins, the active ester had completely dissolved. Stirring was continued at room temperature for a further 66 h. The crude reaction mixture was poured into a large beaker of ice-water and a fine yellow precipitate formed. The suspension was filtered and the solids thus retained were washed with water then air dried under suction. The resulting off-white solid cake was resuspended in ACN and this suspension was stirred at room temperature for 5 mins then filtered. The solids retained were once again air dried, re-pulverised and re-suspended in ACN before being filtered and air dried. The resulting white solid was dissolved in methanol and the methanolic solution was concentrated in vacuo to give BHALys [Lys]$_2$ [Glu]$_4$ [α-Boc]$_4$ [γ-CO$_2$Me]$_4$ (301 mg, 50%) as a colourless solid.

LC/MS (Phobic/TFA): ESI (+ve) m/z=1540.82 [M+H]+, 770.87 [M+2H]/2+; calculated C75H117N11O23 1540.83; Rf (min)=5.96 mins.

ii. BHALys [Lys]$_2$ [Glu]$_4$ [α-NH$_2$.TFA]$_4$ [γ-CO$_2$Me]$_4$

BHALys [Lys]$_2$ [Glu]$_4$ [α-Boc]$_4$ [δ-OMe]$_4$ (236 mg, 0.153 mmol) was suspended in DCM (2.15 ml) and stirred at room temperature. A solution of 1:1 TFA/DCM (1.4 ml) was added slowly, causing the suspension to clear rapidly. Stirring was continued for 17 h. The reaction was terminated by removal of volatiles in vacuo, giving a syrup which was taken up into water (50 ml) and freeze-dried to give BHALys [Lys]$_2$ [Glu]$_4$ [α-NH$_2$.TFA]$_4$ [γ-CO$_2$Me]$_4$ as a colourless lyophilate (261 mg, 107%).

LC/MS (Hydrophilic/TFA): ESI (+ve) m/z=1140.64 [M+H]+, 570.67 [M+2H]/2+; calculated C55H85N11O15 1140.4 g/mol. Data deconvoluted using transform calculation to give mw=1139.50. Rf (min)=6.27.

iii. (−)2-Carboxyethyl 2-deoxy-2-acetamido-3,4,6-tetra-O-acetyl-1-thio-β-D-glucopyranoside

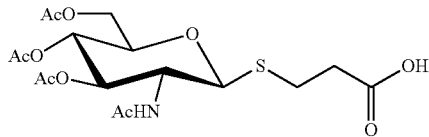

To a stirred solution of 2-deoxy-2-acetamido-3,4,6-O-tri-acetyl-β-D-glucopyranosyl thiouronium hydrochloride (35.7 g, 81 mmol) in acetone (200 ml) and water (200 ml) was added potassium carbonate (16.7 g, 122 mmol) and sodium metabisulfite (15.4 g, 81 mmol) followed by 3-iodopropionic acid (16.1 g, 81 mmol). The reaction was allowed to stir for 2 hours and then an additional portion of sodium metabisulfite (3.0 g, 15.7 mmol) was added. After a further 2 hours, 1N HCl was used to acidify the solution to pH 1 and then the mixture was saturated with solid NaCl. The aqueous mixture was extracted with EtOAc (5×200 ml), the organic extracts were dried (MgSO$_4$) and concentrated under reduced pressure. The residue was suspended in hot toluene and then the toluene decanted. After drying, the product was dissolved in boiling ACN (75 ml) and left to crystallize at −15° C. for 16 hours. The crystalline product was collected and dried under reduced pressure to give 2-carboxyethyl 2-deoxy-2-acetamido-3,4,6-tri-O-acetyl-1-thio-β-D-glucopyranoside as a white solid (26.8 g). The mother liquor was evaporated and the residual product purified by dry flash chromatography then crystallised from ACN to give a further (4.0 g).

[α]$_D^{22}$ −34.9 (c 1.05, MeOH);

IR (nujol): 3303, 1744, 1701, 1659, 1231, 1035, 721 cm$^{-1}$;

$^1$H NMR (300 MHz, d$_6$-DMSO) δ 12.19 (br s, 1H), 7.93 (d, J=9.4 Hz, 1H), 5.06 (dd, J=9.7, 9.7 Hz, 1H), 4.83 (dd, J=9.7, 9.7 Hz, 1H), 4.72 (d, J=10.3 Hz, 1H), 4.13 (dd, J=12.2, 5.2 Hz, 1H), 4.03 (dd, J=12.2, 2.1 Hz, 1H), 3.89-3.78 (m, 2H), 2.90-2.66 (m, 2H), 2.56 (t, J=7.0 Hz, 2H), 2.01 (s, 3H), 1.97 (s, 3H), 1.91 (s, 3H), 1.76 (s, 3H); $^{13}$C NMR (75 MHz, DMSO) 172.9, 169.9, 169.5, 169.1, 169.0, 83.7, 74.4, 73.5, 68.5, 61.9, 51.9, 35.0, 24.9, 22.5, 20.3, 20.3, 20.2;

HRMS calcd for (M+NH$_4^+$, ESI) C$_{17}$H$_{29}$O$_{10}$N$_2$S: 453.1537. found: 453.1528.

iv. NHS—COC2-(perAc)-α-S-GlcNAc

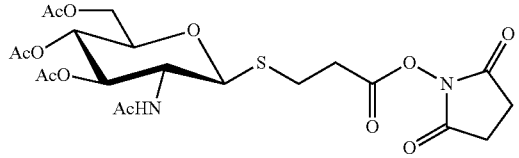

To a stirred solution of 2-carboxyethyl 2-deoxy-2-acetamido-3,4,6-tri-O-acetyl-1-thio-β-D-glucopyranoside (5.0 g, 11.4 mmol) in EtOAc (25 ml) and ACN (25 ml) was added N-hydroxysuccinimide (1.98 g, 17.2 mmol) then dicyclohexylcarbodiimide (2.83 g, 13.7 mmol). The reaction was allowed to stir for 3 hours and then the precipitated urea removed by filtration. The urea was washed well with EtOAc, the filtrate concentrated under reduced pressure and the residue purified by flash chromatography to give NHS—COC2-(perAc)-α-S-GlcNAc as a colourless crystalline solid (4.82 g, 79%).

$^1$H NMR (300 MHz, CHCl$_3$) δ 6.04 (br d, J=9.5 Hz, 1H), 5.15 (dd, J=9.5, 9.5 Hz, 1H), 5.07 (dd, J=9.5, 9.5 Hz, 1H), 4.73 (d, J=10.3 Hz, 1H), 4.24-4.05 (m, 3H), 3.70 (ddd, J=9.5, 4.8, 2.5 Hz, 1H), 3.20-2.82 (m, 4H), 2.87 (s, 4H), 2.07 (s, 3H), 2.02 (s, 3H), 2.01 (s, 3H), 1.94 (s, 3H);

HRMS calcd for (M+NH$_4^+$, ESI) C$_{21}$H$_{32}$N$_3$O$_{12}$S: 550.1701. found: 550.1684; (M+H$^+$) C$_{21}$H$_{29}$N$_2$O$_{12}$S: 533.1454. found: 533.1494;

v. BHALys [Lys]$_2$ [Glu]$_4$ [α-COC2-α-S-GlcNAc]$_4$ [γ-CO$_2$H]$_4$

| Surface Topology | Surface Stoichiometry | |
|---|---|---|
| (((Sacc CO$_2$H)(Sacc CO$_2$H))$^4$((Sacc CO$_2$H)(Sacc CO$_2$H))$^4$)$^8$ | 4 | COC2-α-S-GlcNAc = Sacc |
| | 4 | CO$_2$H |

To a stirred solution of BHALys [Lys]$_2$ [Glu]$_4$ [α-NH$_2$.TFA]$_4$ [γ-CO$_2$Me]$_4$ (107 mg, 0.067 mmol) dissolved in DMF (5 ml) was added NHS—COC2-(perAc)-α-S-GlcNAc (214 mg, 0.40 mmol) followed by DIPEA (69 mg, 0.53 mmol). The reaction mixture was allowed to stir for 2 hours and then diluted with water (10 ml) and the precipitated solid collected under vacuum. The precipitate was washed with water then suspended in hot CHCl$_3$. After cooling the solid was collected then suspended in methanol (5 ml) and CH$_2$Cl$_2$ (5 ml) and 30% NaOMe (5 drops) added. The mixture was sonicated for 5 minutes and then shaken for 15 minutes. The mixture did not appear to dissolve so the mixture was concentrated under vacuum and diluted with water (5 ml) and potassium carbonate (185 mg) added. The mixture was stirred overnight and then 2N NaOH (100 μl) added as not all intermediate had dissolved. The mixture was left for a further 4 hours then acidified to pH 1 with TFA. The volatiles were removed under reduced pressure and the product purified by RP-HPLC (Phenomenex Synergi, 95:5 to 50:50 0.1% formic acid:MeOH over 60 minutes at 20 ml/min). The cleanest fractions containing product were combined and concentrated under reduced pressure and the residue dissolved in water and lyophilized to give BHALys [Lys]$_2$ [Glu]$_4$ [α-COC2-α-S-GlcNAc]$_4$ [γ-CO$_2$H]$_4$ as a colourless solid (33 mg, 39%); HPLC ret time 14.0 min, purity 90% (Waters Symmetry, 70:30 to 30:70 0.1% TFA in water:MeOH over 30 minutes);

$^1$H NMR (300 MHz, D$_2$O) δ 7.44-7.23 (m, 10H), 6.09 (s, 1H), 4.40-4.06 (m, 7H), 3.99-3.33 (m, 24H), 0.32-3.00 (m, 6H), 3.04-2.87 (m, 8H), 2.70-2.56 (m, 8H), 2.14-1.60 (m, 14H), 2.00 (br s, 12H), 1.59-1.20 (m, 12H);

MS calcd for (M−H, Q-TOF) C$_{95}$H$_{144}$N$_{15}$O$_{39}$S$_4$: 2246.86. Found: 2246.81.

Example 67

BHALys [Lys]$_4$ [Glu]$_8$ [α-COC2-α-S-GlcNAc]$_8$ [δ-CO$_2$H]$_8$ i. BHALys [Lys]$_4$ [Glu]$_8$ [α-Boc]$_8$ [γ-CO$_2$Me]$_8$

To a magnetically stirred solution of BHALys [Lys]$_4$ [NH$_2$.TFA]$_5$ (400 mg, 0.201 mmol), TEA (0.560 ml, 4.01 mmol) and DMF (10 ml) was added PNPO-Glu-α-Boc-δ-OMe (737 mg, 1.93 mmol) as a solid and in one portion at room temperature. The reaction suspension immediately turned bright yellow in colour and after stirring for ca. 3 mins, the active ester had completely dissolved. Stirring was continued at room temperature for a further 17 h. The crude reaction mixture was poured into a beaker of ice-water and a fine yellow precipitate formed. The suspension was stirred until the ice melted then filtered and the solids thus retained were washed with water (3×30 ml), ACN (2×25 ml) then methanol (3×30 ml). The remaining solids were air dried under suction, giving BHALys [Lys]$_4$ [Glu]$_8$ [α-Boc]$_8$ [γ-CO$_2$Me]$_8$ (460 mg, 76%) as a white solid.

LC/MS (Phobic/TFA): ESI (+ve) m/z=1514.43 [M+2H]/2+, 1009.61 [M+3H]/3+; calculated C143H233N23O31 3026.58. Data deconvoluted using transform calculation to give mw=3025.83. Rf (min)=6.66 mins.

ii. BHALys [Lys]$_4$ [Glu]$_8$ [α-NH$_2$.TFA]$_8$ [γ-CO$_2$Me]$_8$

BHALys [Lys]$_4$ [Glu]$_8$ [α-Boc]$_8$ [γ-CO$_2$Me]$_8$ (460 mg, 0.152 mmol) was suspended in DCM (2.8 ml) and stirred at room temperature. A solution of 1:1 TFA/DCM (2.8 ml) was added slowly, causing the suspension to clear rapidly. Stirring was continued for 3 h. The reaction was terminated by removal of volatiles in vacuo, giving a syrup which was triturated with Ether (50 ml). The resulting cloudy white suspension was filtered and the pellet thus obtained was washed with Ether (2×50 ml) and air-dried to give BHALys [Lys]$_4$ [Glu]$_8$ [α-NH$_2$.TFA]$_8$ [γ-CO$_2$Me]$_8$ as a white solid (423 mg, 89%).

LC/MS (Hydrophilic/TFA): ESI (+ve) m/z=1113.59 [M+2H]/2+, 742.77 [M+3H]/3+; calculated C103H169N23O31 2225.63 g/mol. Data deconvoluted using transform calculation to give mw=2224.37. Rf (min)=5.94.

iii. HO—COC2-α-S-GlcNAc

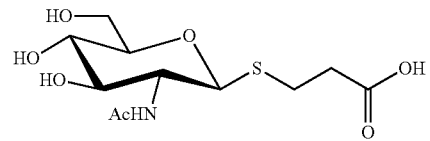

A solution of (−)2-Carboxyethyl 2-deoxy-2-acetamido-3,4,6-tetra-O-acetyl-1-thio-α-D-glucopyranoside (1.30 g, 2.98 mmol) was dissolved in a solution of 7N methanolic ammonia (20 ml) and the resulting solution stirred for 16 hours. The white precipitate formed was collected by vacuum filtration and washed with 1:1 methanol/CH$_2$Cl$_2$ (20 ml). The precipitate was dissolved in water (50 ml) and Amberjet 1200H strongly acidic ion exchange resin (10 g) added. The suspension was stirred for 15 minutes and then the resin was filtered and washed well with water. The aqueous washing were concentrated under reduced pressure to afford HO—COC2-α-S-GlcNAc as a colourless gum which crystallised upon standing (800 mg, 87%);

$[α]_D^{22}$ −41.4 (c 1.5, H$_2$O);

$^1$H NMR (300 MHz, D$_2$O) δ 4.61 (d, J=10.4 Hz, 1H), 3.88 (d, J=12.4 Hz, 1H), 3.75-3.66 (m, 2H), 3.56-3.40 (m, 3H), 3.01-2.83 (m, 2H), 2.72 (t, J=6.7 Hz, 2H), 1.99 (s, 3H);

HRMS calcd for (M−H$^+$, ESI) C$_{11}$H$_{18}$NO$_7$S: 308.0809. found: 308.0809; Anal calcd for C$_{11}$H$_{19}$NO$_7$S: C, 42.71; H, 6.19; N, 4.53. Found: C, 42.40; H, 6.31; N, 4.81.

iv. BHALys [Lys]$_4$ [Glu]$_8$ [α-COC2-α-S-GlcNAc]$_8$ [γ-CO$_2$H]$_8$

| Surface Topology | | Surface Stoichiometry | |
|---|---|---|---|
| ((((Sacc CO$_2$H)(Sacc CO$_2$H))$^4$((Sacc CO$_2$H)(Sacc CO$_2$H))$^4$)$^8$(((Sacc CO$_2$H)(Sacc CO$_2$H))$^4$((Sacc CO$_2$H)(Sacc CO$_2$H))$^4$)$^8$)$^{16}$ | | 8 8 | COC2-α-S-GlcNAc = Sacc CO$_2$H |

To a stirred solution of BHALys [Lys]$_4$ [Glu]$_8$ [α-NH$_2$.TFA]$_8$ [γ-CO$_2$H]$_8$ (82 mg, 0.036 mmol) and HO—COC2-α-S-GlcNAc (137 mg, 0.44 mmol) in DMF (5 ml) were added DIPEA (190 mg, 1.47 mmol) followed by PyBOP (307 mg, 0.59 mmol). The reaction mixture was left to stir for 16 hours and then diluted with ACN and the precipitated solid collected by vacuum filtration. The precipitate was dissolved in water (10 ml) and basified with 1N NaOH (4 ml) and left to stir for several hours. The mixture was then acidified with Amberjet 1200 H resin, the resin removed by filtration and the product lyophilized. The residue was purified by RP-HPLC to give 2 fractions, one containing pure BHALys [Lys]$_4$ [Glu]$_8$ [α-COC2-α-S-GlcNAc]$_8$ [γ-CO$_2$H]$_8$ (19 mg) and one which was only 70% pure (29 mg); HPLC ret time 12.0 min, purity>99% (220 nm, Waters Symmetry, 70:30 to 30:70 0.1% TFA in water:MeOH over 30 minutes);

$^1$H NMR (300 MHz, D$_2$O) δ 7.43-7.21 (m, 10H), 6.08 (s, 1H), 4.36-4.05 (m, 15H), 4.00-3.84 (m, 8H), 3.80-3.31 (m, 40H), 3.27-2.81 (m, 30H), 2.63 (br s, 16H), 2.49-2.35 (m, 16H), 2.16-1.15 (m, 58H), 1.99 (br s, 12H), 1.98 (br s, 12H);

MS calcd for (M−3H, Q-TOF) $C_{183}H_{288}N_{31}O_{79}S$: m/z 1479.235. Found: 1479.219.

Example 68

BHALys [Lys]$_2$ [Glu]$_4$
[α-COC2CO-2-N-α-OMe-Glc]$_4$ [γ-CO$_2$H]$_4$ i. BHALys [Lys]$_2$ [Glu]$_4$ [α-Boc]$_4$ [γ-CO$_2$Fm]$_4$

To a magnetically stirred solution of HO-Glu-α-Boc-δ-OFm (831 mg, 1.95 mmol), DCC (338 mg, 1.64 mmol), HOBT (222 mg, 1.64 mmol) and DMF (7 ml) was added a solution of BHALys [Lys]$_2$ [NH$_2$.TFA]$_4$ (400 mg, 0.391 mmol), DIPEA (0.278 ml, 1.56 mmol) in DMF (3 ml) at 0° C. The reaction was allowed to warm to room temperature and stirred for 18 hrs. The crude reaction mixture was filtered, with the solid pellet being rinsed with DMF (10 ml). The combined filtrates were concentrated in vacuo to give an off-white syrup which was triturated with Ether (100 ml) to give a cloudy white suspension. This suspension was filtered and air-dried, giving BHALys [Lys]$_2$ [Glu]$_4$ [α-Boc]$_4$ [γ-CO$_2$Fm]$_4$ (1.02 g, 119%) as a white solid. Excess mass is due to residual solvent.

LC/MS (Phobic/TFA): ESI (+ve) m/z=1099.67 [M+2H]/2+; calculated C127H149N11O23 2197.66. Data deconvoluted using transform calculation to give mw=2197.25. Rf (Min)=9.07 mins.

ii. BHALys [Lys]$_2$ [Glu]$_4$ [α-NH$_2$.TFA]$_4$ [γ-CO$_2$Fm]$_4$

BHALys [Lys]$_2$ [Glu]$_4$ [α-Boc]$_4$ [γ-CO$_2$Fm]$_4$ (1.02 g, i.e. 858 mg, 0.390 mmol) was suspended in DCM (3.6 ml) and stirred at room temperature. A solution of 1:1 TFA/DCM (3.6 ml) was added slowly, causing the suspension to clear rapidly. Stirring was continued for 3 h. The reaction was terminated by removal of volatiles in vacuo, giving a syrup which was triturated with Ether (50 ml), giving a white suspension. The solids were collected from the suspension by filtration, and washed with Ether (2×50 ml) then air-dried to give and freeze-dried to give BHALys [Lys]$_2$ [Glu]$_4$ [α-NH$_2$.TFA]$_4$ [γ-CO$_2$Fm]$_4$ as a white solid (829 mg, 94%).

LC/MS (Hydrophilic/TFA): ESI (+ve) m/z=1979.78 [M+H]+, 899.34 [M+2H]/2+; calculated C107H117N11O15 1797.19 g/mol. Data deconvoluted using transform calculation to give mw=1796.93. Rf (min)=10.90.

iii. Methyl 2-deoxy-2-[3-(methoxycarbonyl)propanamido]-α-D-glucopyranoside

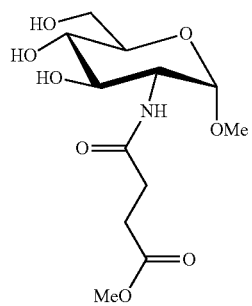

To a stirred solution of glucosamine hydrochloride (20.0 g, 92 mmol) dissolved in acetone (40 ml) and water (100 ml) was added sodium bicarbonate (31 g, 370 mmol) followed by succinic anhydride (13.8 g, 138 mmol). The mixture was stirred for 2 hours and then the mixture acidified to pH 1 with Amberjet 1200 H. The resin was removed by filtration and the filtrate concentrated under reduced pressure. The residue was suspended in hot acetone and collected by filtration, then taken up in methanol (200 ml) and amberjet 1200 H (30 g) added to the mixture which was heated under reflux overnight. The mixture was filtered, then concentrated under reduced pressure to give a colourless gum which was absorbed onto silica gel and purified by dry flash chromatography to give a colourless solid (8.2 g). The product was isolated clean by crystallization from EtOAc to give methyl 2-deoxy-2-[3-(methoxycarbonyl)propanamido]-α-D-glucopyranoside as a colourless solid (3.5 g, 12%);

$[α]_D^{22}$+89 (c 1.0, H$_2$O); R$_f$ 0.43 (90:10 CHCl$_3$:MeOH);
$^1$H NMR (300 MHz, D$_2$O) δ 4.72 (d, J=3.6 Hz, 1H), 3.89 (dd, J=10.6, 3.4 Hz, 1H), 3.85 (dd, J=12.5, 2.2 Hz, 1H), 3.79-3.60 (m, 3H), 3.67 (s, 3H), 3.44 (dd, J=9.3, 9.3 Hz, 1H), 3.36 (s, 3H), 2.69-2.56 (m, 4H);
HRMS calcd for (M+H$^+$, ESI) $C_{12}H_{21}NO_8$: 308.1339. found: 308.1326.

iv. HO—COC2CO-2-N-α-OMe-Glc

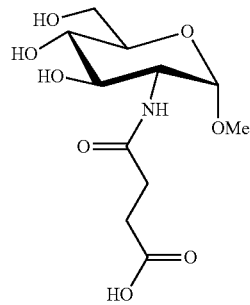

To a stirred solution of methyl 2-deoxy-2-[3-(methoxycarbonyl)propanamido]-α-D-glucopyranoside (3.54 g, 11.5 mmol) dissolved in water (10 ml) was added 2N sodium hydroxide solution (10 ml). The reaction mixture was allowed to stir for 16 hours and then acidified with Amberjet 1200 H resin. The resin was removed by filtration through a sintered glass funnel. The solvent was then removed under reduced pressure leaving HO—COC2CO-2-N-α-OMe-Glc as a white crystalline solid (3.37 g, 94%);

$[α]_D^{22}$+107.2 (c 1.0, H$_2$O);
$^1$H NMR (300 MHz, D$_2$O) δ 4.71 (d, J=3.6 Hz, 1H), 3.89 (dd, J=10.6, 3.6 Hz, 1H), 3.85 (dd, J=12.4, 2.3 Hz, 1H), 3.78-3.60 (m, 3H), 3.44 (dd, J=9.5, 9.5 Hz, 1H), 3.35 (s, 3H), 2.60-2.48 (m, 4H);
HRMS calcd for (M−H$^+$, ESI) $C_{11}H_{19}NO_8Na_1$: 316.1006. Found: 316.1008.

v. BHALys [Lys]$_2$ [Glu]$_4$
[α-COC2CO-2-N-α-OMe-Glc]$_4$ [γ-CO$_2$H]$_4$

| Surface Topology | | Surface Stoichiometry | |
|---|---|---|---|
| (((Sacc CO$_2$H)(Sacc CO$_2$H))$^4$((Sacc CO$_2$H)(Sacc CO$_2$H))$^4$)$^8$ | 4 | COC$_2$CO-2-N-α-OMe-Glc = Sacc | |
| | 4 | CO$_2$H | |

To a stirred solution of BHALys [Lys]$_2$ [Glu]$_4$ [α-NH$_2$.TFA]$_4$ [γ-CO$_2$Fm]$_4$ (100 mg, 0.044 mmol) in DMF (5 ml) was added HO—COC2CO-2-N-α-OMe-Glc (78 mg, 0.26 mmol) and DIPEA (68 mg, 0.53 mmol) followed by PyBOP (138 mg, 0.26 mmol). The reaction mixture was left to stir for 16 hours and then piperidine (0.50 ml) was added and the reaction was left for a further 1 hour. The mixture was diluted with chloroform and the precipitated solid collected. The solid was suspended in water (10 ml) and potassium carbonate (200 mg) added. A colloidal suspension formed and so 1N NaOH (4 ml) was added. The reaction was stirred for 2 hours and then stored at 4° C. for 16 hours before being acidified with Amberjet 1200 H. The reaction mixture was filtered, the volatiles removed under reduced pressure and the residue fractionated by RP-HPLC (Phenomenex Synergi, 1200 H, 70:30 to 30:70 0.1% TFA in water:MeOH over 55 minutes) to give BHALys [Lys]$_2$ [Glu]$_4$ [α-COC2CO-2-N-α-OMe-Glc]$_4$ [γ-CO$_2$H]$_4$ as a colourless solid (32 mg, 33%); HPLC ret time 15.3 min, purity>99% (220 nm, Waters symmetry, 70:30 to 30:70 0.1% TFA in water:MeOH over 37 minutes);

$^1$H NMR (300 MHz, D$_2$O) 7.43-7.24 (m, 10H), 6.07 (s, 1H), 4.37-4.08 (m, 7H), 3.92-3.80 (m, 8H), 3.77-3.60 (m, 12H), 3.48-3.38 (m, 4H), 3.34 (m, 12H), 3.18-3.00 (m, 6H), 2.62-2.48 (m, 16H), 2.46-2.34 (m, 8H), 2.11-1.59 (m, 14H), 1.57-1.13 (m, 12H);

HRMS calcd for (M−2H, Q-TOF) C$_{95}$H$_{143}$N$_{15}$O$_{43}$: m/z 1090.9737. Found: 1090.9701.

Example 69

BHALys [Lys]$_4$ [Glu]$_8$ [α-COC2CO-2-N-α-OMe-Glc]$_8$ [γ-CO$_2$H]$_8$

| Surface Topology | Surface Stoichiometry | |
|---|---|---|
| (((((Sacc CO$_2$H)(Sacc CO$_2$H))$^4$((COC2CO-2-N-α-OMe-Glc CO$_2$H)(Sacc CO$_2$H))$^4$)$^8$(((Sacc CO$_2$H)(Sacc CO$_2$H))$^4$((Sacc CO$_2$H)(Sacc CO$_2$H))$^4$)$^8$)$^{16}$ | 8<br>8 | COC2CO-2-N-α-OMe-Glc = Sacc<br>CO$_2$H |

To a stirred solution of BHALys [Lys]$_4$ [Glu]$_8$ [α-NH$_2$.TFA]$_8$ [γ-CO$_2$Me]$_8$ (100 mg, 0.036 mmol) in DMF (3 ml) was added HO—COC2CO-2-N-α-OMe-Glc (150 mg, 0.51 mmol) followed by DIPEA (99 mg, 0.76 mmol) then PyBOP (265 mg, 0.52 mmol). The reaction mixture was left to stir overnight then diluted with DCM (15 ml) and the precipitated solid collected under vacuum. The product was taken up in water (10 ml) and potassium carbonate (300 mg) added. The mixture was stirred overnight and then 2N NaOH (4 ml, 4.0 mmol) added to drive the reaction to completion. The mixture was diluted to (40 ml), filtered through a 0.45 mm syringe filter and then ultra-filtered through a tangential flow filtration cartridge (mw cutoff 650 da) keeping the volume constant at 40 ml, until the solution was pH 9 (200 ml filtrate). The retentate was lyophilized and then purified by RP-HPLC (Phenomenex Synergi, 1200 H, 70:30 to 30:70 0.1% TFA in water:MeOH over 55 minutes). The fractions containing pure product were combined and concentrated under reduced pressure then the residue was taken up in water and lyophilized giving BHALys [Lys]$_4$ [Glu]$_8$ [α-COC2CO-2-N-α-OMe-Glc]$_8$[γ-CO$_2$H]$_8$ as a colourless solid (12 mg, 9%);

$^1$H NMR (300 MHz, D$_2$O) 7.42-7.23 (m, 10H), 6.07 (s, 1H), 4.39-4.11 (m, 15H), 3.96-3.79 (m, 16H), 3.78-3.57 (m, 24H), 3.48-3.38 (m, 8H), 3.34 (s, 24H), 3.21-3.00 (m, 14H), 2.56 (br s, 32H), 2.37 (br s, 16H), 2.13-1.82 (m, 16H), 1.69 (br s, 14H), 1.54-1.18 (m, 28H);

MS calcd for (M−2H, Q-TOF) C$_{183}$H$_{287}$N$_{31}$O$_{87}$: m/z 2155.449. Found 2155.737.

Example 70

BHALys [Lys]$_4$ [Glu]$_8$ [α-COC5-α-S-GlcNAc]$_8$ [γ-CO$_2$Na]$_8$ i. BHALys [Lys]$_4$ [Glu]$_8$ [α-Boc]$_8$ [γ-CO$_2$Bn]$_8$

To a magnetically stirred solution of BHALys [Lys]$_4$ [NH$_2$.TFA]$_a$ (400 mg, 0.201 mmol), TEA (0.560 ml, 4.01 mmol) and DMF (10 ml) was added PNPO-Glu-α-Boc-δ-OBn (936 mg, 1.93 mmol) as a solid and in one portion at room temperature. The reaction and product isolation were carried out according to the method of Example 1.i to give BHALys [Lys]$_4$ [Glu]$_8$ [α-Boc]$_8$ [γ-CO$_2$Bn]$_8$ (648 mg, 89%) as a white solid.

ii. BHALys [Lys]$_4$ [Glu]$_8$ [α-NH$_2$.TFA]$_8$ [γ-CO$_2$Bn]$_8$

BHALys [Lys]$_4$ [Glu]$_8$ [α-Boc]$_8$ [γ-CO$_2$Bn]$_8$ (648 mg, 0.178 mmol) was suspended in DCM (3.3 ml) and stirred at room temperature. A solution of 1:1 TFA/DCM (3.3 ml) was added slowly, causing the suspension to clear rapidly. Stirring was continued for 4 h. The reaction was terminated by removal of volatiles in vacuo, giving a syrup which was taken up in 1:1 methanol/water, concentrated in vacuo, then taken up in water, freeze-dried, re-suspended in methanol and concentrated to give BHALys [Lys]$_4$ [Glu]$_8$ [α-NH$_2$.TFA]$_8$ [γ-CO$_2$Bn]$_8$ as a colourless foam (677 mg, 101%).

LC/MS: ESI (+ve) m/z=1418.35 [M+2H]/2+, 945.64 [M+3H]/3+, 709.64 [M+4H]/4+; calculated C151H201N23O31 2834.42 g/mol. Data deconvoluted using transform calculation to give mw=2834.00. Rf (min)=8.53.

iii. 5-carboxypentyl 2-acetamido-3,4,6-tri-O-acetyl-2-deoxy-1-thio-β-D-glucopyranoside

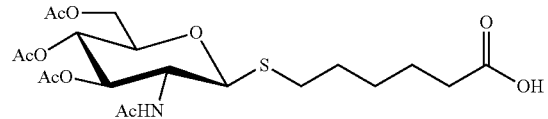

To a stirred solution of S-(2-acetamido-3,4,6-tri-O-acetyl-2-deoxy-γ-D-glucopyranosyl)thiouronium chloride (6.5 g, 16.03 mmol) dissolved in acetone (25 ml) and water (25 ml) was added potassium carbonate (5.54 g, 40.1 mmol) and sodium metabisulfite (3.09 ml, 24.05 mmol) followed by 6-bromohexanoic acid (3.75 g, 19.24 mmol). The reaction mixture was left to stir for 2 h then acetone (25 ml) added and the mixture filtered. The residue was concentrated under reduced pressure and then acidified with 1N HCl. The product crystallized from solution and was collected. Additional product was isolated by extracting the mother liquor with EtOAc (2×25 ml). The combined product was further purified by flash chromatography giving a colourless solid (4.67 g, 61%).

[α]$_D^{22}$ −45.9 (c 1.71, CH$_2$Cl$_2$). $^1$H NMR (300 MHz, CDCl$_3$) δ 5.68 (d, J=9.4 Hz, 1H), 5.15 (dd, J=9.5, 9.5 Hz, 1H), 5.08 (dd, J=9.5, 9.5 Hz, 1H), 4.58 (d, J=10.3 Hz, 1H), 4.23

(dd, J=12.4, 4.8 Hz, 1H), 4.16-4.03 (m, 2H), 3.68 (ddd, J=9.5, 4.9, 2.4 Hz, 1H), 2.78-2.62 (m, 2H), 2.35 (t, J=7.0 Hz, 2H), 2.07 (s, 3H), 2.03 (s, 3H), 2.02 (s, 3H), 1.96 (s, 3H), 1.71-1.56 (m, 4H), 1.52-1.37 (m, 2H). $^{13}$C NMR (300 MHz, CDCl$_3$) δ 177.8, 171.1, 170.8, 170.3, 169.3, 84.4, 75.9, 73.9, 68.4, 62.3, 53.2, 33.6, 29.5, 28.9, 27.9, 24.1, 23.1, 20.7, 20.6, 19.5. HRMS ESI (+ve) m/z=500.1577 [M+Na]+; calculated C$_{20}$H$_{31}$N$_1$O$_{10}$Na$_1$S$_1$ 500.1566 g/mol.

iv. PNPO—COC5-α-S-(perAc)-GlcNAc

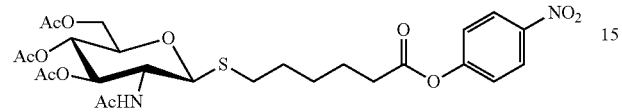

To a stirred solution of 5-carboxypentyl 2-acetamido-3,4, 6-tri-O-acetyl-2-deoxy-1-thio-β-D-glucopyranoside (1.20 g, 2.44 mmol) dissolved in ethyl acetate (10 ml) and dichloromethane (10 ml) was added 4-nitrophenol (0.50 g, 3.66 mmol) and then EDC (0.70 g, 3.66 mmol). The reaction mixture was stirred for 16 h and then concentrated under reduced pressure and purified by flash chromatography to give PNPO—COC5-α-S-(perAc)-GlcNAc as a colourless solid (0.96 g, 64%).

[α]$_D^{22}$ −35.4 (c 1.67, CH$_2$Cl$_2$). $^1$H NMR (300 MHz, CDCl$_3$) δ 8.30-8.25 (m, 2H), 7.31-7.26 (m, 2H), 5.49 (d, J=9.2 Hz, 1H), 5.16 (dd, J=9.3, 9.3 Hz, 1H), 5.09 (dd, J=9.3, 9.3 Hz, 1H), 4.57 (d, J=10.2 Hz, 1H), 4.24 (dd, J=12.4, 5.0 Hz, 1H), 4.18-4.05 (m, 2H), 3.68 (ddd, J=9.3, 4.7, 2.3 Hz, 1H), 2.82-2.68 (m, 2H), 2.61 (dd, J=2.35 (t, J=7.2 Hz, 2H), 2.08 (s, 3H), 2.04 (s, 3H), 2.03 (s, 3H), 1.95 (s, 3H), 1.84-1.47 (m, 6H). $^{13}$C NMR (300 MHz, CDCl$_3$) δ 171.0, 170.5, 169.9, 169.2, 155.4, 145.3, 125.2, 122.4, 84.5, 76.0, 73.8, 68.3, 62.3, 53.2, 34.0, 29.5, 29.0, 27.9, 24.1, 23.2, 20.7, 20.6, 20.5. HRMS ESI (+ve) m/z=620.1731 [M+Na]+; calculated C$_{26}$H$_{34}$N$_2$Na$_1$O$_{12}$S$_1$ 621.1730 g/mol.

v. BHALys [Lys]$_4$ [Glu]$_8$ [α-COC5-α-S-GlcNAc]$_8$ [γ-CO$_2$Na]$_8$

| Surface Topology | Surface Stoichiometry |
|---|---|
| (((((Sacc CO$_2$H)(Sacc CO$_2$H))$^4$((COC2CO-2-N-α-OMe-Glc CO$_2$H)(Sacc CO$_2$H))$^4$)$^8$(((Sacc CO$_2$H)(Sacc CO$_2$H))$^4$((Sacc CO$_2$H)(Sacc CO$_2$H))$^4$)$^8$)$^{16}$ | 8 COC5-α-S-(perAc)-GlcNAc = Sacc<br>8 CO$_2$H |

To a stirred solution of BHALys [Lys]$_4$ [Glu]$_8$ [α-NH$_2$.TFA]$_8$[γ-CO$_2$Bn]$_8$ (59 mg, 15.7 μmol) and PNPO—COC5-α-S-(perAc)-GlcNAc (155 mg, 253 μmol) in DMF (3 ml) was added DIPEA (88 μl, 505 μmol). The reaction mixture was left to stir for 16 h and then the intermediate peracetate precipitated with ether and collected. The filtrate was concentrated under reduced pressure and the residue washed with methanol. The combined isolated solids were suspended in water (10 ml) and 2N NaOH (5 ml) added. The reaction mixture was allowed to stir for 5 h at which time all material had dissolved. The mixture was then filtered through a 0.4 micron syringe filter to remove particulate matter, diluted to (40 ml) with water and purified by tangential flow filtration using a 1 KDa cutoff membrane, dialysing with water (600 ml). The retentate was freeze dried giving BHALys [Lys]$_4$ [Glu]$_8$[α-COC5-α-S-GlcNAc]$_8$ [γ-CO$_2$Na]$_8$ as a slightly yellow solid (28 mg, 35%).

$^1$H NMR (300 MHz, D$_2$O) δ 7.44-7.20 (m, 10H), 6.09 (s, 1H), 4.57 (d, J=10.5 Hz, 8H), 4.37-4.05 (m, 15H), 3.95-3.80 (m, 8H), 3.80-3.63 (m, 16H), 3.59-3.48 (m, 8H), 3.49-3.31 (m, 16H), 3.23-2.99 (m, 14H), 2.76-2.55 (m, 16H), 2.34-2.14 (m, 32H), 2.08-1.22 (m, 106H), 2.00 (s, 24H). HRMS ESI (+ve) calculated C$_{207}$H$_{337}$N$_{31}$O$_{79}$S$_8$ 4777.10 g/mol. Data deconvoluted using transform calculation to give mw=4777.12.

Example 71

BHALys [Lys]$_8$ [Glu]$_{16}$ [α-COC5-α-S-GlcNAc]$_{16}$ [γ-CO$_2$Na]$_{16}$ i. BHALys [Lys]$_8$ [Glu]$_{16}$ [α-Boc]$_{16}$ [γ-CO$_2$Bn]$_{16}$

To a magnetically stirred solution of BHALys [Lys]$_8$ [NH$_2$.TFA]$_{16}$ (400 mg, 0.102 mmol), TEA (0.567 ml, 4.07 mmol) and DMF (10 ml) was added PNPO-Glu-α-Boc-δ-OBn (949 mg, 1.95 mmol) as a solid and in one portion at room temperature. Stirring was continued at room temperature for 64 h. The crude reaction mixture was concentrated in vacuo to give a syrup, which was triturated with water (50 ml) to give a beige-coloured gum. The water was decanted off the gum, which was triturated with ACN (100 ml) giving a white suspension. The white solid was collected by filteration under suction, washed with ACN (2×50 ml) and air-dried to give BHALys [Lys]$_8$ [Glu]$_{16}$ [α-Boc]$_{16}$ [γ-CO$_2$Bn]$_{16}$ (757 mg, 103%) as a colourless solid.

ii. BHALys [Lys]$_8$ [Glu]$_{16}$ [α-NH$_2$.TFA]$_{16}$ [γ-CO$_2$Bn]$_{16}$

BHALys [Lys]$_8$ [Glu]$_{16}$ [α-Boc]$_{16}$ [γ-CO$_2$Bn]$_{16}$ (500 mg, 0.069 mmol) was suspended in DCM (4 ml) and stirred at room temperature. A solution of 1:1 TFA/DCM (2.6 ml) was added slowly, causing the suspension to clear rapidly. Stirring was continued for 17 h. The reaction was terminated by removal of volatiles in vacuo, giving a syrup which was triturated with Ether (50 ml), resulting in a white suspension. The solid was collected by filtration under suction and washed with Ether (2×50 ml) then air-dried to give BHALys [Lys]$_8$ [Glu]$_{16}$ [α-NH$_2$.TFA]$_{16}$ [γ-CO$_2$Bn]$_{16}$ as an off-white solid (486 mg, 94%).

LC/MS: ESI (+ve) m/z=1872.14 [M+3H]/3+, 1404.36 [M+4H]/4+, 1123.76 [M+5H]/5+, 936.43 [M+6H]/6+, 802.97 [M+7H]/7+; calculated C295H401N47O63 5613.76 g/mol. Data deconvoluted using transform calculation to give mw=5612.83. Rf (min)=5.43.

iii. BHALys [Lys]$_8$ [Glu]$_{16}$ [α-COC5-α-S-GlcNAc]$_{16}$ [γ-CO$_2$Na]$_{16}$

| Surface Topology | Surface Stoichiometry |
|---|---|
| (((((Sacc CO$_2$H)(Sacc CO$_2$H))$^4$((COC2CO-2-N-α-OMe-Glc CO$_2$H)(Sacc CO$_2$H))$^4$)$^8$(((Sacc CO$_2$H)(Sacc CO$_2$H))$^4$((Sacc CO$_2$H)(Sacc CO$_2$H))$^4$)$^8$)$^{16}$ | 16 COC5-α-S-(perAc)-GlcNAc = Sacc |
| (((((Sacc CO$_2$H)(Sacc CO$_2$H))$^4$((COC2CO- | 16 CO$_2$H |

| Surface Topology | Surface Stoichiometry |
|---|---|
| 2-N-α-OMe-Glc $CO_2H$)(Sacc $CO_2H$))$^4$)$^8$(((Sacc $CO_2H$)(Sacc $CO_2H$))$^4$((Sacc $CO_2H$)(Sacc $CO_2H$))$^4$)$^8$)$^{16}$ | |

To a stirred solution of BHALys [Lys]$_8$ [Glu]$_{16}$ [α-$NH_2$.TFA]$_{16}$ [γ-$CO_2$Bn]$_{16}$ (58.2 mg, 7.83 µmol) and PNPO—COC5-α-S-(perAc)-GlcNAc (150 mg, 251 µmol) in DMF (3 ml) was added DIPEA (87 µl, 501 µmol). The reaction was left to stir for 16 h and then the product precipitated using water (25 ml). The precipitate was collected, suspended in water (10 ml) and methanol (2 ml) and 2N NaOH added (3 ml). The reaction was allowed to stir for 5 h at which time all of the starting material had dissolved and the solution was yellow from residual 4-nitrophenol. The mixture was diluted with water to a volume of 50 ml and then concentrated using tangential flow filtration to 30 ml and then dialysed against water (400 ml), 5% $Na_2CO_3$ solution (100 ml) then water (600 ml) until the solution was neutral and colourless. The retentate was freeze dried to give BHALys [Lys]$_8$ [Glu]$_{16}$ [α-COC5-α-S-GlcNAc]$_{16}$ [γ-$CO_2$Na]$_{16}$ as a colourless solid (67 mg, 87%).

$^1$H NMR (300 MHz, $D_2O$) 7.40-7.23 (m, 10H), 6.08 (s, 1H), 4.57 (d, J=10.4 Hz, 16H), 4.34-4.10 (m, 31H), 3.87 (br d, J=12.2 Hz, 16H), 3.76-3.65 (m, 32H), 3.58-3.50 (m, 16H), 3.48-3.38 (m, 32H), 3.20-3.05 (m, 30H), 2.78-2.56 (m, 32H), 2.34-2.14 (m, 64H), 2.08-1.22 (m, 218H), 2.01 (s, 48H). MS ESI (+ve) calculated $C_{407}H_{673}N_{63}O_{159}S_{16}$ 9507.2 g/mol. Data deconvoluted using transform calculation to give mw=9504.2. MS ESI (+ve) calculated $C_{407}H_{672}N_{63}O_{159}S_{16}Na$ 9529.0 g/mol. Data deconvoluted using transform calculation to give mw=9525.1.

Example 72

BHALys [Lys]$_2$ [α-GlyLys]$_2$ [CO-3,5-Ph($CO_2Me$)$_2$]$_4$ [ε-GlyLys]$_2$ [α-CO-3,5-Ph($CO_2Me$)$_2$]$_2$ [ε-[Glu]$_2$ [α-Boc]$_2$ [γ-$CO_2Me$]$_2$ i. BnO-GlyLys [α-Fmoc] [ε-Boc]

To a magnetically stirred solution of H-Gly-OBn.HCl (1.63 g, 8.06 mmol) and PFP-Lys-α-Fmoc-ε-Boc (4.65 g, 7.33 mmol) in DMF (60 ml) was slowly added a solution of DIPEA (1.27 ml, 7.33 mmol) in DMF (40 ml) at room temperature. Stirring was continued at room temperature for 18 h. A solution of DIPEA (64 µl, 0.367 mmol) in DMF (1 ml) was added and stirring was continued for a further 4 h. The reaction was poured onto iced water (400 ml), the suspension was filtered and solids washed well with water then collected under suction and air-dried then dried in a vacuum oven at 40° C. and 20 mm Hg to give BnO-GlyLys [α-Fmoc] [ε-Boc] (4.04 g, 90%).

LC/MS (Hydrophobic/TFA): ESI (+ve) m/z=1249.61 [2M+NH4]+, 1231.59 [2M+H]+, 616.25 [M+H]+; calculated $C_{35}H_{41}N_3O_7$ 615.73 g/mol. Rf (min)=5.66.

ii. BnO-GlyLys [α-NH2] [ε-Boc]

BnO-GlyLys [α-Fmoc] [ε-Boc] (1.5 g, 2.44 mmol) was dissolved in DMF (100 ml) and stirred at room temperature. A solution of piperidine (3.75 ml) in DMF (46.25 ml) was added slowly, and stirring was continued at room temperature for 4 h before the reaction was stored at −18° C. for 66 h. The reaction was terminated by removal of volatiles in vacuo, giving an off-white residue which was triturated with Ether (50 ml), resulting in a white suspension. The etheric solution was collected by filtration, then concentrated under reduced pressure to give an off-white solid under suction then air-dried to give BnO-GlyLys [α-NH2] [ε-Boc] as an off-white solid (assume 639 mg, 100%) contaminated with Fmoc-Piperidine. This crude mixture was used without further purification.

LC/MS (Hydrophilic/TFA): ESI (+ve) m/z=787.32 [2M+H]+, 394.19 [M+H]+; calculated C20H31N3O5 393.49 g/mol. Rf (min)=7.00.

iii. BnO-GlyLys [α-CO-3,5-Ph($CO_2Me$)$_2$][ε-Boc]

To a solution of BnO-GlyLys [α-NH2] [ε-Boc] (500 mg, 1.27 mmol) and 1,3-dimethyl 5-(4-nitrophenyl)benzene-1,3,5-tricarboxylate (456 mg, 1.27 mmol in DMF (25 ml), stirring at room temperature, was added TEA (0.186 ml, 1.33 mmol). The reaction and product isolation were carried out according to the method of Example 13.iii to give BnO-GlyLys [α-CO-3,5-Ph($CO_2Me$)$_2$] [ε-Boc] as a clear, pale yellow glass (495 mg, crude).

LC/MS (Hydrophobic/TFA): ESI (+ve) m/z=1250.35 [2M+Na]+, 636.25 [M+Na]+, 614.30 [M+H]+; calculated C31H39N3O10 613.67 g/mol. Rf (min)=4.37.

iv. BnO-GlyLys [α-CO-3,5-Ph($CO_2Me$)$_2$] [ε-$NH_2$.TFA]

BnO-GlyLys [α-CO-3,5-Ph($CO_2Me$)$_2$][ε-Boc] (486 mg, 0.792 mmol) was dissolved in 1:1 TFA/DCM (6 ml) and stirred at room temperature for 4 h. The reaction was concentrated and the residue was triturated with Ether (30 ml), resulting in a white suspension, which was collected by suction and washed with acetonitrile. The acetonitrile washings were concentrated to dryness, yielding BnO-GlyLys [α-CO-3,5-Ph($CO_2Me$)$_2$] [ε-$NH_2$.TFA] as an orange foam (191 mg, 38%).

LC/MS (Hydrophilic/TFA): ESI (+ve) m/z=1027.28 [2M+H]+, 514.09 [M+H]+; calculated C26H31N3O8 513.55 g/mol. Rf (min)=7.05.

v. BnO-GlyLys [α-CO-3,5-Ph($CO_2Me$)$_2$][ε-Glu] [α-Boc] [γ-$CO_2Me$]

To a solution of BnO-GlyLys [α-CO-3,5-Ph($CO_2Me$)$_2$] [ε-$NH_2$.TFA] (191 mg, 0.304 mmol) in DMF (5 ml), stirring at room temperature, was added TEA (0.106 ml, 0.761 mmol) followed by PNPO-Glu-α-Boc-δ-Me (140 mg, 0.365 mmol). The reaction and product isolation were carried out according to the method of Example 13.iii to give BnO-GlyLys [α-CO-3,5-Ph($CO_2Me$)$_2$] [ε-Glu] [α-Boc] [γ-$CO_2Me$] as an orange foam (181 mg, 79%).

LC/MS (Hydrophobic/TFA): ESI (+ve) m/z=1536.48 [2M+Na]+, 1514.43 [2M+H]+, 779.20 [M+Na]+, 757.16 [M+H]+; calculated C37H48N4O13 756.81 g/mol. Rf (min) =4.04.

vi. HO-GlyLys [α-CO-3,5-Ph($CO_2Me$)$_2$] [ε-Glu] [α-Boc] [γ-$CO_2Me$]

BnO-GlyLys [α-CO-3,5-Ph($CO_2Me$)$_2$] [ε-Glu] [α-Boc] [γ-$CO_2Me$] (90 mg, 0.119 mmol) was dissolved in 2,2,2-trifluoroethanol (4 ml) and stirred at room temperature. Non-Degussa Pd/C (10%, 0.030 mmol, 32 mg) was added to the degassed solution and the system was stirred under hydrogen gas (1 atm) for 24 h. The catalyst was removed by filtration and the filtrate was concentrated to dryness to give HO-GlyLys [α-CO-3,5-Ph(CO$_2$Me)$_2$] [ε-Glu] [α-Boc] [γ-CO$_2$Me] as an orange glass (81 mg, 102%).

LC/MS (Hydrophilic/TFA): ESI (+ve) m/z=1556.52 [2M+Na]+, 1333.43 [2M+H]+, 689.16 [M+Na]+, 667.21 [M+H]+; calculated C30H42N4O13 666.69 g/mol. Rf (min)=7.45.

vii. BnO-GlyLys [Boc]$_2$

To a magnetically stirred solution of H-Gly-OBn.HCl (2.50 g, 12.4 mmol) in DMF (80 ml) was added TEA (4.4 ml, 31.0 mmol) followed by PNPO-Lys(Boc)$_2$ (6.96 g, 14.9 mmol). The reaction and product isolation were carried out according to the method of Example 72.i to give BnO-GlyLys [Boc]$_2$ as a pale yellow foam (6.42 g, 105%).

LC/MS (Hydrophobic/TFA): ESI (+ve) m/z=987.45 [2M+H]+, 494.22 [M H]+; calculated C25H39N3O7 493.61 g/mol. Rf (min)=4.30.

viii. BnO-GlyLys [NH$_2$.TFA]$_2$

BnO-GlyLys [Boc]$_2$ (6.12 g, 12.4 mmol) was suspended in 90 ml DCM and stirred at room temperature while 1:1 TFA/DCM (60 ml) was slowly added. After stirring for 18 h, the reaction was concentrated and the residue triturated with Ether (80 ml). The gum was lyophilised from water (100 ml) yielding BnO-GlyLys [NH$_2$.TFA]$_2$ as a hygroscopic off-white foam (6.51 g, 101%).

LC/MS (Hydrophilic/TFA): ESI (+ve) m/z=587.30 [2M+H]+, 294.25 [M+H]+; calculated C15H23N3O3 293.37 g/mol. Rf (min)=3.84.

ix. BnO-GlyLys [CO-3,5-Ph(CO$_2$Me)$_2$]$_2$

To a magnetically stirred solution of BnO-GlyLys [NH$_2$.TFA]$_2$ (600 mg, 1.15 mmol) in DMF (35 ml) was added TEA (0.802 ml, 5.75 mmol) followed by 1,3-dimethyl 5-(4-nitrophenyl)benzene-1,3,5-tricarboxylate (990 mg, 2.76 mmol). Stirring was continued at room temperature for 18 h. The reaction mixture was concentrated to dryness and the resulting oil was triturated with Ether (100 ml) to give a precipitate which was collected by suction, washed with diethyl ether and air-dried to yield BnO-GlyLys [CO-3,5-Ph(CO$_2$Me)$_2$]$_2$ as a white solid (754 mg, 89%).

LC/MS (Hydrophobic/TFA): ESI (+ve) m/z=1490.35 [2M+Na]+, 1468.36 [2M+H]+, 756.10 [M+Na]+, 734.16 [M+H]+; calculated C37H39N3O13 733.74 g/mol. Rf (min)= 3.86.

x. HO-GlyLys [CO-3,5-Ph(CO$_2$Me)$_2$]$_2$

BnO-GlyLys [CO-3,5-Ph(CO$_2$Me)$_2$]$_2$ (750 mg, 1.02 mmol) was dissolved in 2,2,2-trifluoroethanol (35 ml) and stirred at room temperature. Non-Degussa Pd/C (10%, 0.255 mmol, 271 mg) was added to the degassed solution and the system was stirred under hydrogen gas (1 atm) for 66 h. The catalyst was removed by filtration and the filtrate was concentrated to dryness to give HO-GlyLys [CO-3,5-Ph(CO$_2$Me)$_2$]$_2$ as a yellow foam (624 mg, 94%).

LC/MS (Hydrophilic/TFA): ESI (+ve) m/z=1288.30 [2M+H]+, 644.09 [M+H]+; calculated C30H33N3O13 643.61 g/mol. Rf (min)=7.19.

xi. BHALys [Lys]$_2$ [ε-Boc]$_2$ [α-GlyLys]$_2$ [CO-3,5-Ph(CO$_2$Me)$_2$]$_4$

A magnetically stirred solution of BHALys [Lys]$_2$ [α-NH$_2$]$_2$ [ε-Boc]$_2$ (16.4 mg, 0.0213 mmol) and HO-GlyLys [CO-3,5-Ph(CO$_2$Me)$_2$]$_2$ (37.0 mg, 0.0575 mmol) in DMF (5 ml) was cooled to 0° C., then PyBOP (30.0 mg, 0.0575 mmol) was added, followed by DIPEA (19 µl, 0.107 mmol). Stirring was continued at 0° C. for 30 mins, then the reaction was warmed to room temperature and stirred for 66 h. The reaction was quenched with methanol (2 ml) and stirred overnight before being applied to a Sephadex LH20 column for purification (eluent:methanol) to give BHALys [Lys]$_2$ [ε-Boc]$_2$ [α-GlyLys]$_2$ [CO-3,5-Ph(CO$_2$Me)$_2$]$_4$ as a clear glass (33.7 mg, 75%), which was characterised by removal of the Boc groups in the following step.

xii. BHALys [Lys]$_2$ [ε-NH$_2$.TFA]$_2$ [α-GlyLys]$_2$ [CO-3,5-Ph(CO$_2$Me)$_2$]$_4$ BHALys [Lys]$_2$ [ε-Boc]$_2$ [α-GlyLys]$_2$ [CO-3,5-Ph(CO$_2$Me)$_2$]$_4$ dissolved in 1:1 TFA/DCM (2 ml) and stirred at room temperature for 4 h. The reaction was concentrated in vacuo, triturated with Ether and dried to give BHALys [Lys]$_2$ [ε-NH$_2$.TFA]$_2$ [α-GlyLys]$_2$ [CO-3,5-Ph(CO$_2$Me)$_2$]$_4$ as a clear glass (32.0 mg, 100%).

LC/MS (Hydrophilic/TFA): ESI (+ve) m/z=1819.82 [M+H]+, 910.16 [M+2H]/2+; calculated C91H111N13O27 1818.97 g/mol. Data deconvoluted using transform calculation to give mw=1818.58. Rf (min)=9.14.

xiii. BHALys [Lys]$_2$ [α-GlyLys]$_2$ [CO-3,5-Ph(CO$_2$Me)$_2$]$_4$ [ε-GlyLys]$_2$ [α-CO-3,5-Ph(CO$_2$Me)$_2$]$_2$ [ε-[Glu]$_2$ [α-Boc]$_2$ [γ-CO$_2$Me]$_2$

| Surface Topology | Surface Stoichiometry | |
|---|---|---|
| ((((Dianion Ø)(Dianion Ø))$^4$((Dianion Ø)(Anion Boc))$^4$)$^8$(((Dianion Ø)(Dianion Ø))$^4$((Dianion Ø)(Anion Boc))$^4$)$^8$)$^{16}$ | 6 | CO-3,5-Ph(CO$_2$Me)$_2$ = Dianion |
| | 2 | Glutamate CO$_2$Me = Anion |
| | 2 | Boc |

A magnetically stirred solution of BHALys [Lys]$_2$ [ε-NH$_2$.TFA]$_2$ [α-GlyLys]$_2$ [CO-3,5-Ph(CO$_2$Me)$_2$]$_4$ (32 mg, 0.0156 mmol) and HO-GlyLys [α-CO-3,5-Ph(CO$_2$Me)$_2$]$_2$ [ε-[Glu]$_2$ [α-Boc]$_2$ [γ-CO$_2$Me]$_2$ (28 mg, 0.0422 mmol) in DMF (3 ml) was cooled to 0° C., then PyBOP (22 mg, 0.0422 mmol) was added, followed by DIPEA (14 µl, 0.0782 mmol). Stirring was continued at 0° C. for 15 mins, then the reaction was warmed to room temperature and stirred for 18 h. The reaction was quenched with methanol (2 ml) and stirred for 66 h before being applied to a Sephadex LH20 column for purification (eluent:methanol) to give BHALys [Lys]$_2$ [α-GlyLys]$_2$ [CO-3,5-Ph(CO$_2$Me)$_2$]$_4$ [ε-GlyLys]$_2$ [α-CO-3,5-Ph(CO$_2$Me)$_2$]$_2$ [ε-[Glu]$_2$ [α-Boc]$_2$ [γ-CO$_2$Me]$_2$ as a clear glass (31 mg, 63%).

LC/MS (Hydrophobic/TFA): ESI (+ve) m/z=1558.93 [M+2H]/2+, 1039.87 [M+3H]/3+, 1006.20 [M−Boc+3H]/3+, 972.66 [M−2Boc+3H]/3+; calculated C151H191N21O51 3116.32 g/mol. Data deconvoluted using transform calculation to give mw=3116.22. Rf (min)=5.97.

Example 73

Assays for Anti-Inflammatory Activity

Methods
1. Cell Culture

THP-1 cells were cultured in RPMI 1640 medium (ICN) containing 10% heat inactivated foetal calf serum (FCS), 1.5 g/L sodium bicarbonate (ICN), 10 nM HEPES buffer (Sigma), 1 mM sodium pyruvate (JRH), 0.05 mM 2-Mercaptoethanol (Sigma), 2 mM L-glutamine and Penicillin/Streptomycin (Life Technologies). They were maintained in medium TC flasks (Cellstar) at a density of <1×10⁶ cells/mL. All experiments were performed in cells with passage numbers between 3-8.

2. Experimental Procedure

Cells from one or more TC flasks were collected, counted and transferred to a new TC flask in low-serum medium (0.5% FCS/RPMI). The next day, the cells were counted and seeded into wells of a 24-well plate (Sarstedt) at $5\times10^5$ cells/well in 0.5% FCS/RPMI.

Compound treatments, vehicle controls and dexamethasone (Dex) were immediately added to the appropriate wells. The plate was then incubated at 37 degrees, 5% CO2 for 30 minutes. Lipopolysaccharide (LPS-Sigma) was then added to appropriate wells and the plate incubated for a further 4 hours at 37 degrees, 5% CO2.

After 4 hours, the contents of each well were collected into 1.5 mL tubes (Eppendorf) and centrifuged to pellet the cells. The supernatant was then collected and stored at −80° C.

3. Enzyme-Linked Immunosorbent Assay (ELISA) Procedure

Supernatants were assayed to determine levels of MIP-1beta and TNF-alpha by standard ELISAs.

3.i TNF Alpha ELISA
Day 1:
ELISA plates coated with monoclonal anti-TNFα capture antibody (R&D Systems) in a volume of 100 uL at 4 ug/mL in PBS. Plates incubated overnight at 4° C.
Day 2:
Plates washed (×3) with 0.05% Tween 20/PBS
Plates blocked for 2 hrs in 0.1% BSA/PBS
Plates washed (×3) with 0.05% Tween 20/PBS
Supernatants, diluted in 1% BSA/PBS added to plate (100 uL volume/well) along with recombinant human TNF (R&D Systems) as reference standard. Plates incubated overnight at 4° C.
Day 3:
Plates washed (×3) with 0.05% Tween 20/PBS
100 uL of anti-human TNF biotinylated affinity purified polyclonal antibody (R&D Systems) added to each well at 300 ng/mL in 1% BSA/PBS
Plates washed (×3) with 0.05% Tween 20/PBS
100 uL Streptavidin HRP (Chemicon) added to each well (diluted 1/1000 in 1% BSA/PBS).
Plate incubated for 2 hrs at room temperature, then washed (×3) with 0.05% Tween 20/PBS.
100 uL TMB substrate solution added to each well and plate incubated in the dark for 10-20 minutes.
100 uL of stop solution (0.5M $H_2SO_4$) added to each well; plates read immediately on Victor3 plate reader at a wavelength of 450 nm.

3.ii MIP-1b ELISA
Day 1:
ELISA plates coated with monoclonal anti-MIP-1b capture antibody (R&D Systems) in a volume of 100 uL at 1 ug/mL in phosphate buffered saline (PBS).
Plates incubated overnight at 4° C.
Day 2:
Plates washed (×3) with 0.05% Tween 20/PBS
Plates blocked for 2 hrs in 0.1% BSA/PBS
Plates washed (×3) with 0.05% Tween 20/PBS
Supernatants, diluted in 1% BSA/PBS added to plate in duplicate wells (100 uL volume/well).
Recombinant human MIP-1b (R&D Systems) added as reference standard. Plates incubated overnight at 4° C.
Day 3:
Plates washed (×3) with 0.05% Tween 20/PBS 100 uL of anti-human MIP-1b biotinylated affinity purified polyclonal antibody (R&D Systems) added to each well at 50 ng/mL in 1% BSA/PBS
Plates washed (×3) with 0.05% Tween 20/PBS
100 uL Streptavidin HRP (Chemicon) added to each well (diluted 1/1000 in 1% BSA/PBS).
Plate incubated for 2 hrs at room temperature.
Plates washed (×3) with 0.05% Tween 20/PBS
100 uL TMB substrate solution added to each well. Plate incubated in the dark for 10-20 minutes.
100 uL of stop solution (0.5M H2SO4) added to each well.
Plates read immediately on Victor3 plate reader at a wavelength of 450 nm.

3.iii Standard Curves for TNF and MIP-1b
Stock recombinant protein at 10 µg/mL
Dilute stock 2 µL/1000 uL 1% BSA/PBS (1)
Dilute (1) 50 µL/1000 uL 1% BSA/PBS (Standard A 1 ng/mL)
Dilute A 220 µL/440 uL 1% BSA/PBS (Standard B 0.5 ng/mL)
Dilute B 220 µL/440 uL 1% BSA/PBS (Standard C 0.25 ng/mL)
Dilute C 220 µL/440 uL 1% BSA/PBS (Standard D 0.125 ng/mL)
Dilute D 220 µL/440 uL 1% BSA/PBS (Standard E 0.0625 ng/mL)
Dilute E 220 µL/440 uL 1% BSA/PBS (Standard F 0.0312 ng/mL)
Dilute F 220 µL/440 uL 1% BSA/PBS (Standard G 0.0156 ng/mL)
Blank (1% BSA/PBS alone)

4. Data Analysis

Data were analysed for statistically significant inhibition of cytokine release by 1-way ANOVA with Tukey's post test, and if applicable IC50 were derived. GraphPad Prism® 4 software was used.

TABLE 27

Anti-Inflammatory activity of selected Examples.

| Compound # | Name | TNF-α $IC_{50}$ (µg/ml) | MIP-1β $IC_{50}$ (µg/ml) |
|---|---|---|---|
| 73.1[a] | BHALys [Lys]$_{16}$ [COC2CO-2-N-α-OMe-Glc]$_{32}$ | NA | NA |
| 73.2[a] | BHALys [Lys]$_{16}$ [COC2-β-S-GlcNAc]$_{32}$ | Weak | NS @ [max] |
| 73.3[a] | BHALys [Lys]$_4$ [COC2-β-S-GlcNAc]$_8$ | NA | NA |
| 73.4[a] | BHALys [Lys]$_8$ [COC2CO-2-N-Glc]$_{16}$ | NA | NA |
| 73.5[a] | BHALys [Lys]$_8$ [COC2CO-2-N-α-OMe-Glc]$_{16}$ | NA | NA |
| 73.6[a] | BHALys [Lys]$_8$ [COC2-β-S-GlcNAc]$_{16}$ | NA | NA |
| 73.7[a] | MorphLys [Lys]$_8$ [COC2-β-S-GlcNAc]$_{16}$ | NA | NA |
| 73.8[a] | BHALys [Lys]$_4$ [COC2CO-2-N-α-OMe-Glc]$_8$ | 64.8 | 84.8 |
| 73.9[a] | MorphLys [Lys]$_4$ [COC2CO-2-N-α-OMe-Glc]$_8$ | NA | NA |

TABLE 27-continued

Anti-Inflammatory activity of selected Examples.

| Compound # | Name | TNF-α IC$_{50}$ (µg/ml) | MIP-1β IC$_{50}$ (µg/ml) |
|---|---|---|---|
| 73.10[a] | MorphLys [Lys]$_4$ [COC2-β-S-GlcNAc]$_8$ | NA | NA |
| 73.11[b] | [BHAlys] [Lys]16 [CONH-Ph-3,5-(SO3Na)2]32 | 56.7 | 74.7 |
| 73.12[b] | BHALys [Lys]16 [A-3,5-BDC]32 | 132.3 | 202.2 |

[a]The preparation of these compounds has been described in Provisional patent application: AU2006XXXXXXX
[b]The preparation of these compounds has been described in AU2005905858

This data indicates that macromolecules with controlled stoichiometry/topology of Functional Moieties that are either anionic or are N-Acetyl Glucose or analogues thereof, may have anti-inflammatory properties.

What is claimed is:

1. A process for preparing a macromolecule, wherein the macromolecule comprises at least one dendritic motif; which process includes:
    (i) providing a growing macromolecule including at least one reactable amine group;
    a first building compound having a hydrocarbon backbone, and bearing an apex carbonyl group and having a first amino group bearing a first functional moiety and a second amino group bearing a second functional moiety, wherein the first and second functional moieties are different, and wherein the first and second functional moieties are attached to the first and second amino groups, optionally through a linker, by an amide bond;
    (ii) activating the apex carbonyl group of the first building compound; and
    (iii) reacting the at least one reactable amine group of the growing macromolecule with the activated apex carbonyl group of the first building compound.

2. A process according to claim 1 wherein the growing macromolecule is a core including at least one reactable amine group.

3. A process according to claim 1 wherein the growing macromolecule comprises a core and at least one layer of building compounds.

4. A process according to claim 1 wherein the first and second functional moieties are amino protecting groups.

5. A process according to claim 4 wherein one of the amino protecting groups is inert to cleavage conditions required to remove the other amine protecting group.

6. A process according to claim 5 further comprising the steps of
    (i) deprotecting one of the amine protecting groups;
    (ii) reacting the deprotected amine group with a first functional moiety selected from the group consisting of ligands for extraceullar receptors; property modifiers; biological targeting groups; signalling groups; antigenic materials; genetic materials; pharmaceutically active agents; groups adapted to mediate binding to a second entity, end stopping moieties and linkers;
    (iii) deprotecting the other amine protecting group; and
    (iv) reacting the deprotected amine group with a second functional moiety selected from the group consisting of ligands for extraceullar receptors; property modifiers; biological targeting groups; signalling groups; antigenic materials; genetic materials; pharmaceutically active agents; groups adapted to mediate binding to a second entity, end stopping moieties and linkers;
    wherein the first and second functional moieties are different.

7. A process according to claim 4 wherein the amine protecting groups are selected from t-butyloxycarbamate (BOC), (benzylcarboxy) carbamate (CBz), (9-fluorenylmethyl) carbamate (Fmoc), 2-halo-CBz, (allyl) carbamate (Alloc), Me$_3$SiEtSO$_2$, trichoroethyl carbamate (Troc), o-NO$_2$PhSO$_2$, 2,4-dinitrobenzene-sulfonyl, 4-nitro-CBz and N-2-(4,4-dimethyl-2,6-dioxocyclohexylidene)ethylamine (Dde).

8. A process according to claim 4 further comprising the steps of
    (i) providing a second building compound having a hydrocarbon backbone and bearing an apex carbonyl group and having at least one amine group bearing a functional moiety being a protecting group;
    (ii) deprotecting the at least one amine on the first building compound of the macromolecule;
    (iii) activating the apex carbonyl group of the second building compound; and
    (iv) reacting the deprotected macromolecule with the apex carbonyl group of the second building compound.

9. A process according to claim 8 wherein the second building compound is a lysine or lysine analogue.

10. A process according to claim 9 wherein steps (i) to (iv) are repeated with the first or second building compound.

11. A process according to claim 1 wherein the first and second functional moieties are selected from the group consisting of ligands for extraceullar receptors; property modifiers; biological targeting groups; signalling groups; antigenic materials; genetic materials; pharmaceutically active agents; groups adapted to mediate binding to a second entity, end stopping moieties, protecting groups and linkers.

12. A process according to claim 11 wherein the functional moiety is attached to the amine group through a linker.

13. A process according to claim 1 wherein the first building compound is a compound including at least one dendritic motif, the motif having a surface layer and at least one sub-surface layer.

14. A process according to claim 13 wherein the surface layer comprises lysine or a lysine analogue and one of the first and second functional moieties is attached to one of the lysine or lysine analogue amino groups, optionally through a linker, by an amide bond and the other of the first and second functional moieties is attached to the other lysine or lysine analogue amino group, optionally through a linker, by an amide bond.

15. A process according to claim 14 wherein the first and second functional moieties are amine protecting groups.

16. A process according to claim 15 wherein one of the amine protecting groups is inert to cleavage conditions required to remove the other amine protecting group.

17. A process according to claim 16 further comprising the steps of
    (i) deprotecting one of the amine protecting groups;
    (ii) reacting the deprotected amine group with a first functional moiety selected from the group consisting of ligands for extraceullar receptors; property modifiers; biological targeting groups; signalling groups; antigenic materials; genetic materials; pharmaceutically active agents; groups adapted to mediate binding to a second entity, end stopping moieties and linkers;
    (iii) deprotecting the other amine protecting group; and
    (iv) reacting the deprotected amine group with a second functional moiety selected from the group consisting of ligands for extraceullar receptors; property modifiers; biological targeting groups; signalling groups; antigenic materials; genetic materials; pharmaceutically active agents; groups adapted to mediate binding to a second entity, end stopping moieties and linkers;

wherein the first and second functional moieties are different.

18. A process according to claim 17 wherein the amine protecting groups are selected from BOC, CBz, Fmoc, 2-halo-CBz, Alloc, Me$_3$SiEtSO$_2$, Troc, o-NO$_2$PhSO$_2$, 2,4-dinitrobenzene-sulfonyl, 4-nitro-CBz and Dde.

19. A process according to claim 17 wherein the first and second functional moieties are selected from the group consisting of ligands for extraceullar receptors; property modifiers; biological targeting groups; signalling groups; antigenic materials; genetic materials; pharmaceutically active agents; groups adapted to mediate binding to a second entity, end stopping moieties, protecting groups and linkers.

20. A process according to claim 1 wherein the functional moiety is attached to the amine group through a linker.

21. A process according to claim 1 wherein the growing macromolecule includes a second reactable amine group.

22. A process according to claim 8 wherein the first building compound is a lysine or lysine analogue.

23. A process according to claim 1 wherein the growing macromolecule is a dendrimer.

24. A process according to claim 23 wherein the dendrimer has 3 to 5 generations.

25. A process according to claim 1 wherein the first functional moiety is selected from the group consisting of ligands for extraceullar receptors; property modifiers; biological targeting groups; signalling groups; antigenic materials; genetic materials; pharmaceutically active agents; groups adapted to mediate binding to a second entity, end stopping moieties, protecting groups and linkers and the second functional moiety is selected from the group consisting of ligands for extraceullar receptors; property modifiers; biological targeting groups; signalling groups; antigenic materials; genetic materials; pharmaceutically active agents; groups adapted to mediate binding to a second entity, end stopping moieties, protecting groups and linkers; wherein the first functional moiety and second functional moiety are selected from different groups.

26. A process according to claim 1 wherein the first and second functional moieties are independently selected from the group consisting of ligands for extraceullar receptors; property modifiers; biological targeting groups; signalling groups; genetic materials; pharmaceutically active agents; groups adapted to mediate binding to a second entity, end stopping moieties, protecting groups and linkers; wherein the first and second functional moieties are different.

27. A process according to claim 1 wherein one of the first and second functional moieties is a property modifier selected to modify the pharmacokinetics of the macromolecule.

28. A process according to claim 27, wherein the property modifier is polyethylene glycol (PEG).

29. A process according to claim 1 wherein the process is performed in solution.

30. A process according to claim 1 wherein when there are only two different functional moieties, the number of first functional moieties does not equal the number of second functional moieties.

* * * * *